US007626009B2

(12) United States Patent
Weaver et al.

(10) Patent No.: US 7,626,009 B2
(45) Date of Patent: Dec. 1, 2009

(54) PUFA POLYKETIDE SYNTHASE SYSTEMS AND USES THEREOF

(75) Inventors: Craig A. Weaver, Boulder, CO (US); Ross Zirkle, Longmont, CO (US); James G. Metz, Longmont, CO (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 11/689,459

(22) Filed: Mar. 21, 2007

(65) Prior Publication Data

US 2008/0026437 A1 Jan. 31, 2008

Related U.S. Application Data

(60) Division of application No. 10/965,017, filed on Oct. 13, 2004, now Pat. No. 7,217,856, which is a continuation-in-part of application No. 10/810,352, filed on Mar. 26, 2004, now Pat. No. 7,211,418, and a continuation-in-part of application No. 10/124,800, filed on Apr. 16, 2002, now Pat. No. 7,247,461, and a continuation-in-part of application No. 09/231,899, filed on Jan. 14, 1999, now Pat. No. 6,566,583.

(60) Provisional application No. 60/457,979, filed on Mar. 26, 2003, provisional application No. 60/284,066, filed on Apr. 16, 2001, provisional application No. 60/298,796, filed on Jun. 15, 2001, provisional application No. 60/323,269, filed on Sep. 18, 2001.

(51) Int. Cl.

| | |
|---|---|
| *C12N 15/52* | (2006.01) |
| *C12N 15/53* | (2006.01) |
| *C12N 15/74* | (2006.01) |
| *C12N 15/80* | (2006.01) |
| *C12N 15/81* | (2006.01) |
| *C12N 15/82* | (2006.01) |
| *C12N 5/04* | (2006.01) |

(52) U.S. Cl. ...................... 536/23.2; 435/183; 435/189; 435/252.3; 435/320.1; 435/410

(58) Field of Classification Search ....................... None
See application file for complete search history.

(56) References Cited

U.S. PATENT DOCUMENTS 5,130,242 A 7/1992 Barclay et al.

(Continued)

FOREIGN PATENT DOCUMENTS

CA 2520795 10/2004

(Continued)

OTHER PUBLICATIONS

Abbadi et al., Eur. J. Lipid Sci. Technol., 103:106-113 (2001).

(Continued)

*Primary Examiner*—Anand U Desai
*Assistant Examiner*—William W Moore
(74) *Attorney, Agent, or Firm*—Sheridan Ross P.C.

(57) ABSTRACT

Disclosed are the complete polyunsaturated fatty acid (PUFA) polyketide synthase (PKS) systems from the bacterial microorganisms *Shewanella japonica* and *Shewanella olleyana*, and biologically active fragments and homologues thereof. More particularly, this invention relates to nucleic acids encoding such PUFA PKS systems, to proteins and domains thereof that comprise such PUFA PKS systems, to genetically modified organisms (plants and microorganisms) comprising such PUFA PKS systems, and to methods of making and using the PUFA PKS systems disclosed herein. This invention also relates to genetically modified plants and microorganisms and methods to efficiently produce lipids enriched in various polyunsaturated fatty acids (PUFAs) as well as other bioactive molecules by manipulation of a PUFA polyketide synthase (PKS) system.

22 Claims, 4 Drawing Sheets

37895 nt
orf1 orf2 orf3 orf4 orf5 orf6 orf7 orf8 orf9
Shewanella SCRC-2738

39669 nt
orf1 orf3 orf5 pfaE orf7 pfaA pfaB pfaC pfaD orf8 orf9 orf10
orf2 orf4 orf6
Shewanella japonica
(cosmid 3F3)

38794 nt
orf1 orf3orf5 orf7 orf9 pfaE orf12 pfaA pfaB pfaC pfaD
orf2orf4 orf6 orf8 orf10 orf11
Shewanella olleyana
(cosmid 9A10)

U.S. PATENT DOCUMENTS

| | | | |
|---|---|---|---|
| 5,246,841 | A | 9/1993 | Yazawa et al. |
| 5,310,242 | A | 5/1994 | Golder |
| 5,639,790 | A | 6/1997 | Voelker et al. |
| 5,672,491 | A | 9/1997 | Khosla et al. |
| 5,683,898 | A | 11/1997 | Yazawa et al. |
| 5,798,259 | A | 8/1998 | Yazawa et al. |
| 5,908,622 | A | 6/1999 | Barclay |
| 6,033,883 | A | 3/2000 | Barr et al. |
| 6,140,486 | A | 10/2000 | Facciotti et al. |
| 6,503,706 | B1 | 1/2003 | Abken et al. |
| 6,566,583 | B1 | 5/2003 | Facciotti et al. |
| 6,677,145 | B2 | 1/2004 | Mukerji et al. |
| 7,001,772 | B2 | 2/2006 | Roessler et al. |
| 7,087,432 | B2 | 8/2006 | Qiu et al. |
| 7,125,672 | B2 | 10/2006 | Picataggio et al. |
| 7,208,590 | B2 | 4/2007 | Mukerji et al. |
| 7,211,418 | B2 | 5/2007 | Metz et al. |
| 7,214,853 | B2 | 5/2007 | Facciotti et al. |
| 7,217,856 | B2 | 5/2007 | Weaver et al. |
| 7,247,461 | B2 | 7/2007 | Metz et al. |
| 7,256,022 | B2 | 8/2007 | Metz et al. |
| 7,256,023 | B2 | 8/2007 | Metz et al. |
| 7,259,295 | B2 | 8/2007 | Metz et al. |
| 7,271,315 | B2 | 9/2007 | Metz et al. |
| 2004/0005672 | A1 | 1/2004 | Santi et al. |
| 2004/0010817 | A1 | 1/2004 | Shockey et al. |
| 2004/0139498 | A1 | 7/2004 | Jaworski et al. |
| 2004/0172682 | A1 | 9/2004 | Kinney et al. |
| 2005/0089865 | A1 | 4/2005 | Napier et al. |
| 2005/0164192 | A1 | 7/2005 | Graham et al. |
| 2007/0244192 | A1 | 10/2007 | Metz |
| 2007/0245431 | A1 | 10/2007 | Metz et al. |
| 2007/0256146 | A1 | 11/2007 | Metz et al. |
| 2007/0266455 | A1 | 11/2007 | Weaver et al. |
| 2007/0270494 | A1 | 11/2007 | Metz et al. |
| 2008/0022422 | A1 | 1/2008 | Weaver et al. |
| 2008/0026434 | A1 | 1/2008 | Weaver et al. |
| 2008/0026435 | A1 | 1/2008 | Weaver et al. |
| 2008/0026436 | A1 | 1/2008 | Weaver et al. |
| 2008/0026438 | A1 | 1/2008 | Metz et al. |
| 2008/0026439 | A1 | 1/2008 | Metz et al. |
| 2008/0026440 | A1 | 1/2008 | Metz et al. |
| 2008/0032296 | A1 | 2/2008 | Weaver et al. |
| 2008/0032338 | A1 | 2/2008 | Weaver et al. |
| 2008/0032351 | A1 | 2/2008 | Metz et al. |
| 2008/0032367 | A1 | 2/2008 | Weaver et al. |
| 2008/0032368 | A1 | 2/2008 | Weaver et al. |
| 2008/0032369 | A1 | 2/2008 | Weaver et al. |
| 2008/0038378 | A1 | 2/2008 | Metz et al. |
| 2008/0038379 | A1 | 2/2008 | Metz et al. |
| 2008/0038790 | A1 | 2/2008 | Metz et al. |
| 2008/0038791 | A1 | 2/2008 | Metz et al. |
| 2008/0038792 | A1 | 2/2008 | Metz et al. |
| 2008/0038793 | A1 | 2/2008 | Metz et al. |
| 2008/0038794 | A1 | 2/2008 | Metz et al. |
| 2008/0038795 | A1 | 2/2008 | Metz et al. |
| 2008/0038796 | A1 | 2/2008 | Metz et al. |
| 2008/0038797 | A1 | 2/2008 | Metz et al. |
| 2008/0038798 | A1 | 2/2008 | Weaver et al. |
| 2008/0038799 | A1 | 2/2008 | Weaver et al. |
| 2008/0040822 | A1 | 2/2008 | Metz et al. |
| 2008/0044867 | A1 | 2/2008 | Metz et al. |
| 2008/0044868 | A1 | 2/2008 | Metz et al. |
| 2008/0044869 | A1 | 2/2008 | Metz et al. |
| 2008/0044870 | A1 | 2/2008 | Metz et al. |
| 2008/0044871 | A1 | 2/2008 | Metz et al. |
| 2008/0044872 | A1 | 2/2008 | Metz et al. |
| 2008/0044873 | A1 | 2/2008 | Metz et al. |
| 2008/0044874 | A1 | 2/2008 | Weaver et al. |
| 2008/0050790 | A1 | 2/2008 | Metz et al. |
| 2008/0050791 | A1 | 2/2008 | Weaver et al. |
| 2008/0148433 | A1 | 6/2008 | Metz et al. |

FOREIGN PATENT DOCUMENTS

| | | |
|---|---|---|
| EP | 0594868 | 5/1994 |
| EP | 0823475 | 2/1998 |
| WO | WO 93/23545 | 11/1993 |
| WO | WO 96/21735 | 7/1996 |
| WO | WO 98/46764 | 10/1998 |
| WO | WO 98/55625 | 12/1998 |
| WO | WO 00/42195 | 7/2000 |
| WO | WO 02/083870 | 10/2002 |
| WO | WO 2004/087879 | 10/2004 |
| WO | WO 2006/008099 | 1/2006 |
| WO | WO 2006/034228 | 3/2006 |

OTHER PUBLICATIONS

Allen et al., Appl. Environ. Microbiol., 65(4):1710-1720 (1999).
Bateman et al., Nucl. Acids Res., 30(1):276-280 (2002).
Bentley et al., Annu. Rev. Microbiol., 53:411-46 (1999).
Bisang et al., Nature, 401:502-505 (1999).
Bork, TIG, 12(10):425-427 (1996).
Brenner, TIG, 15(4):132-133 (1999).
Broun et al., Science, 282:1315-1317 (1998).
Creelman et al., Annu. Rev. Plan Physiol. Plant Mol. Biol., 48:355-81 (1997).
Delong & Yayanos, Appl. Environ. Microbiol, 51(4):730-737 (1986).
Doerks, TIG, 14(6):248-250 (1998).
Facciotti et al., "Cloning and Characterization of Polyunsaturated Fatty Acids (PUFA) Genes from Marine Bacteria" in Proceedings of the international symposium on progress and prospect of marine biotechnology (China Ocean Pres 1999), pp. 404-405 Abstract.
Heath et al., J. Biol. Chem., 271(44):22795-27801 (1996).
Hopwood & Sherman, Annu. Rev. Genet., 24:37-66 (1990).
Hutchinson, Annu. Rev. Microbiol., 49:201-238 (1995).
Jostensen & Landfald, FEMS Microbiology Letters, 151:95-101 (1997).
Katz & Donadio, Annu. Rev. Microbiol., 47:875-912 (1993).
Keating et al., Curr. Opin. Chem. Biol., 3:598-606 (1999).
Kyle et al., HortScience, 25:1523-26 (1990).
Magnuson, Microbil. Rev., 57(3):522-542 (1993) Abstract.
Metz et al., Science, 293:290-293 (2001).
Nakahara, Yukagaku, 44(10):821-7 (1995).
Nasu et al., J. Ferment. Bioeng., 122:467-473 (1997).
Nichols et al., Curr. Opin. Biotechnol., 10:240-246 (1999).
Nogi et al., Extremophiles, 2:1-7 (1998).
Parker-Barnes et al., PNAS, 97(15):8284-8289 (2000).
Sanchez et al., Chemistry & Biolosy, 8:725-738 (2001).
Shanklin et al., Annu. Rev. Plant Physiol. Plant Mol. Biol., 49:611-41 (1998).
Smith et al., Nature Biotechnol., 15:1222-1223 (1997).
Somerville Am. J. Clin. Nutr., 58(2 supp):270S-275S (1993).
Van de Loo, Proc. Natl. Acad. Sci. USA, 92:6743-6747 (1995).
Watanabe et al., J. Biochem., 122:467-473 (1997).
Yalpani et al., The Plant Cell, 13:1401-1409 (2001).
Yazawa, Lipids, 31(supp):S297-S300 (1996).
U.S. Appl. No. 11/674,574, filed Feb. 13, 2007, Facciotti et al.
U.S. Appl. No. 11/777,277, filed Jul. 12, 2007, Metz et al.
U.S. Appl. No. 11/778,594, filed Jul. 16, 2007, Metz et al.
U.S. Appl. No. 11/781,861, filed Jul. 23, 2007, Weaver et al.
U.S. Appl. No. 11/781,882, filed Jul. 23, 2007, Weaver et al.
Allen E.A. et al. 2002 "Structure and regulation of the omega-3 polyunsaturated fatty acid synthase genes from the deep-sea bacterium *Photobacterium profundum* strain SS9" Microbiology vol. 148 pp. 1903-1913.
Cane et al., "Harnessing the Biosynthetic Code: Combinations, Permutations, and Mutations." Science 1998, vol. 282, pp. 63-68.
Chuck et al., "Molecular recognition of diketide substrates by a beta-ketoacyl-acyl carrier protein synthase domain within a bimodular polyketide synthase", Chem and Bio, Current Bio, (London), GB,, vol. 4, No. 10, 1997, pp. 757-766, XP000884721.
Database Geneseq 'Online! Dec. 11, 2000, "*S. aggregatum* PKS cluster ORF6 homolog DNA." XP002368912, retrieved from EBI accession No. GSN:AAA71567Database accession No. AAA71567—& Database Geneseq 'Online! Dec. 11, 2000, "*S. aggregatum* PKS cluster ORF6 homolog protein." XP002368914 retrieved from EBI accession No. GSP:AAB10482 Database accession No. AAB10482 & WO 00/42195 A (Calgene, LLC) Jul 20, 2000.
GenBank Accession No. AF4091 00, (Allen et al.) 2002.
GenBank Accession No. U09865. *Alcaligenes eutrophys* pyruvate dehydrogenase (pdhA), dihydrolipoamide acetyltransferase (pdhB), dihydrolipoamide dehydrogenase (pdhL), and ORF3 genes, complete cds (1994).
Harlow et al. Antibodies: A Laboratory Manual (1988) Cold Spring Harbor Laboratory Press, p. 76.
Jez et al., "Structural control of polyketide formation in plant-specific polyketide synthases", Chem and Bio (London), vol. 7, No. 12, Dec. 2000, pp. 919-930, XP002338564.
Kaulmann et al. "Biosynthesis of Polyunsaturated Fatty Acids by Polyketide Synthases", Angew. Chem. Int. Ed. 2002, 41, No. 11, pp. 1866-1869.
Kealey et al., "Production of a polyketide natural product in non-polyketide-producing prokaryotic and eukaryotic hosts", Proceedings of the National Academy of Sciences of the United States of America, vol. 95, No. 2, Jan. 20, 1998, pp. 505-509, XP002338563.
Khosla et al., "Tolerance and Specificity of Polyketide Synthases", Annu. Rev. Biochem. 1999. 68:219-253.
Leadlay PF. "Combinatorial Approaches to Polyketides Biosynthesis" Current Opinion in Chemical Biology (1997) 1: 162-168.
Nasu et al., "Efficient Transformation of *Marchantia polymorpha* That is Haploid and Has Very Small Genome DNA," Journal of Fermentation and Bioengineering vol. 84, No. 6, 519-523 1997.
Nicholson et al., "Design and utility of oligonucleotide gene probes for fungal polyketide synthases", Chem & Bio (London) vol. 8, No. 2, Feb. 2001, pp. 157-178, XP002338562.
Oliynuk et al. "A hybrid modular polyketide synthase obtained by domain swapping." Chemistry & Biology (1996) 3: 833-839.
Orikasa et al. Characterization of the eicosapentaenoic acid biosynthesis gene cluster from *Shewanella* sp. strain SCRC-2738, Cellular and Molecular Biology (Noisy-le-grand), Jul. 2004, vol. 50, No. 5, pp. 625-630.
Satomi et al. *Shewanelia marinintesina* sp. nov., *Shewanella schlegeliana* sp. nov. and *Shewanelia sairae* sp. nov., novel eicosapentaenoic-acid-producing marine bacteria isolated from see-animal intestines. Internat. J. Syst. Evol. Microbiol. 2003, vol. 53, pp. 491-499.
Takeyama et al. Expression of eicosapentaenoic acid synthesis gene clustter from *Shewanella* sp. in transgenic marine cyanobacterium. *Synechecoccus* sp. Microbiology. 1997, vol. 143, pp. 2725-2731.
UniProt Accession No. Q93CG6_PHOPR, (Allen et al.) 2002.
Wallis et al., "Polyunsaturated fatty acid synthesis: what will they think of next?", Tibs Trends in Bio Sciences, Elsevier Publ., Cambridge, EN, vol. 27, No. 9, Sep. 2002, pp. 467-473, XP004378766.
Wiesmann et al. "The molecular basis of Celmer's rules: the stereochemistry of the condensation step in chain extension on the erythromycin polyketide synthase." Biochemistry (1997) 36: 13849-13855.
Wiesmann et al. "Origin of starter units for erythromycin biosynthesis." Biochemistry (1998) 37: 11012-11017.
Wiesmann et al. "Polyketide synthesis in vitro on a modular polyketide synthase." Chemistry & Biology (Sep. 1995) 2: 583-589.
International Search Report for International (PCT) Patent Application No. PCT/US02/12254, mailed Nov. 15, 2002.
International Preliminary Examination Report for International (PCT) Patent Application No. PCT/US02/12254, mailed Oct. 16, 2006.
International Search Report for International (PCT) Patent Application No. PCT/US00/00956, mailed Jul. 6, 2000.
Written Opinion for International (PCT) Patent Application No. PCT/US00/00956, mailed Dec. 19, 2000.
International Preliminary Examination Report for International (PCT) Patent Application No. PCT/US00/00956, mailed Apr. 19, 2001.
International Search Report for International (PCT) Patent Application No. PCT/US05/36998, mailed Mar. 22, 2007.
Written Opinion for International (PCT) Patent Application No. PCT/US05/36998, mailed Mar. 22, 2007.
International Search Report for International (PCT) Patent Application No. PCT/US08/63835, mailed Nov. 3, 2008.
Written Opinion for International (PCT) Patent Application No. PCT/US08/63835, mailed Nov. 3, 2008.
International Search Report for International (PCT) Patent Application No. PCT/US06/22893, mailed Feb. 29, 2008.
Written Opinion for International (PCT) Patent Application No. PCT/US06/22893, mailed Feb. 29, 2008.
International Search Report for International (PCT) Patent Application No. PCT/US07/64105, mailed Nov. 23, 2007.
Written Opinion for International (PCT) Patent Application No. PCT/US07/64105, mailed Nov. 23, 2007.
International Preliminary Report on Patentability for International (PCT) Patent Application No. PCT/US07/64105, mailed Sep. 25, 2008.
International Search Report for International (PCT) Patent Application No. PCT/US07/64104, mailed Dec. 5, 2008.
Written Opinion for International (PCT) Patent Application No. PCT/US07/64104, mailed Dec. 5, 2008.
International Search Report for International (PCT) Patent Application No. PCT/US2007/064106, mailed Sep. 16, 2008.
Written Opinion for International (PCT) Patent Application No. PCT/US2007/064106, mailed Sep. 16, 2008.
International Preliminary Report on Patentability for International (PCT) Patent Application No. PCT/US2007/064106, mailed Oct. 30, 2008.
Fan K W et al: "Eicosapentaenoic and docosahexaenoic acids production by and okara-utilizing potential of thraustochytrids" Journal of Industrial Microbiology and Biotechnology, Basingstoke, GB, vol. 27, No. 4, Oct. 1, 2001 (Oct. 1, 2001), pp. 199-202, XP002393382 ISSN: 1367-5435.
Wolff et al, Arachidonic, Eicosapentaenoic and Biosynthetically Related Fatty Acids in Seed Lipids from a primitive Gymnosperm, *Agathis robusta*. Lipids 34(10), 1994, 1083-1097.
Grimsley et al, "Fatty acid composition of mutants of the moss *Physcomitrella patens*" Phytochemistry 20(7): 1519-1524, 1981.
Bedford et al, "A functional chimeric modular polyketide synthase generated via domain replacement." Chemistry & Biology 3: 827-831, Oct 1996.

Shewanella SCRC-2738
PPtase
KS
MAT
6X ACP
KRDH
AT
KS
CLF
DH
DH
ER
Orf 2
Orf 5
Orf 6
Orf 7
Orf 8
Shewanella japonica
(cosmid 3F3)
PPtase
KS
MAT
6X ACP
KRDH
AT
KS
CLF
DH
DH
ER
PfaE
PfaA
PfaB
PfaC
PfaD
Shewanella olleyana
(cosmid 9A10)
PPtase
KS
MAT
6X ACP
KRDH
AT
KS
CLF
DH
DH
ER
PfaE
PfaA
PfaB
PfaC
PfaD

FIG. 3A

*pfa*B *pfa*C

Ala Pro Gln Leu Glu Gly Glu Gln Ser ***

Leu Ser Ser Gln Ser Asn Val Pro Lys

GCTCCACAAT TAGAAGGAGA ACAATCTTGA GTTCTCAATC AAACGTTCCC AAA
CGAGGTGTTA ATCTTCCTCT TGTTAGAACT CAAGAGTTAG TTTGCAAGGG TTT

FIG. 3B

*pfa*B *pfa*C

Ala Pro Gln Leu Glu Gly Glu Gln Ser ***

Leu Ser Ser Gln Ser Thr Asn Leu Asn

CCCCTCAA TTAGAAGGAG AACAATCTTG AGTTCTCAAT CAACTAATCT AAAT
GGGGAGTT AATCTTCCTC TTGTTAGAAC TCAAGAGTTA GTTGATTAGA TTTA

```
orf2_ATG    1 ...............................................................MVRGYLR
Sja_pfaE    1 MSYCYYKCEFGLSPLPTIQLEFCPLDTNLLDEKTVSTVRSWLSDAEINKVDRFIQQAAQQQGLMVRGYLR
Sol_pfaE    1 ...........LKPPTVIQLEFCPLNTDLLDESTASIVRSWLPEDEVKKVDRFIQQSSREQGLMVRGYLR
orf2_TTG    1 ................LISLYFCPLTIQECDNQTTELVKSWLPEDELIKVNRYIKQEAKTQGLMVRGYLR
```

FIG. 4

PUFA POLYKETIDE SYNTHASE SYSTEMS AND USES THEREOF

CROSS-REFERENCE TO RELATED APPLICATIONS

This application is a divisional of U.S. patent application Ser. No. 10/965,017, filed Oct. 13, 2004, now U.S. Pat. No. 7,217,856, which is a continuation-in-part of U.S. patent application Ser. No. 10/810,352, filed Mar. 26, 2004, now U.S. Pat. No. 7,211,418, which claims priority under 35 U.S.C. § 119(e) from U.S. Provisional Application Ser. No. 60/457,979, filed Mar. 26, 2003. U.S. application Ser. No. 10/810,352, supra, is also a continuation-in-part of U.S. patent application Ser. No. 10/124,800, filed Apr. 16, 2002, now U.S. Pat. No. 7,247,461, which claims the benefit of priority under 35 U.S.C. § 119(e) to: U.S. Provisional Application Ser. No. 60/284,066, filed Apr. 16, 2001; U.S. Provisional Application Ser. No. 60/298,796, filed Jun. 15, 2001; and U.S. Provisional Application Ser. No. 60/323,269, filed Sep. 18, 2001. U.S. patent application Ser. No. 10/124,800, supra, is also a continuation-in-part of U.S. application Ser. No. 09/231,899, filed Jan. 14, 1999, now U.S. Pat. No. 6,566,583. Each of the above-identified patent applications is incorporated herein by reference in its entirety.

This application does not claim the benefit of priority from U.S. application Ser. No. 09/090,793, filed Jun. 4, 1998, now U.S. Pat. No. 6,140,486, although U.S. application Ser. No. 09/090,793 is incorporated herein by reference in its entirety.

REFERENCE TO SEQUENCE LISTING

This application contains a Sequence Listing submitted as an electronic text file named "Sequence_Listing.txt", having a size in bytes of 373 kb, and created on 12 Oct. 2004. The information contained in this electronic file is hereby incorporated by reference in its entirety pursuant to 37 CFR §1.52 (e)(5).

FIELD OF THE INVENTION

This invention relates to polyunsaturated fatty acid (PUFA) polyketide synthase (PKS) systems from bacterial microorganisms. More particularly, this invention relates to nucleic acids encoding PUFA PKS systems, to proteins and domains thereof that comprise PUFA PKS systems, to genetically modified organisms comprising such PUFA PKS systems, and to methods of making and using the PUFA PKS systems disclosed herein. This invention also relates to genetically modified plants and microorganisms and methods to efficiently produce lipids enriched in various polyunsaturated fatty acids (PUFAs) by manipulation of a PUFA polyketide synthase (PKS) system.

BACKGROUND OF THE INVENTION

Polyketide synthase (PKS) systems are generally known in the art as enzyme complexes related to fatty acid synthase (FAS) systems, but which are often highly modified to produce specialized products that typically show little resemblance to fatty acids. It has now been shown, however, that polyketide synthase systems exist in marine bacteria and certain microalgae that are capable of synthesizing polyunsaturated fatty acids (PUFAs) from acetyl-CoA and malonyl-CoA. The PKS pathways for PUFA synthesis in *Shewanella* and another marine bacteria, *Vibrio marinus*, are described in detail in U.S. Pat. No. 6,140,486. The PKS pathways for PUFA synthesis in the eukaryotic Thraustochytrid, *Schizochytrium* is described in detail in U.S. Pat. No. 6,566,583. The PKS pathways for PUFA synthesis in eukaryotes such as members of Thraustochytriales, including the complete structural description of the PUFA PKS pathway in *Schizochytrium* and the identification of the PUFA PKS pathway in *Thraustochytrium*, including details regarding uses of these pathways, are described in detail in U.S. Patent Application Publication No. 20020194641, published Dec. 19, 2002 (corresponding to U.S. patent application Ser. No. 10/124,800, filed Apr. 16, 2002). U.S. patent application Ser. No. 10/810,352, filed Mar. 24, 2004, discloses the complete structural description of the PUFA PKS pathway in *Thraustochytrium*, and further detail regarding the production of eicosapentaenoic acid (C20:5, ω-3) (EPA) and other PUFAs using such systems.

Researchers have attempted to exploit polyketide synthase (PKS) systems that have been traditionally described in the literature as falling into one of three basic types, typically referred to as: Type I (modular or iterative), Type II, and Type III. For purposes of clarity, it is noted that the Type I modular PKS system has previously also been referred to as simply a "modular" PKS system, and the Type I iterative PKS system has previously also been referred to simply as a "Type I" PKS system. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I iterative PKS systems are similar to the Type II system in that the enzymes are used in an iterative fashion to produce the end product. The Type I iterative differs from Type II in that enzymatic activities, instead of being associated with separable proteins, occur as domains of larger proteins. This system is analogous to the Type I FAS systems found in animals and fungi.

In contrast to the Type II systems, in Type I modular PKS systems, each enzyme domain is used only once in the production of the end product. The domains are found in very large proteins and the product of each reaction is passed on to another domain in the PKS protein. Additionally, in the PKS systems described above, if a carbon-carbon double bond is incorporated into the end product, it is usually in the trans configuration.

Type III systems have been more recently discovered and belong to the plant chalcone synthase family of condensing enzymes. Type III PKSs are distinct from type I and type II PKS systems and utilize free CoA substrates in iterative condensation reactions to usually produce a heterocyclic end product.

Polyunsaturated fatty acids (PUFAs) are critical components of membrane lipids in most eukaryotes (Lauritzen et al., *Prog. Lipid Res.* 40 1 (2001); McConn et al., *Plant J.* 15, 521 (1998)) and are precursors of certain hormones and signaling molecules (Heller et al., *Drugs* 55, 487 (1998); Creelman et al., *Annu. Rev. Plant Physiol. Plant Mol. Biol.* 48, 355 (1997)). Known pathways of PUFA synthesis involve the processing of saturated 16:0 or 18:0 fatty acids (the abbreviation X:Y indicates an acyl group containing X carbon atoms and Y double bonds (usually cis in PUFAs); double-bond positions of PUFAs are indicated relative to the methyl carbon of the fatty acid chain (e.g., ω3 or ω6) with systematic methylene interruption of the double bonds) derived from fatty acid synthase (FAS) by elongation and aerobic desaturation reactions (Sprecher, *Curr. Opin. Clin. Nutr. Metab. Care* 2, 135 (1999); Parker-Barnes et al., *Proc. Natl. Acad. Sci. USA* 97, 8284 (2000); Shanklin et al., *Annu. Rev. Plant Physiol. Plant Nol. Biol.* 49, 611 (1998)). Starting from acetyl-CoA, the synthesis of docosahexaenoic acid (DHA) requires approximately 30 distinct enzyme activities and nearly 70 reactions including the four repetitive steps of the fatty acid synthesis cycle. Polyketide synthases (PKSs) carry out some of the same reactions as FAS (Hopwood et al., *Annu. Rev. Genet.* 24, 37 (1990); Bentley et al., *Annu. Rev. Microbiol.* 53, 411 (1999)) and use the same small protein (or domain), acyl carrier protein (ACP), as a covalent attachment site for the growing carbon chain. However, in these enzyme systems, the complete cycle of reduction, dehydration and reduction seen in FAS is often abbreviated so that a highly derivatized carbon chain is produced, typically containing many keto- and hydroxy-groups as well as carbon-carbon double bonds typically in the trans configuration. The linear products of PKSs are often cyclized to form complex biochemicals that include antibiotics and many other secondary products (Hopwood et al., (1990) supra; Bentley et al., (1999), supra; Keating et al., *Curr. Opin. Chem. Biol.* 3, 598 (1999)).

Very long chain PUFAs such as docosahexaenoic acid (DHA; 22:6ω3) and eicosapentaenoic acid (EPA; 20:5ω3) have been reported from several species of marine bacteria, including *Shewanella* sp (Nichols et al., *Curr. Op. Biotechnol.* 10, 240 (1999); Yazawa, *Lipids* 31, S (1996); DeLong et al., *Appl. Environ. Microbiol.* 51, 730 (1986)). Analysis of a genomic fragment (cloned as plasmid pEPA) from *Shewanella* sp. strain SCRC2738 led to the identification of five open reading frames (Orfs), totaling 20 Kb, that are necessary and sufficient for EPA production in *E. coli* (Yazawa, (1996), supra). Several of the predicted protein domains were homologues of FAS enzymes, while other regions showed no homology to proteins of known function. At least 11 regions within the five Orfs were identifiable as putative enzyme domains (See Metz et al., *Science* 293:290-293 (2001)). When compared with sequences in the gene databases, seven of these were more strongly related to PKS proteins than to FAS proteins. Included in this group were domains putatively encoding malonyl-CoA:ACP acyltransferase (MAT), β-ketoacyl-ACP synthase (KS), β-ketoacyl-ACP reductase (KR), acyltransferase (AT), phosphopantetheine transferase, chain length (or chain initiation) factor (CLF) and a highly unusual cluster of six ACP domains (i.e., the presence of more than two clustered ACP domains had not previously been reported in PKS or FAS sequences). It is likely that the PKS pathway for PUFA synthesis that has been identified in *Shewanella* is widespread in marine bacteria. Genes with high homology to the *Shewanella* gene cluster have been identified in *Photobacterium profundum* (Allen et al., *Appli. Environ. Microbiol.* 65:1710 (1999)) and in *Moritella marina* (*Vibrio marinus*) (see U.S. Pat. No. 6,140,486, ibid., and Tanaka et al., *Biotechnol. Lett.* 21:939 (1999)).

Polyunsaturated fatty acids (PUFAs) are considered to be useful for nutritional, pharmaceutical, industrial, and other purposes. The current supply of PUFAs from natural sources and from chemical synthesis is not sufficient for commercial needs. A major current source for PUFAs is from marine fish; however, fish stocks are declining, and this may not be a sustainable resource. Additionally, contamination, from both heavy metals and toxic organic molecules, is a serious issue with oil derived from marine fish. Vegetable oils derived from oil seed crops are relatively inexpensive and do not have the contamination issues associated with fish oils. However, the PUFAs found in commercially developed plant oils are typically limited to linoleic acid (eighteen carbons with 2 double bonds, in the delta 9 and 12 positions—18:2 delta 9,12) and linolenic acid (18:3 delta 9,12,15). In the conventional pathway for PUFA synthesis, medium chain-length saturated fatty acids (products of a fatty acid synthase (FAS) system) are modified by a series of elongation and desaturation reactions. Because a number of separate desaturase and elongase enzymes are required for fatty acid synthesis from linoleic and linolenic acids to produce the more saturated and longer chain PUFAs, engineering plant host cells for the expression of PUFAs such as EPA and docosahexaenoic acid (DHA) may require expression of several separate enzymes to achieve synthesis. Additionally, for production of useable quantities of such PUFAs, additional engineering efforts may be required, for example, engineering the down regulation of enzymes that compete for substrate, engineering of higher enzyme activities such as by mutagenesis or targeting of enzymes to plastid organelles. Therefore it is of interest to obtain genetic material involved in PUFA biosynthesis from species that naturally produce these fatty acids and to express the isolated material alone or in combination in a heterologous system which can be manipulated to allow production of commercial quantities of PUFAs.

The discovery of a PUFA PKS system in marine bacteria such as *Shewanella* and *Vibrio marinus* (see U.S. Pat. No. 6,140,486, ibid.), discussed above, provided a resource for new methods of commercial PUFA production. However, the marine bacteria containing PUFA PKS systems that have been identified to date have limitations which may ultimately restrict their usefulness on a commercial level. In particular, although U.S. Pat. No. 6,140,486 discloses that these marine bacteria PUFA PKS systems can be used to genetically modify plants, the marine bacteria naturally live and grow in cold marine environments and the enzyme systems of these bacteria do not function well above 22° C. and may optimally function at much lower temperatures. In contrast, many crop plants, which are attractive targets for genetic manipulation using the PUFA PKS system, have normal growth conditions at temperatures above 22° C. and ranging to higher than 40° C. Therefore, the PUFA PKS systems from these marine bacteria are not predicted to be readily adaptable to plant expression under normal growth conditions.

With regard to the production of eicosapentaenoic acid (EPA) in particular, researchers have tried to produce EPA with microbes by growing them in both photosynthetic and heterotrophic cultures. They have also used both classical and directed genetic approaches in attempts to increase the productively of the organisms under culture conditions. Other researchers have attempted to produce EPA in oil-seed crop plants by introduction of genes encoding various desaturase and elongase enzymes.

Researchers have attempted to use cultures of red microalgae (Monodus), diatoms (e.g. *Phaeodactylum*), other microalgae and fungi (e.g. *Mortierella* cultivated at low temperatures). However, in all cases, productivity was low compared to existing commercial microbial production systems for other long chain PUFAs such as DHA. In many cases, the EPA occurred primarily in the phospholipids (PL) rather than the triacylglycerols (TAG) form. Since productivity of microalgae under heterotrophic growth conditions can be much higher than under phototrophic conditions, researchers have attempted, and achieved, trophic conversion by introduction of genes encoding specific sugar transporters. However, even with the newly acquired heterotrophic capability, productivity in terms of oil remained relatively low.

As discussed above, several marine bacteria have been shown to produce PUFAs (EPA as well as DHA). However, these bacteria do not produce significant quantities of TAG, and the EPA is found primarily in the PL membrane form. The levels of EPA produced by these particular bacteria as well as their growth characteristics (discussed above) limit their utility for commercial production of EPA.

There have been many efforts to produce EPA in oil-seed crop plants by modification of the endogenously-produced fatty acids. Genetic modification of these plants with various individual genes for fatty acid elongases and desaturases has produced leaves or seeds containing significant levels of EPA but also containing significant levels of mixed shorter-chain and less unsaturated PUFAs (Qi et al., *Nature Biotech.* 22:739 (2004); PCT Publication No. WO 04/071467; Abbadi et al., *Plant Cell* 16:1 (2004)). In contrast, the known EPA-producing PUFA PKS systems as described herein yield a PUFA profile that is essentially pure EPA.

Therefore, there is a need in the art for other PUFA PKS systems having greater flexibility for commercial use, and for a biological system that efficiently produces quantities of lipids (e.g., PL and TAG) enriched in desired PUFAs, such as EPA, in a commercially useful production process.

SUMMARY OF THE INVENTION

One embodiment of the present invention generally relates to isolated nucleic acid molecules encoding PUFA PKS proteins and domains from *Shewanella japonica* or *Shewanella olleyana*, and biologically active homologues and fragments thereof. In one aspect, the invention includes an isolated nucleic acid molecule comprising a nucleic acid sequence selected from: (a) a nucleic acid sequence encoding an amino acid sequence selected from the group consisting of: SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, and SEQ ID NO: 12; (b) a nucleic acid sequence encoding a fragment of any of the amino acid sequences of (a) having at least one biological activity selected from the group consisting of enoyl-ACP reductase (ER) activity; acyl carrier protein (ACP) activity; β-ketoacyl-ACP synthase (KS) activity; acyltransferase (AT) activity; β-ketoacyl-ACP reductase (KR) activity; FabA-like β-hydroxyacyl-ACP dehydrase (DH) activity; non-FabA-like dehydrase activity; chain length factor (CLF) activity; malonyl-CoA:ACP acyltransferase (MAT) activity; and 4'-phosphopantetheinyl transferase (PPTase) activity; (c) a nucleic acid sequence encoding an amino acid sequence that is at least about 65% identical, and more preferably at least about 75% identical, and more preferably at least about 85% identical, and more preferably at least about 95% identical, to SEQ ID NO:2 or SEQ ID NO:8 and has at least one biological activity selected from the group consisting of: KS activity, MAT activity, KR activity, ACP activity, and non-FabA-like dehydrase activity; (d) a nucleic acid sequence encoding an amino acid sequence that is at least about 60% identical, and more preferably at least about 70% identical, and more preferably at least about 80% identical, and more preferably at least about 90% identical, to SEQ ID NO:3 or SEQ ID NO:9 and has AT biological activity; (e) a nucleic acid sequence encoding an amino acid sequence that is at least about 70% identical and more preferably at least about 80% identical, and more preferably at least about 90% identical, and more preferably at least about 95% identical, to SEQ ID NO:4 or SEQ ID NO:10 and has at least one biological activity selected from the group consisting of KS activity, CLF activity and DH activity; (f) a nucleic acid sequence encoding an amino acid sequence that is at least about 60% identical, and more preferably at least about 70% identical, and more preferably at least about 80% identical, and more preferably at least about 90% identical, to SEQ ID NO:6 or SEQ ID NO:12 and has PPTase biological activity; (g) a nucleic acid sequence encoding an amino acid sequence that is at least about 85% identical, and more preferably at least about 95% identical, and more preferably at least about 96% identical, and more preferably at least about 97% identical, to SEQ ID NO:11, or at least about 95% identical, and more preferably at least about 96% identical, and more preferably at least about 97% identical, and more preferably at least about 98% identical, to SEQ ID NO:5, and has ER biological activity.

In one aspect, the fragment set forth in (b) above is selected from:

(a) a fragment of SEQ ID NO:2 from about position 29 to about position 513 of SEQ ID NO:2, wherein the domain has KS biological activity;

(b) a fragment of SEQ ID NO:2 from about position 625 to about position 943 of SEQ ID NO:2, wherein the domain has MAT biological activity;

(c) a fragment of SEQ ID NO:2 from about position 1264 to about position 1889 of SEQ ID NO:2, and subdomains thereof, wherein the domain or subdomain thereof has ACP biological activity;

(d) a fragment of SEQ ID NO:2 from about position 2264 to about position 2398 of SEQ ID NO:2, wherein the domain has KR biological activity;

(e) a fragment of SEQ ID NO:2 comprising from about position 2504 to about position 2516 of SEQ ID NO:2, wherein the fragment has non-FabA-like dehydrase biological activity;

(f) a fragment of SEQ ID NO:3 from about position 378 to about position 684 of SEQ ID NO:3, wherein the domain has AT biological activity;

(g) a fragment of SEQ ID NO:4 from about position 5 to about position 483 of SEQ ID NO:4, wherein the domain has KS biological activity;

(h) a fragment of SEQ ID NO:4 from about position 489 to about position 771 of SEQ ID NO:4, wherein the domain has CLF biological activity;

(i) a fragment of SEQ ID NO:4 from about position 1428 to about position 1570 of SEQ ID NO:4, wherein the domain has DH biological activity;

(j) a fragment of SEQ ID NO:4 from about position 1881 to about position 2019 of SEQ ID NO:4, wherein the domain has DH biological activity;

(k) a fragment of SEQ ID NO:5 from about position 84 to about position 497 of SEQ ID NO:5, wherein the domain has ER biological activity;

(l) a fragment of SEQ ID NO:6 from about position 40 to about position 186 of SEQ ID NO:6, wherein the domain has PPTase biological activity;

(m) a fragment of SEQ ID NO:8 from about position 29 to about position 513 of SEQ ID NO:8, wherein the domain has KS biological activity;

(n) a fragment of SEQ ID NO:8 from about position 625 to about position 943 of SEQ ID NO:8, wherein the domain has MAT biological activity;

(o) a fragment of SEQ ID NO:8 from about position 1275 to about position 1872 of SEQ ID NO:8, and subdomains thereof, wherein the domain or subdomain thereof has ACP biological activity;

(p) a fragment of SEQ ID NO:8 from about position 2240 to about position 2374 of SEQ ID NO:8, wherein the domain has KR biological activity;

(q) a fragment of SEQ ID NO:8 comprising from about position 2480-2492 of SEQ ID NO:8, wherein the fragment has non-FabA-like dehydrase activity;

(r) a fragment of SEQ ID NO:9 from about position 366 to about position 703 of SEQ ID NO:9, wherein the domain has AT biological activity;

(s) a fragment of SEQ ID NO:10 from about position 10 to about position 488 of SEQ ID NO:10, wherein the domain has KS biological activity;

(t) a fragment of SEQ ID NO:10 from about position 502 to about position 750 of SEQ ID NO:10, wherein the domain has CLF biological activity;

(u) a fragment of SEQ ID NO:10 from about position 1431 to about position 1573 of SEQ ID NO:10, wherein the domain has DH biological activity;

(v) a fragment of SEQ ID NO:10 from about position 1882 to about position 2020 of SEQ ID NO:10, wherein the domain has DH biological activity;

(w) a fragment of SEQ ID NO:11 from about position 84 to about position 497 of SEQ ID NO:11, wherein the domain has ER biological activity; and (x) a fragment of SEQ ID NO:12 from about position 29 to about position 177 of SEQ ID NO:12, wherein the domain has PPTase biological activity.

Also included in the present invention are nucleic acid molecules consisting essentially of a nucleic acid sequence that is fully complementary to any of the above-identified the nucleic acid molecules. One aspect of the invention further relates to a recombinant nucleic acid molecule comprising any of the above-identified nucleic acid molecules, operatively linked to at least one expression control sequence. Another aspect of the invention relates to a recombinant cell transfected with any of the such recombinant nucleic acid molecules.

Another embodiment of the invention relates to a genetically modified plant or a part of the plant, wherein the plant has been genetically modified to recombinantly express a PKS system comprising at least one biologically active protein or domain thereof of a polyunsaturated fatty acid (PUFA) polyketide synthase (PKS) system, wherein the protein or domain is encoded by any of the above-described nucleic acid molecules. In one aspect, the genetically modified plant or part of a plant, as a result of the genetic modification, produces one or more polyunsaturated fatty acids selected from the group consisting of: DHA (docosahexaenoic acid (C22:6, ω-3)), ARA (eicosatetraenoic acid or arachidonic acid (C20:4, n-6)), DPA (docosapentaenoic acid (C22:5, ω-6 or ω-3)), and/or EPA (eicosapentaenoic acid (C20:5, ω-3). In particularly preferred embodiment, the plant or part of a plant produces DHA, EPA, EPA and DHA, ARA and DHA, or ARA and EPA. Genetically modified plants can include, crop plants, and any dicotyledonous plant or monocotyledonous plant. Preferred plants include, but are not limited to, canola, soybean, rapeseed, linseed, corn, safflower, sunflower and tobacco.

Yet another embodiment of the invention relates to a genetically modified microorganism, wherein the microorganism has been genetically modified to recombinantly express any of the above-described isolated nucleic acid molecules. In one aspect, the microorganism, as a result of the genetic modification, produces a polyunsaturated fatty acid selected from the group consisting of: DHA (docosahexaenoic acid (C22:6, ω-3)), ARA (eicosatetraenoic acid or arachidonic acid (C20:4, n-6)), DPA (docosapentaenoic acid (C22:5, ω-6 or ω-3)), and/or EPA (eicosapentaenoic acid (C20:5, ω-3). In a particularly preferred embodiment, the microorganism, as a result of the genetic modification, produces DHA, EPA, EPA and DHA, ARA and DHA or ARA and EPA. In one aspect, the microorganism is a Thraustochytrid, including, but not limited to, *Schizochytrium* and *Thraustochytrium*. In one aspect, the microorganism is a bacterium.

In one aspect, the above-described genetically modified plant or microorganism is genetically modified to recombinantly express a nucleic acid molecule encoding at least one amino acid sequence selected from: (a) an amino acid sequence selected from the group consisting of: SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, and SEQ ID NO:12; and (b) a fragment of any of the amino acid sequences of (a) having at least one biological activity selected from the group consisting of enoyl-ACP reductase (ER) activity; acyl carrier protein (ACP) activity; β-ketoacyl-ACP synthase (KS) activity; acyltransferase (AT) activity; β-ketoacyl-ACP reductase (KR) activity; FabA-like β-hydroxyacyl-ACP dehydrase (DH) activity; non-FabA-like dehydrase activity; chain length factor (CLF) activity; malonyl-CoA:ACP acyltransferase (MAT) activity; and 4'-phosphopantetheinyl transferase (PPTase) activity. In one aspect, the plant is genetically modified to recombinantly express a nucleic acid molecule encoding at least one amino acid sequence selected from: SEQ ID NO:2, SEQ ID NO:3, SEQ ID NO:4, SEQ ID NO:5, and/or SEQ ID NO:6. In another aspect, the plant or microorganism is genetically modified to recombinantly express at least one nucleic acid molecule encoding SEQ ID NO:2, SEQ ID NO:3, SEQ ID NO:4, SEQ ID NO:5, and SEQ ID NO:6. In yet another aspect, the plant or microorganism is genetically modified to recombinantly express a nucleic acid molecule encoding at least one amino acid sequence selected from: SEQ ID NO:8, SEQ ID NO:9, SEQ ID NO:10, SEQ ID NO:11, and/or SEQ ID NO:12. In yet another aspect, the plant or microorganism is genetically modified to recombinantly express at least one nucleic acid molecule encoding SEQ ID NO:8, SEQ ID NO:9, SEQ ID NO:10, SEQ ID NO:11, and SEQ ID NO:12. In another aspect, the plant or microorganism is genetically modified to recombinantly express at least one nucleic acid molecule encoding any of the fragments previously described above.

In one aspect of the genetically modified plant or part of a plant or microorganism embodiments of the invention, the plant or microorganism is additionally genetically modified to express at least one biologically active protein or domain of a polyunsaturated fatty acid (PUFA) polyketide synthase (PKS) system from a Thraustochytrid, including, but not limited to, *Schizochytrium* and *Thraustochytrium*. In one aspect, such a protein or domain comprises an amino acid sequence selected from: (a) SEQ ID NO:14, SEQ ID NO:16, and SEQ ID NO:18; and (b) a fragment of any of the amino acid sequences of (a) having at least one biological activity selected from the group consisting of enoyl-ACP reductase (ER) activity; acyl carrier protein (ACP) activity; β-ketoacyl-ACP synthase (KS) activity; acyltransferase (AT) activity; β-ketoacyl-ACP reductase (KR) activity; FabA-like β-hydroxyacyl-ACP dehydrase (DH) activity; non-FabA-like dehydrase activity; chain length factor (CLF) activity; malonyl-CoA:ACP acyltransferase (MAT) activity; and 4'-phosphopantetheinyl transferase (PPTase) activity. In another aspect, the protein or domain comprises an amino acid sequence selected from: (a) SEQ ID NO:20, SEQ ID NO:22, and SEQ ID NO:24; and (b) a fragment of any of the amino acid sequences of (a) having at least one biological activity selected from the group consisting of enoyl-ACP reductase (ER) activity; acyl carrier protein (ACP) activity; β-ketoacyl-ACP synthase (KS) activity; acyltransferase (AT) activity; β-ketoacyl-ACP reductase (KR) activity; FabA-like β-hydroxyacyl-ACP dehydrase (DH) activity; non-FabA-like dehydrase activity; chain length factor (CLF) activity; malonyl-CoA:ACP acyltransferase (MAT) activity; and 4'-phosphopantetheinyl transferase (PPTase) activity.

In one aspect of the embodiment of the invention related to the genetically modified microorganism, the microorganism comprises an endogenous PUFA PKS system. In this aspect, the endogenous PUFA PKS system can be modified by substitution of another isolated nucleic acid molecule encoding at least one domain of a different PKS system for a nucleic acid sequence encoding at least one domain of the endogenous PUFA PKS system. A different PKS system includes, but is not limited to, a non-bacterial PUFA PKS system, a bacterial PUFA PKS system, a type I modular PKS system, a type I iterative PKS system, a type II PKS system, and a type III PKS system. In another aspect, the endogenous PUFA PKS system has been genetically modified by substitution of any of the above-described isolated nucleic acid molecules of the invention for a nucleic acid sequence encoding at least one domain of the endogenous PUFA PKS system. In another aspect, the microorganism has been genetically modified to recombinantly express a nucleic acid molecule encoding a chain length factor, or a chain length factor plus a β-ketoacyl-ACP synthase (KS) domain, that directs the synthesis of C20 units. In another aspect, the endogenous PUFA PKS system has been modified in a domain or domains selected from the group consisting of a domain encoding FabA-like β-hydroxy acyl-ACP dehydrase (DH) domain and a domain encoding β-ketoacyl-ACP synthase (KS), wherein the modification alters the ratio of long chain fatty acids produced by the PUFA PKS system as compared to in the absence of the modification. Such a modification can include substituting a DH domain that does not possess isomerization activity for a FabA-like β-hydroxy acyl-ACP dehydrase (DH) in the endogenous PUFA PKS system. Such a modification can also include a deletion of all or a part of the domain, a substitution of a homologous domain from a different organism for the domain, and a mutation of the domain. In one aspect, the endogenous PUFA PKS system has been modified in an enoyl-ACP reductase (ER) domain, wherein the modification results in the production of a different compound as compared to in the absence of the modification. In this aspect, such a modification can include a deletion of all or a part of the ER domain, a substitution of an ER domain from a different organism for the ER domain, and a mutation of the ER domain.

Another embodiment of the present invention relates to a method to produce a bioactive molecule that is produced by a polyketide synthase system, comprising growing under conditions effective to produce the bioactive molecule, a genetically modified plant as described above.

Another embodiment of the present invention relates to a method to produce a bioactive molecule that is produced by a polyketide synthase system, comprising culturing under conditions effective to produce the bioactive molecule, a genetically modified microorganism as described above.

In either of the two embodiments directly above, in one aspect, the genetic modification changes at least one product produced by the endogenous PKS system, as compared to a wild-type organism. In another aspect, the organism produces a polyunsaturated fatty acid (PUFA) profile that differs from the naturally occurring organism without a genetic modification. In one aspect, the bioactive molecule is selected from: an anti-inflammatory formulation, a chemotherapeutic agent, an active excipient, an osteoporosis drug, an anti-depressant, an anti-convulsant, an anti-Heliobactor pylori drug, a drug for treatment of neurodegenerative disease, a drug for treatment of degenerative liver disease, an antibiotic, and a cholesterol lowering formulation. In another aspect, the bioactive molecule is an antibiotic. In another aspect, the bioactive molecule is a polyunsaturated fatty acid (PUFA). In yet another aspect, the bioactive molecule is a molecule including carbon-carbon double bonds in the cis configuration. In another aspect, the bioactive molecule is a molecule including a double bond at every third carbon.

Another embodiment of the present invention relates to a method to produce a plant that has a polyunsaturated fatty acid (PUFA) profile that differs from the naturally occurring plant, comprising genetically modifying cells of the plant to express a PKS system comprising at least one recombinant nucleic acid molecule of the present invention described above.

Another embodiment of the present invention relates to a method to produce a recombinant microbe, comprising genetically modifying microbial cells to express at least one recombinant nucleic acid molecule of the present invention described above.

Yet another embodiment of the present invention relates to a method to modify an endproduct to contain at least one fatty acid, comprising adding to the endproduct an oil produced by a recombinant host cell that expresses at least one recombinant nucleic acid molecule of the present invention as described above. For example, the endproduct can include, but is not limited to, a dietary supplement, a food product, a pharmaceutical formulation, a humanized animal milk, and an infant formula.

Yet another embodiment of the present invention relates to a method to produce a humanized animal milk, comprising genetically modifying milk-producing cells of a milk-producing animal with at least one recombinant nucleic acid molecule of the present invention as described above.

Another embodiment of the present invention relates to a recombinant host cell which has been modified to express a recombinant bacterial polyunsaturated fatty acid (PUFA) polyketide synthase (PKS) system, wherein the PUFA PKS catalyzes both iterative and non-iterative enzymatic reactions, and wherein the PUFA PKS system comprises: (a) at least one enoyl ACP-reductase (ER) domain; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; (h) at least one malonyl-CoA:ACP acyltransferase (MAT) domain; and (i) at least one 4'-phosphopantetheinyl transferase (PPTase) domain. The PUFA PKS system produces PUFAs at temperatures of at least about 25° C. In one aspect, the PUFA PKS system comprises: (a) one enoyl ACP-reductase (ER) domain; (b) six acyl carrier protein (ACP) domains; (c) two β-keto acyl-ACP synthase (KS) domains; (d) one acyltransferase (AT) domain; (e) one ketoreductase (KR) domain; (f) two FabA-like β-hydroxy acyl-ACP dehydrase (DH) domains; (g) one chain length factor (CLF) domain; (h) one malonyl-CoA:ACP acyltransferase (MAT) domain; and (i) one 4'-phosphopantetheinyl transferase (PPTase) domain. In one aspect, the PUFA PKS system is a PUFA PKS system from a marine bacterium selected from the group consisting of *Shewanella japonica* and *Shewanella olleyana*.

Yet another embodiment of the present invention relates to a genetically modified organism comprising at least one protein or domain of a bacterial polyunsaturated fatty acid (PUFA) polyketide synthase (PKS) system, wherein the bacterial PUFA PKS system catalyzes both iterative and non-iterative enzymatic reactions, wherein the bacterial PUFA PKS system produces PUFAs at temperatures of at least about 25° C., and wherein the bacterial PUFA PKS system comprises: (a) at least one enoyl ACP-reductase (ER) domain; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; (h) at least one malonyl-CoA:ACP acyltransferase (MAT) domain; and (i) at least one 4'-phosphopantetheinyl transferase (PPTase) domain. The genetic modification affects the activity of the PUFA PKS system. In one aspect, the organism is modified to recombinantly express at least one protein or domain of the bacterial PUFA PKS system. In another aspect, the organism is modified to recombinantly express the bacterial PUFA PKS system. The organism can include a plant or a microorganism. In one aspect, the bacterial PUFA PKS system is a PUFA PKS system from a marine bacterium selected from the group consisting of *Shewanella japonica* and *Shewanella olleyana*. In another aspect, the organism expresses at least one additional protein or domain from a second, different PKS system.

Another embodiment of the present invention relates to an isolated recombinant nucleic acid molecule encoding at least one protein or functional domain of a bacterial (PUFA) polyketide synthase (PKS) system, wherein the bacterial PUFA PKS system catalyzes both iterative and non-iterative enzymatic reactions, wherein the bacterial PUFA PKS system produces PUFAs at temperatures of at least about 25° C., and wherein the bacterial PUFA PKS system comprises: (a) at least one enoyl ACP-reductase (ER) domain; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; (h) at least one malonyl-CoA:ACP acyltransferase (MAT) domain; and (i) at least one 4'-phosphopantetheinyl transferase (PPTase) domain.

BRIEF DESCRIPTION OF THE FIGURES OF THE INVENTION

FIG. 3A is a sequence alignment showing the overlap between the end of pfaB ORF and the start of pfaC ORF (nucleotides 21101-21150 of SEQ ID NO:1, including the complementary strand, is shown) and their corresponding amino acid translation (pfaB: positions 751-759 of SEQ ID NO:3; pfaC: positions 1-9 of SEQ ID NO:4) from *Shewanella japonica* (cosmid 3F3).

FIG. 3B is a sequence alignment showing the overlap between the end of pfaB ORF and the start of pfaC ORF (nucleotides 27943-28008 of SEQ ID NO:7, including the complementary strand, is shown) and their corresponding amino acid translation (pfaB: positions 735-742 of SEQ ID NO:9; pfaC: positions 1-9 of SEQ ID NO:10) from *Shewanella olleyana* (cosmid 9A10).

Figure 1:
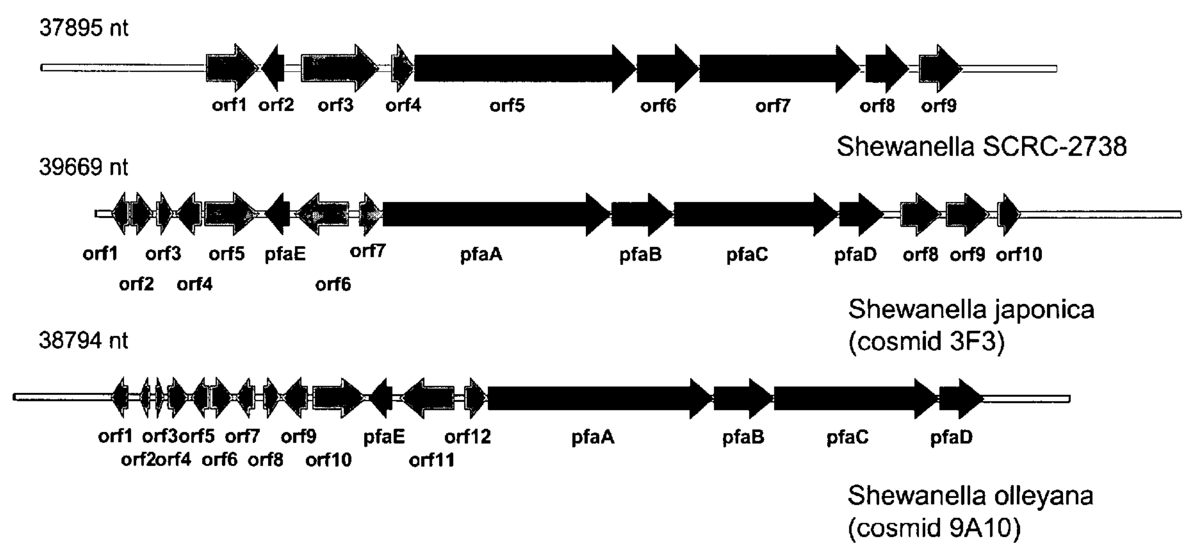
FIG. 1 is a schematic drawing illustrating the open reading frame (ORF) architecture of EPA production clusters from *Shewanella* sp. SCRC-2738, *Shewanella japonica*, and *Shewanella olleyana*.

FIG. 4 is a sequence alignment showing the N-terminal end of the pfaE ORFs (Sja_pfaE: positions 1-70 of SEQ ID NO:6; Sol_pfaE: positions 1-59 of SEQ ID NO:12) versus the annotated start of orf2 from *Shewanella* sp. SCRC-2738 (orf2_ATG: SEQ ID NO:61) and the experimentally functional start of orf2 from *Shewanella* sp. SCRC-2738 (WO 98/55625) (orf2_TTG: SEQ ID NO:62).

DETAILED DESCRIPTION OF THE INVENTION

The present invention generally relates to polyunsaturated fatty acid (PUFA) polyketide synthase (PKS) systems from a subset of marine bacteria that naturally produce EPA and grow well at temperatures up to about 30° C. and possibly higher (e.g., up to 35° C. or beyond), to genetically modified organisms comprising such PUFA PKS systems, to methods of making and using such systems for the production of products of interest, including bioactive molecules and particularly, PUFAs, such as DHA, DPA and EPA.

As used herein, a PUFA PKS system (which may also be referred to as a PUFA synthase system) generally has the following identifying features: (1) it produces PUFAs as a natural product of the system; and (2) it comprises several multifunctional proteins assembled into a complex that conducts both iterative processing of the fatty acid chain as well non-iterative processing, including trans-cis isomerization and enoyl reduction reactions in selected cycles. Reference to a PUFA PKS system refers collectively to all of the genes and their encoded products that work in a complex to produce PUFAs in an organism. Therefore, the PUFA PKS system refers specifically to a PKS system for which the natural products are PUFAs.

More specifically, first, a PUFA PKS system that forms the basis of this invention produces polyunsaturated fatty acids (PUFAs) as products (i.e., an organism that endogenously (naturally) contains such a PKS system makes PUFAs using this system). The PUFAs referred to herein are preferably polyunsaturated fatty acids with a carbon chain length of at least 16 carbons, and more preferably at least 18 carbons, and more preferably at least 20 carbons, and more preferably 22 or more carbons, with at least 3 or more double bonds, and preferably 4 or more, and more preferably 5 or more, and even more preferably 6 or more double bonds, wherein all double bonds are in the cis configuration. It is an object of the present invention to find or create via genetic manipulation or manipulation of the endproduct, PKS systems which produce polyunsaturated fatty acids of desired chain length and with desired numbers of double bonds. Examples of PUFAs include, but are not limited to, DHA (docosahexaenoic acid (C22:6, ω-3)), ARA (eicosatetraenoic acid or arachidonic acid (C20:4, n-6)), DPA (docosapentaenoic acid (C22:5, ω-6 or ω-3)), and EPA (eicosapentaenoic acid (C20:5, ω-3)).

Second, the PUFA PKS system described herein incorporates both iterative and non-iterative reactions, which generally distinguish the system from previously described PKS systems (e.g., type I modular or iterative, type II or type III). More particularly, the PUFA PKS system described herein contains domains that appear to function during each cycle as well as those which appear to function during only some of the cycles. A key aspect of this functionality may be related to the domains showing homology to the bacterial Fab-A enzymes. For example, the Fab-A enzyme of *E. coli* has been shown to possess two enzymatic activities. It possesses a dehydration activity in which a water molecule ($H_2O$) is abstracted from a carbon chain containing a hydroxy group, leaving a trans double bond in that carbon chain. In addition, it has an isomerase activity in which the trans double bond is converted to the cis configuration. This isomerization is accomplished in conjunction with a migration of the double bond position to adjacent carbons. In PKS (and FAS) systems, the main carbon chain is extended in 2 carbon increments. One can therefore predict the number of extension reactions required to produce the PUFA products of these PKS systems. For example, to produce DHA (C22:6, all cis) requires 10 extension reactions. Since there are only 6 double bonds in the end product, it means that during some of the reaction cycles, a double bond is retained (as a cis isomer), and in others, the double bond is reduced prior to the next extension.

Before the discovery of a PUFA PKS system in marine bacteria (see U.S. Pat. No. 6,140,486), PKS systems were not known to possess this combination of iterative and selective enzymatic reactions, and they were not thought of as being able to produce carbon-carbon double bonds in the cis configuration. However, the PUFA PKS system described by the present invention has the capacity to introduce cis double bonds and the capacity to vary the reaction sequence in the cycle.

The present inventors propose to use these features of the PUFA PKS system to produce a range of bioactive molecules that could not be produced by the previously described (Type I iterative or modular, Type II, or Type III) PKS systems. These bioactive molecules include, but are not limited to, polyunsaturated fatty acids (PUFAs), antibiotics or other bioactive compounds, many of which will be discussed below. For example, using the knowledge of the PUFA PKS gene structures described herein, any of a number of methods can be used to alter the PUFA PKS genes, or combine portions of these genes with other synthesis systems, including other PKS systems, such that new products are produced. The inherent ability of this particular type of system to do both iterative and selective reactions will enable this system to yield products that would not be found if similar methods were applied to other types of PKS systems.

In U.S. patent application Ser. No. 10/810,352, supra, the present inventors identified two exemplary marine bacteria (e.g. *Shewanella olleyana* and *Shewanella japonica*) that are particularly suitable for use as sources of PUFA PKS genes, because they have the surprising characteristic of being able to produce PUFAs (e.g., EPA) and grow at temperatures up to about 30° C., in contrast to previously described PUFA PKS-containing marine bacteria, including other species and strains within *Shewanella*, which typically produce PUFAs and grow at much lower temperatures. The inventors have now cloned and sequenced the full-length genomic sequence of all of the PUFA PKS open reading frames (Orfs) in each of *Shewanella olleyana* (Australian Collection of Antarctic Microorganisms (ACAM) strain number 644; Skerratt et al., *Int. J. Syst. Evol. Microbiol.* 52, 2101 (2002)) and *Shewanella japonica* (American Type Culture Collection (ATCC) strain number BAA-316; Ivanova et al., *Int. J. Syst. Evol. Microbiol.* 51, 1027 (2001)), and have identified the domains comprising the PUFA PKS system in these special marine bacteria. Therefore, the present invention solves the above-mentioned problem of providing additional PUFA PKS systems that have the flexibility for commercial use.

The PUFA PKS systems of the present invention can also be used as a tool in a strategy to solve the above-identified problem for production of commercially valuable lipids enriched in a desired PUFA, such as EPA, by the present inventors' development of genetically modified microorganisms and methods for efficiently producing lipids enriched in PUFAs in one or more of their various forms (e.g., triacylglycerols (TAG) and phospholipids (PL)) by manipulation of the polyketide synthase-like system that produces PUFAs in eukaryotes, including members of the order Thraustochytriales such as *Schizochytrium* and *Thraustochytrium*. Specifically, and by way of example, the present inventors describe herein a strain of *Schizochytrium* that has previously been optimized for commercial production of oils enriched in PUFA, primarily docosahexaenoic acid (DHA; C22:6 n-3) and docosapentaenoic acid (DPA; C22:5 n-6), and that will now be genetically modified such that EPA (C20:5 n-3) production (or other PUFA production) replaces the DHA production, without sacrificing the oil productivity characteristics of the organism. One can use the marine bacterial PUFA PKS genes from the marine bacteria described in the present invention in one embodiment to produce such a genetically modified microorganism. This is only one example of the technology encompassed by the invention, as the concepts of the invention can readily be applied to other production organisms and other desired PUFAs as described in detail below.

As used herein, the term "lipid" includes phospholipids; free fatty acids; esters of fatty acids; triacylglycerols; diacylglycerides; phosphatides; sterols and sterol esters; carotenoids; xanthophylls (e.g., oxycarotenoids); hydrocarbons; and other lipids known to one of ordinary skill in the art. The terms "polyunsaturated fatty acid" and "PUFA" include not only the free fatty acid form, but other forms as well, such as the TAG form and the PL form.

Figure 2:
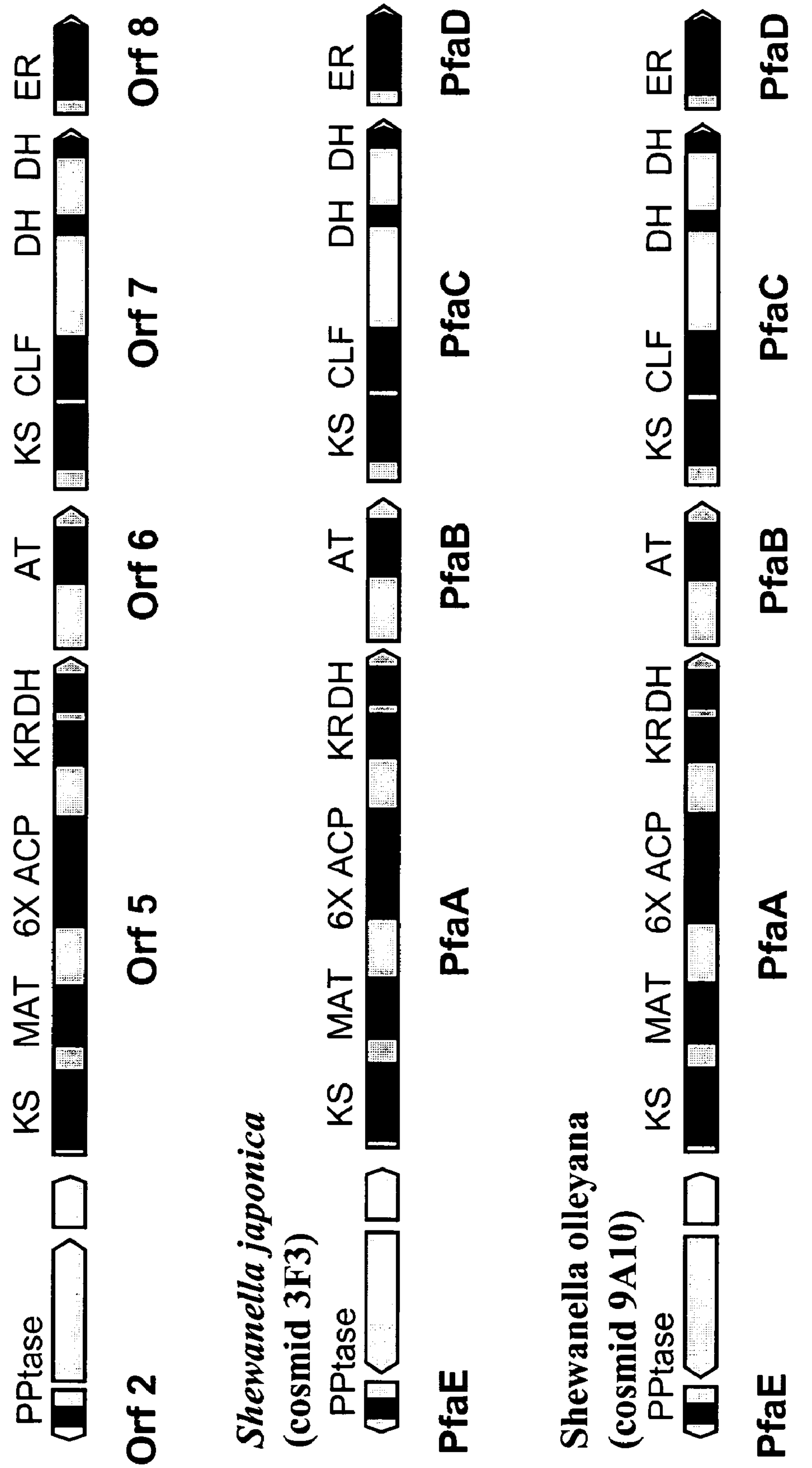
FIG. 2 is a schematic drawing illustrating the domain architecture of the EPA production gene clusters from *Shewanella* sp. SCRC-2738, *Shewanella japonica* and *Shewanella olleyana*.

In one embodiment, a PUFA PKS system according to the present invention comprises at least the following biologically active domains: (a) at least one enoyl-ACP reductase (ER) domain; (b) at least six acyl carrier protein (ACP) domains; (c) at least two β-ketoacyl-ACP synthase (KS) domains; (d) at least one acyltransferase (AT) domain; (e) at least one β-ketoacyl-ACP reductase (KR) domain; (f) at least two FabA-like β-hydroxyacyl-ACP dehydrase (DH) domains; (g) at least one chain length factor (CLF) domain; and (h) at least one malonyl-CoA:ACP acyltransferase (MAT) domain. A PUFA PKS system also comprises at least one 4'-phosphopantetheinyl transferase (PPTase) domain, and such domain can be considered to be a part of the PUFA PKS system or an accessory domain or protein to the PUFA PKS system. In one embodiment a PUFA PKS system according to the present invention also comprises at least one region containing a dehydratase (DH) conserved active site motif. The functions of these domains and motifs are generally individually known in the art and will be described in detail below with regard to the PUFA PKS system of the present invention. The domains of the present invention may be found as a single protein (i.e., the domain and protein are synonymous) or as one of two or more (multiple) domains in a single protein. The domain architecture of the PUFA PKS systems in these *Shewanella* species is described in more detail below and is illustrated in FIG. 2.

In another embodiment, the PUFA PKS system comprises at least the following biologically active domains: (a) at least one enoyl-ACP reductase (ER) domain; (b) multiple acyl carrier protein (ACP) domain(s) (at least from one to four, and preferably at least five, and more preferably at least six, and even more preferably seven, eight, nine, or more than nine); (c) at least two β-ketoacyl-ACP synthase (KS) domains; (d) at least one acyltransferase (AT) domain; (e) at least one β-ketoacyl-ACP reductase (KR) domain; (f) at least two FabA-like β-hydroxyacyl-ACP dehydrase (DH) domains; (g) at least one chain length factor (CLF) domain; (h) at least one malonyl-CoA:ACP acyltransferase (MAT) domain; and (i) at least one 4'-phosphopantetheinyl transferase (PPTase) domain. In one embodiment a PUFA PKS system according to the present invention also comprises at least one region containing a dehydratase (DH) conserved active site motif.

According to the present invention, a domain or protein having β-ketoacyl-ACP synthase (KS) biological activity (function) is characterized as the enzyme that carries out the initial step of the FAS (and PKS) elongation reaction cycle. The term "β-ketoacyl-ACP synthase" can be used interchangeably with the terms "3-keto acyl-ACP synthase", "β-keto acyl-ACP synthase", and "keto-acyl ACP synthase", and similar derivatives. The acyl group destined for elongation is linked to a cysteine residue at the active site of the enzyme by a thioester bond. In the multi-step reaction, the acyl-enzyme undergoes condensation with malonyl-ACP to form -ketoacyl-ACP, $CO_2$ and free enzyme. The KS plays a key role in the elongation cycle and in many systems has been shown to possess greater substrate specificity than other enzymes of the reaction cycle. For example, *E. coli* has three distinct KS enzymes—each with its own particular role in the physiology of the organism (Magnuson et al., *Microbiol. Rev.* 57, 522 (1993)). The two KS domains of the PUFA-PKS systems described herein could have distinct roles in the PUFA biosynthetic reaction sequence.

As a class of enzymes, KS's have been well characterized. The sequences of many verified KS genes are known, the active site motifs have been identified and the crystal structures of several have been determined. Proteins (or domains of proteins) can be readily identified as belonging to the KS family of enzymes by homology to known KS sequences.

According to the present invention, a domain or protein having malonyl-CoA:ACP acyltransferase (MAT) biological activity (function) is characterized as one that transfers the malonyl moiety from malonyl-CoA to ACP. The term "malonyl-CoA:ACP acyltransferase" can be used interchangeably with "malonyl acyltransferase" and similar derivatives. In addition to the active site motif (G×S×G), these enzymes possess an extended motif (R and Q amino acids in key positions) that identifies them as MAT enzymes (in contrast to the AT domain, discussed below). In some PKS systems (but not the PUFA PKS domain), MAT domains will preferentially load methyl- or ethyl-malonate on to the ACP group (from the corresponding CoA ester), thereby introducing branches into the linear carbon chain. MAT domains can be recognized by their homology to known MAT sequences and by their extended motif structure.

According to the present invention, a domain or protein having acyl carrier protein (ACP) biological activity (function) is characterized as being a small polypeptide (typically, 80 to 100 amino acids long), that functions as a carrier for growing fatty acyl chains via a thioester linkage to a covalently bound co-factor of the protein. These polypeptides occur as separate units or as domains within larger proteins. ACPs are converted from inactive apo-forms to functional holo-forms by transfer of the phosphopantetheinyl moiety of CoA to a highly conserved serine residue of the ACP. Acyl groups are attached to ACP by a thioester linkage at the free terminus of the phosphopantetheinyl moiety. ACPs can be identified by labeling with radioactive pantetheine and by sequence homology to known ACPs. The presence of variations of an active site motif (LGIDS*; e.g., see amino acids 1296-1300 of SEQ ID NO:2) is also a signature of an ACP.

According to the present invention, a domain or protein having β-ketoacyl-ACP reductase (KR) activity is characterized as one that catalyzes the pyridine-nucleotide-dependent reduction of 3-ketoacyl forms of ACP. The term "β-ketoacyl-ACP reductase" can be used interchangeably with the terms "ketoreductase", "3-ketoacyl-ACP reductase", "keto-acyl ACP reductase" and similar derivatives of the term. It is the first reductive step in the de novo fatty acid biosynthesis elongation cycle and a reaction often performed in polyketide biosynthesis. Significant sequence similarity is observed with one family of enoyl-ACP reductases (ER), the other reductase of FAS (but not the ER family present in the PUFA PKS system), and the short-chain alcohol dehydrogenase family. Pfam analysis of this PUFA PKS region may reveal the homology to the short-chain alcohol dehydrogenase family in the core region. Blast analysis of the same region may reveal matches in the core area to known KR enzymes as well as an extended region of homology to domains from the other characterized PUFA PKS systems.

According to the present invention, a domain or protein is referred to as a chain length factor (CLF) based on the following rationale. The CLF was originally described as characteristic of Type II (dissociated enzymes) PKS systems and was hypothesized to play a role in determining the number of elongation cycles, and hence the chain length, of the end product. CLF amino acid sequences show homology to KS domains (and are thought to form heterodimers with a KS protein), but they lack the active site cysteine. The role of CLF in PKS systems has been controversial. Evidence (C. Bisang et al., *Nature* 401, 502 (1999)) suggests a role in priming the PKS systems (by providing the initial acyl group to be elongated). In this role, the CLF domain is thought to decarboxylate malonate (as malonyl-ACP), thus forming an acetate group that can be transferred to the KS active site. This acetate therefore acts as the 'priming' molecule that can undergo the initial elongation (condensation) reaction. Homologues of the Type II CLF have been identified as 'loading' domains in some type I modular PKS systems. However, other recent evidence suggests a genuine role of the CLF domains in determining chain length (Yi et al., *J. Am. Chem. Soc.* 125: 12708 (2003). A domain with the sequence features of the CLF is found in all currently identified PUFA PKS systems and in each case is found as part of a multidomain protein.

Reference to an "acyltransferase" or "AT" refers to a general class of enzymes that can carry out a number of distinct acyl transfer reactions. The term "acyltransferase" can be used interchangeably with the term "acyl transferase". The *Schizochytrium* domain shows good homology to a domain present in all of the other PUFA PKS systems currently examined and very weak homology to some acyltransferases whose specific functions have been identified (e.g. to malonyl-CoA:ACP acyltransferase, MAT). In spite of the weak homology to MAT, the AT domain is not believed to function as a MAT because it does not possess an extended motif structure characteristic of such enzymes (see MAT domain description, above). For the purposes of this disclosure, the functions of the AT domain in a PUFA PKS system include, but are not limited to: transfer of the fatty acyl group from the OrfA ACP domain(s) to water (i.e. a thioesterase—releasing the fatty acyl group as a free fatty acid), transfer of a fatty acyl group to an acceptor such as CoA, transfer of the acyl group among the various ACP domains, or transfer of the fatty acyl group to a lipophilic acceptor molecule (e.g. to lysophosphadic acid).

According to the present invention, a protein or domain having enoyl-ACP reductase (ER) biological activity reduces the trans-double bond (introduced by the DH activity) in the fatty acyl-ACP, resulting in fully saturating those carbons. The ER domain in the PUFA-PKS shows homology to a newly characterized family of ER enzymes (Heath et al., *Nature* 406, 145 (2000)). According to the present invention, the term "enoyl-ACP reductase" can be used interchangeably with "enoyl reductase", "enoyl ACP-reductase" and "enoyl acyl-ACP reductase". Heath and Rock identified this new class of ER enzymes by cloning a gene of interest from *Streptococcus pneumoniae*, purifying a protein expressed from that gene, and showing that it had ER activity in an in vitro assay. The bacterial PUFA PKS systems described herein contain one ER domain.

According to the present invention, a protein or domain having dehydrase or dehydratase (DH) activity catalyzes a dehydration reaction. As used generally herein, reference to DH activity typically refers to FabA-like β-hydroxyacyl-ACP dehydrase (DH) biological activity. FabA-like β-hydroxyacyl-ACP dehydrase (DH) biological activity removes HOH from a β-ketoacyl-ACP and initially produces a trans double bond in the carbon chain. The term "FabA-like β-hydroxyacyl-ACP dehydrase" can be used interchangeably with the terms "FabA-like β-hydroxy acyl-ACP dehydrase", "β-hydroxyacyl-ACP dehydrase", "dehydrase" and similar derivatives. The DH domains of the PUFA PKS systems show homology to bacterial DH enzymes associated with their FAS systems (rather than to the DH domains of other PKS systems). A subset of bacterial DH's, the FabA-like DH's, possesses cis-trans isomerase activity (Heath et al., *J. Biol. Chem.,* 271, 27795 (1996)). It is the homology to the FabA-like DH proteins that indicate that one or all of the DH domains described herein is responsible for insertion of the cis double bonds in the PUFA PKS products.

A protein of the invention may also have dehydratase activity that is not characterized as FabA-like (e.g., the cis-trans activity described above is associated with FabA-like activity), generally referred to herein as non-FabA-like DH activity, or non-FabA-like β-hydroxyacyl-ACP dehydrase (DH) biological activity. More specifically, a conserved active site motif (~13 amino acids long: L*xxHxxxGxxxxP; amino acids 2504-2516 of SEQ ID NO:2; *in the motif, L can also be I) is found in dehydratase domains in PKS systems (Donadio S, Katz L. Gene. 1992 Feb. 1; 111(1):51-60). This conserved motif, also referred to herein as a dehydratase (DH) conserved active site motif or DH motif, is found in a similar region of all known PUFA-PKS sequences described to date and in the PUFA PKS sequences described herein (e.g., amino acids 2504-2516 of SEQ ID NO:2, or amino acids 2480-2492 of SEQ ID NO:8), but it is believed that his motif has been previously undetected until the present invention. This conserved motif is within an uncharacterized region of high homology in the PUFA-PKS sequence. The proposed biosynthesis of PUFAs via the PUFA-PKS requires a non-FabA like dehydration, and this motif may be responsible for the reaction.

According to the present invention, a domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopantetheine group forms thioesters with the growing acyl chains. The PPTases are a family of enzymes that have been well characterized in fatty acid synthesis, polyketide synthesis, and non-ribosomal peptide synthesis. The sequences of many PPTases are known, and crystal structures have been determined (e.g., Reuter K, Mofid M R, Marahiel M A, Ficner R. "Crystal structure of the surfactin synthetase-activating enzyme sfp: a prototype of the 4'-phosphopantetheinyl transferase superfamily" EMBO J. 1999 Dec. 1; 18(23): 6823-31) as well as mutational analysis of amino acid residues important for activity (Mofid M R, Finking R, Essen L O, Marahiel M A. "Structure-based mutational analysis of the 4'-phosphopantetheinyl transferases Sfp from *Bacillus subtilis*: carrier protein recognition and reaction mechanism" Biochemistry. 2004 Apr. 13; 43(14):4128-36). These invariant and highly conserved amino acids in PPTases are contained within the pfaE ORFs from both *Shewanella* strains described herein. Additionally, the pfaE ORF homolog in *Shewanella* sp. SCRC-2738 orf2 has been shown to be required for activity in the native strain (Yazawa K. "Production of eicosapentaenoic acid from marine bacteria". Lipids. 1996 Mar.; 31 Suppl:S297-300.) and labeling experiments confirming its PPTase activity (WO 98/55625).

The PUFA PKS systems of particular marine bacteria (e.g., *Shewanella olleyana* and *Shewanella japonica*) that produce PUFAs and grow well at temperatures of up to about 25-30° C., and possibly higher (e.g., 35° C.), are the basis of the present invention, although the present invention does contemplate the use of domains from these bacterial PUFA PKS systems in conjunction with domains from other bacterial and non-bacterial PUFA PKS systems that have been described, for example, in U.S. Pat. No. 6,140,486, U.S. Pat. No. 6,566,583, U.S. patent application Ser. No. 10/124,800, and U.S. patent application Ser. No. 10/810,352. More particularly, the PUFA PKS systems of the present invention can be used with other PUFA PKS systems to produce hybrid constructs and genetically modified microorganisms and plants for improved and or modified production of biological products by such microorganisms and plants. For example, according to the present invention, genetically modified organisms can be produced which incorporate non-bacterial PUFA PKS functional domains with bacterial PUFA PKS functional domains (preferably those of the present invention), as well as PKS functional domains or proteins from other PKS systems (type I, type II, type III) or FAS systems.

Reference herein to a "non-bacterial PUFA PKS" system is reference to a PUFA PKS system that has been isolated from an organism that is not a bacterium, or is a homologue of, or derived from, a PUFA PKS system from an organism that is not a bacterium, such as a eukaryote or an archaebacterium. Eukaryotes are separated from prokaryotes based on the degree of differentiation of the cells, with eukaryotes having more highly differentiated cells and prokaryotes having less differentiated cells. In general, prokaryotes do not possess a nuclear membrane, do not exhibit mitosis during cell division, have only one chromosome, their cytoplasm contains 70S ribosomes, they do not possess any mitochondria, endoplasmic reticulum, chloroplasts, lysosomes or Golgi apparatus, their flagella (if present) consists of a single fibril. In contrast, eukaryotes have a nuclear membrane, they do exhibit mitosis during cell division, they have many chromosomes, their cytoplasm contains 80S ribosomes, they do possess mitochondria, endoplasmic reticulum, chloroplasts (in algae), lysosomes and Golgi apparatus, and their flagella (if present) consists of many fibrils. In general, bacteria are prokaryotes, while algae, fungi, protist, protozoa and higher plants are eukaryotes.

Non-bacterial PUFA PKS systems include those that have been described in the above identified patents and applications, and particularly include any PUFA PKS system isolated or derived from any Thraustochytrid. In U.S. Pat. No. 6,566,583, several cDNA clones from *Schizochytrium* showing homology to *Shewanella* sp. strain SCRC2738 PKS genes were sequenced, and various clones were assembled into nucleic acid sequences representing two partial open reading frames and one complete open reading frame. Further sequencing of cDNA and genomic clones by the present inventors allowed the identification of the full-length genomic sequence of each of OrfA, OrfB and OrfC in *Schizochytrium* and the complete identification of the domains in *Schizochytrium* with homology to those in *Shewanella*. These genes are described in detail in U.S. patent application Ser. No. 10/124,800, supra and are described in some detail below. Similarly, U.S. patent application Ser. No. 10/810,352 describes in detail the full-length genomic sequence of the genes encoding the PUFA PKS system in a *Thraustochytrium* (specifically, *Thraustochytrium* sp. 23B (ATCC 20892)) as well as the domains comprising the PUFA PKS system in *Thraustochytrium.*

According to the present invention, the phrase "open reading frame" is denoted by the abbreviation "Orf". It is noted that the protein encoded by an open reading frame can also be denoted in all upper case letters as "ORF" and a nucleic acid sequence for an open reading frame can also be denoted in all lower case letters as "orf", but for the sake of consistency, the spelling "Orf" is preferentially used herein to describe either the nucleic acid sequence or the protein encoded thereby. It will be obvious from the context of the usage of the term whether a protein or nucleic acid sequence is referenced.

FIG. 1 shows the architecture of the PUFA PKS (also referred to as "EPA production") clusters from *Shewanella* sp. SCRC-2738 ("Yazawa" strain; Yazawa K. "Production of eicosapentaenoic acid from marine bacteria" Lipids. 1996 Mar.; 31 Suppl:S297-300.) versus the gene clusters of the present invention from *Shewanella japonica* (cosmid 3F3) and *Shewanella olleyana* (cosmid 9A10). FIG. 2 shows the domain architecture of the PUFA PKS gene clusters from *Shewanella* sp. SCRC-2738 ("Yazawa" strain) verses that encoded by the gene clusters from *Shewanella japonica* (cosmid 3F3) and *Shewanella olleyana* (cosmid 9A10). The domain structure of each open reading frame is described below.

*Shewanella Japonica* PUFA PKS

SEQ ID NO:1 is the nucleotide sequence for *Shewanella japonica* cosmid 3F3 and is found to contain 15 ORFs as detailed in Table 1 (see Example 2). The ORFs related to the PUFA PKS system in this microorganism are characterized as follows.

pfaA (nucleotides 10491-18854 of SEQ ID NO:1) encodes PFAS A (SEQ ID NO:2), a PUFA PKS protein harboring the following domains: β-ketoacyl-synthase (KS) (nucleotides 10575-12029 of SEQ ID NO:1, amino acids 29-513 of SEQ ID NO:2); malonyl-CoA: ACP acyltransferase (MAT) (nucleotides 12366-13319 of SEQ ID NO:1, amino acids 625-943 of SEQ ID NO:2); six tandem acyl-carrier proteins (ACP) domains (nucleotides 14280-16157 of SEQ ID NO:1, amino acids 1264-1889 of SEQ ID NO:2); β-ketoacyl-ACP reductase (KR) (nucleotides 17280-17684 of SEQ ID NO:1, amino acids 2264-2398 of SEQ ID NO:2); and a region of the PFAS A protein between amino acids 2399 and 2787 of SEQ ID NO:2 containing a dehydratase (DH) conserved active site motif LxxHxxxGxxxxP (amino acids 2504-2516 of SEQ ID NO:2), referred to herein as DH-motif region.

In PFAS A, a KS active site DXAC* is located at amino acids 226-229 of SEQ ID NO:2 with the C* being the site of the acyl attachment. A MAT active site, GHS*XG, is located at amino acids 721-725 of SEQ ID NO:2, with the S* being the acyl binding site. ACP active sites of LGXDS* are located at the following positions: amino acids 1296-1300, amino acids 1402-1406, amino acids 1513-1517, amino acids 1614-1618, amino acids 1728-1732, and amino acids 1843-1847 in SEQ ID NO:2, with the S* being the phosphopantetheine attachment site. Between amino acids 2399 and 2787 of SEQ ID NO:2, the PFAS A also contains the dehydratase (DH) conserved active site motif LxxHxxxGxxxxP (amino acids 2504-2516 of SEQ ID NO:2) referenced above.

pfaB (nucleotides 18851-21130 of SEQ ID NO:1) encodes PFAS B (SEQ ID NO:3), a PUFA PKS protein harboring the following domain: acyltransferase (AT) (nucleotides 19982-20902 of SEQ ID NO:1, amino acids 378-684 of SEQ ID NO:3).

In PFAS B, an active site GXS*XG motif is located at amino acids 463-467 of SEQ ID NO:3, with the S* being the site of acyl-attachment.

pfaC (nucleotides 21127-27186 of SEQ ID NO:1) encodes PFAS C (SEQ ID NO:4), a PUFA PKS protein harboring the following domains: KS (nucleotides 21139-22575 of SEQ ID NO:1, amino acids 5-483 of SEQ ID NO:4); chain length factor (CLF) (nucleotides 22591-23439 of SEQ ID NO:1, amino acids 489-771 of SEQ ID NO:4); and two FabA 3-hydroxyacyl-ACP dehydratases, referred to as DH1 (nucleotides 25408-25836 of SEQ ID NO:1, amino acids 1428-1570 of SEQ ID NO:4) and DH2 (nucleotides 26767-27183 of SEQ ID NO:1, amino acids 1881-2019 of SEQ ID NO:4).

In PFAS C, a KS active site DXAC* is located at amino acids 211-214 of SEQ ID NO:4 with the C* being the site of the acyl attachment.

pfaD (nucleotides 27197-28825 of SEQ ID NO:1) encodes the PFAS D (SEQ ID NO:5), a PUFA PKS protein harboring the following domain: an enoyl reductase (ER) (nucleotides 27446-28687 of SEQ ID NO:1, amino acids 84-497 of SEQ ID NO:5).

pfaE (nucleotides 6150-7061 of SEQ ID NO:1 on the reverse complementary strand) encodes PFAS E (SEQ ID NO:6), a 4'-phosphopantetheinyl transferase (PPTase) with the identified domain (nucleotides 6504-6944 of SEQ ID NO:1, amino acids 40-186 of SEQ ID NO:6).

*Shewanella Olleyana* PUFA PKS

SEQ ID NO:7 is the nucleotide sequence for *Shewanella olleyana* cosmid 9A10 and was found to contain 17 ORFs as detailed in Table 2 (see Example 2). The ORFs related to the PUFA PKS system in this microorganism are characterized as follows.

pfaA (nucleotides 17437-25743 of SEQ ID NO:7) encodes PFAS A (SEQ ID NO:8), a PUFA PKS protein harboring the following domains: β-ketoacyl-synthase (KS) (nucleotides 17521-18975 of SEQ ID NO:7, amino acids 29-513 of SEQ ID NO:8); malonyl-CoA: ACP acyltransferase (MAT) (nucleotides 19309-20265 of SEQ ID NO:7, amino acids 625-943 of SEQ ID NO:8); six tandem acyl-carrier proteins (ACP) domains (nucleotides 21259-23052 of SEQ ID NO:7, amino acids 1275-1872 of SEQ ID NO:8); β-ketoacyl-ACP reductase (KR) (nucleotides 24154-24558 of SEQ ID NO:7, amino acids 2240-2374 of SEQ ID NO:8); and a region of the PFAS A protein between amino acids 2241 and 2768 of SEQ ID NO:8 containing a dehydratase (DH) conserved active site motif LxxHxxxGxxxxP (amino acids 2480-2492 of SEQ ID NO:8), referred to herein as DH-motif region.

In PFAS A, a KS active site DXAC* is located at AA 226-229 of SEQ ID NO:8 with the C* being the site of the acyl attachment. A MAT active site, GHS*XG, is located at amino acids 721-725 of SEQ ID NO:8 with the S* being the acyl binding site. ACP active sites of LGXDS* are located at: amino acids 1307-1311, amino acids 1408-1412, amino acids 1509-1513, amino acids 1617-1621, amino acids 1721-1725, and amino acids 1826-1830 in SEQ ID NO:8, with the S* being the phosphopantetheine attachment site. Between amino acids 2241 and 2768 of SEQ ID NO:8, the PFAS A also contains the dehydratase (DH) conserved active site motif LxxHxxxGxxxxP (amino acids 2480-2492 of SEQ ID NO:8) referenced above.

pfaB (nucleotides 25740-27971 of SEQ ID NO:7) encodes PFAS B (SEQ ID NO:9), a PUFA PKS protein harboring the following domain: acyltransferase (AT) (nucleotides 26837-27848 of SEQ ID NO:1, amino acids 366-703 of SEQ ID NO:9).

In PFAS B, an active site GXS*XG motif is located at amino acids 451-455 of SEQ ID NO:9 with the S* being the site of acyl-attachment.

pfaC (nucleotides 27968-34030 of SEQ ID NO:7) encodes PFAS C (SEQ ID NO:10), a PUFA PKS protein harboring the following domains: KS (nucleotides 27995-29431 SEQ ID NO:7, amino acids 10-488 SEQ ID NO:10); chain length factor (CLF) (nucleotides 29471-30217 SEQ ID NO:7, amino acids 502-750 SEQ ID NO:10); and two FabA 3-hydroxyacyl-ACP dehydratases, referred to as DH1 (nucleotides 32258-32686 SEQ ID NO:7, amino acids 1431-1573 SEQ ID NO:10), and DH2 (nucleotides 33611-34027 of SEQ ID NO:7, amino acids 1882-2020 of SEQ ID NO:10).

In PFAS C, a KS active site DXAC* is located at amino acids 216-219 of SEQ ID NO:10 with the C* being the site of the acyl attachment.

pfaD (nucleotides 34041-35669 of SEQ ID NO:7) encodes the PFAS D (SEQ ID NO:11), a PUFA PKS protein harboring the following domain: an enoyl reductase (ER) (nucleotides 34290-35531 of SEQ ID NO:7, amino acids 84-497 of SEQ ID NO:11).

pfaE (nucleotides 13027-13899 of SEQ ID NO:7 on the reverse complementary strand) encodes PFAS E (SEQ ID NO:12), a 4'-phosphopantetheinyl transferase (PPTase) with the identified domain (nucleotides 13369-13815 of SEQ ID NO:7, amino acid 29-177 of SEQ ID NO:12).

The pfaC ORF from both *Shewanella* strains described above and the pfaE ORF from *Shewanella olleyana* are predicted to have TTG as their start codon. While TTG is a less common start codon in bacteria then ATG and GTG, it has been predicted to be the start codon for 1.1% of *E. coli* genes and 11.2% of *Bacillus subtilis* genes (Hannenhalli S S, Hayes W S, Hatzigeorgiou A G, Fickett J W. "Bacterial start site prediction". Nucleic Acids Res. 1999 Sep. 1; 27(17):3577-82). There are several lines of evidence to annotate these ORFs start with a TTG codon. First, both computational gene finding tools (EasyGene and GeneMark.hmm) predicted the TTG start codon for these three ORFs. Second, translation from the TTG start in these three ORFs conserves the spacing and range of identical and similar protein residues to homologous genes in the GenBank database. Another line of evidence for the TTG start codon in these genes is the predicted ribosome binding sites (RBS). The RBS is approximately 7 to 12 nucleotides upstream of the start codon and is usually purine rich. Table 5 (see Example 2) shows the upstream regions of all the pfa ORFs and possible RBS. Both pfaC ORFs show very high homology to canonical RBS upstream of the TTG start codon. Alternative starting codons and RBS for these three ORFs annotated with the TTG start codon are also shown in Table 5. It is also noted that the pfaE ORFs from the *Shewanella* strains described here are homologous to orf2 from the EPA biosynthetic cluster from *Shewanella* sp. SCRC-2738 (GenBank accession numberU73935). Expression of the *Shewanella* sp. SCRC-2738 orf2 from the annotated ATG was shown not to support EPA production in a heterologous expression system (see PCT Publication No. WO 98/55625). When an alternate upstream start codon of TTG was used in the expression, EPA production was seen in a heterologous expression system. The annotated start codons for both pfaE ORFs described here encode similar and identical amino acids to those encoded from the alternate TTG start codon from orf2 of *Shewanella* sp. SCRC-2738 (FIG. 4). This also supports the TTG start annotation for pfaE ORF from *Sh. olleyana*. Lastly, the pfaC ORF start codons from both *Shewanella* strains overlap with the pfaB stop codons (FIG. 3). The overlap of ORFs is a common feature in bacterial operons and is thought to be one means for coupling two or more genes at the transcriptional level.

One embodiment of the present invention relates to an isolated protein or domain from a bacterial PUFA PKS system described herein, a homologue thereof, and/or a fragment thereof. Also included in the invention are isolated nucleic acid molecules encoding any of the proteins, domains or peptides described herein (discussed in detail below). According to the present invention, an isolated protein or peptide, such as a protein or peptide from a PUFA PKS system, is a protein or a fragment thereof (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. An isolated peptide can be produced synthetically (e.g., chemically, such as by peptide synthesis) or recombinantly. In addition, and by way of example, a "*Shewanella japonica* PUFA PKS protein" refers to a PUFA PKS protein (generally including a homologue of a naturally occurring PUFA PKS protein) from a *Shewanella japonica* microorganism, or to a PUFA PKS protein that has been otherwise produced from the knowledge of the structure (e.g., sequence), and perhaps the function, of a naturally occurring PUFA PKS protein from *Shewanella japonica*. In other words, general reference to a *Shewanella japonica* PUFA PKS protein includes any PUFA PKS protein that has substantially similar structure and function of a naturally occurring PUFA PKS protein from *Shewanella japonica* or that is a biologically active (i.e., has biological activity) homologue of a naturally occurring PUFA PKS protein from *Shewanella japonica* as described in detail herein. As such, a *Shewanella japonica* PUFA PKS protein can include purified, partially purified, recombinant, mutated/modified and synthetic proteins. The same description applies to reference to other proteins or peptides described herein, such as the PUFA PKS proteins and domains from *Shewanella olleyana*.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with another compound. Such modifications can be considered to be mutations, for example, if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can have either enhanced, decreased, or substantially similar properties as compared to the naturally occurring protein or peptide. Preferred homologues of a PUFA PKS protein or domain are described in detail below. It is noted that homologues can include synthetically produced homologues, naturally occurring allelic variants of a given protein or domain, or homologous sequences from organisms other than the organism from which the reference sequence was derived.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157:105 (1982)), or on the basis of the ability to assume similar polypeptide secondary structure (Chou and Fasman, *Adv. Enzymol.* 47: 45 (1978)).

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications or mutations in protein homologues, as compared to the wild-type protein, either increase, decrease, or do not substantially change, the basic biological activity of the homologue as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Biological activities of PUFA PKS systems and the individual proteins/domains that make up a PUFA PKS system have been described in detail elsewhere herein. Modifications of a protein, such as in a homologue, may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same biological activity as the wild-type protein, but at a reduced or increased level of activity as compared to the wild-type protein. A functional domain of a PUFA PKS system is a domain (i.e., a domain can be a portion of a protein) that is capable of performing a biological function (i.e., has biological activity).

Methods of detecting and measuring PUFA PKS protein or domain biological activity include, but are not limited to, measurement of transcription of a PUFA PKS protein or domain, measurement of translation of a PUFA PKS protein or domain, measurement of posttranslational modification of a PUFA PKS protein or domain, measurement of enzymatic activity of a PUFA PKS protein or domain, and/or measurement production of one or more products of a PUFA PKS system (e.g., PUFA production). It is noted that an isolated protein of the present invention (including a homologue) is not necessarily required to have the biological activity of the wild-type protein. For example, a PUFA PKS protein or domain can be a truncated, mutated or inactive protein, for example. Such proteins are useful in screening assays, for example, or for other purposes such as antibody production. In a preferred embodiment, the isolated proteins of the present invention have a biological activity that is similar to that of the wild-type protein (although not necessarily equivalent, as discussed above).

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. *Anal. Biochem.* 212:457 (1993); Schuster et al., *Nature* 365:343 (1993)). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

In one embodiment, the present invention relates to an isolated protein comprising, consisting essentially of, or consisting of, an amino acid sequence selected from: any one of SEQ ID NOs:2-6 or 8-12, or biologically active domains or fragments thereof. The domains contained within the PUFA PKS proteins represented by SEQ ID NOs:2-6 and 8-12 have been described in detail above. In another embodiment, the present invention relates to an isolated homologue of a protein represented by any one of SEQ ID NOs:2-6 and 8-12. Such a homologue comprises, consists essentially of, or consists of, an amino acid sequence that is at least about 60% identical to any one of SEQ ID NOs:2-6 or 8-12 and has a biological activity of at least one domain that is contained within the corresponding protein represented by SEQ ID NOs:2-6 or 8-12. In a further embodiment, the present invention relates to a homologue of a domain of a PUFA PKS protein represented by any one of SEQ ID NO:2-6 or 8-12, wherein the homologue comprises, consists essentially of, or consists of, an amino acid sequence that is at least about 60% identical to a domain from any one of SEQ ID NOs:2-6 or 8-12, and which has a biological activity of such domain from any one of SEQ ID NOs:2-6 or 8-12. In additional embodiments, any of the above-described homologues is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to any one of SEQ ID NOs:2-6 or 8-12, or to a domain contained within these sequences. As above, the homologue preferably has a biological activity of the protein or domain from which it is derived or related (i.e., the protein or domain having the reference amino acid sequence).

One embodiment of the invention relates to an isolated homologue of a protein represented by SEQ ID NO:2 that comprises, consists essentially of, or consists of, an amino acid sequence that is at least about 65% identical to SEQ ID NO:2 or to a biologically active domain within SEQ ID NO:2 as previously described herein, wherein the homologue has a biological activity of at least one domain that is contained within the corresponding protein represented by SEQ ID NO:2. In additional embodiments, the homologue is at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 65% and 99%, in whole single percentage increments) to SEQ ID NO:2 or a domain thereof.

Another embodiment of the invention relates to an isolated homologue of a protein represented by SEQ ID NO:3 that comprises, consists essentially of, or consists of, an amino acid sequence that is at least about 60% identical to SEQ ID NO:3 or to a biologically active domain within SEQ ID NO:3 as previously described herein, wherein the homologue has a biological activity of at least one domain that is contained within the corresponding protein represented by SEQ ID NO:3. In additional embodiments, the homologue is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:3 or a domain thereof.

Another embodiment of the invention relates to an isolated homologue of a protein represented by SEQ ID NO:4 that comprises, consists essentially of, or consists of, an amino acid sequence that is at least about 70% identical to SEQ ID NO:4 or to a biologically active domain within SEQ ID NO:4 as previously described herein, wherein the homologue has a biological activity of at least one domain that is contained within the corresponding protein represented by SEQ ID NO:4. In additional embodiments, the homologue is at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:4 or a domain thereof.

Another embodiment of the invention relates to an isolated homologue of a protein represented by SEQ ID NO:5 that comprises, consists essentially of, or consists of, an amino acid sequence that is at least about 95% identical to SEQ ID NO:5 or to a biologically active domain within SEQ ID NO:5 as previously described herein, wherein the homologue has a biological activity of at least one domain that is contained within the corresponding protein represented by SEQ ID NO:5. In additional embodiments, the homologue is at least about 96% identical, and more preferably at least about 97% identical, and more preferably at least about 98% identical, and more preferably at least about 99% identical to SEQ ID NO:5 or a domain thereof.

Another embodiment of the invention relates to an isolated homologue of a protein represented by SEQ ID NO:6 that comprises, consists essentially of, or consists of, an amino acid sequence that is at least about 60% identical to SEQ ID NO:6 or to a biologically active domain within SEQ ID NO:6 as previously described herein, wherein the homologue has a biological activity of at least one domain that is contained within the corresponding protein represented by SEQ ID NO:6. In additional embodiments, the homologue is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:6 or a domain thereof.

Another embodiment of the invention relates to an isolated homologue of a protein represented by SEQ ID NO:8 that comprises, consists essentially of, or consists of, an amino acid sequence that is at least about 65% identical to SEQ ID NO:8 or to a biologically active domain within SEQ ID NO:8 as previously described herein, wherein the homologue has a biological activity of at least one domain that is contained within the corresponding protein represented by SEQ ID NO:8. In additional embodiments, the homologue is at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:8 or a domain thereof.

Another embodiment of the invention relates to an isolated homologue of a protein represented by SEQ ID NO:9 that comprises, consists essentially of, or consists of, an amino acid sequence that is at least about 60% identical to SEQ ID NO:9 or to a biologically active domain within SEQ ID NO:9 as previously described herein, wherein the homologue has a biological activity of at least one domain that is contained within the corresponding protein represented by SEQ ID NO:9. In additional embodiments, the homologue is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:9 or a domain thereof.

Another embodiment of the invention relates to an isolated homologue of a protein represented by SEQ ID NO:10 that comprises, consists essentially of, or consists of, an amino acid sequence that is at least about 70% identical to SEQ ID NO:10 or to a biologically active domain within SEQ ID NO:10 as previously described herein, wherein the homologue has a biological activity of at least one domain that is contained within the corresponding protein represented by SEQ ID NO:10. In additional embodiments, the homologue is at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:10 or a domain thereof.

Another embodiment of the invention relates to an isolated homologue of a protein represented by SEQ ID NO:11 that comprises, consists essentially of, or consists of, an amino acid sequence that is at least about 85% identical to SEQ ID NO:11 or to a biologically active domain within SEQ ID NO:11 as previously described herein, wherein the homologue has a biological activity of at least one domain that is contained within the corresponding protein represented by SEQ ID NO:11. In additional embodiments, the homologue is at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO:11 or a domain thereof.

Another embodiment of the invention relates to an isolated homologue of a protein represented by SEQ ID NO:12 that comprises, consists essentially of, or consists of, an amino acid sequence that is at least about 60% identical to SEQ ID NO: 12 or to a biologically active domain within SEQ ID NO: 12 as previously described herein, wherein the homologue has a biological activity of at least one domain that is contained within the corresponding protein represented by SEQ ID NO: 12. In additional embodiments, the homologue is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical (or any percentage between 60% and 99%, in whole single percentage increments) to SEQ ID NO: 12 or a domain thereof.

In one aspect of the invention, a PUFA PKS protein or domain encompassed by the present invention, including a homologue of a particular PUFA PKS protein or domain described herein, comprises an amino acid sequence that includes at least about 100 consecutive amino acids of the amino acid sequence chosen from any one of SEQ ID NOs: 2-6 or 8-12, wherein the amino acid sequence of the homologue has a biological activity of at least one domain or protein as described herein. In a further aspect, the amino acid sequence of the protein is comprises at least about 200 consecutive amino acids, and more preferably at least about 300 consecutive amino acids, and more preferably at least about 400 consecutive amino acids, and more preferably at least about 500 consecutive amino acids, and more preferably at least about 600 consecutive amino acids, and more preferably at least about 700 consecutive amino acids, and more preferably at least about 800 consecutive amino acids, and more preferably at least about 900 consecutive amino acids, and more preferably at least about 1000 consecutive amino acids of any of SEQ ID NOs:2-6 or 8-12.

In a preferred embodiment of the present invention, an isolated protein or domain of the present invention comprises, consists essentially of, or consists of, an amino acid sequence chosen from: SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, or any biologically active fragments or domains thereof.

In one embodiment, a biologically active domain of a PUFA PKS system as described herein and referenced above comprises, consists essentially of, or consists of, an amino acid sequence chosen from: (1) from about position 29 to about position 513 of SEQ ID NO:2, wherein the domain has KS biological activity; (2) from about position 625 to about position 943 of SEQ ID NO:2, wherein the domain has MAT biological activity; (3) from about position 1264 to about position 1889 of SEQ ID NO:2, and subdomains thereof, wherein the domain or subdomain thereof has ACP biological activity; (4) from about position 2264 to about position 2398 of SEQ ID NO:2, wherein the domain has KR biological activity; (5) a sequence comprising from about position 2504 to about position 2516 of SEQ ID NO:2, wherein the domain has DH biological activity, and preferably, non-FabA-like DH activity; (6) from about position 378 to about position 684 of SEQ ID NO:3, wherein the domain has AT biological activity; (7) from about position 5 to about position 483 of SEQ ID NO:4, wherein the domain has KS biological activity; (8) from about position 489 to about position 771 of SEQ ID NO:4, wherein the domain has CLF biological activity; (9) from about position 1428 to about position 1570 of SEQ ID NO:4, wherein the domain has DH biological activity, and preferably, FabA-like DH activity; (10) from about position 1881 to about position 2019 of SEQ ID NO:4, wherein the domain has DH biological activity, and preferably, FabA-like DH activity; (11) from about position 84 to about position 497 of SEQ ID NO:5, wherein the domain has ER biological activity; (12) from about position 40 to about position 186 of SEQ ID NO:6, wherein the domain has PPTase biological activity; (13) from about position 29 to about position 513 of SEQ ID NO:8, wherein the domain has KS biological activity; (14) from about position 625 to about position 943 of SEQ ID NO:8, wherein the domain has MAT biological activity; (15) from about position 1275 to about position 1872 of SEQ ID NO:8, and subdomains thereof, wherein the domain or subdomain thereof has ACP biological activity; (16) from about position 2240 to about position 2374 of SEQ ID NO:8, wherein the domain has KR biological activity; (17) a sequence comprising from about position 2480-2492 of SEQ ID NO:8, wherein the sequence has DH biological activity, and preferably, non-FabA-like DH activity; (18) from about position 366 to about position 703 of SEQ ID NO:9, wherein the domain has AT biological activity; (19) from about position 10 to about position 488 of SEQ ID NO:10, wherein the domain has KS biological activity; (20) from about position 502 to about position 750 of SEQ ID NO:10, wherein the domain has CLF biological activity; (21) from about position 1431 to about position 1573 of SEQ ID NO:10, wherein the domain has DH biological activity, and preferably, FabA-like DH activity; (22) from about position 1882 to about position 2020 of SEQ ID NO:10, wherein the domain has DH biological activity, and preferably, FabA-like DH activity; (23) from about position 84 to about position 497 of SEQ ID NO:11, wherein the domain has ER biological activity; or (24) from about position 29 to about position 177 of SEQ ID NO:12, wherein the domain has PPTase biological activity.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, "Blast 2 sequences—a new tool for comparing protein and nucleotide sequences", *FEMS Microbiol Lett.* 174:247 (1999), incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:

Reward for match=1

Penalty for mismatch=−2

Open gap (5) and extension gap (2) penalties gap x_dropoff (50) expect (10) word size (11) filter (on)

For blastp, using 0 BLOSUM62 matrix:

Open gap (11) and extension gap (1) penalties gap x_dropoff (50) expect (10) word size (3) filter (on).

According to the present invention, an amino acid sequence that has a biological activity of at least one domain of a PUFA PKS system is an amino acid sequence that has the biological activity of at least one domain of the PUFA PKS system described in detail herein (e.g., a KS domain, an AT domain, a CLF domain, etc.). Therefore, an isolated protein useful in the present invention can include: the translation product of any PUFA PKS open reading frame, any PUFA PKS domain, any biologically active fragment of such a translation product or domain, or any homologue of a naturally occurring PUFA PKS open reading frame product or domain which has biological activity.

In another embodiment of the invention, an amino acid sequence having the biological activity of at least one domain of a PUFA PKS system of the present invention includes an amino acid sequence that is sufficiently similar to a naturally occurring PUFA PKS protein or polypeptide that is specifically described herein that a nucleic acid sequence encoding the amino acid sequence is capable of hybridizing under moderate, high, or very high stringency conditions (described below) to (i.e., with) a nucleic acid molecule encoding the naturally occurring PUFA PKS protein or polypeptide (i.e., to the complement of the nucleic acid strand encoding the naturally occurring PUFA PKS protein or polypeptide). Preferably, an amino acid sequence having the biological activity of at least one domain of a PUFA PKS system of the present invention is encoded by a nucleic acid sequence that hybridizes under moderate, high or very high stringency conditions to the complement of a nucleic acid sequence that encodes any of the above-described amino acid sequences for a PUFA PKS protein or domain. Methods to deduce a complementary sequence are known to those skilled in the art. It should be noted that since amino acid sequencing and nucleic acid sequencing technologies are not entirely error-free, the sequences presented herein, at best, represent apparent sequences of PUFA PKS domains and proteins of the present invention.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press (1989). Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., *Anal. Biochem.* 138, 267 (1984); Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6X SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6X SSC (0.9 M $Na^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6X SSC (50% formamide) at about 42° C., followed by washing steps that include one or more washes at room temperature in about 2X SSC, followed by additional washes at higher temperatures and lower ionic strength (e.g., at least one wash as about 37° C. in about 0.1X–0.5X SSC, followed by at least one wash at about 68° C. in about 0.1X–0.5X SSC).

The present invention also includes a fusion protein that includes any PUFA PKS protein or domain or any homologue or fragment thereof attached to one or more fusion segments. Suitable fusion segments for use with the present invention include, but are not limited to, segments that can: enhance a protein's stability; provide other desirable biological activity; and/or assist with the purification of the protein (e.g., by affinity chromatography). A suitable fusion segment can be a domain of any size that has the desired function (e.g., imparts increased stability, solubility, biological activity; and/or simplifies purification of a protein). Fusion segments can be joined to amino and/or carboxyl termini of the protein and can be susceptible to cleavage in order to enable straight-forward recovery of the desired protein. Fusion proteins are preferably produced by culturing a recombinant cell transfected with a fusion nucleic acid molecule that encodes a protein including the fusion segment attached to either the carboxyl and/or amino terminal end of the protein of the invention as discussed above.

In one embodiment of the present invention, any of the above-described PUFA PKS amino acid sequences, as well as homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The minimum size of a protein or domain and/or a homologue or fragment thereof of the present invention is, in one aspect, a size sufficient to have the requisite biological activity, or sufficient to serve as an antigen for the generation of an antibody or as a target in an in vitro assay. In one embodiment, a protein of the present invention is at least about 8 amino acids in length (e.g., suitable for an antibody epitope or as a detectable peptide in an assay), or at least about 25 amino acids in length, or at least about 50 amino acids in length, or at least about 100 amino acids in length, or at least about 150 amino acids in length, or at least about 200 amino acids in length, or at least about 250 amino acids in length, or at least about 300 amino acids in length, or at least about 350 amino acids in length, or at least about 400 amino acids in length, or at least about 450 amino acids in length, or at least about 500 amino acids in length, and so on, in any length between 8 amino acids and up to the full length of a protein or domain of the invention or longer, in whole integers (e.g., 8, 9, 10, . . . 25, 26, . . . 500, 501, . . . ). There is no limit, other than a practical limit, on the maximum size of such a protein in that the protein can include a portion of a PUFA PKS protein, domain, or biologically active or useful fragment thereof, or a full-length PUFA PKS protein or domain, plus additional sequence (e.g., a fusion protein sequence), if desired.

One embodiment of the present invention relates to isolated nucleic acid molecules comprising, consisting essentially of, or consisting of nucleic acid sequences that encode any of the PUFA PKS proteins or domains described herein, including a homologue or fragment of any of such proteins or domains, as well as nucleic acid sequences that are fully complementary thereto. In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome, with the exception of other genes that encode other proteins of the PUFA PKS system as described herein. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on PUFA PKS system biological activity as described herein. Protein homologues (e.g., proteins encoded by nucleic acid homologues) have been discussed in detail above.

A nucleic acid molecule homologue can be produced using a number of methods known to those skilled in the art (see, for example, Sambrook et al., *Molecular Cloning: A Laboratory Manual*, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule of the present invention, or of a size sufficient to encode an amino acid sequence having a biological activity of at least one domain of a PUFA PKS system according to the present invention. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a PUFA PKS system, an entire domain of a PUFA PKS system, several domains within an open reading frame (Orf) of a PUFA PKS system, an entire single- or multi-domain protein of a PUFA PKS system, or more than one protein of a PUFA PKS system.

In one embodiment of the present invention, an isolated nucleic acid molecule comprises, consists essentially of, or consists of a nucleic acid sequence encoding any of the above-described amino acid sequences, including any of the amino acid sequences, or homologues thereof, from *Shewanella japonica* or *Shewanella olleyana* described herein. In one aspect, the nucleic acid sequence is selected from the group of: SEQ ID NO:1 or SEQ ID NO:7 or any fragment (segment, portion) of SEQ ID NO:1 or SEQ ID NO:7 that encodes one or more domains or proteins of the PUFA PKS systems described herein. In another aspect, the nucleic acid sequence includes any homologues of SEQ ID NO:1 or SEQ ID NO:7 or any fragment of SEQ ID NO:1 or SEQ ID NO:7 that encodes one or more domains or proteins of the PUFA PKS systems described herein (including sequences that are at least about 50%, 55%, 60%, 65%, 70%, 75%, 80%, 85%, 90%, 95%, 96%, 97%, 98%, or 99% identical to such sequences). In yet another aspect, fragments and any complementary sequences of such nucleic acid sequences are encompassed by the invention.

Another embodiment of the present invention includes a recombinant nucleic acid molecule comprising a recombinant vector and a nucleic acid sequence encoding protein or peptide having a biological activity of at least one domain (or homologue or fragment thereof) of a PUFA PKS protein as described herein. Such nucleic acid sequences are described in detail above. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a PUFA PKS domain or protein) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector that enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete, inactivate, or replace an endogenous gene or portion of a gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to associate with the target gene such that the target gene and the insert may undergo homologous recombination, whereby the endogenous target gene is deleted, inactivated, attenuated (i.e., by at least a portion of the endogenous target gene being mutated or deleted), or replaced. The use of this type of recombinant vector to replace an endogenous *Schizochytrium* gene, for example, with a recombinant gene is described in the Examples section, and the general technique for genetic transformation of Thraustochytrids is described in detail in U.S. patent application Ser. No. 10/124,807, published as U.S. Patent Application Publication No. 20030166207, published Sep. 4, 2003. Genetic transformation techniques for plants are well-known in the art. It is an embodiment of the present invention that the marine bacterial genes described herein can be used to transform plants or microorganisms such as Thraustochytrids to improve and/or alter (modify, change) the PUFA PKS production capabilities of such plants or microorganisms.

Typically, a recombinant nucleic acid molecule includes at least one nucleic acid molecule of the present invention operatively linked to one or more expression control sequences. As used herein, the phrase "recombinant molecule" or "recombinant nucleic acid molecule" primarily refers to a nucleic acid molecule or nucleic acid sequence operatively linked to a expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those that are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

One or more recombinant molecules of the present invention can be used to produce an encoded product (e.g., a PUFA PKS domain, protein, or system) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. In one embodiment of the invention, a preferred host cell is a Thraustochytrid host cell (described in detail below) or a plant host cell. Host cells can be either untransfected cells or cells that are already transfected with at least one other recombinant nucleic acid molecule.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast, or into plant cells. In microbial and plant systems, the term "transformation" is used to describe an inherited change due to the acquisition of exogenous nucleic acids by the microorganism or plant and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass transfection of animal cells, and transformation of microbial cells or plant cells, to the extent that the terms pertain to the introduction of exogenous nucleic acids into a cell. Therefore, transfection techniques include, but are not limited to, transformation, particle bombardment, diffusion, active transport, bath sonication, electroporation, microinjection, lipofection, adsorption, infection and protoplast fusion.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

General discussion above with regard to recombinant nucleic acid molecules and transfection of host cells is intended to be applied to any recombinant nucleic acid molecule discussed herein, including those encoding any amino acid sequence having a biological activity of at least one domain from a PUFA PKS system, those encoding amino acid sequences from other PKS systems, and those encoding other proteins or domains.

Polyunsaturated fatty acids (PUFAs) are essential membrane components in higher eukaryotes and the precursors of many lipid-derived signaling molecules. The PUFA PKS system of the present invention uses pathways for PUFA synthesis that do not require desaturation and elongation of saturated fatty acids. The pathways catalyzed by PUFA PKS systems are distinct from previously recognized PKS systems in both structure and mechanism. Generation of cis double bonds is suggested to involve position-specific isomerases; these enzymes are believed to be useful in the production of new families of antibiotics.

To produce significantly high yields of one or more desired polyunsaturated fatty acids or other bioactive molecules, an organism, preferably a microorganism or a plant, can be genetically modified to alter the activity and particularly, the end product, of the PUFA PKS system in the microorganism or plant or to introduce a PUFA PKS system into the microorganism or plant.

Therefore, one embodiment of the present invention relates to a genetically modified microorganism, wherein the microorganism expresses a PKS system comprising at least one biologically active domain of a polyunsaturated fatty acid (PUFA) polyketide synthase (PKS) system as described herein (e.g., at least one domain or protein, or biologically active fragment or homologue thereof, of a PUFA PKS system from *Shewanella japonica* or *Shewanella olleyana*). The genetic modification of the microorganism affects the activity of the PKS system in the organism. The domain of the PUFA PKS system can include any of the domains, including homologues thereof, for the marine bacterial PUFA PKS systems as described above, and can also include any domain of a PUFA PKS system from any other bacterial or non-bacterial microorganism, including any eukaryotic microorganism, and particularly including any Thraustochytrid microorganism or any domain of a PUFA PKS system from a microorganism identified by a screening method as described in U.S. patent application Ser. No. 10/124,800, supra. Briefly, the screening process described in U.S. patent application Ser. No. 10/124,800 includes the steps of: (a) selecting a microorganism that produces at least one PUFA; and, (b) identifying a microorganism from (a) that has an ability to produce increased PUFAs under dissolved oxygen conditions of less than about 5% of saturation in the fermentation medium, as compared to production of PUFAs by the microorganism under dissolved oxygen conditions of greater than about 5% of saturation, and preferably about 10%, and more preferably about 15%, and more preferably about 20% of saturation in the fermentation medium. Proteins, domains, and homologues thereof for other bacterial PUFA PKS systems are described in U.S. Pat. No. 6,140,486, supra, incorporated by reference in its entirety. Proteins, domains, and homologues thereof for Thraustochytrid PUFA PKS systems are described in detail in U.S. Pat. No. 6,566,583, supra; U.S. patent application Ser. No. 10/124,800, supra; and U.S. patent application Ser. No. 10/810,352, supra, each of which is incorporated herein by reference in its entirety.

In one aspect of the invention, a genetically modified organism can endogenously contain and express a PUFA PKS system, and the genetic modification can be a genetic modification of one or more of the functional domains of the endogenous PUFA PKS system, whereby the modification has some effect on the activity of the PUFA PKS system. For example, the *Shewanella japonica* or *Shewanella olleyana* species described herein may be genetically modified by modifying an endogenous PUFA PKS gene or genes that results in some alteration (change, modification) of the PUFA PKS function in that microorganism.

In another aspect of the invention, a genetically modified organism can endogenously contain and express a PUFA PKS system, and the genetic modification can be an introduction of at least one exogenous nucleic acid sequence (e.g., a recombinant nucleic acid molecule), wherein the exogenous nucleic acid sequence encodes at least one biologically active domain or protein from a second PKS system (including a PUFA PKS system or another type of PKS system) and/or a protein that affects the activity of the PUFA PKS system. In this aspect of the invention, the organism can also have at least one modification to a gene or genes comprising its endogenous PUFA PKS system.

In yet another aspect of the invention, the genetically modified organism does not necessarily endogenously (naturally) contain a PUFA PKS system, but is genetically modified to introduce at least one recombinant nucleic acid molecule encoding an amino acid sequence having the biological activity of at least one domain of a PUFA PKS system. Preferably, the organism is genetically modified to introduce more than one recombinant nucleic acid molecule which together encode the requisite components of a PUFA PKS system for production of a PUFA PKS system product (bioactive molecule, such as a PUFA or antibiotic), or to introduce a recombinant nucleic acid molecule encoding multiple domains comprising the requisite components of a PUFA PKS system for production of a PUFA PKS product. Various embodiments associated with each of these aspects will be discussed in greater detail below.

It is to be understood that a genetic modification of a PUFA PKS system or an organism comprising a PUFA PKS system can involve the modification and/or utilization of at least one domain of a PUFA PKS system (including a portion of a domain), more than one or several domains of a PUFA PKS system (including adjacent domains, non-contiguous domains, or domains on different proteins in the PUFA PKS system), entire proteins of the PUFA PKS system, and the entire PUFA PKS system (e.g., all of the proteins encoded by the PUFA PKS genes) or even more than one PUFA PKS system (e.g., one from an organism that naturally produces DHA and one from an organism that naturally produces EPA). As such, modifications can include, but are not limited to: a small modification to a single domain of an endogenous PUFA PKS system; substitution of, deletion of or addition to one or more domains or proteins of an endogenous PUFA PKS system; introduction of one or more domains or proteins from a recombinant PUFA PKS system; introduction of a second PUFA PKS system in an organism with an endogenous PUFA PKS system; replacement of the entire PUFA PKS system in an organism with the PUFA PKS system from a different organism; or introduction of one, two, or more entire PUFA PKS systems to an organism that does not endogenously have a PUFA PKS system. One of skill in the art will understand that any genetic modification to a PUFA PKS system is encompassed by the invention.

As used herein, a genetically modified microorganism can include a genetically modified bacterium, protist, microalgae, fungus, or other microbe, and particularly, any of the genera of the order Thraustochytriales (e.g., a Thraustochytrid), including any microorganism in the families Thraustochytriaceae and Labyrinthulaceae described herein (e.g., *Schizochytrium, Thraustochytrium, Japonochytrium, Labyrinthula, Labyrinthuloides*, etc.). Such a genetically modified microorganism has a genome which is modified (i.e., mutated or changed) from its normal (i.e., wild-type or naturally occurring) form such that the desired result is achieved (i.e., increased or modified PUFA PKS activity and/or production of a desired product using the PKS system). Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. These include, but are not limited to, *Escherichia coli*, which can be useful in fermentation processes. Alternatively, and only by way of example, a host such as a *Lactobacillus* species or *Bacillus* species can be used as a host.

Particularly preferred host cells for use in the present invention include microorganisms from a genus including, but not limited to: *Thraustochytrium, Japonochytrium, Aplanochytrium, Elina* and *Schizochytrium* within the Thraustochytriaceae, and *Labyrinthula, Labyrinthuloides*, and *Labyrinthomyxa* within the Labyrinthulaceae. Preferred species within these genera include, but are not limited to: any species within *Labyrinthula,* including *Labyrinthula* sp., *Labyrinthula algeriensis, Labyrinthula cienkowskii, Labyrinthula chattonii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula roscoffensis, Labyrinthula valkanovii, Labyrinthula vitellina, Labyrinthula vitellina pacifica, Labyrinthula vitellina vitellina, Labyrinthula zopfii*; any *Labyrinthuloides* species, including *Labyrinthuloides* sp., *Labyrinthuloides minuta, Labyrinthuloides schizochytrops*; any *Labyrinthomyxa* species, including *Labyrinthomyxa* sp., *Labyrinthomyxa pohlia, Labyrinthomyxa sauvageaui*, any *Aplanochytrium* species, including *Aplanochytrium* sp. and *Aplanochytrium kerguelensis*; any *Elina* species, including *Elina* sp., *Elina marisalba, Elina sinorifica*; any *Japonochytrium* species, including *Japonochytrium* sp., *Japonochytrium marinum*; any *Schizochytrium* species, including *Schizochytrium* sp., *Schizochytrium aggregatum, Schizochytrium limacinum, Schizochytrium minutum, Schizochytrium octosporum*; and any *Thraustochytrium* species, including *Thraustochytrium* sp., *Thraustochytrium aggregatum, Thraustochytrium arudimentale, Thraustochytrium aureum, Thraustochytrium benthicola, Thraustochytrium globosum, Thraustochytrium kinnei, Thraustochytrium motivum, Thraustochytrium pachydermum, Thraustochytrium proliferum, Thraustochytrium roseum, Thraustochytrium striatum, Ulkenia* sp., *Ulkenia minuta, Ulkenia profunda, Ulkenia radiate, Ulkenia sarkariana*, and *Ulkenia visurgensis*. Particularly preferred species within these genera include, but are not limited to: any *Schizochytrium* species, including *Schizochytrium aggregatum, Schizochytrium limacinum, Schizochytrium minutum*; or any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207).

According to the present invention, the terms/phrases "Thraustochytrid", "Thraustochytriales microorganism" and "microorganism of the order Thraustochytriales" can be used interchangeably and refer to any members of the order Thraustochytriales, which includes both the family Thraustochytriaceae and the family Labyrinthulaceae. The terms "Labyrinthulid" and "Labyrinthulaceae" are used herein to specifically refer to members of the family Labyrinthulaceae. To specifically reference Thraustochytrids that are members of the family Thraustochytriaceae, the term "Thraustochytriaceae" is used herein. Thus, for the present invention, members of the Labyrinthulids are considered to be included in the Thraustochytrids.

Developments have resulted in frequent revision of the taxonomy of the Thraustochytrids. Taxonomic theorists generally place Thraustochytrids with the algae or algae-like protists. However, because of taxonomic uncertainty, it would be best for the purposes of the present invention to consider the strains described in the present invention as Thraustochytrids to include the following organisms: Order: Thraustochytriales; Family: Thraustochytriaceae (Genera: *Thraustochytrium, Schizochytrium, Japonochytrium, Aplanochytrium*, or *Elina*) or Labyrinthulaceae (Genera *Labyrinthula, Labyrinthuloides*, or *Labyrinthomyxa*). Also, the following genera are sometimes included in either family Thraustochytriaceae or Labyrinthulaceae: *Althornia, Corallochytrium, Diplophyrys*, and *Pyrrhosorus*), and for the purposes of this invention are encompassed by reference to a Thraustochytrid or a member of the order Thraustochytriales. It is recognized that at the time of this invention, revision in the taxonomy of Thraustochytrids places the genus *Labyrinthuloides* in the family of Labyrinthulaceae and confirms the placement of the two families Thraustochytriaceae and Labyrinthulaceae within the Stramenopile lineage. It is noted that the Labyrinthulaceae are sometimes commonly called labyrinthulids or labyrinthula, or labyrinthuloides and the Thraustochytriaceae are commonly called thraustochytrids, although, as discussed above, for the purposes of clarity of this invention, reference to Thraustochytrids encompasses any member of the order Thraustochytriales and/or includes members of both Thraustochytriaceae and Labyrinthulaceae. Recent taxonomic changes are summarized below.

Strains of certain unicellular microorganisms disclosed herein are members of the order Thraustochytriales. Thraustochytrids are marine eukaryotes with an evolving taxonomic history. Problems with the taxonomic placement of the Thraustochytrids have been reviewed by Moss (in "*The Biology of Marine Fungi*", Cambridge University Press p. 105 (1986)), Bahnweb and Jackle (ibid. p. 131) and Chamberlain and Moss (BioSystems 21:341 (1988)).

For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids were retained in the Oomycetes (the biflagellate zoosporic fungi). It was initially assumed that the Oomycetes were related to the heterokont algae, and eventually a wide range of ultrastructural and biochemical studies, summarized by Barr (Barr. *Biosystems* 14:359 (1981)) supported this assumption. The Oomycetes were in fact accepted by Leedale (Leedale. *Taxon* 23:261 (1974)) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis, 1970, *Origin of Eukaryotic Cells*. Yale University Press, New Haven); e.g., mitochondria were derived from bacterial endosymbionts, chloroplasts from cyanophytes, and flagella from spirochaetes. The other theory suggests a gradual evolution of the membrane-bound organelles from the non-membrane-bounded systems of the prokaryote ancestor via an autogenous process (Cavalier-Smith, 1975, *Nature* (Lond.) 256:462-468). Both groups of evolutionary biologists however, have removed the Oomycetes and Thraustochytrids from the fungi and place them either with the chromophyte algae in the kingdom Chromophyta (Cavalier-Smith *BioSystems* 14:461 (1981)) (this kingdom has been more recently expanded to include other protists and members of this kingdom are now called Stramenopiles) or with all algae in the kingdom Protoctista (Margulis and Sagen. *Biosystems* 18:141 (1985)).

With the development of electron microscopy, studies on the ultrastructure of the zoospores of two genera of Thraustochytrids, *Thraustochytrium* and *Schizochytrium*, (Perkins, 1976, pp. 279-312 in "*Recent Advances in Aquatic Mycology*" (ed. E. B. G. Jones), John Wiley & Sons, New York; Kazama. *Can. J. Bot.* 58:2434 (1980); Barr, 1981, Biosystems 14:359-370) have provided good evidence that the Thraustochytriaceae are only distantly related to the Oomycetes. Additionally, genetic data representing a correspondence analysis (a form of multivariate statistics) of 5-S ribosomal RNA sequences indicate that Thraustochytriales are clearly a unique group of eukaryotes, completely separate from the fungi, and most closely related to the red and brown algae, and to members of the Oomycetes (Mannella et al. *Mol. Evol.* 24:228 (1987)). Most taxonomists have agreed to remove the Thraustochytrids from the Oomycetes (Bartnicki-Garcia. p. 389 in "*Evolutionary Biology of the Fungi*" (eds. Rayner, A. D. M., Brasier, C. M. & Moore, D.), Cambridge University Press, Cambridge).

In summary, employing the taxonomic system of Cavalier-Smith (Cavalier-Smith. BioSystems 14:461 (1981); Cavalier-Smith. *Microbiol. Rev.* 57:953 (1993)), the Thraustochytrids are classified with the chromophyte algae in the kingdom Chromophyta (Stramenopiles). This taxonomic placement has been more recently reaffirmed by Cavalier-Smith et al. using the 18s rRNA signatures of the Heterokonta to demonstrate that Thraustochytrids are chromists not Fungi (Cavalier-Smith et al. *Phil. Tran. Roy. Soc. London Series BioSciences* 346:387 (1994)). This places the Thraustochytrids in a completely different kingdom from the fungi, which are all placed in the kingdom Eufungi.

Currently, there are 71 distinct groups of eukaryotic organisms (Patterson. Am. Nat. 154:S96(1999)) and within these groups four major lineages have been identified with some confidence: (1) Alveolates, (2) Stramenopiles, (3) a Land Plant-green algae-Rhodophyte_Glaucophyte ("plant") clade and (4) an Opisthokont clade (Fungi and Animals). Formerly these four major lineages would have been labeled Kingdoms but use of the "kingdom" concept is no longer considered useful by some researchers.

As noted by Armstrong, Stramenopile refers to three-parted tubular hairs, and most members of this lineage have flagella bearing such hairs. Motile cells of the Stramenopiles (unicellular organisms, sperm, zoospores) are asymmetrical having two laterally inserted flagella, one long, bearing three-parted tubular hairs that reverse the thrust of the flagellum, and one short and smooth. Formerly, when the group was less broad, the Stramenopiles were called Kingdom Chromista or the heterokont (=different flagella) algae because those groups consisted of the Brown Algae or Phaeophytes, along with the yellow-green Algae, Golden-brown Algae, Eustigmatophytes and Diatoms. Subsequently some heterotrophic, fungal-like organisms, the water molds, and labyrinthulids (slime net amoebas), were found to possess similar motile cells, so a group name referring to photosynthetic pigments or algae became inappropriate. Currently, two of the families within the Stramenopile lineage are the Labyrinthulaceae and the Thraustochytriaceae. Historically, there have been numerous classification strategies for these unique microorganisms and they are often classified under the same order (i.e., Thraustochytriales). Relationships of the members in these groups are still developing. Porter and Leander have developed data based on 18S small subunit ribosomal DNA indicating the thraustochytrid-labyrinthulid lade in monophyletic. However, the clade is supported by two branches; the first contains three species of *Thraustochytrium* and *Ulkenia profunda*, and the second includes three species of *Labyrinthula*, two species of *Labyrinthuloides* and *Schizochytrium aggregatum.*

The taxonomic placement of the Thraustochytrids as used in the present invention is therefore summarized below:

Kingdom: Chromophyta (Stramenopiles)

Phylum: Heterokonta

Order: Thraustochytriales (Thraustochytrids)

Family: Thraustochytriaceae or Labyrinthulaceae

Genera: *Thraustochytrium, Schizochytrium, Japonochytrium, Aplanochytrium, Elina, Labyrinthula, Labyrinthuloides*, or *Labyrinthulomyxa*

Some early taxonomists separated a few original members of the genus *Thraustochytrium* (those with an amoeboid life stage) into a separate genus called *Ulkenia*. However it is now known that most, if not all, Thraustochytrids (including *Thraustochytrium* and *Schizochytrium*), exhibit amoeboid stages and as such, *Ulkenia* is not considered by some to be a valid genus. As used herein, the genus *Thraustochytrium* will include *Ulkenia.*

Despite the uncertainty of taxonomic placement within higher classifications of Phylum and Kingdom, the Thraustochytrids remain a distinctive and characteristic grouping whose members remain classifiable within the order Thraustochytriales.

Another embodiment of the present invention relates to a genetically modified plant, wherein the plant has been genetically modified to recombinantly express a PKS system comprising at least one biologically active domain or protein of a polyunsaturated fatty acid (PUFA) polyketide synthase (PKS) system as described herein. The domain of the PUFA PKS system can include any of the domains, including homologues thereof, for PUFA PKS systems as described above (e.g., for *Shewanella japonica* and/or *Shewanella olleyana*), and can also include any domain of a PUFA PKS system from any bacterial or non-bacterial microorganism (including any eukaryotic microorganism and any Thraustochytrid microorganism, such as *Schizochytrium* and/or *Thraustochytrium*) or any domain of a PUFA PKS system from a microorganism identified by a screening method as described in U.S. patent application Ser. No. 10/124,800, supra. The plant can also be further modified with at least one domain or biologically active fragment thereof of another PKS system, including, but not limited to, Type I PKS systems (iterative or modular), Type II PKS systems, and/or Type III PKS systems. The modification of the plant can involve the modification and/or utilization of at least one domain of a PUFA PKS system (including a portion of a domain), more than one or several domains of a PUFA PKS system (including adjacent domains, non-contiguous domains, or domains on different proteins in the PUFA PKS system), entire proteins of the PUFA PKS system, and the entire PUFA PKS system (e.g., all of the proteins encoded by the PUFA PKS genes) or even more than one PUFA PKS system (e.g., one from an organism that naturally produces DHA and one from an organism that naturally produces EPA).

As used herein, a genetically modified plant can include any genetically modified plant including higher plants and particularly, any consumable plants or plants useful for producing a desired bioactive molecule of the present invention. "Plant parts", as used herein, include any parts of a plant, including, but not limited to, seeds, pollen, embryos, flowers, fruits, shoots, leaves, roots, stems, explants, etc. A genetically modified plant has a genome which is modified (i.e., mutated or changed) from its normal (i.e., wild-type or naturally occurring) form such that the desired result is achieved (i.e., increased or modified PUFA PKS activity and/or production of a desired product using the PKS system). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art. A preferred plant to genetically modify according to the present invention is preferably a plant suitable for consumption by animals, including humans.

Preferred plants to genetically modify according to the present invention (i.e., plant host cells) include, but are not limited to any higher plants, including both dicotyledonous and monocotyledonous plants, and particularly consumable plants, including crop plants and especially plants used for their oils. Such plants can include, for example: canola, soybeans, rapeseed, linseed, corn, safflowers, sunflowers and tobacco. Other preferred plants include those plants that are known to produce compounds used as pharmaceutical agents, flavoring agents, nutraceutical agents, functional food ingredients or cosmetically active agents or plants that are genetically engineered to produce these compounds/agents.

According to the present invention, a genetically modified microorganism or plant includes a microorganism or plant that has been modified using recombinant technology or by classical mutagenesis and screening techniques. As used herein, genetic modifications that result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

The genetic modification of a microorganism or plant according to the present invention preferably affects the activity of the PKS system expressed by the microorganism or plant, whether the PKS system is endogenous and genetically modified, endogenous with the introduction of recombinant nucleic acid molecules into the organism (with the option of modifying the endogenous system or not), or provided completely by recombinant technology. To alter the PUFA production profile of a PUFA PKS system or organism expressing such system includes causing any detectable or measurable change in the production of any one or more PUFAs (or other bioactive molecule produced by the PUFA PKS system) by the host microorganism or plant as compared to in the absence of the genetic modification (i.e., as compared to the unmodified, wild-type microorganism or plant or the microorganism or plant that is unmodified at least with respect to PUFA synthesis—i.e., the organism might have other modifications not related to PUFA synthesis). To affect the activity of a PKS system includes any genetic modification that causes any detectable or measurable change or modification in the PKS system expressed by the organism as compared to in the absence of the genetic modification. A detectable change or modification in the PKS system can include, but is not limited to: a change or modification (introduction of, increase or decrease) of the expression and/or biological activity of any one or more of the domains in a modified PUFA PKS system as compared to the endogenous PUFA PKS system in the absence of genetic modification; the introduction of PKS system activity (i.e., the organism did not contain a PKS system or a PUFA PKS system prior to the genetic modification) into an organism such that the organism now has measurable/detectable PKS system activity, such as production of a product of a PUFA PKS system; the introduction into the organism of a functional domain from a different PKS system than the PKS system endogenously expressed by the organism such that the PKS system activity is modified (e.g., a bacterial PUFA PKS domain as described herein is introduced into an organism that endogenously expresses a non-bacterial PUFA PKS system, such as a Thraustochytrid); a change in the amount of a bioactive molecule (e.g., a PUFA) produced by the PKS system (e.g., the system produces more (increased amount) or less (decreased amount) of a given product as compared to in the absence of the genetic modification); a change in the type of a bioactive molecule (e.g., a change in the type of PUFA) produced by the PKS system (e.g., the system produces an additional or different PUFA, a new or different product, or a variant of a PUFA or other product that is naturally produced by the system); and/or a change in the ratio of multiple bioactive molecules produced by the PKS system (e.g., the system produces a different ratio of one PUFA to another PUFA, produces a completely different lipid profile as compared to in the absence of the genetic modification, or places various PUFAs in different positions in a triacylglycerol as compared to the natural configuration). Such a genetic modification includes any type of genetic modification and specifically includes modifications made by recombinant technology and/or by classical mutagenesis.

It should be noted that reference to increasing the activity of a functional domain or protein in a PUFA PKS system refers to any genetic modification in the organism containing the domain or protein (or into which the domain or protein is to be introduced) which results in increased functionality of the domain or protein system and can include higher activity of the domain or protein (e.g., specific activity or in vivo enzymatic activity), reduced inhibition or degradation of the domain or protein system, and overexpression of the domain or protein. For example, gene copy number can be increased, expression levels can be increased by use of a promoter that gives higher levels of expression than that of the native promoter, or a gene can be altered by genetic engineering or classical mutagenesis to increase the activity of the domain or protein encoded by the gene.

Similarly, reference to decreasing the activity of a functional domain or protein in a PUFA PKS system refers to any genetic modification in the organism containing such domain or protein (or into which the domain or protein is to be introduced) which results in decreased functionality of the domain or protein and includes decreased activity of the domain or protein, increased inhibition or degradation of the domain or protein and a reduction or elimination of expression of the domain or protein. For example, the action of domain or protein of the present invention can be decreased by blocking or reducing the production of the domain or protein, "knocking out" the gene or portion thereof encoding the domain or protein, reducing domain or protein activity, or inhibiting the activity of the domain or protein. Blocking or reducing the production of a domain or protein can include placing the gene encoding the domain or protein under the control of a promoter that requires the presence of an inducing compound in the growth medium. By establishing conditions such that the inducer becomes depleted from the medium, the expression of the gene encoding the domain or protein (and therefore, of protein synthesis) could be turned off. The present inventors demonstrate the ability to delete (knock out) targeted genes in a Thraustochytrid microorganism in the Examples section. Blocking or reducing the activity of domain or protein could also include using an excision technology approach similar to that described in U.S. Pat. No. 4,743,546, incorporated herein by reference. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In one embodiment of the present invention, the endogenous PUFA PKS system of a microorganism is genetically modified by, for example, classical mutagenesis and selection techniques and/or molecular genetic techniques, include genetic engineering techniques. Genetic engineering techniques can include, for example, using a targeting recombinant vector to delete a portion of an endogenous gene (demonstrated in the Examples) or to replace a portion of an endogenous gene with a heterologous sequence (demonstrated in the Examples). Examples of heterologous sequences that could be introduced into a host genome include sequences encoding at least one functional PUFA PKS domain or protein from another PKS system or even an entire PUFA PKS system (e.g., all genes associated with the PUFA PKS system). A heterologous sequence can also include a sequence encoding a modified functional domain (a homologue) of a natural domain from a PUFA PKS system. Other heterologous sequences that can be introduced into the host genome include a sequence encoding a protein or functional domain that is not a domain of a PKS system per se, but which will affect the activity of the endogenous PKS system. For example, one could introduce into the host genome a nucleic acid molecule encoding a phosphopantetheinyl transferase. Specific modifications that could be made to an endogenous PUFA PKS system are discussed in detail herein.

With regard to the production of genetically modified plants, methods for the genetic engineering of plants are also well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

Another generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.,* 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

In one aspect of this embodiment of the invention, the genetic modification of an organism (microorganism or plant) can include: (1) the introduction into the host of a recombinant nucleic acid molecule encoding an amino acid sequence having a biological activity of at least one domain of a PUFA PKS system; and/or (2) the introduction into the host of a recombinant nucleic acid molecule encoding at least one protein or functional domain that affects the activity of a PUFA PKS system. The host can include: (1) a host cell that does not express any PKS system, wherein all functional domains of a PKS system are introduced into the host cell, and wherein at least one functional domain is from a PUFA PKS system as described herein; (2) a host cell that expresses a PKS system (endogenous or recombinant) having at least one functional domain of a PUFA PKS system described herein; and (3) a host cell that expresses a PKS system (endogenous or recombinant) which does not necessarily include a domain function from a PUFA PKS system described herein (in this case, the recombinant nucleic acid molecule introduced to the host cell includes a nucleic acid sequence encoding at least one functional domain of the PUFA PKS system described herein). In other words, the present invention intends to encompass any genetically modified organism (e.g., microorganism or plant), wherein the organism comprises (either endogenously or introduced by recombinant modification) at least one domain from a PUFA PKS system described herein (e.g., from or derived from *Shewanella japonica* or *Shewanella olleyana*), wherein the genetic modification has a measurable effect on the PUFA PKS activity in the host cell.

The present invention relates particularly to the use of PUFA PKS systems and portions thereof from the marine bacteria described herein to genetically modify microorganisms and plants to affect the production of PUFA PKS products by the microorganisms and plants. As discussed above, the bacteria that are useful in the embodiments of the present invention can grow at, and have PUFA PKS systems that are capable of producing PUFAs at (e.g., enzymes and proteins that function well at), temperatures approximating or exceeding about 20° C., preferably approximating or exceeding about 25° C. and even more preferably approximating or exceeding about 30° C. (or any temperature between 20° C. and 30° C. or higher, in whole degree increments, e.g., 21° C., 22° C., 23° C. . . . ). In a preferred embodiment, such bacteria produce PUFAs at such temperatures. As described previously herein, the marine bacteria, other *Shewanella* sp. (e.g., strain SCRC2738) and *Vibrio* marinus, described in U.S. Pat. No. 6,140,486, do not produce PUFAs (or produce substantially less or no detectable PUFAs) and do not grow well, if at all, at higher temperatures (e.g., temperatures at or above 20° C.), which limits the usefulness of PUFA PKS systems derived from these bacteria, particularly in plant applications under field conditions.

In one embodiment of the present invention, one can identify additional bacteria that have a PUFA PKS system and the ability to grow and produce PUFAs at high temperatures. For example, inhibitors of eukaryotic growth such as nystatin (antifungal) or cycloheximide (inhibitor of eukaryotic protein synthesis) can be added to agar plates used to culture/select initial strains from water samples/soil samples collected from the types of habitats/niches such as marine or estuarian habits, or any other habitat where such bacteria can be found. This process would help select for enrichment of bacterial strains without (or minimal) contamination of eukaryotic strains. This selection process, in combination with culturing the plates at elevated temperatures (e.g. 20-30° C. or 25-30° C.), and then selecting strains that produce at least one PUFA would initially identify candidate bacterial strains with a PUFA PKS system that is operative at elevated temperatures (as opposed to those bacterial strains in the prior art which only exhibit PUFA production at temperatures less than about 20° C. and more preferably below about 5° C.). To evaluate PUFA PKS function at higher temperatures for genes from any bacterial source, one can produce cell-free extracts and test for PUFA production at various temperatures, followed by selection of microorganisms that contain PUFA PKS genes that have enzymatic/biological activity at higher temperature ranges (e.g., 15° C., 20° C., 25° C., or 30° C. or even higher). The present inventors have identified two exemplary bacteria (e.g. *Shewanella olleyana* and *Shewanella japonica*; see Examples) that are particularly suitable as sources of PUFA PKS genes, and others can be readily identified or are known to comprise PUFA PKS genes and may be useful in an embodiment of the present invention (e.g., *Shewanella gelidimarina*).

Using the PUFA PKS systems from the particular marine bacteria described herein, as well as previously described non-bacterial PUFA PKS systems that, for example, make use of PUFA PKS genes from Thraustochytrid and other eukaryotic PUFA PKS systems, gene mixing can be used to extend the range of PUFA products to include EPA, DHA, ARA, GLA, SDA and others (described in detail below), as well as to produce a wide variety of bioactive molecules, including antibiotics, other pharmaceutical compounds, and other desirable products. The method to obtain these bioactive molecules includes not only the mixing of genes from various organisms but also various methods of genetically modifying the PUFA PKS genes disclosed herein. Knowledge of the genetic basis and domain structure of the bacterial PUFA PKS system of the present invention provides a basis for designing novel genetically modified organisms which produce a variety of bioactive molecules. In particular, the use of the bacterial PUFA PKS genes described herein extends that ability to produce modified PUFA PKS systems that function and produce high levels of product at higher temperatures than would be possible using the PUFA PKS genes from previously described marine bacteria. Although mixing and modification of any PKS domains and related genes are contemplated by the present inventors, by way of example, various possible manipulations of the PUFA-PKS system are discussed below with regard to genetic modification and bioactive molecule production.

Particularly useful PUFA PKS genes and proteins to use in conjunction with the marine bacterial PUFA PKS genes described above include the PUFA PKS genes from Thraustochytrids, such as those that have been identified in *Schizochytrium* and *Thraustochytrium*. Such genes are especially useful for modification, targeting, introduction into a host cell and/or otherwise for the gene mixing and modification discussed above, in combination with various genes, portions thereof and homologues thereof from the marine bacterial genes described herein. These are described in detail in U.S. patent application Ser. No. 10/810,352, supra (*Thraustochytrium*), in U.S. patent application Ser. No. 10/124,800, supra (*Schizochytrium*), and in U.S. Pat. No. 6,566,583, supra (*Schizochytrium*). The PUFA PKS genes in both *Schizochytrium* and *Thraustochytrium* are organized into three multi-domain-encoding open reading frames, referred to herein as OrfA, OrfB and OrfC.

The complete nucleotide sequence for *Schizochytrium* OrfA is represented herein as SEQ ID NO:13. OrfA is a 8730 nucleotide sequence (not including the stop codon) which encodes a 2910 amino acid sequence, represented herein as SEQ ID NO:14. Within OrfA are twelve domains: (a) one β-ketoacyl-ACP synthase (KS) domain (represented by about position 1 to about position 500 of SEQ ID NO:14); (b) one malonyl-CoA:ACP acyltransferase (MAT) domain (represented by about position 575 to about position 1000 of SEQ ID NO:14); (c) nine acyl carrier protein (ACP) domains (represented by about position 1095 to about 2096 of SEQ ID NO:14; and the locations of the active site serine residues (i.e., the pantetheine binding site) for each of the nine ACP domains, with respect to the amino acid sequence of SEQ ID NO:14, are as follows: ACP1=$S_{1157}$; ACP2=$S_{1266}$; ACP3=$S_{1377}$; ACP4=$S_{1488}$; ACP5=$S_{1604}$; ACP6=$S_{1715}$; ACP7=$S_{1819}$; ACP8=$S_{1930}$; and ACP9=$S_{2034}$); and (d) one β-ketoacyl-ACP reductase (KR) domain (represented by about position 2200 to about position 2910 of SEQ ID NO:14).

The complete nucleotide sequence for *Schizochytrium* OrfB is represented herein as SEQ ID NO:15. OrfB is a 6177 nucleotide sequence (not including the stop codon) which encodes a 2059 amino acid sequence, represented herein as SEQ ID NO:16. Within OrfB are four domains: (a) one β-ketoacyl-ACP synthase (KS) domain (represented by about position 1 to about position 450 of SEQ ID NO:16); (b) one chain length factor (CLF) domain (represented by about position 460 to about position 900 of SEQ ID NO:16); (c) one acyltransferase (AT) domain (represented by about position 901 to about position 1400 of SEQ ID NO:16); and, (d) one enoyl-ACP reductase (ER) domain (represented by about position 1550 to about position 2059 of SEQ ID NO:16).

The complete nucleotide sequence for *Schizochytrium* OrfC is represented herein as SEQ ID NO:17. OrfC is a 4509 nucleotide sequence (not including the stop codon) which encodes a 1503 amino acid sequence, represented herein as SEQ ID NO:18. Within OrfC are three domains: (a) two FabA-like β-hydroxyacyl-ACP dehydrase (DH) domains (represented by about position 1 to about position 450 of SEQ ID NO:18; and represented by about position 451 to about position 950 of SEQ ID NO:18); and (b) one enoyl-ACP reductase (ER) domain (represented by about position 1000 to about position 1502 of SEQ ID NO:18).

The complete nucleotide sequence for *Thraustochytrium* OrfA is represented herein as SEQ ID NO:19. OrfA is a 8433 nucleotide sequence (not including the stop codon) which encodes a 2811 amino acid sequence, represented herein as SEQ ID NO:20. Within OrfA are 11 domains: (a) one β-ketoacyl-ACP synthase (KS) domain (represented by about position 1 to about position 500 of SEQ ID NO:20); (b) one malonyl-CoA:ACP acyltransferase (MAT) domain (represented by about position 501 to about position 1000 of SEQ ID NO:20); (c) eight acyl carrier protein (ACP) domains (represented by about position 1069 to about 1998 of SEQ ID NO:20; and the locations of the active site serine residues (i.e., the pantetheine binding site) for each of the nine ACP domains, with respect to the amino acid sequence of SEQ ID NO:20, are as follows: 1128 (ACP1), 1244 (ACP2), 1360 (ACP3), 1476 (ACP4), 1592 (ACP5), 1708 (ACP6), 1824 (ACP7) and 1940 (ACP8)); and (d) one β-ketoacyl-ACP reductase (KR) domain (represented by about position 2001 to about position 2811 of SEQ ID NO:20).

The complete nucleotide sequence for *Thraustochytrium* OrfB is represented herein as SEQ ID NO:21. OrfB is a 5805 nucleotide sequence (not including the stop codon) which encodes a 1935 amino acid sequence, represented herein as SEQ ID NO:22. Within OrfB are four domains: (a) one β-ketoacyl-ACP synthase (KS) domain (represented by about position 1 to about position 500 of SEQ ID NO:22); (b) one chain length factor (CLF) domain (represented by about position 501 to about position 1000 of SEQ ID NO:22); (c) one acyltransferase (AT) domain (represented by about position 1001 to about position 1500 of SEQ ID NO:22); and, (d) one enoyl-ACP reductase (ER) domain (represented by about position 1501 to about position 1935 of SEQ ID NO:22).

The complete nucleotide sequence for *Thraustochytrium* OrfC is represented herein as SEQ ID NO:23. OrfC is a 4410 nucleotide sequence (not including the stop codon) which encodes a 1470 amino acid sequence, represented herein as SEQ ID NO:24. Within Orfc are three domains: (a) two FabA-like β-hydroxyacyl-ACP dehydrase (DH) domains (represented by about position 1 to about position 500 of SEQ ID NO:24; and represented by about position 501 to about position 1000 of SEQ ID NO:24); and (b) one enoyl-ACP reductase (ER) domain (represented by about position 1001 to about position 1470 of SEQ ID NO:24).

Accordingly, encompassed by the present invention are methods to genetically modify microbial or plant cells by: genetically modifying at least one nucleic acid sequence in the organism that encodes at least one functional domain or protein (or biologically active fragment or homologue thereof) of a bacterial PUFA PKS system described herein (e.g., from or derived from the *Shewanella japonica* or *Shewanella olleyana* PUFA PKS systems described herein), and/or expressing at least one recombinant nucleic acid molecule comprising a nucleic acid sequence encoding such domain or protein. Various embodiments of such sequences, methods to genetically modify an organism, and specific modifications have been described in detail above. Typically, the method is used to produce a particular genetically modified organism that produces a particular bioactive molecule or molecules.

A particularly preferred embodiment of the present invention relates to a genetically modified plant or part of a plant, wherein the plant has been genetically modified using the PUFA PKS genes described herein so that the plant produces a desired product of a PUFA PKS system (e.g., a PUFA or other bioactive molecule). Knowledge of the genetic basis and domain structure of the bacterial PUFA PKS system of the present invention combined with the knowledge of the genetic basis and domain structure for various Thraustochytrid PUFA PKS systems provides a basis for designing novel genetically modified plants which produce a variety of bioactive molecules. For example, one can now design and engineer a novel PUFA PKS construct derived from various combinations of domains from the PUFA PKS systems described herein. Such constructs can first be prepared in microorganisms such as *E. coli*, a yeast, or a Thraustochytrid, in order to demonstrate the production of the desired bioactive molecule, for example, followed by isolation of the construct and use of the same to transform plants to impart similar bioactive molecule production properties onto the plants. Plants are not known to endogenously contain a PUFA PKS system, and therefore, the PUFA PKS systems of the present invention represent an opportunity to produce plants with unique fatty acid production capabilities. It is a particularly preferred embodiment of the present invention to genetically engineer plants to produce one or more PUFAs in the same plant, including, EPA, DHA, DPA, ARA, GLA, SDA and others. The present invention offers the ability to create any one of a number of "designer oils" in various ratios and forms. Moreover, the disclosure of the PUFA PKS genes from the particular marine bacteria described herein offer the opportunity to more readily extend the range of PUFA production and successfully produce such PUFAs within temperature ranges used to grow most crop plants.

Another embodiment of the present invention relates to a genetically modified Thraustochytrid microorganism, wherein the microorganism has an endogenous polyunsaturated fatty acid (PUFA) polyketide synthase (PKS) system, and wherein the endogenous PUFA PKS system has been genetically modified to alter the expression profile of a polyunsaturated fatty acid (PUFA) by the microorganism as compared to the Thraustochytrid microorganism in the absence of the modification. Thraustochytrid microorganisms useful as host organisms in the present invention endogenously contain and express a PUFA PKS system. The genetic modification based on the present invention includes the introduction into the Thraustochytrid of at least one recombinant nucleic acid sequence encoding a PUFA PKS domain or protein (or homologue or functional fragment thereof) from a bacterial PUFA PKS system described herein. The Thraustochytrid may also contain genetic modifications within its endogenous PUFA PKS genes, including substitutions, additions, deletions, mutations, and including a partial or complete deletion of the Thraustochytrid PUFA PKS genes and replacement with the PUFA PKS genes from the preferred marine bacteria of the present invention.

This embodiment of the invention is particularly useful for the production of commercially valuable lipids enriched in a desired PUFA, such as EPA, via the present inventors' development of genetically modified microorganisms and methods for efficiently producing lipids (triacylglycerols (TAG) as well as membrane-associated phospholipids (PL)) enriched in PUFAs. Such microorganisms are also useful as "surrogate" hosts to determine optimum gene combinations for later use in the transformation of plant cells, although other microorganisms, including many bacterial and yeast hosts, for example, can also be used as "surrogate" hosts This particular embodiment of the present invention is derived in part from the following knowledge: (1) utilization of the inherent TAG production capabilities of selected microorganisms, and particularly, of Thraustochytrids, such as the commercially developed *Schizochytrium* strain ATCC 20888; (2) the present inventors' detailed understanding of PUFA PKS biosynthetic pathways (i.e., PUFA PKS systems) in eukaryotes and in particular, in members of the order Thraustochytriales, and in the marine bacteria used in the present invention; and, (3) utilization of a homologous genetic recombination system in *Schizochytrium*. Based on the inventors' knowledge of the systems involved, the same general approach may be exploited to produce PUFAs other than EPA.

For example, in one embodiment of the invention, the endogenous Thraustochytrid PUFA PKS genes, such as the *Schizochytrium* genes encoding PUFA PKS enzymes that normally produce DHA and DPA, are modified by random or targeted mutagenesis, replaced with genes from other organisms that encode homologous PKS proteins (e.g., from bacteria or other sources), such as the marine bacterial PUFA PKS genes from *Shewanella japonica* or *Shewanella olleyana* described in detail herein, and/or replaced with genetically modified *Schizochytrium, Thraustochytrium* or other Thraustochytrid PUFA PKS genes. As discussed above, combinations of nucleic acid molecules encoding various domains from the marine bacterial and Thraustochytrid or other PKS systems can be "mixed and matched" to create a construct(s) that will result in production of a desired PUFA or other bioactive molecule. The product of the enzymes encoded by these introduced and/or modified genes can be EPA, for example, or it could be some other related molecule, including other PUFAs. One feature of this method is the utilization of endogenous components of Thraustochytrid PUFA synthesis and accumulation machinery that is essential for efficient production and incorporation of the PUFA into PL and TAG, while taking further advantage of the ability of the marine bacterial genes, for example, to produce EPA. In particular, this embodiment of the invention is directed to the modification of the type of PUFA produced by the organism, while retaining the high oil productivity of the parent strain.

Although some of the following discussion uses the organism *Schizochytrium* as an exemplary host organism, any Thraustochytrid can be modified according to the present invention, including members of the genera *Thraustochytrium, Labyrinthuloides*, and *Japonochytrium.* For example, *Thraustochytrium* as described above can also serve as a host organism for genetic modification using the methods described herein, although it is more likely that the *Thraustochytrium* PUFA PKS genes will be used to modify the endogenous PUFA PKS genes of another Thraustochytrid, such as *Schizochytrium*. Furthermore, using methods for screening organisms as set forth in U.S. application Ser. No. 10/124,800, supra, one can identify other organisms useful in the present method and all such organisms are encompassed herein. Moreover, PUFA PKS systems can be constructed using the exemplary information provided herein, produced in other microorganisms, such as bacteria or yeast, and transformed into plants cells to produce genetically modified plants. The concepts discussed herein can be applied to various systems as desired.

This embodiment of the present invention can be illustrated as follows. By way of example, based on the present inventors' current understanding of PUFA synthesis and accumulation in *Schizochytrium*, the overall biochemical process can be divided into three parts.

First, the PUFAs that accumulate in *Schizochytrium* oil (DHA and DPA) are the product of a PUFA PKS system as discussed above. The PUFA PKS system in *Schizochytrium* converts malonyl-CoA into the end product PUFA without release of significant amounts of intermediate compounds. In *Schizochytrium* and also in *Thraustochytrium*, three genes have previously been identified (Orfs A, B and C; also represented by SEQ ID NOs:13, 15 and 17 in *Schizochytrium* and by SEQ ID NOs: 19, 21 and 23 in *Thraustochytrium*, respectively) that encode all of the enzymatic domains known to be required for actual synthesis of PUFAs in these organisms. Similar sets of genes (encoding proteins containing homologous sets of enzymatic domains) have been cloned and characterized from several other non-eukaryotic organisms that produce PUFAs, namely, several strains of marine bacteria, and now in the present invention, the present inventors have identified and sequenced PUFA PKS genes in two particularly useful strains of marine bacteria, *Shewanella japonica* and *Shewanella olleyana*. The PUFA products of these marine bacteria are EPA. It is an embodiment of the invention that any PUFA PKS gene set or combinations thereof could be envisioned to substitute for the *Schizochytrium* genes described in the example herein, as long as the physiological growth requirements of the production organism (e.g., *Schizochytrium*) in fermentation conditions were satisfied. In particular, the PUFA-producing bacterial strains described above grow well at relatively high temperatures (e.g., greater than 25° C.) which further indicates that their PUFA PKS gene products will function at standard growth temperatures for *Schizochytrium* (25-30° C.). It will be apparent to those skilled in the art from this disclosure that other currently unstudied or unidentified PUFA-producing bacteria could also contain PUFA PKS genes useful for modification of Thraustochytrids.

Second, in addition to the genes that encode the enzymes directly involved in PUFA synthesis, an "accessory" enzyme is required. The gene encodes a phosphopantetheine transferase (PPTase) that activates the acyl-carrier protein (ACP) domains present in the PUFA PKS complex. Activation of the ACP domains by addition of this co-factor is required for the PUFA PKS enzyme complex to function. All of the ACP domains of the PUFA PKS systems identified so far show a high degree of amino acid sequence conservation and, without being bound by theory, the present inventors believe that the PPTase of *Schizochytrium* and other Thraustochytrids will recognize and activate ACP domains from other PUFA PKS systems, and vice versa. This gene is identified and included as part of the PUFA PKS system in the marine bacterial PUFA PKS systems described herein and can be used in the genetic modification scenarios encompassed by the invention. As proof of principle that heterologous PPTases and PUFA PKS genes can function together to produce a PUFA product, the present inventors have demonstrated the use of two different heterologous PPTases with the PUFA PKS genes from *Schizochytrium* to produce a PUFA in a bacterial host cell.

Third, in *Schizochytrium* and other Thraustochytrids, the products of the PUFA PKS system are efficiently channeled into both the phospholipids (PL) and triacylglycerols (TAG). The present inventors' data suggest that the PUFA is transferred from the ACP domains of the PKS complex to coenzyme A (CoA). As in other eukaryotic organisms, this acyl-CoA would then serve as the substrate for the various acyl-transferases that form the PL and TAG molecules. In contrast, the data indicate that in bacteria, transfer to CoA does not occur; rather, there is a direct transfer from the ACP domains of the PKS complex to the acyl-transferases that form PL. The enzymatic system in *Schizochytrium* that transfers PUFA from ACP to CoA clearly can recognize both DHA and DPA and therefore, the present inventors believe that it is predictable that any PUFA product of the PUFA PKS system (as attached to the PUFA PKS ACP domains) will serve as a substrate.

Therefore, in one embodiment of the present invention, the present inventors propose to alter the genes encoding the components of the PUFA PKS enzyme complex in a Thraustochytrid host (e.g., by introducing at least one recombinant nucleic acid molecule encoding at least one domain or functional portion thereof from a marine bacteria PUFA PKS of the present invention) while utilizing the endogenous PPTase from *Schizochytrium*, another Thraustochytrid host, or the PPTase from the marine bacteria of the invention; and PUFA-ACP to PUFA-CoA transferase activity and TAG/PL synthesis systems (or other endogenous PUFA ACP to TAG/PL mechanism. These methods of the present invention are supported by experimental data, some of which are presented in the Examples section in detail.

The present inventors and others have previously shown that the PUFA PKS system can be transferred between organisms, and that some parts are interchangeable. More particularly, it has been previously shown that the PUFA PKS pathways of the marine bacteria, *Shewanella* SCR2738 (Yazawa Lipids 31:S297 (1996)) and *Vibrio* marinus (along with the PPTase from *Shewanella*) (U.S. Pat. No. 6,140,486), can be successfully transferred to a heterologous host (i.e., to *E. coli*). Additionally, the degree of structural homology between the subunits of the PUFA PKS enzymes from these two organisms (*Shewanella* SCRC2738 and *Vibrio* marinus) is such that it has been possible to mix and match genes from the two systems (U.S. Pat. No. 6,140,486, supra). The functional domains of all of the PUFA PKS enzymes identified so far show some sequence homology to one another. Similarly, these data indicated that PUFA PKS systems, including those from the marine bacteria, can be transferred to, and will function in, *Schizochytrium* and other Thraustochytrids.

The present inventors have now expressed the PUFA PKS genes (Orfs A, B and C) from *Schizochytrium* in an *E. coli* host and have demonstrated that the cells made DHA and DPA in about the same ratio as the endogenous production of these PUFAs in *Schizochytrium* (see Example 3). Therefore, it has been demonstrated that the recombinant *Schizochytrium* PUFA PKS genes encode a functional PUFA synthesis system. Additionally, all or portions of the *Thraustochytrium* 23B OrfA and OrfC genes have been shown to function in *Schizochytrium* (see Example 7). Furthermore, the present inventors have also replaced the entire *Schizochytrium* orfC coding sequence completely and exactly by the *Thraustochytrium* 23B orfC coding sequence, which resulted in a PUFA production profile in the *Schizochytrium* host that was shifted toward that of *Thraustochytrium* (see Example 8).

The present inventors have previously found that PPTases can activate heterologous PUFA PKS ACP domains. Production of DHA in *E. coli* transformed with the PUFA PKS genes from *Vibrio* marinus occurred only when an appropriate PPTase gene (in this case, from *Shewanella* SCRC2738) was also present (see U.S. Pat. No. 6,140,486, supra). This demonstrated that the *Shewanella* PPTase was able to activate the *Vibrio* PUFA PKS ACP domains. Additionally, the present inventors have now demonstrated the activation (pantetheinylation) of ACP domains from *Schizochytrium* Orf A using a PPTase (sfp) from *Bacillus subtilus* (see Example 3). The present inventors have also demonstrated activation (pantetheinylation) of ACP domains from *Schizochytrium* Orf A by a PPTase called Het I from Nostoc (see Example 3). The HetI enzyme was additionally used as the PPTase in the experiments discussed above for the production of DHA and DPA in *E. coli* using the recombinant *Schizochytrium* PUFA PKS genes (Example 3).

The data also indicate that DHA-CoA and DPA-CoA may be metabolic intermediates in the *Schizochytrium* TAG and PL synthesis pathway. Published biochemical data suggest that in bacteria, the newly synthesized PUFAs are transferred directly from the PUFA PKS ACP domains to the phospholipid synthesis enzymes. In contrast, the present inventors' data indicate that in *Schizochytrium*, a eukaryotic organism, there may be an intermediate between the PUFA on the PUFA PKS ACP domains and the target TAG and PL molecules. The typical carrier of fatty acids in the eukaryotic cytoplasm is CoA. The inventors examined extracts of *Schizochytrium* cells and found significant levels of compounds that co-migrated during HPLC fractionation with authentic standards of DHA-CoA, DPA-CoA, 16:0-CoA and 18:1-CoA. The identity of the putative DHA-CoA and DPA-CoA peaks were confirmed using mass spectroscopy. In contrast, the inventors were not able to detect DHA-CoA in extracts of *Vibrio* marinus, again suggesting that a different mechanism exists in bacteria for transfer of the PUFA to its final target (e.g., direct transfer to PL). The data indicate a mechanism likely exists in *Schizochytrium* for transfer of the newly synthesized PUFA to CoA (probably via a direct transfer from the ACP to CoA). Both TAG and PL synthesis enzymes could then access this PUFA-CoA. The observation that both DHA and DPA CoA are produced suggests that the enzymatic transfer machinery may recognize a range of PUFAs.

The present inventors have also created knockouts of Orf A, Orf B, and Orf C in *Schizochytrium* (see Example 4). The knockout strategy relies on the homologous recombination that has been demonstrated to occur in *Schizochytrium* (see U.S. patent application Ser. No. 10/124,807, supra). Several strategies can be employed in the design of knockout constructs. The specific strategy used to inactivate these three genes utilized insertion of a Zeocin™ resistance gene coupled to a tubulin promoter (derived from pMON50000, see U.S. patent application Ser. No. 10/124,807) into a cloned portion of the Orf. The new construct containing the interrupted coding region was then used for the transformation of wild type *Schizochytrium* cells via particle bombardment (see U.S. patent application Ser. No. 10/124,807). Bombarded cells were spread on plates containing both Zeocin™ and a supply of PUFA (see below). Colonies that grew on these plates were then streaked onto Zeocin™ plates that were not supplemented with PUFAs. Those colonies that required PUFA supplementation for growth were candidates for having had the PUFA PKS Orf inactivated via homologous recombination. In all three cases, this presumption was confirmed by rescuing the knockout by transforming the cells with a full-length genomic DNA clones of the respective *Schizochytrium* Orfs. Furthermore, in some cases, it was found that in the rescued transformants the Zeocin™ resistance gene had been removed (see Example 6), indicating that the introduced functional gene had integrated into the original site by double homologous recombination (i.e. deleting the resistance marker). One key to the success of this strategy was supplementation of the growth medium with PUFAs. In the present case, an effective means of supplementation was found to be sequestration of the PUFA by mixing with partially methylated beta-cyclodextrin prior to adding to the growth medium (see Example 6). Together, these experiments demonstrate the principle that one of skill in the art, given the guidance provided herein, can inactivate one or more of the PUFA PKS genes in a PUFA PKS-containing microorganism such as *Schizochytrium*, and create a PUFA auxotroph which can then be used for further genetic modification (e.g., by introducing other PKS genes) according to the present invention (e.g., to alter the fatty acid profile of the recombinant organism).

One element of the genetic modification of the organisms of the present invention is the ability to directly transform a Thraustochytrid genome. In U.S. application Ser. No. 10/124,807, supra, transformation of *Schizochytrium* via single crossover homologous recombination and targeted gene replacement via double crossover homologous recombination were demonstrated. As discussed above, the present inventors have now used this technique for homologous recombination to inactivate Orf A, Orf B and OrfC of the PUFA-PKA system in *Schizochytrium*. The resulting mutants are dependent on supplementation of the media with PUFA. Several markers of transformation, promoter elements for high level expression of introduced genes and methods for delivery of exogenous genetic material have been developed and are available. Therefore, the tools are in place for knocking out endogenous PUFA PKS genes in Thraustochytrids and other eukaryotes having similar PUFA PKS systems and replacing them with genes from other organisms, such as the marine bacterial genes described herein and as proposed above.

In one approach for production of EPA-rich TAG, the PUFA PKS system of *Schizochytrium* can be altered by the addition of heterologous genes encoding a PUFA PKS system whose product is EPA, such as the genes from *Shewanella japonica* and *Shewanella olleyana* described herein. It is anticipated that the endogenous PPTase will activate the ACP domains of that heterologous PUFA PKS system, but the inventors have also cloned and sequenced the PPTase from the marine bacteria, which could also be introduced into the host. Additionally, it is anticipated that the EPA will be converted to EPA-CoA and will readily be incorporated into *Schizochytrium* TAG and PL membranes. Therefore, in one embodiment, genes encoding a heterologous PUFA PKS system that produce EPA (e.g., from the marine bacteria above) can be introduced into a microorganism that naturally produces DHA (e.g., *Schizochytrium*) so that the resulting microorganism produces both EPA and DHA. This technology can be further applied to genetically modified plants, for example, by introducing the two different PUFA PKS systems described above into plant cells to produce a plant that produces both EPA and DHA, or whatever combination of PUFAs is desired.

In one modification of this approach, techniques can be used to modify the relevant domains of the endogenous

*Schizochytrium* system (either by introduction of specific regions of heterologous genes or by mutagenesis of the *Schizochytrium* genes themselves) such that its end product is EPA rather than DHA and DPA, or alternatively, so that the endproduct is both EPA and DHA and/or DPA, or so that the endproduct is EPA and ARA instead of DHA and DPA. This is an exemplary approach, as this technology can be applied to the production of other PUFA end products and to any eukaryotic microorganism that comprises a PUFA PKS system and that has the ability to efficiently channel the products of the PUFA PKS system into both the phospholipids (PL) and triacylglycerols (TAG). In particular, the invention is applicable to any Thraustochytrid microorganism or any other eukaryote that has an endogenous PUFA PKS system, which is described in detail below by way of example. In addition, the invention is applicable to any suitable host organism, into which the modified genetic material for production of various PUFA profiles as described herein can be transformed. For example, in the Examples, the PUFA PKS system from *Schizochytrium* is transformed into an *E. coli*. Such a transformed organism could then be further modified to alter the PUFA production profile using the methods described herein.

The present invention particularly makes use can make use of genes and nucleic acid sequences which encode proteins or domains from PKS systems other than the PUFA PKS system described herein and in prior applications and includes genes and nucleic acid sequences from bacterial and non-bacterial PKS systems, including PKS systems of Type I (iterative or modular), Type II or Type III, described above. Organisms which express each of these types of PKS systems are known in the art and can serve as sources for nucleic acids useful in the genetic modification process of the present invention.

In a preferred embodiment, genes and nucleic acid sequences which encode proteins or domains from PKS systems other than the PUFA PKS system or from other PUFA PKS systems are isolated or derived from organisms which have preferred growth characteristics for production of PUFAs. In particular, it is desirable to be able to culture the genetically modified Thraustochytrid microorganism at temperatures at or greater than about 15° C., at or greater than 20° C., at or greater than 25° C., or at or greater than 30° C., or up to about 35° C., or in one embodiment, at any temperature between about 20° C. and 35° C., in whole degree increments. Therefore, PKS proteins or domains having functional enzymatic activity at these temperatures are preferred. The PUFA PKS genes from *Shewanella olleyana* or *Shewanella japonica* described herein naturally produce EPA and grow at temperatures up to 25° C., 30° C., or 35° C., which makes them particularly useful for this embodiment of the invention (see Examples 1-2).

In another preferred embodiment, the genes and nucleic acid sequences that encode proteins or domains from a PUFA PKS system that produces one fatty acid profile are used to modify another PUFA PKS system and thereby alter the fatty acid profile of the host. For example, *Thraustochytrium* 23B (ATCC 20892) is significantly different from *Schizochytrium* sp. (ATCC 20888) in its fatty acid profile. *Thraustochytrium* 23B can have DHA:DPA(n-6) ratios as high as 40:1 compared to only 2-3:1 in *Schizochytrium* (ATCC 20888). *Thraustochytrium* 23B can also have higher levels of C20:5(n-3). However, *Schizochytrium* (ATCC 20888) is an excellent oil producer as compared to *Thraustochytrium* 23B. *Schizochytrium* accumulates large quantities of triacylglycerols rich in DHA and docosapentaenoic acid (DPA; 22:5ω6); e.g., 30% DHA+DPA by dry weight. Therefore, the present inventors describe herein the modification of the *Schizochytrium* endogenous PUFA PKS system with *Thraustochytrium* 23B PUFA PKS genes to create a genetically modified *Schizochytrium* with a DHA:DPA profile more similar to *Thraustochytrium* 23B (i.e., a "super-DHA-producer" *Schizochytrium*, wherein the production capabilities of the *Schizochytrium* combine with the DHA:DPA ratio of *Thraustochytrium*). This modification is demonstrated in Example 8.

Therefore, the present invention makes use of genes from certain marine bacterial and any Thraustochytrid or other eukaryotic PUFA PKS systems, and further utilizes gene mixing to extend and/or alter the range of PUFA products to include EPA, DHA, DPA, ARA, GLA, SDA and others. The method to obtain these altered PUFA production profiles includes not only the mixing of genes from various organisms into the Thraustochytrid PUFA PKS genes, but also various methods of genetically modifying the endogenous Thraustochytrid PUFA PKS genes disclosed herein. Knowledge of the genetic basis and domain structure of the Thraustochytrid PUFA PKS system and the marine bacterial PUFA PKS system provides a basis for designing novel genetically modified organisms that produce a variety of PUFA profiles. Novel PUFA PKS constructs prepared in microorganisms such as a Thraustochytrid can be isolated and used to transform plants to impart similar PUFA production properties onto the plants.

Any one or more of the endogenous Thraustochytrid PUFA PKS domains can be altered or replaced according to the present invention (for example with a domain from a marine bacterium of the present invention), provided that the modification produces the desired result (i.e., alteration of the PUFA production profile of the microorganism). Particularly preferred domains to alter or replace include, but are not limited to, any of the domains corresponding to the domains in *Schizochytrium* OrfB or OrfC (β-keto acyl-ACP synthase (KS), acyltransferase (AT), FabA-like β-hydroxy acyl-ACP dehydrase (DH), chain length factor (CLF), enoyl ACP-reductase (ER), an enzyme that catalyzes the synthesis of trans-2-acyl-ACP, an enzyme that catalyzes the reversible isomerization of trans-2-acyl-ACP to cis-3-acyl-ACP, and an enzyme that catalyzes the elongation of cis-3-acyl-ACP to cis-5-O-keto-acyl-ACP). In one embodiment, preferred domains to alter or replace include, but are not limited to, β-keto acyl-ACP synthase (KS), FabA-like β-hydroxy acyl-ACP dehydrase (DH), and chain length factor (CLF).

In one aspect of the invention, Thraustochytrid PUFA-PKS PUFA production is altered by modifying the CLF (chain length factor) domain. This domain is characteristic of Type II (dissociated enzymes) PKS systems. Its amino acid sequence shows homology to KS (keto synthase pairs) domains, but it lacks the active site cysteine. CLF may function to determine the number of elongation cycles, and hence the chain length, of the end product. In this embodiment of the invention, using the current state of knowledge of FAS and PKS synthesis, a rational strategy for production of ARA by directed modification of the non-bacterial PUFA-PKS system is provided. There is controversy in the literature concerning the function of the CLF in PKS systems (Bisang et al., *Nature* 401:502 (1999); Yi et al., *J. Am. Chem. Soc.* 125:12708 (2003)) and it is realized that other domains may be involved in determination of the chain length of the end product. However, it is significant that *Schizochytrium* produces both DHA (C22:6, ω-3) and DPA (C22:5, ω-6). In the PUFA-PKS system the cis double bonds are introduced during synthesis of the growing carbon chain. Since placement of the ω-3 and ω-6 double bonds occurs early in the synthesis of the molecules, one would not expect that they would affect subsequent end-product chain length determination. Thus, without being bound by theory, the present inventors believe that introduction of a factor (e.g. CLF) that directs synthesis of C20 units (instead of C22 units) into the *Schizochytrium* PUFA-PKS system will result in the production of EPA (C20:5, ω-3) and ARA (C20:4, ω-6). For example, in heterologous systems, one could exploit the CLF by directly substituting a CLF from an EPA producing system (such as one from *Photobacterium*, or preferably from a microorganism with the preferred growth requirements as described below) into the *Schizochytrium* gene set. The fatty acids of the resulting transformants can then be analyzed for alterations in profiles to identify the transformants producing EPA and/or ARA.

By way of example, in this aspect of the invention, one could construct a clone with the CLF of OrfB replaced with a CLF from a C20 PUFA-PKS system, such as the marine bacterial systems described in detail herein. A marker gene could be inserted downstream of the coding region. More specifically, one can use the homologous recombination system for transformation of Thraustochytrids as described herein and in detail in U.S. patent application Ser. No. 10/124,807, supra. One can then transform the wild type Thraustochytrid cells (e.g., *Schizochytrium* cells), select for the marker phenotype, and then screen for those that had incorporated the new CLF. Again, one would analyze these transformants for any effects on fatty acid profiles to identify transformants producing EPA and/or ARA. Alternatively, and in some cases, preferably, such screening for the effects of swapped domains can be carried out in *E. coli* (as described below) or in other systems such as, but not limited to, yeast. If some factor other than those associated with the CLF is found to influence the chain length of the end product, a similar strategy could be employed to alter those factors. In another embodiment of the invention, an organism is modified by introducing both a chain length factor plus a β-ketoacyl-ACP synthase (KS) domain.

In another aspect of the invention, modification or substitution of the β-hydroxy acyl-ACP dehydrase/keto synthase pairs is contemplated. During cis-vaccenic acid (C18:1, Δ11) synthesis in *E. coli*, creation of the cis double bond is believed to depend on a specific DH enzyme, β-hydroxy acyl-ACP dehydrase, the product of the fabA gene. This enzyme removes HOH from a β-keto acyl-ACP and initially produces a trans double bond in the carbon chain. A subset of DH's, FabA-like, possess cis-trans isomerase activity (Heath et al., 1996, supra). A novel aspect of bacterial and non-bacterial PUFA-PKS systems is the presence of two FabA-like DH domains. Without being bound by theory, the present inventors believe that one or both of these DH domains will possess cis-trans isomerase activity (manipulation of the DH domains is discussed in greater detail below).

Another aspect of the unsaturated fatty acid synthesis in *E. coli* is the requirement for a particular KS enzyme, β-ketoacyl-ACP synthase, the product of the fabB gene. This is the enzyme that carries out condensation of a fatty acid, linked to a cysteine residue at the active site (by a thio-ester bond), with a malonyl-ACP. In the multi-step reaction, $CO_2$ is released and the linear chain is extended by two carbons. It is believed that only this KS can extend a carbon chain that contains a double bond. This extension occurs only when the double bond is in the cis configuration; if it is in the trans configuration, the double bond is reduced by enoyl-ACP reductase (ER) prior to elongation (Heath et al., 1996, supra). All of the PUFA-PKS systems characterized so far have two KS domains, one of which shows greater homology to the FabB-like KS of *E. coli* than the other. Again, without being bound by theory, the present inventors believe that in PUFA-PKS systems, the specificities and interactions of the DH (FabA-like) and KS (FabB-like) enzymatic domains determine the number and placement of cis double bonds in the end products. Because the number of 2-carbon elongation reactions is greater than the number of double bonds present in the PUFA-PKS end products, it can be determined that in some extension cycles complete reduction occurs. Thus the DH and KS domains can be used as targets for alteration of the DHA/DPA ratio or ratios of other long chain fatty acids. These can be modified and/or evaluated by introduction of homologous domains from other systems or by mutagenesis of these gene fragments. In one embodiment, the FabA-like DH domain may not require a KS partner domain at all.

In another embodiment, the ER (enoyl-ACP reductase—an enzyme which reduces the trans-double bond in the fatty acyl-ACP resulting in fully saturated carbons) domains can be modified or substituted to change the type of product made by the PKS system. For example, the present inventors know that *Schizochytrium* PUFA-PKS system differs from the previously described bacterial systems in that it has two (rather than one) ER domains. Without being bound by theory, the present inventors believe these ER domains can strongly influence the resulting PKS production product. The resulting PKS product could be changed by separately knocking out the individual domains or by modifying their nucleotide sequence or by substitution of ER domains from other organisms, such as the ER domain from the marine bacteria described herein.

In another aspect of the invention, substitution of one of the DH (FabA-like) domains of the PUFA-PKS system for a DH domain that does not posses isomerization activity is contemplated, potentially creating a molecule with a mix of cis- and trans-double bonds. The current products of the *Schizochytrium* PUFA PKS system are DHA and DPA (C22:5 ω6). If one manipulated the system to produce C20 fatty acids, one would expect the products to be EPA and ARA (C20:4 ω6). This could provide a new source for ARA. One could also substitute domains from related PUFA-PKS systems that produced a different DHA to DPA ratio—for example by using genes from *Thraustochytrium* 23B (the PUFA PKS system of which is identified in U.S. patent application Ser. No. 10/124,800, supra).

Additionally, in one embodiment, one of the ER domains is altered in the Thraustochytrid PUFA PKS system (e.g. by removing or inactivating) to alter the end product profile. Similar strategies could be attempted in a directed manner for each of the distinct domains of the PUFA-PKS proteins using more or less sophisticated approaches. Of course one would not be limited to the manipulation of single domains. Finally, one could extend the approach by mixing domains from the PUFA-PKS system and other PKS or FAS systems (e.g., type I, type II, type III) to create an entire range of new PUFA end products.

As an example of how the bacterial PUFA PKS genes described in detail herein can be used to modify PUFA production in *Schizochytrium*, the following discussion is provided. Again, all of the examples described herein may be equally applied to the production of other genetically modified microorganisms or to the production of genetically modified plants. All presently-known examples of PUFA PKS genes from bacteria exist as four closely linked genes that contain the same domains as in the three-gene *Schizochytrium* set. Indeed, the present inventors have demonstrated that the PUFA PKS genes from *Shewanella olleyana* and *Shewanella japonica* are found in this tightly clustered arrangement. The DNA sequences of the bacterial PUFA PKS genes described herein can now be used to design vectors for transformation of *Schizochytrium* strains defective in the endogenous PUFA PKS genes (e.g., see Examples 4, 6 and 7). Whole bacterial genes (coding sequences) may be used to replace whole *Schizochytrium* genes (coding sequences), thus utilizing the *Schizochytrium* gene expression regions, and the fourth bacterial gene may be targeted to a different location within the genome. Alternatively, individual bacterial PUFA PKS functional domains may be "swapped" or exchanged with the analogous *Schizochytrium* domains by similar techniques of homologous recombination. As yet another alternative, bacterial PUFA PKS genes may even be added to PUFA PKS systems from Thraustochytrids to produce organisms having more than one PUFA synthase activity. It is understood that the sequence of the bacterial PUFA PKS genes or domains may have to be modified to accommodate details of *Schizochytrium* codon usage, but this is within the ability of those of skill in the art.

It is recognized that many genetic alterations, either random or directed, which one may introduce into a native (endogenous, natural) PKS system, will result in an inactivation of enzymatic functions. Therefore, in order to test for the effects of genetic manipulation of a Thraustochytrid PUFA PKS system in a controlled environment, one could first use a recombinant system in another host, such as *E. coli*, to manipulate various aspects of the system and evaluate the results. For example, the FabB strain of *E. coli* is incapable of synthesizing unsaturated fatty acids and requires supplementation of the medium with fatty acids that can substitute for its normal unsaturated fatty acids in order to grow (see Metz et al. (2001), supra). However, this requirement (for supplementation of the medium) can be removed when the strain is transformed with a functional PUFA-PKS system (i.e. one that produces a PUFA product in the *E. coli* host—see (Metz et al. (2001), supra, FIG. 2A of that publication). The transformed FabB strain now requires a functional PUFA-PKS system (to produce the unsaturated fatty acids) for growth without supplementation. The key element in this example is that production of a wide range of unsaturated fatty acid will suffice (even unsaturated fatty acid substitutes such as branched chain fatty acids). Therefore, in another preferred embodiment of the invention, one could create a large number of mutations in one or more of the PUFA PKS genes disclosed herein, and then transform the appropriately modified FabB strain (e.g. create mutations in an expression construct containing an ER domain and transform a FabB strain having the other essential domains on a separate plasmid—or integrated into the chromosome) and select only for those transformants that grow without supplementation of the medium (i.e., that still possessed an ability to produce a molecule that could complement the FabB defect). The FabA strain of *E. coli* has a similar phenotype to the FabB strain and could also be used as an alternative strain in the example described above.

One test system for genetic modification of a PUFA PKS is exemplified in the Examples section. Briefly, a host microorganism such as *E. coli* is transformed with genes encoding a PUFA PKS system including all or a portion of a Thraustochytrid PUFA PKS system (e.g., Orfs A, B and C of *Schizochytrium*) and a gene encoding a phosphopantetheinyl transferases (PPTase), which is required for the attachment of a phosphopantetheine cofactor to produce the active, holo-ACP in the PKS system. The genes encoding the PKS system can be genetically engineered to introduce one or more modifications to the Thraustochytrid PUFA PKS genes and/or to introduce nucleic acids encoding domains from other PKS systems into the Thraustochytrid genes (including genes from non-Thraustochytrid microorganisms and genes from different Thraustochytrid microorganisms). The PUFA PKS system can be expressed in the *E. coli* and the PUFA production profile measured. In this manner, potential genetic modifications can be evaluated prior to manipulation of the Thraustochytrid PUFA production organism.

The present invention includes the manipulation of endogenous nucleic acid molecules in a Thraustochytrid PUFA PKS system and/or the use of isolated nucleic acid molecules comprising a nucleic acid sequence from a *Shewanella japonica* PUFA PKS system, from a *Shewanella olleyana* PUFA PKS system, and can additionally include a nucleic acid sequence from a Thraustochytrid PUFA PKS system, or homologues of any of such nucleic acid sequences. In one aspect, the present invention relates to the modification and/or use of a nucleic acid molecule comprising a nucleic acid sequence encoding a domain from a PUFA PKS system having a biological activity of at least one of the following proteins: malonyl-CoA:ACP acyltransferase (MAT), β-keto acyl-ACP synthase (KS), ketoreductase (KR), acyltransferase (AT), FabA-like β-hydroxy acyl-ACP dehydrase (DH), phosphopantetheine transferase, chain length factor (CLF), acyl carrier protein (ACP), enoyl ACP-reductase (ER), an enzyme that catalyzes the synthesis of trans-2-acyl-ACP, an enzyme that catalyzes the reversible isomerization of trans-2-acyl-ACP to cis-3-acyl-ACP, and/or an enzyme that catalyzes the elongation of cis-3-acyl-ACP to cis-5-β-keto-acyl-ACP. Preferred domains to modify in order to alter the PUFA production profile of a host Thraustochytrid have been discussed previously herein.

The genetic modification of an organism according to the present invention preferably affects the type, amounts, and/or activity of the PUFAs produced by the organism, whether the organism has an endogenous PUFA PKS system that is genetically modified, and/or whether recombinant nucleic acid molecules are introduced into the organism. According to the present invention, to affect an activity of a PUFA PKS system, such as to affect the PUFA production profile, includes any genetic modification in the PUFA PKS system or genes that interact with the PUFA PKS system that causes any detectable or measurable change or modification in any biological activity the PUFA PKS system expressed by the organism as compared to in the absence of the genetic modification. According to the present invention, the phrases "PUFA profile", "PUFA expression profile" and "PUFA production profile" can be used interchangeably and describe the overall profile of PUFAs expressed/produced by a organism. The PUFA expression profile can include the types of PUFAs expressed by the organism, as well as the absolute and relative amounts of the PUFAs produced. Therefore, a PUFA profile can be described in terms of the ratios of PUFAs to one another as produced by the organism, in terms of the types of PUFAs produced by the organism, and/or in terms of the types and absolute or relative amounts of PUFAs produced by the organism.

As discussed above, the host organism can include any prokaryotic or eukaryotic organism with or without an endogenous PUFA PKS system and preferably is a eukaryotic microorganism with the ability to efficiently channel the products of the PUFA PKS system into both the phospholipids (PL) and triacylglycerols (TAG). A preferred host microorganism is any member of the order Thraustochytriales, including the families Thraustochytriaceae and Labyrinthulaceae. Particularly preferred host cells of these families have been described above. Preferred host plant cells include plant cells from any crop plant or plant that is commercially useful.

In one embodiment of the present invention, it is contemplated that a genetic engineering and/or mutagenesis program could be combined with a selective screening process to obtain a Thraustochytrid microorganism with the PUFA production profile of interest. The mutagenesis methods could include, but are not limited to: chemical mutagenesis, shuffling of genes, switching regions of the genes encoding specific enzymatic domains, or mutagenesis restricted to specific regions of those genes, as well as other methods.

For example, high throughput mutagenesis methods could be used to influence or optimize production of the desired PUFA profile. Once an effective model system has been developed, one could modify these genes in a high throughput manner. Utilization of these technologies can be envisioned on two levels. First, if a sufficiently selective screen for production of a product of interest (e.g., EPA) can be devised, it could be used to attempt to alter the system to produce this product (e.g., in lieu of, or in concert with, other strategies such as those discussed above). Additionally, if the strategies outlined above resulted in a set of genes that did produce the PUFA profile of interest, the high throughput technologies could then be used to optimize the system. For example, if the introduced domain only functioned at relatively low temperatures, selection methods could be devised to permit removing that limitation.

As described above, in one embodiment of the present invention, a genetically modified microorganism or plant includes a microorganism or plant which has an enhanced ability to synthesize desired bioactive molecules (products) or which has a newly introduced ability to synthesize specific products (e.g., to synthesize a specific antibiotic). According to the present invention, “an enhanced ability to synthesize” a product refers to any enhancement, or up-regulation, in a pathway related to the synthesis of the product such that the microorganism or plant produces an increased amount of the product (including any production of a product where there was none before) as compared to the wild-type microorganism or plant, cultured or grown, under the same conditions. Methods to produce such genetically modified organisms have been described in detail above and indeed, any exemplary modifications described using any of the PUFA PKS systems can be adapted for expression in plants.

One embodiment of the present invention is a method to produce desired bioactive molecules (also referred to as products or compounds) by growing or culturing a genetically modified microorganism or plant of the present invention (described in detail above). Such a method includes the step of culturing in a fermentation medium or growing in a suitable environment, such as soil, a microorganism or plant, respectively, that has a genetic modification as described previously herein and in accordance with the present invention. Preferred host cells for genetic modification related to the PUFA PKS system of the invention are described above.

One embodiment of the present invention is a method to produce desired PUFAs by culturing a genetically modified microorganism of the present invention (described in detail above). Such a method includes the step of culturing in a fermentation medium and under conditions effective to produce the PUFA(s) a microorganism that has a genetic modification as described previously herein and in accordance with the present invention. An appropriate, or effective, medium refers to any medium in which a genetically modified microorganism of the present invention, including Thraustochytrids and other microorganisms, when cultured, is capable of producing the desired PUFA product(s). Such a medium is typically an aqueous medium comprising assimilable carbon, nitrogen and phosphate sources. Such a medium can also include appropriate salts, minerals, metals and other nutrients. Any microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for Thraustochytrid microorganisms according to the present invention are well known in the art and are described in detail, for example, in U.S. Pat. Nos. 5,130,242, 5,340,742, and 5,698,244, each of which is incorporated herein by reference in its entirety.

In one embodiment, the genetically modified microorganism is cultured at a temperature of at or greater than about 15° C., and in another embodiment, at or greater than about 20° C., and in another embodiment, at or greater than about 25° C., and in another embodiment, at or greater than about 30° C., and in another embodiment, up to about 35° C. or higher, and in another embodiment, at any temperature between about 20° C. and 35° C., in whole degree increments.

The desired PUFA(s) and/or other bioactive molecules produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, phase separation, membrane separation, electrodialysis, reverse osmosis, distillation, chemical derivatization and crystallization. Alternatively, microorganisms producing the PUFA(s), or extracts and various fractions thereof, can be used without removal of the microorganism components from the product.

Preferably, a genetically modified microorganism of the invention produces one or more polyunsaturated fatty acids including, but not limited to, EPA (C20:5, ω-3), DHA (C22:6, ω-3), DPA (C22:5, ω-6), ARA (C20:4, ω-6), GLA (C18:3, n-6), and SDA (C18:4, n-3)). In one preferred embodiment, a *Schizochytrium* that, in wild-type form, produces high levels of DHA and DPA, is genetically modified according to the invention to produce high levels of EPA. As discussed above, one advantage of using genetically modified Thraustochytrid microorganisms to produce PUFAs is that the PUFAs are directly incorporated into both the phospholipids (PL) and triacylglycerides (TAG).

Preferably, PUFAs are produced in an amount that is greater than about 5% of the dry weight of the microorganism, and in one aspect, in an amount that is greater than 6%, and in another aspect, in an amount that is greater than 7%, and in another aspect, in an amount that is greater than 8%, and in another aspect, in an amount that is greater than 9%, and in another aspect, in an amount that is greater than 10%, and so on in whole integer percentages, up to greater than 90% dry weight of the microorganism (e.g., 15%, 20%, 30%, 40%, 50%, and any percentage in between).

In the method for production of desired bioactive compounds of the present invention, a genetically modified plant is cultured in a fermentation medium or grown in a suitable medium such as soil. An appropriate, or effective, fermentation medium has been discussed in detail above. A suitable growth medium for higher plants includes any growth medium for plants, including, but not limited to, soil, sand, any other particulate media that support root growth (e.g. vermiculite, perlite, etc.) or hydroponic culture, as well as suitable light, water and nutritional supplements which optimize the growth of the higher plant. The genetically modified plants of the present invention are engineered to produce significant quantities of the desired product through the activity of the PKS system that is genetically modified according to the present invention. The compounds can be recovered through purification processes which extract the compounds from the plant. In a preferred embodiment, the compound is recovered by harvesting the plant. In this embodiment, the plant can be consumed in its natural state or further processed into consumable products.

Many genetic modifications useful for producing bioactive molecules will be apparent to those of skill in the art, given the present disclosure, and various other modifications have been discussed previously herein. The present invention contemplates any genetic modification related to a PUFA PKS system as described herein which results in the production of a desired bioactive molecule.

Bioactive molecules, according to the present invention, include any molecules (compounds, products, etc.) that have a biological activity, and that can be produced by a PKS system that comprises at least one amino acid sequence having a biological activity of at least one functional domain of a non-bacterial PUFA PKS system as described herein. Such bioactive molecules can include, but are not limited to: a polyunsaturated fatty acid (PUFA), an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. One advantage of the PUFA PKS system of the present invention is the ability of such a system to introduce carbon-carbon double bonds in the cis configuration, and molecules including a double bond at every third carbon. This ability can be utilized to produce a variety of compounds.

Preferably, bioactive compounds of interest are produced by the genetically modified microorganism in an amount that is greater than about 0.05%, and preferably greater than about 0.1%, and more preferably greater than about 0.25%, and more preferably greater than about 0.5%, and more preferably greater than about 0.75%, and more preferably greater than about 1%, and more preferably greater than about 2.5%, and more preferably greater than about 5%, and more preferably greater than about 10%, and more preferably greater than about 15%, and even more preferably greater than about 20% of the dry weight of the microorganism. For lipid compounds, preferably, such compounds are produced in an amount that is greater than about 5% of the dry weight of the microorganism. For other bioactive compounds, such as antibiotics or compounds that are synthesized in smaller amounts, those strains possessing such compounds at of the dry weight of the microorganism are identified as predictably containing a novel PKS system of the type described above. In some embodiments, particular bioactive molecules (compounds) are secreted by the microorganism, rather than accumulating. Therefore, such bioactive molecules are generally recovered from the culture medium and the concentration of molecule produced will vary depending on the microorganism and the size of the culture.

One embodiment of the present invention relates to a method to modify an endproduct so that it contains at least one fatty acid (although the endproduct may already contain at least one fatty acid, whereby at least one additional fatty acid is provided by the present method), comprising adding to the endproduct an oil produced by a recombinant host cell (microbial or plant) that expresses at least one recombinant nucleic acid molecule comprising a nucleic acid sequence encoding at least one biologically active domain of a PUFA PKS system. The PUFA PKS system includes any suitable bacterial or non-bacterial PUFA PKS system described herein, including the bacterial PUFA PKS systems from *Shewanella japonica* or *Shewanella olleyana*, or any PUFA PKS system from other bacteria that normally (i.e., under normal or natural conditions) are capable of growing and producing PUFAs at temperatures above 22° C.

Preferably, the endproduct is selected from the group consisting of a food, a dietary supplement, a pharmaceutical formulation, a humanized animal milk, and an infant formula. Suitable pharmaceutical formulations include, but are not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. In one embodiment, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Suitable food products include, but are not limited to, fine bakery wares, bread and rolls, breakfast cereals, processed and unprocessed cheese, condiments (ketchup, mayonnaise, etc.), dairy products (milk, yogurt), puddings and gelatin desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks.

Yet another embodiment of the present invention relates to a method to produce a humanized animal milk. This method includes the steps of genetically modifying milk-producing cells of a milk-producing animal with at least one recombinant nucleic acid molecule comprising a nucleic acid sequence encoding at least one biologically active domain of a PUFA PKS system as described herein.

Methods to genetically modify a host cell and to produce a genetically modified non-human, milk-producing animal, are known in the art. Examples of host animals to modify include cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

The following examples are provided for the purpose of illustration and are not intended to limit the scope of the present invention.

EXAMPLES

Example 1

The following example shows that certain EPA-producing bacteria contain PUFA PKS-like genes that appear to be suitable for modification of *Schizochytrium.*

Two EPA-producing marine bacterial strains of the genus *Shewanella* have been shown to grow at temperatures typical of *Schizochytrium* fermentations and to possess PUFA PKS-like genes. *Shewanella olleyana* (Australian Collection of Antarctic Microorganisms (ACAM) strain number 644; Skerratt et al., *Int. J. Syst. Evol. Microbiol.* 52, 2101 (2002)) produces EPA and grows up to 25-30° C. *Shewanella*

*japonica* (American Type Culture Collection (ATCC) strain number BAA-316; Ivanova et al., *Int. J. Syst. Evol. Microbiol.* 51, 1027 (2001)) produces EPA and grows up to 30-35° C.

To identify and isolate the PUFA-PKS genes from these bacterial strains, degenerate PCR primer pairs for the KS-MAT region of bacterial orf5/pfaA genes and the DH-DH region of bacterial orf7/pfaC genes were designed based on published gene sequences for *Shewanella* SCRC-2738, *Shewanella oneidensis* MR-1; *Shewanella* sp. GA-22; *Photobacter profundum*, and *Moritella marina* (see discussion above). Specifically, the primers and PCR conditions were designed as follows:

Primers for the KS/AT region; based on the following published sequences: *Shewanella* sp. SCRC-2738; *Shewanella oneidensis* MR-1; *Photobacter profundum; Moritella marina*:

```
prRZ23
GGYATGMTGRTTGGTGAAGG      (forward; SEQ ID NO:25)

prRZ24
TRTTSASRTAYTGYGAACCTTG    (reverse; SEQ ID NO:26)
```

Primers for the DH region; based on the following published sequences: *Shewanella* sp. GA-22; *Shewanella* sp. SCRC-2738; *Photobacter profundum; Moritella marina*:

```
prRZ28
ATGKCNGAAGGTTGTGGCCA      (forward; SEQ ID NO:27)

prRZ29
CCWGARATRAAGCCRTTDGGTTG   (reverse; SEQ ID NO:28)
```

The PCR conditions (with bacterial chromosomal DNA as templates) were as follows:

Reaction Mixture:
0.2 μM dNTPs
0.1 μM each primer
8% DMSO
250 ng chromosomal DNA
2.5 U Herculase® DNA polymerase (Stratagene)
1X Herculase® buffer
50 μL total volume PCR Protocol: (1) 98° C. for 3 min.; (2) 98° C. for 40 sec.; (3) 56° C. for 30 sec.; (4) 72° C. for 90 sec.; (5) Repeat steps 2-4 for 29 cycles; (6) 72° C. for 10 min.; (7) Hold at 6° C.

For both primer pairs, PCR gave distinct products with expected sizes using chromosomal DNA templates from either *Shewanella olleyana* or *Shewanella japonica*. The four respective PCR products were cloned into pCR-BLUNT II-TOPO (Invitrogen) and insert sequences were determined using the M13 forward and reverse primers. In all cases, the DNA sequences thus obtained were highly homologous to known bacterial PUFA PKS gene regions.

The DNA sequences obtained from the bacterial PCR products were compared with known sequences and with PUFA PKS genes from *Schizochytrium* ATCC 20888 in a standard Blastx search (BLAST parameters: Low Complexity filter: On; Matrix: BLOSUM62; Word Size: 3; Gap Costs: Existance11, Extension 1 (BLAST described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety)).

At the amino acid level, the sequences with the greatest degree of homology to the *Shewanella olleyana* ACAM644 ketoacyl synthase/acyl transferase (KS-AT) deduced amino acid sequence were: Photobacter profundum pfaA (identity=70%; positives=81%); *Shewanella* oneidensis MR-1 "multi-domain β-ketoacyl synthase" (identity=66%; positives=77%); and Moritella marina ORF8 (identity=56%; positives=71%). The *Schizochytrium* sp. ATCC20888 orfA was 41% identical and 56% positive to the deduced amino acid sequence for *Shewanella olleyana* KS-AT.

At the amino acid level, the sequences with the greatest degree of homology to the *Shewanella japonica* ATCC BAA-316 ketoacyl synthase/acyl transferase (KS-AT) deduced amino acid sequence were: *Shewanella oneidensis* MR-1 "multi-domain β-ketoacyl synthase" (identity=67%; positives=79%); *Shewanella* sp. SCRC-2738 orf5 (identity=69%; positives=77%); and Moritella marina ORF8 (identity=56%; positives=70%). The *Schizochytrium* sp. ATCC20888 orfA was 41% identical and 55% positive to the deduced amino acid sequence for *Shewanella japonica* KS-AT.

At the amino acid level, the sequences with the greatest degree of homology to the *Shewanella olleyana* ACAM644 dehydrogenase (DH) deduced amino acid sequence were: *Shewanella* sp. SCRC-2738 orf7 (identity=77%; positives=86%); Photobacter profundum pfaC (identity=72%; positives=81%); and *Shewanella* oneidensis MR-1 "multi-domain β-ketoacyl synthase" (identity=75%; positives=83%). The *Schizochytrium* sp. ATCC20888 orfC was 26% identical and 42% positive to the deduced amino acid sequence for *Shewanella olleyana* DH.

At the amino acid level, the sequences with the greatest degree of homology to the *Shewanella japonica* ATCC BAA-316 dehydrogenase (DH) deduced amino acid sequence were: *Shewanella* sp. SCRC-2738 orf7 (identity=77%; positives=86%); Photobacter profundum pfaC (identity=73%; positives=83%) and *Shewanella* oneidensis MR-1 "multi-domain β-ketoacyl synthase" (identity=74%; positives=81%). The *Schizochytrium* sp. ATCC20888 orfC was 27% identical and 42% positive to the deduced amino acid sequence for *Shewanella japonica* DH.

Example 2

The following example demonstrates the generation, identification, sequencing and analysis of DNA clones encoding the complete PUFA PKS systems from *Shewanella japonica* and *Shewanella olleyana.*

*Shewanella japonica* and *Shewanella olleyana* recombinant libraries, consisting of large genomic DNA fragments (approximately 40 kB), were generated by standard methods in the cosmid vector Supercos-1 (Stratagene). The cosmid libraries were screened by standard colony hybridization procedures. The *Sh. olleyana* cosmid library was screened using two separate digoxigenin-labeled probes. Each probe contained a fragment of DNA homologous to a segment of EPA biosynthetic gene clusters described in Example 1 above and respectively represent both ends of the clusters. These probes were generated by PCR using *Sh. olleyana* DNA as a template and primers prRZ23 (SEQ ID NO:25) and prRZ24 (SEQ ID NO:26) for one probe and prRZ28 (SEQ ID NO:27) and prRZ29 (SEQ ID NO:28) for a second probe. Example 1 above describes these degenerate primers and the derived PCR products containing DNA fragments homologous to segments of EPA biosynthetic genes. *Sh. japonica* specific probes were generated in a similar manner and the cosmid library was screened. In all cases, strong hybridization of the individual probes to certain cosmids indicated clones containing DNA homologous to EPA biosynthetic gene clusters.

Clones with strong hybridization to both probes were then assayed for heterologous production of EPA in *E. coli*. Cells of individual isolates of *E. coli* cosmid clones were grown in 2 mL of LB broth overnight at 30° C. with 200 rpm shaking. 0.5 mL of this subculture was used to inoculate 25 mL of LB broth and the cells were grown at 20° C. for 20 hours. The cells were then harvested via centrifugation and dried by lyophilization. The dried cells were analyzed for fat content and fatty acid profile and content using standard gas chromatography procedures. No EPA was detected in fatty acids prepared from control cells of *E. coli* containing the empty Supercos-1 vector. *E. coli* strains containing certain cosmids from *S. japonica* and *S. olleyana* typically produced between 3-8% EPA of total fatty acids.

Cosmid 9A10 from *Sh. olleyana* and cosmid 3F3 from *Sh. japonica* were selected for total random sequencing. The cosmid clones were randomly fragmented and subcloned, and the resulting random clones were sequenced. The chromatograms were analyzed and assembled into contigs with the Phred, Phrap and Consed programs (Ewing, et al., Genome Res. 8(3):175-185 (1998); Ewing, et al., Genome Res. 8(3): 186-194 (1998); Gordon et al., Genome Res. 8(3): 195-202 (1998)). Each nucleotide base pair of the final contig was covered with at least a minimum aggregated Phred score of 40 (confidence level 99.995%).

The nucleotide sequence of the 39669 bp contig from cosmid 3F3 is shown as SEQ ID NO:1. The nucleotide sequence of the 38794 bp contig from cosmid 9A10 is shown as SEQ ID NO:7. The sequences of the various domains and proteins for the PUFA PKS gene clusters from *Shewanella japonica* (cosmid 3F3) and *Shewanella olleyana* (cosmid 9A10) are described in detail previously herein, and are represented in SEQ ID NOs:2-6 and 8-12, respectively.

Protein comparisons described herein were performed using standard BLAST analysis (BLAST parameters: Blastp, low complexity filter On, program—BLOSUM62, Gap cost—Existence: 11, Extension 1; (BLAST described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402)). Domain identification was performed using the Conserved Domain Database and Search Service (CD-Search), v2.01. The CD-Search is a public access program available through the public database for the National Center for Biotechnology Information, sponsored by the National Library of Medicine and the National Institutes of Health. The CD-Search contains protein domains from various databases. The CD-Search uses a BLAST algorithm to identify domains in a queried protein sequence (Marchler-Bauer A, Bryant S H. "CD-Search: protein domain annotations on the fly." Nucleic Acids Res. 32:W327-331 (2004)). Finally, Open Reading Frame (ORF) identification was aided by the use of the EasyGene 1.0 Server (Larsen T S, Krogh A. "EasyGene—a prokaryotic gene finder that ranks ORFs by statistical significance", BMC Bioinformatics 2003, 4:21) and GeneMark.hmm 2.1 (Lukashin A. and Borodovsky M., "GeneMark.hmm: new solutions for gene finding" Nucleic Acids Res., Vol. 26, No. 4, pp. 1107-1115. 1998). The default settings were used in the EasyGene analysis and *Vibrio cholerae* was used as the reference organism. The default settings were used with the GeneMark.hmm program and the Pseudonative.model as the setting for the model organism. These programs use a Hidden Markov Models algorithms to predict bacterial genes.

Table 1 shows an overview/analysis of ORFs from cosmid 3F3 from *Shewanella japonica*, including start and stop codon coordinates based on SEQ ID NO:1, total nucleotide length of each ORF, total amino acids for each predicted protein, calculated molecular weight of each predicted protein, highest homolog in a BLASTp query against the public GenBank database, GI accession number ("GenInfo Identifier" sequence identification number) of the most homologous entry in the GenBank database, and proposed function (if related to EPA production).

Table 2 shows an overview/analysis of ORFs from cosmid 9A10 from *Shewanella olleyana*, including start and stop codon coordinates based on SEQ ID NO:7, and the same additional information that was presented in Table 1 for *Shewanella japonica.*

Table 3 shows the percent identity of deduced proteins from EPA clusters of *Shewanella japonica* (cosmid 3F3) compared to *Shewanella olleyana* (cosmid 9A10) and also compared to proteins from EPA-producing organisms having the highest levels of identity in the public sequence database. Table 4 shows the same analysis as Table 3 with regard to nucleotide identity.

Table 5 shows the 23 nucleotides upstream from all of the annotated pfa ORFs with possible ribosome binding sites being underlined, as well as the alternative start codon and upstream nucleotides for ORFs that are annotated to start with the TTG start codon.

TABLE 1

ORF analysis of cosmid 3F3 from *Shewanella japonica*

| ORF | Start Codon | Stop Codon | total nt length | total AA | MW | Homology of deduced protein | Accession Number | Proposed function of deduced protein |
|---|---|---|---|---|---|---|---|---|
| orf1* | 1195 | 548 | 648 | 215 | 24561.35 | syd protein *Shewanella oneidensis* MR-1 | GI: 24373178 | |
| orf2 | 1255 | 2109 | 855 | 284 | 32825.47 | conserved hypothetical protein *Shewanella oneidensis* MR-1 | GI: 24373177 | |
| orf3 | 2196 | 2834 | 639 | 212 | 23779.30 | pseudouridylate synthase *Nostoc punctiforme* | GI: 23123676 | |
| orf4* | 3832 | 2873 | 960 | 319 | 36135.31 | LysR transcriptional regulator *Shewanella oneidensis* MR-1 | GI: 24373176 | |
| orf5 | 3962 | 5956 | 1995 | 664 | 73468.40 | metallo-beta-lactamase superfamily protein *Shewanella oneidensis* MR-1 | GI: 24373175 | |
| pfaE* | 7061 | 6150 | 912 | 303 | 34678.40 | orf2 *Shewanella* sp. SCRC-2738 | GI: 2529415 | phosphopantetheinyl transferase |
| orf6* | 9249 | 7222 | 2028 | 675 | 73367.16 | Translation elongation factor *Vibrio vulnificus* CMCP6 | GI: 27358908 | |

TABLE 1-continued

ORF analysis of cosmid 3F3 from *Shewanella japonica*

| ORF | Start Codon | Stop Codon | total nt length | total AA | MW | Homology of deduced protein | Accession Number | Proposed function of deduced protein |
|---|---|---|---|---|---|---|---|---|
| orf7 | 9622 | 10494 | 873 | 290 | 32540.64 | putative transcriptional regulator *Shewanella oneidensis* MR-1 | GI: 24373172 | |
| pfaA | 10491 | 18854 | 8364 | 2787 | 294907.67 | PfaA polyunsaturated fatty acid synthase *Photobacterium profundum* | GI: 46913082 | EPA synthase |
| pfaB | 18851 | 21130 | 2280 | 759 | 82727.25 | PfaB polyunsaturated fatty acid synthase *Photobacterium profundum* | GI: 46913081 | EPA synthase |
| pfaC | 21127 | 27186 | 6060 | 2019 | 219255.74 | PfaC polyunsaturated fatty acid synthase *Photobacterium profundum* | GI: 15488033 | EPA synthase |
| pfaD | 27197 | 28825 | 1692 | 542 | 59116.36 | orf8 *Shewanella* sp. SCRC-2738 | GI: 2529421 | EPA synthase |
| orf8 | 29445 | 30926 | 1482 | 493 | 56478.03 | putative cellulosomal protein *Clostridium thermocellum* | GI: 7208813 | |
| orf9 | 31105 | 32712 | 1608 | 535 | 59618.32 | methyl-accepting chemotaxis protein *Shewanella oneidensis* MR-1 | GI: 24374914 | |
| orf10 | 32988 | 33845 | 858 | 285 | 32119.88 | Glutathione S-transferase *Vibrio vulnificus* CMCP6 | GI: 27359215 | |

*on the reverse complementary strand

TABLE 2

ORF analysis of cosmid 9A10 from *Shewanella olleyana*

| ORF | Start Codon | Stop Codon | total nt length | total AA | MW | Homology of deduced protein | Accession Number | Proposed function of deduced protein |
|---|---|---|---|---|---|---|---|---|
| orf1* | 4160 | 3531 | 630 | 209 | 23724.40 | acetyltransferase, GNAT family *Shewanella oneidensis* MR-1 | GI: 24373183 | |
| orf2* | 4992 | 4606 | 387 | 128 | 14034.86 | hypothetical protein *Shewanella oneidensis* MR-1 | GI: 24373181 | |
| orf3 | 5187 | 5522 | 336 | 111 | 12178.79 | hypothetical protein *Shewanella oneidensis* MR-1 | GI: 24373180 | |
| orf4 | 5644 | 6417 | 774 | 257 | 29674.73 | hypothetical protein *Shewanella oneidensis* MR-1 | GI: 24373179 | |
| orf5* | 7148 | 6495 | 654 | 217 | 24733.33 | syd protein *Shewanella oneidensis* MR-1 | GI: 24373178 | |
| orf6 | 7208 | 8062 | 855 | 284 | 32749.29 | hypothetical protein *Shewanella oneidensis* MR-1 | GI: 24373177 | |
| orf7 | 8841 | 8131 | 711 | 236 | 26178.32 | putative phosphatase *Vibrio parahaemolyticus* | GI: 28899965 | |
| orf8 | 9167 | 9808 | 642 | 213 | 23849.14 | pseudouridylate synthase *Nostoc punctiforme* | GI: 23123676 | |
| orf9* | 10797 | 9805 | 993 | 330 | 37337.29 | LysR transcriptional regulator *Shewanella oneidensis* MR-1 | GI: 24373176 | |
| orf10 | 10968 | 12962 | 1995 | 664 | 72982.72 | metallo-beta-lactamase superfamily protein *Shewanella oneidensis* MR-1 | GI: 24373175 | |
| pfaE* | 13899 | 13027 | 873 | 290 | 32864.30 | orf2 *Shewanella* sp. SCRC-2738 | GI: 2529415 | phosphopantetheinyl transferase |
| orf11* | 16195 | 14156 | 2040 | 679 | 74070.34 | Translation elongation factor *Vibrio vulnificus* CMCP6 | GI: 27358908 | |
| orf12 | 16568 | 17440 | 873 | 290 | 32741.82 | putative transcriptional regulator *Shewanella oneidensis* MR-1 | GI: 24373172 | |
| pfaA | 17437 | 25743 | 8307 | 2768 | 293577.27 | PfaA polyunsaturated fatty acid synthase *Photobacterium profundum* | GI: 46913082 | EPA synthase |
| pfaB | 25740 | 27971 | 2232 | 743 | 80446.82 | PfaB polyunsaturated fatty acid synthase *Photobacterium profundum* | GI: 46913081 | EPA synthase |
| pfaC | 27968 | 34030 | 6063 | 2020 | 218810.57 | PfaC polyunsaturated fatty acid synthase *Photobacterium profundum* | GI: 15488033 | EPA synthase |
| pfaD | 34041 | 35669 | 1629 | 542 | 59261.59 | orf8 *Shewanella* sp. SCRC-2738 | GI: 2529421 | EPA synthase |

*on the reverse complementary strand

TABLE 3

| Amino Acid Percent Identity | | |
|---|---|---|
| | *Shewanella japonica* (3F3) | *Shewanella olleyana* (9A10) |
| PfaA | | |
| *Shewanella japonica* (3F3) | | 87.7 |
| *Shewanella olleyana* (9A10) | 87.7 | |
| *Shewanella* sp. SCRC-2738 Orf5 | 63 | 63.4 |
| *Photobacterium profundum* S9 PfaA | 60.9 | 62.2 |
| *Moritella marina* Orf8 | 41.6 | 42.9 |
| PfaB | | |
| *Shewanella japonica* (3F3) | | 70.3 |
| *Shewanella olleyana* (9A10) | 70.3 | |
| *Shewanella* sp. SCRC-2738 Orf6 | 39.8 | 38.4 |
| *Photobacterium profundum* S9 PfaB | 39 | 39.6 |
| *Moritella marina* Orf9 | 19 | 18.4 |
| PfaC | | |
| *Shewanella japonica* (3F3) | | 85.7 |
| *Shewanella olleyana* (9A10) | 85.7 | |
| *Shewanella* sp. SCRC-2738 Orf7 | 65.1 | 64.8 |
| *Photobacterium profundum* S9 PfaC | 64.6 | 64.6 |
| *Moritella marina* Orf10 | 47.3 | 47.1 |
| PfaD | | |
| *Shewanella japonica* (3F3) | | 98.2 |
| *Shewanella olleyana* (9A10) | 98.2 | |
| *Shewanella* sp. SCRC-2738 Orf8 | 84.2 | 84 |
| *Photobacterium profundum* S9 PfaD | 93.8 | 64.6 |
| *Moritella marina* Orf11 | 63 | 62.6 |
| PfaE | | |
| *Shewanella japonica* (3F3) | | 61.2 |
| *Shewanella olleyana* (9A10) | 61.2 | |
| *Shewanella* sp. SCRC-2738 Orf2 | 36.7 | 38 |
| *Anabaena* sp. PCC 7120 HetI | 22.6 | 24.8 |
| *Bacillus subtilis* Sfp | 20.1 | 20.7 |

TABLE 4

| Nucleic Acid Percent Identity | | |
|---|---|---|
| | *Shewanella japonica* (3F3) | *Shewanella olleyana* (9A10) |
| pfaA | | |
| *Shewanella japonica* (3F3) | | 83.1 |
| *Shewanella olleyana* (9A10) | 83.1 | |
| *Shewanella* sp. SCRC-2738 orf5 | 65.5 | 65.5 |
| *Photobacterium profundum* S9 pfaA | 63.5 | 64.4 |
| *Moritella marina* orf8 | 56 | 56.2 |
| pfaB | | |
| *Shewanella japonica* (3F3) | | 70.4 |
| *Shewanella olleyana* (9A10) | 70.4 | |
| *Shewanella* sp. SCRC-2738 orf6 | 54.7 | 54.5 |
| *Photobacterium profundum* S9 pfaB | 53.4 | 52.6 |
| *Moritella marina* orf9 | 42.2 | 40.6 |
| pfaC | | |
| *Shewanella japonica* (3F3) | | 79.6 |
| *Shewanella olleyana* (9A10) | 79.6 | |
| *Shewanella* sp. SCRC-2738 orf7 | 66.2 | 67.2 |
| *Photobacterium profundum* S9 pfaC | 66 | 66.7 |
| *Moritella marina* orf10 | 58.3 | 58.8 |
| pfaD | | |
| *Shewanella japonica* (3F3) | | 89.5 |
| *Shewanella olleyana* (9A10) | 89.5 | |
| *Shewanella* sp. SCRC-2738 orf8 | 77.4 | 77.8 |
| *Photobacterium profundum* S9 pfaD | 75.9 | 76.0 |
| *Moritella marina* orf11 | 63.5 | 62.9 |
| pfaE | | |
| *Shewanella japonica* (3F3) | | 65 |
| *Shewanella olleyana* (9A10) | 65 | |
| *Shewanella* sp. SCRC-2738 orf2 | 43 | 44.4 |
| *Anabaena* sp. PCC 7120 hetI | 43.1 | 38.6 |
| *Bacillus subtilis* sfp | 34.6 | 32.9 |

TABLE 5

Predicted start sites of ORFs from EPA biosynthesis clusters (start codons shown in bold) Possible ribosome binding sites are underlined

| Sequence | Start | ORF | SEQ ID |
|---|---|---|---|
| ALL pfa ORFs | | | |
| 3F3 | | | |
| CTGAACACTGGAGACTCAAA | **ATG** | pfaA | SEQ ID NO:33 |
| GCTGACTTGCAGGAGTCTGT | **GTG** | pfaB | SEQ ID NO:34 |
| CAATTAGAAGGAGAACAATC | **TTG** | pfaC | SEQ ID NO:35 |
| AGAGGCATAAAGGAATAATA | **ATG** | pfaD | SEQ ID NO:36 |
| GCGACCTAGAACAAGCGACA | **ATG** | pfaE | SEQ ID NO:37 |
| 9A10 | | | |
| CTGAACACTGGAGACTCAAA | **ATG** | pfaA | SEQ ID NO:38 |
| GCTGATTTGCAGGAGTCTGT | **GTG** | pfaB | SEQ ID NO:39 |
| CAATTAGAAGGAGAACAATC | **TTG** | pfaC | SEQ ID NO:40 |
| AGAGGCATAAAGGAATAATA | **ATG** | pfaD | SEQ ID NO:41 |
| CAATTTAGCCTGAGCCTAGT | **TTG** | pfaE | SEQ ID NO:42 |
| pfaC Alternate Start Comparisons | | | |
| 3F3 | | | |
| CAATTAGAAGGAGAACAATC | **TTG** | pfaC | |
| TAAATCGCACTGGTATTGTC | **ATG** | pfaC alternate #1 | SEQ ID NO:43 |
| AAGCACTCAATGATGCTGGT | **GTG** | pfaC alternate #2 | SEQ ID NO:44 |

TABLE 5-continued

Predicted start sites of ORFs from EPA biosynthesis clusters (start codons shown in bold) Possible ribosome binding sites are underlined

```
pfaC alternate #1 starts at nucleotide 21514 of SEQ ID NO:1
This is 387 nucleotides downstream of annotated pfaC start

pfaC alternate #2 starts at nucleotide 21460 of SEQ ID NO:1
This is 333 nucleotides downstream of annotated pfaC start

9A10
CAATTAGAAGGAGAACAATC TTG   pfaC
TAAACCGCACCGGTATTGTC ATG   pfaC alternate #1   SEQ ID NO:45
ACCCAGCTGACTATCAAGGT GTG   pfaC alternate #2   SEQ ID NO:46

pfaC alternate #1 starts at nucleotide 28370 of SEQ ID NO:7
This is 402 nucleotides downstream of annotated pfaC start

pfaC alternate #2 starts at nucleotide 28151 of SEQ ID NO:7
This is 183 nucleotides downstream of annotated pfaC start

pfaE Alternate Start Comparisons

9 A 10
CAATTTAGCCTGAGCCTAGT TTG   pfaE
ATGAATCGACTGCGTCTATT GTG   pfaE alternate #1   SEQ ID NO:47
CATCTAGAGAACAAGGTTTA ATG   pfaE alternate #2   SEQ ID NO:48

pfaE alternate #1 starts at nucleotide 13821 of SEQ ID NO:7
This is 78 nucleotides upstream of the annotated pfaE start

pfaE alternate #2 starts at nucleotide 13743 of SEQ ID NO:7
This is 156 nucleotides upstream of the annotated pfaE start
```

Example 3

The following example demonstrates that *Schizochytrium* Orfs A, B and C encode a functional DHA/DPA synthesis enzyme via functional expression in *E. coli.*

General Preparation of *E. coli* Transformants

The three genes encoding the *Schizochytrium* PUFA PKS system that produce DHA and DPA (Orfs A, B & C; SEQ ID NO:13, SEQ ID NO:15 and SEQ ID NO:17, respectively) were cloned into a single *E. coli* expression vector (derived from pET21c (Novagen)). The genes are transcribed as a single message (by the T7 RNA-polymerase), and a ribosome-binding site cloned in front of each of the genes initiates translation. Modification of the Orf B coding sequence was needed to obtain production of a full-length Orf B protein in *E. coli* (see below). An accessory gene, encoding a PPTase (see below) was cloned into a second plasmid (derived from pACYC184, New England Biolabs).

The Orf B gene is predicted to encode a protein with a mass of ~224 kDa. Initial attempts at expression of the gene in *E. coli* resulted in accumulation of a protein with an apparent molecular mass of ~165 kDa (as judged by comparison to proteins of known mass during SDS-PAGE). Examination of the Orf B nucleotide sequence revealed a region containing 15 sequential serine codons—all of them being the TCT codon. The genetic code contains 6 different serine codons, and three of these are used frequently in *E. coli*. The present inventors used four overlapping oligonucleotides in combination with a polymerase chain reaction protocol to resynthesize a small portion of the Orf B gene (a ~195 base pair, BspHI to SacII restriction enzyme fragment) that contained the serine codon repeat region. In the synthetic Orf B fragment, a random mixture of the 3 serine codons commonly used by *E. coli* was used, and some other potentially problematic codons were changed as well (i.e., other codons rarely used by *E. coli*). The BspHI to SacII fragment present in the original Orf B was replaced by the resynthesized fragment (to yield Orf B*) and the modified gene was cloned into the relevant expression vectors. The modified OrfB* still encodes the amino acid sequence of SEQ ID NO:16. Expression of the modified Orf B* clone in *E. coli* resulted in the appearance of a ~224 kDa protein, indicating that the full-length product of OrfB was produced. The sequence of the resynthesized Orf B* BspHI to SacII fragment is represented herein as SEQ ID NO:29. Referring to SEQ ID NO:29, the nucleotide sequence of the resynthesized BspHI to SacII region of Orf B is shown. The BspHI restriction site and the SacII restriction site are identified. The BspHI site starts at nucleotide 4415 of the Orf B CDS (SEQ ID NO:15) (note: there are a total of three BspHI sites in the Orf B CDS, while the SacII site is unique).

The ACP domains of the Orf A protein (SEQ ID NO:14 in *Schizochytrium*) must be activated by addition of phosphopantetheine group in order to function. The enzymes that catalyze this general type of reaction are called phosphopantetheine transferases (PPTases). *E. coli* contains two endogenous PPTases, but it was anticipated that they would not recognize the Orf A ACP domains from *Schizochytrium*. This was confirmed by expressing Orfs A, B* (see above) and C in *E. coli* without an additional PPTase. In this transformant, no DHA production was detected. The inventors tested two heterologous PPTases in the *E. coli* PUFA PKS expression system: (1) sfp (derived from *Bacillus subtilis*) and (2) Het I (from the cyanobacterium Nostoc strain 7120).

The sfp PPTase has been well characterized and is widely used due to its ability to recognize a broad range of substrates. Based on published sequence information (Nakana, et al., 1992, *Molecular and General Genetics* 232:313-321), an expression vector for sfp was built by cloning the coding region, along with defined up- and downstream flanking DNA sequences, into a pACYC-184 cloning vector. The oligonucleotides:

```
CGGGGTACCCGGGAGCCGCCTTGGCTTTGT
(forward; SEQ ID NO:30);
and

AAACTGCAGCCCGGGTCCAGCTGGCAGGCACCCTG
(reverse; SEQ ID NO:31),
```

were used to amplify the region of interest from genomic *B. subtilus* DNA. Convenient restriction enzyme sites were included in the oligonucleotides to facilitate cloning in an intermediate, high copy number vector and finally into the EcoRV site of pACYC184 to create the plasmid: pBR301. Examination of extracts of *E. coli* transformed with this plasmid revealed the presence of a novel protein with the mobility expected for sfp. Co-expression of the sfp construct in cells expressing the Orf A, B*, C proteins, under certain conditions, resulted in DHA production. This experiment demonstrated that sfp was able to activate the *Schizochytrium* Orf A ACP domains. In addition, the regulatory elements associated with the sfp gene were used to create an expression cassette into which other genes could be inserted. Specifically, the sfp coding region (along with three nucleotides immediately upstream of the ATG) in pBR301 was replaced with a 53 base pair section of DNA designed so that it contains several unique (for this construct) restriction enzyme sites. The initial restriction enzyme site in this region is NdeI. The ATG sequence embedded in this site is utilized as the initiation methionine codon for introduced genes. The additional restriction sites (Bg1LL, NotI, SmaI, Pme1I, HindIII, SpeI and XhoI) were included to facilitate the cloning process. The functionality of this expression vector cassette was tested by using PCR to generate a version of sfp with a NdeI site at the 5' end and an XhoI site ate the 3' end. This fragment was cloned into the expression cassette and transferred into *E. coli* along with the Orf A, B* and C expression vector. Under appropriate conditions, these cells accumulated DHA, demonstrating that a functional sfp had been produced.

To the present inventors' knowledge, Het I had not been tested previously in a heterologous situation. Het I is present in a cluster of genes in Nostoc known to be responsible for the synthesis of long chain hydroxy-fatty acids that are a component of a glyco-lipid layer present in heterocysts of that organism. The present inventors, without being bound by theory, believe that Het I activates the ACP domains of a protein, Hg1 E, present in that cluster. The two ACP domains of Hg1 E have a high degree of sequence homology to the ACP domains found in *Schizochytrium* Orf A. SEQ ID NO:32 represents the amino acid sequence of the Nostoc Het I protein. The endogenous start codon of Het I has not been identified (there is no methionine present in the putative protein). There are several potential alternative start codons (e.g., TTG and ATT) near the 5' end of the open reading frame. No methionine codons (ATG) are present in the sequence. A Het I expression construct was made by using PCR to replace the furthest 5' potential alternative start codon (TTG) with a methionine codon (ATG, as part of the above described NdeI restriction enzyme recognition site), and introducing an XhoI site at the 3' end of the coding sequence. The modified HetI coding sequence was then inserted into the NdeI and XhoI sites of the pACYC184 vector construct containing the sfp regulatory elements. Expression of this Het I construct in *E. coli* resulted in the appearance of a new protein of the size expected from the sequence data. Co-expression of Het I with *Schizochytrium* Orfs A, B*, C in *E. coli* under several conditions resulted in the accumulation of DHA and DPA in those cells. In all of the experiments in which sfp and Het I were compared, more DHA and DPA accumulated in the cells containing the Het I construct than in cells containing the sfp construct.

Production of DHA and DPA in *E. coli* Transformants

The two plasmids encoding: (1) the *Schizochytrium* PUFA PKS genes (Orfs A, B* and C) and (2) the PPTase (from sfp or from Het I) were transformed into *E. coli* strain BL21 which contains an inducible T7 RNA polymerase gene. Synthesis of the *Schizochytrium* proteins was induced by addition of IPTG to the medium, while PPTase expression was controlled by a separate regulatory element (see above). Cells were grown under various defined conditions and using either of the two heterologous PPTase genes. The cells were harvested and the fatty acids were converted to methyl-esters (FAME) and analyzed using gas-liquid chromatography.

Under several conditions, DHA and DPA were detected in *E. coli* cells expressing the *Schizochytrium* PUFA PKS genes, plus either of the two heterologous PPTases (data not shown). No DHA or DPA was detected in FAMEs prepared from control cells (i.e., cells transformed with a plasmid lacking one of the Orfs). The ratio of DHA to DPA observed in *E. coli* approximates that of the endogenous DHA and DPA production observed in *Schizochytrium*. The highest level of PUFA (DHA plus DPA), representing ~17% of the total FAME, was found in cells grown at 32° C. in 765 medium (recipe available from the American Type Culture Collection) supplemented with 10% (by weight) glycerol. PUFA accumulation was also observed when cells were grown in Luria Broth supplemented with 5 or 10% glycerol, and when grown at 20° C. Selection for the presence of the respective plasmids was maintained by inclusion of the appropriate antibiotics during the growth, and IPTG (to a final concentration of 0.5 mM) was used to induce expression of Orfs A, B* and C.

Example 4

The following example demonstrates that genes encoding the *Schizochytrium* PUFA PKS enzyme complex can be selectively inactivated (knocked out), and that it is a lethal phenotype unless the medium is supplemented with polyunsaturated fatty acids.

Homologous recombination has been demonstrated in *Schizochytrium* (see copending U.S. patent application Ser. No. 10/124,807, incorporated herein by reference in its entirety). A plasmid designed to inactivate *Schizochytrium* Orf A (SEQ ID NO:13) was made by inserting a Zeocin™ resistance marker into the Sma I site of a clone containing the Orf A coding sequence. The Zeocin™ resistance marker was obtained from the plasmid pMON50000—expression of the Zeocin™ resistance gene is driven by a *Schizochytrium* derived tubulin promoter element (see U.S. patent application Ser. No. 10/124,807, ibid.). The knock-out construct thus consists of: 5' *Schizochytrium* Orf A coding sequence, the tub-Zeocin™ resistance element and 3' *Schizochytrium* Orf A coding sequence, all cloned into pBluescript II SK (+) vector (Stratagene).

The plasmid was introduced into *Schizochytrium* cells by particle bombardment and transformants were selected on plates containing Zeocin™ and supplemented with polyunsaturated fatty acids (PUFA) (see Example 5). Colonies that grew on the Zeocin™ plus PUFA plates were tested for ability to grow on plates without the PUFA supplementation and several were found that required the PUFA. These PUFA auxotrophs are putative Orf A knockouts. Northern blot analysis of RNA extracted from several of these mutants confirmed that a full-length Orf A message was not produced in these mutants.

These experiments demonstrate that a *Schizochytrium* gene (e.g., Orf A) can be inactivated via homologous recombination, that inactivation of Orf A results in a lethal phenotype, and that those mutants can be rescued by supplementation of the media with PUFA.

Similar sets of experiments directed to the inactivation of *Schizochytrium* Orf B (SEQ ID NO:15) and Orf C (SEQ ID NO:17) have yielded similar results. That is, Orf B and Orf C can be individually inactivated by homologous recombination and those cells require PUFA supplementation for growth.

Example 5

The following example shows that PUFA auxotrophs can be maintained on medium supplemented with EPA, demonstrating that EPA can substitute for DHA in *Schizochytrium*.

As indicated in Example 4, *Schizochytrium* cells in which the PUFA PKS complex has been inactivated required supplementation with PUFA to survive. Aside from demonstrating that *Schizochytrium* is dependent on the products of this system for growth, this experimental system permits the testing of various fatty acids for their ability to rescue the mutants. It was discovered that the mutant cells (in which any of the three genes have been inactivated) grew as well on media supplemented with EPA as they did on media supplemented with DHA. This result indicates that, if the endogenous PUFA PKS complex which produces DHA were replaced with one whose product was EPA, the cells would be viable. Additionally, these mutant cells could be rescued by supplementation with either ARA or GLA, demonstrating the feasibility of producing genetically modified *Schizochytrium* that produce these products. It is noted that a preferred method for supplementation with PUFAs involves combining the free fatty acids with partially methylated beta-cyclodextrin prior to addition of the PUFAs to the medium.

Example 6

The following example shows that inactivated PUFA genes can be replaced at the same site with active forms of the genes in order to restore PUFA synthesis.

Double homologous recombination at the acetolactate synthase gene site has been demonstrated in *Schizochytrium* (see U.S. patent application Ser. No. 10/124,807, supra). The present inventors tested this concept for replacement of the *Schizochytrium* PUFA PKS genes by transformation of a *Schizochytrium* Orf A knockout strain (described in Example 3) with a full-length *Schizochytrium* Orf A genomic clone. The transformants were selected by their ability to grow on media without supplemental PUFAs. These PUFA prototrophs were then tested for resistance to Zeocin™ and several were found that were sensitive to the antibiotic. These results indicate that the introduced *Schizochytrium* Orf A has replaced the Zeocin™ resistance gene in the knockout strain via double homologous recombination. This experiment demonstrates the proof of concept for gene replacement within the PUFA PKS genes. Similar experiments for *Schizochytrium* Orf B and Orf C knock-outs have given identical results.

Example 7

This example shows that all or some portions of the *Thraustochytrium* 23B PUFA PKS genes can function in *Schizochytrium*.

As described in U.S. patent application Ser. No. 10/124,800 (supra), the DHA-producing protist *Thraustochytrium* 23B (Th. 23B) has been shown to contain orfA, orfb, and orfC homologs. Complete genomic clones of the three Th. 23B genes were used to transform the Zeocin™-resistant *Schizochytrium* strains containing the cognate orf "knock-out" (see Example 4). Direct selection for complemented transformants was carried out in the absence of PUFA supplementation. By this method, it was shown that the Th. 23B orfA and orfC genes could complement the *Schizochytrium* orfA and orfC knock-out strains, respectively, to PUFA prototrophy. Complemented transformants were found that either retained or lost Zeocin™ resistance (the marker inserted into the *Schizochytrium* genes thereby defining the knock-outs). The Zeocin™-resistant complemented transformants are likely to have arisen by a single cross-over integration of the entire *Thraustochytrium* gene into the *Schizochytrium* genome outside of the respective orf region. This result suggests that the entire *Thraustochytrium* gene is functioning in *Schizochytrium*. The Zeocin™-sensitive complemented transformants are likely to have arisen by double cross-over events in which portions (or conceivably all) of the *Thraustochytrium* genes functionally replaced the cognate regions of the *Schizochytrium* genes that had contained the disruptive Zeocin™ resistance marker. This result suggests that a fraction of the *Thraustochytrium* gene is functioning in *Schizochytrium*.

Example 8

In this example, the entire *Schizochytrium* orfC coding sequence is completely and exactly replaced by the *Thraustochytrium* 23B orfC coding sequence resulting in a PUFA profile shifted toward that of *Thraustochytrium*.

To delete the *Schizochytrium* orfC coding sequence, approximately 2 kb of DNA immediately upstream (up to but not including the ATG start codon) and immediately downstream (beginning just after the TAA stop codon) were cloned around the Zeocin™ resistance marker. The upstream and downstream regions provide homology for double crossover recombination effectively replacing the orfC coding sequence with the marker. Transformants are selected for Zeocin™ resistance in the presence of supplemental PUFA, screened for PUFA auxotrophy, and characterized by PCR and Southern blot analysis. Similarly, a plasmid was constructed in which the same upstream and downstream sequences of the *Schizochytrium* orfC gene region were cloned around the Th. 23B orf C coding sequence (SEQ ID NO:23). Transformation of this plasmid into the Zeocin™ resistant PUFA auxotroph described above was carried out with selection for PUFA prototrophy, thus relying on the Th. 23B orfC gene to function correctly in *Schizochytrium* and complement the PUFA auxotrophy. Subsequent screening for Zeocin™ sensitive transformants identified those likely to have arisen from a replacement of the Zeocin™ resistance marker with the Th. 23B orfC gene. The DHA:DPA ratio in these orfC replacement strains was on average 8.3 versus a normal ("wild type") value of 2.3. This higher ratio approximates the value of 10 for *Thraustochytrium* 23B under these growth conditions. Therefore, it is shown that the PUFA profile of *Schizochytrium* can be manipulated by substituting components of the PUFA synthase enzyme complex.

More specifically, the first pair of plasmids captures the regions immediately "upstream" and "downstream" of the *Schizochytrium* orfC gene and was used to construct both the orfC deletion vector as well as the Th. 23B replacement vector.

Primers prRZ15 (SEQ ID NO:49) and prRZ16 (SEQ ID NO:50) were used to amplify a 2000 bp fragment upstream of the orfC coding region from a clone of the *Schizochytrium* orfC region. Primer prRZ15 incorporates a KpnI site at the 5-prime end of the fragment and prRZ16 contains homology to *Schizochytrium* sequence up to but not including the ATG start codon and incorporates a BamHI site at the 3-prime end of the fragment. The PCR product was cloned into pCR-Blunt II (Invitrogen) resulting in plasmid pREZ21. In a similar manner, primers prRZ17 (SEQ ID NO:51) and prRZ18 (SEQ ID NO:52) were used to amplify a 1991 bp fragment immediately downstream of the orfC coding region (not containing the TAA stop codon) but incorporating a BamHI site at the 5-prime end and a XbaI site at the 3-prime end. This PCR fragment was cloned into pCR-Blunt II (Invitrogen) to create pREZ18. In a three-component ligation, the upstream region from pREZ21 (as a KpnI-BamHI fragment) and the downstream region from pREZ18 (as a BamHI-XbaI fragment) were cloned into the KpnI-XbaI site of pBlueScriptII SK(+) to yield pREZ22. The Zeocin™ resistance marker from pTUBZEO11-2 (a.k.a. pMON50000; see U.S. patent application Ser. No. 10/124,807, supra) as an 1122 bp BamHI fragment was inserted into the BamHI site of pREZ22 to produce pREZ23A and pREZ23B (containing the Zeocin™ resistance marker in either orientation). The pREZ23 plasmids were then used to create the precise deletion of the orfC coding region by particle bombardment transformation as described above. A strain with the desired structure is named B32-Z1.

To develop the plasmid for insertion of the Th. 23B orfC gene, intermediate constructs containing the precise junctions between 1) the *Schizochytrium* upstream region and the 5-prime end of the Th. 23B orfC coding region and 2) the 3-prime end of the Th. 23B orfC coding region and the *Schizochytrium* downstream region are first produced. Then, the internal section of the Th. 23B orfC coding region is introduced.

Primers prRZ29a (SEQ ID NO:53) and prRZ30 (SEQ ID NO:54) are used to amplify approximately 100 bp immediately upstream of the *Schizochytrium* orfC coding sequence. Primer prRZ29a includes the SpeI restriction site approximately 95 bp upstream of the *Schizochytrium* orfC ATG start codon, and prRZ30 contains homology to 19 bp immediately upstream of the *Schizochytrium* orfC ATG start codon and 15 bp homologous to the start of the Th. 23B orfC coding region (including the start ATG). Separately, an approximately 450 bp PCR product is generated from the 5-prime end of the Th. 23B orfC coding region using the cloned Th. 23B gene as a template. Primer prRZ31 contains 15 bp of the *Schizochytrium* orfC coding sequence immediately upstream of the start ATG and homology to 17 bp at the start of the Th. 23B orfC coding region, and primer prRZ32 incorporates the NruI site located at approximately 450 bp downstream of the Th. 23B orfC ATG start codon and further includes an artificial SwaI restriction site just downstream of the NruI site. These two PCR products therefore have about 30 bp of overlapping homology with each other at the start ATG site essentially comprising the sequences of prRZ30 (SEQ ID NO:54) and prRZ31 (SEQ ID NO:55). A second round of PCR using a mix of the two first-round PCR products (prRZ29a (SEQ ID NO:53) X prRZ30 (SEQ ID NO:54); ca. 100 bp; prRZ31 (SEQ ID NO:55) X prRZ32 (SEQ ID NO:56); ca. 450 bp) as template and the outside primers prRZ29a (SEQ ID NO:53) and prRZ32 (SEQ ID NO:56) resulted in an approximately 520 bp product containing the "perfect stitch" between the upstream *Schizochytrium* orfC region and the start of the Th. 23B orf C coding region. This PCR product was cloned into plasmid pCR-Blunt II to create pREZ28, and the sequence of the insert was confirmed.

Primers prRZ33 (SEQ ID NO:57) and prRZ34 (SEQ ID NO:58) were used for PCR to generate a fragment of approximately 65 bp at the 3-prime end of the Th. 23B orf C coding region using the cloned Th. 23B gene as a template. The upstream end of this fragment (from prRZ33) contains an artificial SwaI restriction site and encompasses the SphI restriction site at approximately 60 bp upstream of the Th. 23B orfC TAA termination codon. The downstream end of this fragment (from prRZ34) contains 16 bp at the 3-prime end of the Th. 23B orf C coding region and 18 bp with homology to *Schizochytrium* sequences immediately downstream from the orfC coding region (including the termination codon). Primers prRZ35 (SEQ ID NO:59) and prRZ36 (SEQ ID NO:60) were used to generate a fragment of approximately 250 bp homologous to *Schizochytrium* DNA immediately downstream of the orfC coding region. The upstream end of this PCR fragment (from prRZ35) contained 15 bp homologous to the end of the Th. 23B orf C coding region (counting the TAA stop codon), and the downstream end contained the SalI restriction site about 240 bp downstream of the *Schizochytrium* stop codon. A second round of PCR using a mix of the two first-round PCR products (prRZ33 (SEQ ID NO:57) X prRZ34 (SEQ ID NO:58); ca. 65 bp; prRZ35 (SEQ ID NO:59) X prRZ36 (SEQ ID NO:60); ca. 250 bp) as template and the outside primers prRZ33 (SEQ ID NO:57) and prRZ36 (SEQ ID NO:60) resulted in an approximately 310 bp product containing the "perfect stitch" between the end of the *Thraustochytrium* 23B orfC coding region and the region of *Schizochytrium* DNA immediately downstream of the orfC coding region. This PCR product was cloned into plasmid pCR-Blunt II to create pREZ29, and the sequence of the insert was confirmed.

Next, the upstream and downstream "perfect stitch" regions were combined into pREZ22 (see above). In a three component ligation, the SpeI/SwaI fragment from pREZ28 and the SwaI/SalI fragment of pREZ29 were cloned into the SpeI/SalI sites of pREZ22 to create pREZ32. Lastly, the internal bulk of the *Thraustochytrium* 23B orfC coding region was cloned into pREZ32 as a NruI/SphI fragment to create pREZ33. This plasmid was then used to transform the orfC knock-out strain B32-Z1 with selection for PUFA prototrophy.

Each publication cited or discussed herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule comprising a nucleic acid sequence encoding an amino acid sequence that is at least 95% identical to amino acid positions 2264-2398 of SEQ ID NO:2 or that is an enzymatically active fragment of amino acid positions 2264-2398 of SEQ ID NO:2, wherein said amino acid sequence has β-ketoacyl-ACP reductase (KR) activity.

2. The isolated nucleic acid molecule of claim 1, comprising a nucleic acid sequence encoding an amino acid sequence that is at least 95% identical to amino acid positions 2264-2398 of SEQ ID NO:2, wherein said amino acid sequence has β-ketoacyl-ACP reductase (KR) activity.

3. The isolated nucleic acid molecule of claim 1, consisting of a nucleic acid sequence encoding an amino acid sequence that is at least 95% identical to amino acid positions 2264-2398 of SEQ ID NO:2, wherein said amino acid sequence has β-ketoacyl-ACP reductase (KR) activity.

4. The isolated nucleic acid molecule of claim 1, comprising a nucleic acid sequence encoding an amino acid sequence that is at least 96% identical to amino acid positions 2264-2398 of SEQ ID NO:2, wherein said amino acid sequence has β-ketoacyl-ACP reductase (KR) activity.

5. The isolated nucleic acid molecule of claim 1, consisting of a nucleic acid sequence encoding an amino acid sequence that is at least 96% identical to amino acid positions 2264-2398 of SEQ ID NO:2, wherein said amino acid sequence has β-ketoacyl-ACP reductase (KR) activity.

6. The isolated nucleic acid molecule of claim 1, comprising a nucleic acid sequence encoding an amino acid sequence that is at least 97% identical to amino acid positions 2264-2398 of SEQ ID NO:2, wherein said amino acid sequence has β-ketoacyl-ACP reductase (KR) activity.

7. The isolated nucleic acid molecule of claim 1, consisting of a nucleic acid sequence encoding an amino acid sequence that is at least 97% identical to amino acid positions 2264-

2398 of SEQ ID NO:2, wherein said amino acid sequence has β-ketoacyl-ACP reductase (KR) activity.

8. The isolated nucleic acid molecule of claim 1, comprising a nucleic acid sequence encoding an amino acid sequence that is at least 98% identical to amino acid positions 2264-2398 of SEQ ID NO:2, wherein said amino acid sequence has β-ketoacyl-ACP reductase (KR) activity.

9. The isolated nucleic acid molecule of claim 1, consisting of a nucleic acid sequence encoding an amino acid sequence that is at least 98% identical to amino acid positions 2264-2398 of SEQ ID NO:2, wherein said amino acid sequence has β-ketoacyl-ACP reductase (KR) activity.

10. The isolated nucleic acid molecule of claim 1, comprising a nucleic acid sequence encoding an amino acid sequence that is at least 99% identical to amino acid positions 2264-2398 of SEQ ID NO:2, wherein said amino acid sequence has β-ketoacyl-ACP reductase (KR) activity.

11. The isolated nucleic acid molecule of claim 1, consisting of a nucleic acid sequence encoding an amino acid sequence that is at least 99% identical to amino acid positions 2264-2398 of SEQ ID NO:2, wherein said amino acid sequence has β-ketoacyl-ACP reductase (KR) activity.

12. The isolated nucleic acid molecule of claim 1, comprising a nucleic acid sequence encoding amino acid positions 2264-2398 of SEQ ID NO:2.

13. The isolated nucleic acid molecule of claim 1, consisting of a nucleic acid sequence encoding amino acid positions 2264-2398 of SEQ ID NO:2.

14. The isolated nucleic acid molecule of claim 1, wherein the nucleic acid molecule comprises nucleotides 17280-17684 of SEQ ID NO:1.

15. The isolated nucleic acid molecule of claim 1, wherein the nucleic acid molecule consists of nucleotides 17280-17684 of SEQ ID NO:1.

16. A recombinant nucleic acid molecule comprising the nucleic acid molecule of claim 1 and a transcription control sequence.

17. A recombinant plant cell that expresses the nucleic acid molecule of claim 1.

18. A recombinant microbial cell that expresses a recombinant vector comprising the nucleic acid molecule of claim 1 and a transcription control sequence.

19. The recombinant microbial cell of claim 18, wherein the microbial cell is a bacterium.

20. The recombinant microbial cell of claim 18, wherein the microbial cell is a Thraustochytriales microorganism.

21. The recombinant microbial cell of claim 20, wherein the Thraustochytriales microorganism is a *Schizochytrium* or a *Thraustochytrium*.

22. A method to produce at least one polyunsaturated fatty acid (PUFA), comprising culturing under conditions effective to produce the PUFA, a plant cell or a microbial cell that expresses a PKS system for production of PUFAs, wherein the plant cell or microbial cell expresses a recombinant vector comprising the nucleic acid molecule of claim 1.

* * * * *

SEQUENCE LISTING

<160> NUMBER OF SEQ ID NOS: 62

<210> SEQ ID NO 1
<211> LENGTH: 39669
<212> TYPE: DNA
<213> ORGANISM: Sh. japonica

<400> SEQUENCE: 1

```
gatctggcga taacttactc cccattccac tgtatcagct gcctgcaacc tttaacggcg      60
atcataaacg cgtcattcgc tggcagacag agtggcaagc ctgtgatgaa ttacaaatgg     120
cagcggccac aaaggctgaa tttgcagcat tagaagaaat taccagtcat caaagtgatt     180
tatttagacg gggctgggat atcaggggcg gagttgagta tttaactaaa atcccaactt     240
attattattt ataccgtgtc ggtggcgaaa accttgccag tgaaaaaaac cgagcttgtc     300
cacgttgcgg ctcaaaagcg tggcgtttag atgagccatt attagacatg ttccacttta     360
ggtgcgagcc atgtcgaatt gtatcgaata tctcatggga tcatcagtaa aattatcttc     420
tcgtcaatag atactaatac aacgagttag ctgataacgc attatcggtt cattcaataa     480
aaaagccaga ccgcatctat agcctgatct atagcctggc ttttttattt tatgtccgaa     540
taagcaatta tttcttgcct ttaatcaaat cattccacat cattttcatt cgctgccaaa     600
tacctggatg agcaacatat tcctctacaa tcggctctac cggcggcgtt actcgtggtg     660
ttagcgcatc aataaattcc gcaagactat cggctaattt atctttgggc ctatcacctg     720
gaatttcaat ccacacactg ccatcttcat tatcgacagt aatcatctgt tcgccatcac     780
ctaaaacgcc aacaaaccaa gttggtgctt gtttaagctt tttcttcatc attaagtggc     840
caattacatt ttgttgcaaa gattcaaaat cttgctggtt ccaaacctgc agtaactccc     900
cttcgcccca tttagaatcg aaaaaaagtg gcgcagaaaa aaactcacca taaaaggcat     960
taatgtcttg atgaagcttg atgtctaatg catgttctac attactgaaa tctgaattac    1020
tttttcgttt taccgctttc caaaaaaccg caccgtcaga ttcaagatca tacttgcctt    1080
caatacaagc ggatccttgc ccaagtggga aataacgggg taactcgtct aatacatcct    1140
gataagcttg tatataacgg ctagaaaaat gttccaatga agttgaacaa gacacttaag    1200
atgctccagt tttgggttat aataaaagtc tattttgaca cggaaacaga ctagatgaca    1260
cacaatcacg accccctatag tgatgcagat gcacttaaag gactcacttt aggtcaatcg   1320
acgcaatatc aagcagaata tgatgcttca ctgctgcaag gggttcctcg taaacttaat    1380
cgcgacgcta ttgaattaac tgatactctg ccgtttcaag gggcagatat ttggactggc    1440
tacgagttat cttggttgaa cgccaaaggt aaacctatgg tcgcaatgat tgaagtttac    1500
cttgctatcg aaagtgataa tttaatcgaa tcaaaatcgt tcaagttgta tttaaacagc    1560
tttaaccaaa cacgttttga cagtgtagac cacgttcagc aaaccttaac cactgactta    1620
agccaatgcg ctaatggtaa ggtaacagtg aaagtgattg agcctaagca tttcaatact    1680
caacgtattg ttgaactacc tggcaattgt atcgatgagc tagatattga agtcaatgat    1740
tatgaattta accctgagta cttgcaagac agcactgaag agaaaaatgt tgtcgaaaca    1800
ctcacatcaa acttattaaa atctaactgt ttaatcactt cacagcctga ttggggaagt    1860
gtgatgatcc gttatcaagg cccaaagatt aatcatgaaa agctattgcg ctatttaatc    1920
tcattccgcc aacataatga atttcatgag caatgtgtag agcgtatttt taccgaccta    1980
aaacgatact gtcattgtac taagctcact gtttatgcac gttatactcg ccgcggtgga    2040
```

-continued

```
ttggatatca acccattcag aagcgacctt gagcaacctc cagagacgca ccgtttagca   2100
agacaataaa tagcttattc atcaatcagc ttaatgaata aagcctaatc cctaggcttt   2160
attcatttat tttctgtcgt aataccgagc ccttcatgcc tacagacaat gttacttgtt   2220
taacaccaac aactgacgat attcagtccc ataagcattt caaaatattt aaaccctttg   2280
gtttttaag tcagtttgtg cctgaaactc gaaagaaaaa acacttattg ggcgagttat   2340
gtcagtttcc agataaaacc atggcaattg gtcgattaga ccatgattct gaaggcttat   2400
tactgctaac aactgacggc atgatgagcc ataaagtgag aagtaaaggc atcgaaaaag   2460
aatattatgt tcaagtggat ggcgatatcg atgacaaggc gatgtcacaa ctacaaaacg   2520
gagttgaaat tggcattaat agcacgaaat atctcactca gccctgtaaa gcagtcaagc   2580
taaacgcaga gccaatactt ccctcacgcg gtaaaaaaat ccgcgatcca agacatggcc   2640
ccaccagctg ggtttcaatc acattaactg aaggtaaaaa ccgtcaaatc agaaaaatga   2700
ccgctgccgt tggctttgcc acattaaggc ttgttagggt cagaattggt aatatacata   2760
ttgatgatat gcgagctggc gacgttattg aactcaataa cttagattca gtaataaacc   2820
ctaaccttag ctaacccata aaacggggct attcatttat cggcttacct tactagttat   2880
tggttaaata cactttctcc atcgcagact ccaccagctc ccgtaaccac tttatcgcag   2940
ggtcttgatg attacgtgtt ggccaaatac tgtaaatcga aatcacttgg ctttcaaaag   3000
gcaagtccat caaaattaaa ttaaaaatag attgatagtt tttcgcgtag gtataaggcg   3060
caatacatat ggcatcggat ttactcacgc cagataacat cgtcagtaaa gaggattttt   3120
caccatacat atctcgttca ggtaaatggt ctgttgaaat catctctgca actcgctggt   3180
tatgacgatg aagtcgataa aacagatgct tagcagcgaa gtacgacact tcatctattc   3240
catgtttaaa ttgcgggtgc tcagccctag caacacaaac aagcttttcg gtggcaattt   3300
gcttactggt aaagctcgct tcagttggcg caacaatatc tagcgctaaa tcaatttgct   3360
gatttttaag ggcttgatat aaattaccct catctaaaat cgcttctgta aaaatgattt   3420
caacgccttt atccgtcagt gacttttcga tatctgcttc aatcaaatca ataattgatt   3480
cattagcgct gacatgaaat atccgttttg acaacgaagg gtcaaaggct ttaacgctat   3540
taatgcattg ttcgatttcg atgagtggca aacttaactg tcggtgcaag tgctgaccta   3600
tcgcagtgag agctatccct cttccttgcc taataaatag ttcaacaccc acaaccgctt   3660
taaaccgatt gatagcatta ctgactgacg actgagttaa tgcaaggtgc tccgctgcaa   3720
gcgtaataga ttgataatca catacacagc aaaaaactct aataaggtta agatccaact   3780
taagtaattg ttgttgcata agagcatcag actctaagtt ctcttgcttc atcacttctc   3840
ccataacaca tatcgccaaa tacattcaca cggtaaatgt attaaccatt tttagccata   3900
gttatatttg ggctttttat tgttaactta tctttaacaa taaaaagtac ccgaggccta   3960
catgagaaaa acacgagttg ctttagtcat cagtttatca tttaccaatg cagtggctgc   4020
tgcgcagcac gaacatgacc acatcagtct tgattaccag ggtaagcctg cgacgcccat   4080
taccgcagag cacaacaaag ccatagcaca aaagttaccg ttcgaagata aatccgcttt   4140
tgagcgcttt agtcgacata aaattgcctc ttttgatgaa gccaccgcca agatactgcg   4200
tgcagaattt aactttatca gtgacacgct tcctgattca gtcaaccctt cgttatatcg   4260
ccaagctcaa cttaatatgg taccagacgg gctctataaa gtgactgatg gcatttacca   4320
agtacgaggc actgacttat ctaacttaac ccttattcga ggtaaaacgg gttggattgt   4380
```

-continued

```
atatgacgtt ttattaacta aagaagctgt tcagcaatca ttaacatttg cttttgctca   4440
cttgcctgag ggcaaagatt tacctgttgt ggcaatgatt tactctcaca gccatgcaga   4500
tcatttcggt ggtgcccgtg gcgttcagga acgctaccct gatgtcaaag tgtatggttc   4560
atataatatt acccaagaga tagtggatga aaatgtactc gcgggtaatg tcatgagccg   4620
gcgagctgct taccaatacg gcgttacact cgataaacac aatcacggaa ttgtcgatgc   4680
agcgttagca aaaggtttat caaaaggcga aatcacttac gtcaaacctg attatgaact   4740
tcatcatcaa ggcaaatggg aaaccttgac cattgatggt cttgaaatgg tctttatgga   4800
tgcatctggc actgaagctg ccagtgaaat gatcacatat ataccatcta tgaaggcgct   4860
atggtcaggc gaattaacat atgatggtat gcacaatatt tataccttac gaggcgctaa   4920
agttcgcgac gcattaaaat ggtctaaaga cattaacgag atgattaatg catttggcga   4980
aaatgttcag gtactatttg cttcacattc tgcgccggta tggggaaata aagaaattaa   5040
tcattacctt cgcatgcagc gagataatta tggcctcgtt cataatcaat ctttacgttt   5100
agccaatgaa ggtgtggtaa tacaagatat tggtgatgca atcatggaaa ccattccaca   5160
aaatgtccaa gacgaatggt acaccaatgg ttatcacggt acatacagcc ataacgctaa   5220
agctgtgtac aacatgtatt taggctattt tgatatgaat ccagccaact taaacccctt   5280
acctacaaag gctgaagcaa ttaagtttgt agaatatatg ggcggcgcca acaatgtagt   5340
atcaaaagcg caagcagact tcaatcaagg cgagtatcgg tttgtcgcca ctgcattaaa   5400
taaggtggtc atggccgaac cacaacaccc ccaagcccga gaattacttg ccgataccta   5460
tgagcaactt ggctaccaag ccgaaggagc tggttggcga aatatttact taacaggtgc   5520
gcaagagtta cgtattggca ttaaacctgg cgcacctaaa tccgcatccg ctgatgttat   5580
cagcgaaatg gacatgtcca ctttatttga ctttctcgcg gttaaagttg acagcattaa   5640
cgccgccaag cttggcaata tcactttaaa tgtggtgaca caaagcggcg ataaaactga   5700
cacgctcttt gtagagttaa gtaacggaaa cttgagtaat atcaaagtag acgaggctaa   5760
aaaagccgat gccacactga caattaataa gtctgatgtc gttgcaatat tattaggtaa   5820
agcagatatg aaagcgttaa tgcaatcagg agctgcgagt atgcaaggtg acaaattagc   5880
atttgccaaa attgcatcaa cactggtgca atttaatcct gattttgaaa tcgtaccgct   5940
acagcatact cattagctca taacttaacg aaattcggct gcgaagtttt tcactctgct   6000
tctttgctta tattcactag tttaccaaga gtaatggcat gagagtttaa agcaaaaatg   6060
accgactaag acaagtgagg gaagattgtt ctgataagcc gtttttgatt agcagttaaa   6120
catccaaaaa accttaacag ttcgataaat cagttggttt ttatgaacat ttttatttgt   6180
tcatgccagc tgattttttt tgcctttaat tgaagtgtta atggcttttc gccaaaagcg   6240
aactcgccca cactcacagc aaatcgatat gaattattaa gcttacctaa acaacattgc   6300
cataaaggtg agacttcata aaaagactca acatcattag tctgttcaag ctcatcaacg   6360
tctgtaggct tcaataagct aagtgaaata tcatgctgaa ttggcaacaa ctgatcatct   6420
attgttaagt tagctaagct cggtgcagat aagtcaaatg caaacgattt aagcgacaag   6480
gccagtccca gtccctttgc tttaatataa gattctttca gtgcccataa atcgaaaaat   6540
cgctcacgct gctgactttc aggtaacgcc aataatgcag tttcttctgg ttttgaaaaa   6600
tagtgatgta aaattgaatg gatattcgtg ctttctcggc gacgttcaat atcgaccccc   6660
aattgaatgg gcattgaagc gtcctctttg gagtgaatga caccaataag caaccagtta   6720
ccactgtgac ttaaattaaa ctgtaagccc gtttgtttat attgcacagc cgatagccta   6780
```

-continued

```
ggtttgccct tctcaccata ctcaaattgc caatcgtctg gttcgatatt tgcaaagttc   6840
gataatacgc tgcgcaaata cccacgcacc attaaccctt gctgttgagc agcctgttga   6900
ataaaacgat ccactttatt tatctcagca tcagataacc atgaacgcac tgtagagacg   6960
gttttctcat ctaataaatt ggtatctaaa ggacaaaaaa ataattgaat agtgggtaaa   7020
gggctcaaac caaactcgca tttataatag caataagaca ttgtcgcttg ttctaggtcg   7080
ctaattcaac acataaacaa tcttgattga aaatgtcgtc taaggtttaa acaaataaag   7140
gaaggtttag acaaataaaa aagggttaag ccatccttaa ccctttgcat atcatctgtt   7200
atttcaataa gtattagcca atcaatctac cagtgctttt accgcctttt taggtaaaac   7260
atcataacgg ctaaactgca ttgaaaactg accttctcca cctgtcatag atttaagctt   7320
tgaagagtag ctactgacat tggcaagtgg cacttcaacg ctgacttcaa caagtccatt   7380
ggcatttgcc tgcgttccac aaataatgcc tctagatgca ctaatgtcac ctgtcacttc   7440
gccgacatgc tcttgcccaa ctaaaatgct catatcaact aatggttcta acattacagg   7500
ttttgctaac gatactgctt ctataaaagc tttttaccc gccatcacaa aagcaatttc   7560
tttagagtct acactgtggt gtttgccatc caataacgtg acttttatgt cttgtaatgg   7620
atagccacct aactcaccgg ctagcatggc ttctcgcacg cctttctcta ctgctggaat   7680
atattgactt ggcactgagc caccaaccac cttcgaaata aactcaaagc cttcaccacg   7740
ctcaagtggc tcaatggcta attcaacttc accaaattgg ccagatccgc ctgattgttt   7800
tttatggcga taacggcatt gtgctttctc ggtgatggtt tctcgataag ccaccgccgg   7860
cgtatcagta tccatgtcga ggtggaacat attttgcgct ttttcaagcg caatttttaa   7920
atgcaaatcc ccttgacctt gcaatacggt ttgcccttca acctcacttc gagtgatgtg   7980
taaacttgga tcttcagcga ccagtttatt gagaacatcg gagatctttt gttcatcacc   8040
acgacgcttg gctgatacag ccaaaccaaa aataggttgc ggcacttcca gttctggtaa   8100
atgaaattca tcttcatcat ggctatcatg cagtacagaa ccaacactta atgcatccaa   8160
ttttgcaata gcgcaaatat cgccaggaaa cgcttgggat acattaattt gtttatcgcc   8220
ttgaagcttc attaagtgag agactttgaa aggtttgcgg ccttggccaa taagcagctt   8280
catgccaaca ttcagcgtcc cttggtacaa cctaaatacg cccagtcttc ctaaaaatgg   8340
gtcaattgaa acgctaaaca catgggctaa aacatgatct gttgcctttt gtgtcactgt   8400
tactggtgtc gactgttcac caaatccttt cataaattgt ggtgcattgg cttcaagtgg   8460
acttggcatg agtttgatca acatttctaa caatgaacta atcccaatat cttgttctgc   8520
acttgtaaag cagactggca ctaagtgccc cattctgagt gctttttcta gcggagcatg   8580
aagctgctga ggcgttaacg actcaccttg ctctaaatac aaggtcatta acgcttcatc   8640
ttcttcaagt accgtatcaa ctagctcatc tctagcacta gcaggttgac taaataatgt   8700
ctctgcactt tcatcacaat gtaaataaca atcaacaacg gcttttccat cggcactggg   8760
caagttaacc ggtaaacatc ggtgtccaaa ttgatgctga atgtcgatca tcacatctga   8820
cactcgcgtg agattactgt cgaggtggtt aatggcaata atcaccgctt taccttgcgc   8880
tcttgcagct tcaaaagcac gtttagtcac agactctata ccaacggcgg cattaataac   8940
caacagtact gactcaacgg caggcaaagg taataaggct cgcccgaaaa agtcaggtaa   9000
acctggcgtg tcgataaaat tgatatgatg ctgttgatac tgaaggtgta aaaatgaagg   9060
ctctaaactg tgacggtggg atttttcttg ggcagtgaaa tcagcatgat ttgtgccctt   9120
```

-continued

```
gtcgaccctg ccttttaacg atattgcctt agctctatac agcaatgctt caagcaagga   9180
tgatttgcct gctccaacat gtccgagcac agccaaatta cgggtttgct cagtagtaaa   9240
ctcagccata atggcctcct gttttcacat tattaaactt tccatattct tgtctaactt   9300
tgtttacgtt tggctattta ttgcgcataa aaatagcata cggggctaac aactcagatg   9360
aattgaccta gatcagtgtt tacatcggca acgtttttta taacaaaatc acccattcgg   9420
cttacaagtg ttagctaatt ctggtcgtat cagtgattaa ttagtttcgg gtgattgtat   9480
cgacccgaaa cctcaggtac tctgcatgct cgattgtgct aaaacgctaa ttttgaagat   9540
gaacaaacgt taatcttcac gtttttatac cgagtcccaa cagattgtac ggagtattca   9600
tcgaactatg gcagtcctta aatgaccgca aatagaaaag ctcacgctgt aactcaaaca   9660
gccgctaaga aagccacatc agaaaccgat gttgcgatgg cccctgttcg ccatagcaat   9720
gcaacaacga ctcctgaaat gcgtcaattt attcagactt ctgatttcag tgttagtcaa   9780
ttggctaaga ttcttaatat ctcggaagcc actgtcagaa agtggcgcaa gcgcgactca   9840
atcagtgata cgcccaatac tccacatcat ttgaaaacca cgctttcacc aatggaagaa   9900
tacgtggttg tgggacttcg ttatcaatta aaaatgtcac tggatagatt gcttcacgtc   9960
acacaacaat ttatcaaccc taacgtctct cgctctggtt tagcccgatg tttaaagcgc  10020
tacggcatat caaaactaga tgaatttgaa agccctcatg tgcctgagtg ttattttaat  10080
cagctgccta ttgttcaggg tacagatgta gcgacttata cactgaaccc tgaaacgctc  10140
gctaaaaccc ttgcattacc tgaagcgaca ccagataacg ttgtacaggt tgtatcgtta  10200
acgattccac ctcaactcac tcaagcggac agttattcca ttttgctcgg tgtcgacttt  10260
gcaaccgact gggtgtatct cgacatatat caagacaatc acacacaagc gacaaatcgt  10320
tatatcgctt atgtgttaaa gcacggcccg tttcatttac gtaagttatt agtcaaaaat  10380
taccacacct ttttagcccg ctttcctggc gcaacagttt tacaatccac ggaagcggca  10440
aaccaaaaaa ataaatcagc taaggatcag ctgaacactg gagactcaaa atgagccaag  10500
cccctacaaa tcctgagaca agctctcaag ataataacga gtcgcaagat acaagactga  10560
ataaacgtct taaagacatg cccattgcca ttgtcggcat ggccagtatc tttgccaact  10620
ctcgttacct gaataagttt tgggacttaa tcagcgaaaa aattgatgct attaccgaag  10680
tacctgatac ccactggcgc gctgaagatt actttgatgc tgacaagagc accccagata  10740
agagctactg taaacgcggt ggttttatcc ctgaagtgga ctttaaccca atggaatttg  10800
gcctgccgcc aaatatccta gaactgaccg atacttcgca attattgtca ttagtgattg  10860
ccaaagaagt gctagcagat gctggtgtca cttctgaata tgacactgat aaaatcggta  10920
ttactttagg tgtgggcggt ggccaaaaaa ttaatgccag cctaacagca cgtctgcaat  10980
accctgtgct taaaaaagta tttaaaagca gcggcctaag cgatgccgac agcgacatgc  11040
ttatcaaaaa attccaagac caatacattc actgggaaga aaactcgttc ccaggatcgc  11100
ttggtaatgt tattgctggt cgtattgcta accgctttga cttaggcggc atgaactgtg  11160
tggttgatgc ggcatgtgca ggttcacttg cggcaatgcg tatggcgtta accgaactgg  11220
ttgaaggccg cagcgaaatg atgatcactg gtggcgtatg taccgataac tcgccatcga  11280
tgtacatgag tttttcaaaa accccagcgt ttaccaccaa tgaaacgatt cagccatttg  11340
atatcgactc aaaaggcatg atgattggtg aaggcattgg catggtggca ttaaaacgtc  11400
ttgaagatgc tgagcgtgac ggtgaccgta tttactcagt cattaaaggg gtcggcgctt  11460
catctgatgg taagttcaaa tcaatttatg cacctcgacc tgaaggccaa gctaaagcgc  11520
```

-continued

```
tgaagcgtgc ttatgatgac gccggctttg cacctgaaac cgttggctta attgaagctc  11580
acggaacagg cactgcagcg ggtgatgtgg cagaatttaa tggtcttaaa tctgtatttg  11640
gtgagaatga ctcaacaaag caacacattg ctttaggttc agttaagtca caagtgggcc  11700
atactaaatc aactgcggga accgcgggtg tgattaaagc ggcgttagca ctgcatcata  11760
aagtgctgcc gccaaccatc aacgtctcta agcctaaccc taagcttaat gttgaggatt  11820
caccgttttt cattaacact gaaactcgcc cttggatgcc tcgccctgat ggcacaccac  11880
gccgagctgg tataagttcg ttcggttttg gtggcacaaa cttccactta gtactagaag  11940
aatacagccc agagcacagc cgtgatgaga aatatcgtca gcgccaagta gcacaaagct  12000
tattgattag cgctgacaat aaagctgagc tcattgcaga aatcaacaag cttaacgctg  12060
acatcagcgc gcttaaaggc acagataaca gcagcatcga acaagctgaa cttgcccgca  12120
ttgctaaact atatgctgtt cgcactttag atacttcagc agcccgtttg ggtcttgtgg  12180
tctcaagcct taatgaatta accactcaac ttggtttagc gttaaagcag ctaagtaacg  12240
acgctgaagc atggcaatta ccatcaggta cgagctatcg ctcatctgcg ctcatcacga  12300
ttaatgccaa ccaaaagacg actaaaggta aaaaagcagc taacacaccg aaagtagcag  12360
cattatttgc aggtcaaggt tctcagtacg tcaacatggg gattgatgtt gcttgtcact  12420
tccctgaaat gcgccagcaa ttaatcaaag ccgacaaggt atttgcaagc tttgataaaa  12480
cgccattatc gcaagtgatg ttcccaattc cagcctttga aaaagcagat aaagatgcgc  12540
aagcagcttt actcaccagc actgataacg cgcaaagcgc cattggtgta atgagcatga  12600
gccaatacca actgtttact caatcaggtt ttagcgcaga tatgtttgca ggtcacagct  12660
ttggtgagct ttcagctctt tgcgctgctg gcgttatttc taatgacgac tactaccaat  12720
tatcctatgc tcgcggcgct tcaatggccg catcagcagt tgataaagat ggcaatgaat  12780
tagataaagg cacgatgtac gccattatct tgccagctaa tgaaaatgat gcagcaaata  12840
gcgataacat cgctaaatta gaaagctgca ttagcgagtt tgaaggcgtt aaggtggcta  12900
actacaactc agccactcag ctagttattg caggcccaac acaaagctgc gccgatgcag  12960
ctaaagccat tgccgcttta ggctttaaag ctatcgcgct acctgtttct ggcgccttcc  13020
acacaccact tgtggggcat gcgcaaaagc catttgctaa agccattgat aaagctaagt  13080
tcacggcgag caaagtcgac ctgttctcaa atgccactgg tgacaaacac ccaagtgacg  13140
ctaaatcaat taaagccgct ttcaagcaac atatgctgca atcagttcgt tttactgatc  13200
agctgaacaa tatgtacgat gcgggagcgc gcgtatttgt cgagttcggc cctaagaaca  13260
ttctgcaaaa actggttgaa gcgaccctag gtaataaagc tgaagcggta tccgttatca  13320
gtatcaatcc aaaccctaag ggcaacagtg atgtgcaact tcgtgttgca gctatgcaac  13380
ttagcgtttt aggtgcgcca ctctcaagca ttgaccctta tcaagctgaa atcgcagctc  13440
ctgcggtacc aaaaggcatg aacgttaaac tcaatgcaac caaccacatc agtgcaccta  13500
ctcgtgccaa gatggaaaaa tcattagcaa caggccaagt aacctctcaa gttgtcgaaa  13560
caattgttga gaaagttatc gaaaaacctg ttgaaaaagt agtagagaag atcgtggaaa  13620
aagaagtcat taaaactgaa tatgttgaag ttgccacatc tggcgcaaca acagtgtcta  13680
acgttgcgcc tcaagcaata gcacctcatg catcagctca ggctgctcct gcttctggca  13740
gtttagaagc gttctttaat gcacaacagc aagccgctga tctgcatcag caattcttag  13800
cgattccgca gcaatatggt gacaccttta ctcacttgat ggcagagcaa agtaaaatgg  13860
```

-continued

```
ttgctgcagg ccaagccatt cctgaaagct tgcaacgctc gattgagtta ttccatcagc  13920
atcaagcgca aacgctacaa agtcacaccc tgtttttaga acaacaagct caggcaagcc  13980
aaaatgcatt aaacatgcta acgggtcaaa cacctgttac tgctcctgtt gttaacgcac  14040
caattgttaa ttcaccagta gttgaagcgg tgaaagtagc acctcctgta caaactcctg  14100
tcgtaaacac gccagtagta ccagcagtaa aggccacacc tgtagctcaa cctgctgcga  14160
tggccgctcc aaccccacct gttgaaccaa ttaaagcacc tgctcctgta gccgctcctg  14220
tagtaagtgc acctgtagtt cctacccctg ctggcttaag cgcacaaaca gccctgagct  14280
cacaaaaagt tctggatact atgttagaag tggttgcaga aaaaaccggt tacccaactg  14340
aaatgcttga acttagcatg gacatggaag cagacttagg catcgattca attaaacgtg  14400
ttgaaatatt aggtactgtt caagacgaac taccaacact gccagaactc agtcctgaag  14460
atttagctga gtgtcgtaca ttgggcgaaa tcgttgacta tatgggtagt aaactaccgg  14520
ccgcaggcgc tatgaacagc gacactgcaa atgcaactca cacagccgtt tccgcccctg  14580
ccgcttcagg tcttagcgca gaaacagtac tcaacactat gcttgaagtg gttgcagaaa  14640
aaacaggtta tccaactgaa atgcttgaac taagcatgga catggaagcc gatttaggca  14700
tcgattcaat taaacgtgtt gaaatattag gtactgttca agacgaactg ccaacaccgc  14760
cagagctaag ccctgaagat ttagctgagt gtcgtacact gggtgaaatc gtatcttata  14820
tgggtagtaa actacccgcc gcaggcgcta tgaactctaa acttcctgca agtgccgctg  14880
aagtagctca accccaaacc gcgccagttc aagctgcatc tggccttagc gctgaaacag  14940
ttctgaatac catgctagaa gtcgttgcag aaaaaaccgg ttacccaact gaaatgcttg  15000
aactcagcat ggacatggaa gccgatttag gcatcgattc aattaaacgt gttgaaatat  15060
taggtactgt tcaagacgaa ctgccaacac tgccagagct aagccctgaa gatttagctg  15120
agtgtcgtac tcttggtgaa atcgttgact acatgaactc taagctaccc gctgctggtt  15180
ctgccccagt tgcatcacca gttcagtctg cgactccggt atctggtctt agcgctgaaa  15240
cagttttgaa taccatgcta gaagtcgttg ctgaaaagac tggttatccg actgatatgc  15300
ttgaattaag catggatatg gaagccgatt taggcatcga ttcaatcaag cgtgttgaga  15360
tattaggtac tgttcaagac gagctgccaa cactacctga actcagccct gaagatttag  15420
ctgagtgtcg tactcttggc gagatcgttg actatatggg tagtaaacta cccgccgcag  15480
gcgctatgaa cactaagctt cctgctgaag gcgctaatac acaggccgcc gcaggcgctg  15540
ctcaagtagc agctactcaa acatcaggtt taagtgcgga acaagttcaa agcactatga  15600
tgacagtggt tgctgagaag accggttacc cgactgaaat gcttgaatta agcatggata  15660
tggaagcgga tttaggcatc gattcaatca agcgagttga gatcttaggt acagttcaag  15720
atgaacttcc gacgctacca gaacttaacc ctgaagattt agctgagtgt cgtacacttg  15780
gtgagatcgt ttcgtacatg ggtggtaaac tacccgccgc aggcgctatg aacactaagc  15840
tacctgctga aggcgctaat acacaggccg cagcaggcgc ttctcaagta gctgcctcaa  15900
ccgcagaaac agccctgagc gctgagcaag ttcaaagcac catgatgact gtggttgctg  15960
aaaaaaccgg ttacccaact gaaatgcttg aattgagcat ggatatggaa gcggatttag  16020
gcatcgattc aatcaagcgt gttgaaattt tagggacggt tcaagacgag cttccgggct  16080
tacctgaatt aaatcctgaa gatttagcag agtgtcgcac cctaggcgaa atcgtatctt  16140
atatgggcgc taaactgcca gccgcaggcg ctatgaacaa aaagcaagcg agcgttgaaa  16200
ctcaatctgc acccgcagca gagttagcaa ctgacttacc tcctcatcag gaagttgcgc  16260
```

-continued

```
taaaaaagct accagcggcg gataagttag ttgacggttt ttcaaaagac gcctgtatcg  16320
ttatcaatga tgacggccat aacgcaggtg ttttagctga aaaattagta gcaacaggcc  16380
taaccgtcgc cgttattcgt agccctgagt cagtgacatc tgcgcaatca ccgcttagca  16440
gtgatattgc cagcttcact ttatctgcgg tcaatgacga cgcgattagc gatgtcattg  16500
ctcaaattag caagcagcat aagatcgccg gttttgttca cctacaacct caactaacag  16560
cacaaggagc tttgccttta agtgatgctg gttttgtagc agtagagcaa gctttcttga  16620
tggctaaaca cctacagaaa ccatttgctg agctagcaaa aactgagcgt gtcagcttta  16680
tgactgtcag ccgcatcgat ggtggctttg gttacttaaa cacggctgaa cttgccaaag  16740
cagagctaaa ccaagctgca ttatcaggtt taactaaaac attaggtcat gagtggccaa  16800
ctgtgttctg tagagcattg gatattaccc caagctttga agctgtcgag ttagcacaag  16860
ccgttattgc agagctattt gatgttgata cagcaacagc tgaagtgggt attagcgacc  16920
aaggtcgtca tactttatca gctacggcaa ctgctcaaac ccgttaccaa accacatctt  16980
taaacagtga agatactgta ttggtgactg gcggtgctaa aggcgtcaca tttgaatgtg  17040
cccttactct tgccaaacaa actcagtcgc actttatttt agcgggtcgc agtgagcatt  17100
tagccggtaa tttaccgact tgggcaaaga gtgtcatagc ggctgcgcct aacgttagtg  17160
aagtaaacac aagtcagtta aaagcagcag caatcggatt tattcaatct caaggtaaca  17220
agccaacacc taagcaaatt gatgccttag tttggccgat taccagcagt ttagaaattg  17280
atcgctcatt agcagcattt aaagctgtcg gtgcaagtgc tgagtacatc agcatggatg  17340
tcagctcaga tgcagccatc aagcaatctc ttgcaggtgt taaaccgatt acaggcatca  17400
ttcatggtgc aggtgtactc gctgataaac atattcaaga caaaacctta gctgagttag  17460
gccgtgtata tggcactaaa gtgtcgggct ttgcaggtat catcaatgcg attgatgcaa  17520
gcaagttaaa actggttgct atgttctcat cagcagccgg cttctatggc aatactggcc  17580
aaagtgacta ctcaatgtct aatgagatcc tcaacaagac agcacttcaa cttgcagcta  17640
actacccgca agctaaagta atgagcttta actggggccc ttgggatggc ggaatggtca  17700
gttcagcatt gaagaaaatg tttgttgagc gcggcgtata cgttattcca ctcgataaag  17760
gcgcaaactt gtttgctcac agcctattgt ctgagtcggg cgtacagtta ttaattggtt  17820
caagcatgca gggctcaagc tcagcagata aaacaggcgc agctgtaaaa aagcttaatg  17880
cggactcttc gcttaatgcc gagggttcgc tgattctttc ttttactact cctgctaacc  17940
gtgttgtcaa caacgcggtt actgttgaac gtgtactaaa cccagtagca atgcccttcc  18000
ttgaagatca ttgcatcgcg ggtaatccag tactaccgac agtgtgcgcc atacaatgga  18060
tgcgtgaaac agcgcaacaa ttgtgtggtc tgcctgtgac tgttcaagat tataaattgc  18120
tgaaaggcat tattttcgag actaaagagc cgcaagtatt aacgctaaca ttgacgcaaa  18180
ctgaatcagg cttaaaagca ctgatcgcga gtcgtatgca tcgcgatcca atggatagct  18240
tgctaagacc tcagtatcaa gcaaaccttg tgatcaatga agccgtcatt aacggtcaaa  18300
ctttaacaac acagccaact atcgttgcgg atgcacaaca gttagcaagt gcaggtaaag  18360
tgattagcac tgacagcgaa ctttattcaa acggtagctt atttcatgga ccacgcctgc  18420
aaggcatcaa gcaagtcttg attgctgatg acacacaact ggtttgcaac gtggaattac  18480
cacatattag ttccgcagat tgcgcaggct ttgcgcctaa tctgtccata ggtggcagcc  18540
aagcatttgc tgaagatttg ctactgcaag ccatgttagt gtgggcacga attaaccatg  18600
```

-continued

```
atgctgcaag cttaccatcg actattggta agttaacgac ttattcacca tttgcatcag  18660
gcgataaagg ttacttggtg ttatctgtgc ttaagagtac cagccgttcg ttaacagctg  18720
atattgcact ttatcaccaa gatggtcgct tgagttgcac tatgagcagt gcaaaaacaa  18780
caattagcaa aagcttaaat gaggcatttc ttgcccctgc taaagcaatt gctgacttgc  18840
aggagtctgt gtgagcactc aactgactgc aaaaacggct gcaatcaata gtattcgtat  18900
agccttaaaa ctggtcgcga atgatcaaac atcattcgca ccagcacaaa atgctgatga  18960
catattttca gccataaaac cgtgttcatt agcgcaggtc attggcgagt ctgccattga  19020
ccttgaaatt gatgtatcaa gcttagatgc aggcatagat aaccttgcta cagcaagcca  19080
acaaacgctt agctttagtg attattttgc ccaagcgatt gcccatattg agcagcaaca  19140
tactgtgtta ctgagccatc cagcaatacc gtatcgagta ttgatgatgc cagcgattgt  19200
tgcagctaag catcgctgtc atccccatgc ctatttaacg ggtttgggag aagctgatga  19260
tatgcaatgc gctatgcaaa acgctttagc acaagctaaa cgtgagcaca ttactcctac  19320
cttggtcgat gtcactgagt taacttgtta taaagacaag tttactcagc ttgtcatgtt  19380
gataagccgt attgctgcgc gtcgtttacc tgacactaca ttgcctactg tcactagtga  19440
caagcagaac aatagcaatc aagccaatgc caaatattgg tttacccaaa tgcaccaaaa  19500
ccgtgttgct agctttaact ttacagaaaa tggcaagcaa cacgctgccg tttttgttca  19560
aggtactgaa ctggcccagg ccagctcgat gcttgatgaa aacagactat tcttcccctt  19620
agcagccaat acatctgctt gcatgatcca atctttgcat gagctattag tggcgctcaa  19680
taggcttaat cagcaacaaa gcaatccgtt agacagccag cggcttctaa acaagcctag  19740
ccatgttatc tctttaatgc tcaattactt aaaggcattt gatcaaacca aatccttgtc  19800
tgcagttatc atagccaact ctgtagtcac tgcaatcgca gaaattgagg ccatgttagc  19860
caaaatcagt acagcaagtg atgacacctc tggatcgata aatgaacttg agtacaaaac  19920
gccttcgggt agttgtttaa ccatcactca tcatgaagcg cttggtcgca gcggcgtgtg  19980
ttttgtgtat ccgggtgtgg gtacggttta tccgcaaatg tttgcacaac tgccacagta  20040
cttccccgct ctgtttgctc aacttgaacg tgatggcgat gtaaaagcca tgcttcaagc  20100
tgattgtatt tatgcagaaa atgccaaaac ctcagacatg aatttaggcg agcttgctat  20160
tgctggggtt ggcgcaagtt atatattaac taaagtgctt accgaacact ttgccattaa  20220
gcctgatttt gcaatgggct attctatggg tgaagcatca atgtgggcca gccttaatgt  20280
ctggaaaacg cctcacaata tgattgaagc cactcaaact aatagtattt tcacctctga  20340
tatttcaggc cgactcgact gcgtccgtca agcatggcaa ctcgaacagg gtgaagatat  20400
tgtttggaat agctttgttg tgcgtgctgc gccgactgaa atagaagccg tgcttgccga  20460
ttaccctcgc gcatatttag cgattataca aggtgatacc tgtgtattag cgggttgtga  20520
gcaaagctgt aaagccttat tgaaacaaat cggtaaacgt ggcattgcag caaatcgtgt  20580
cacagccatg cacacgcaac ccgccatgct tattcgtgat aatgttcaag cgttttatca  20640
gcaagctttg cacgaccaag atgtgcttga tgcacaagca agtagcatca aattcattag  20700
tgctgcgagt caaataccta tttcattgac cagtcaggac atcgccaatt ccattgcaga  20760
tacattttgt cagccactga acttcactaa actggtgaat aatgctcgtc atttaggtgc  20820
acgtttattt gttgaaattg gcgcagatag gcaaaccagt accttgatag ataaaattgc  20880
ccgcactgca gctaataccg attcacattt aaacgcgcca ctgtcagcca ttgcaatcaa  20940
tgccaaaggt gatgatcaaa cagcgctgct taaatgtatc gctcagctta tctcgcataa  21000
```

-continued

```
agtgccttta tctctacaat atctaactga gaatttatcc catttgttga ccgctagcat  21060
tactcgcgaa aaccgtcagc aaagccaaac cgctcagtta gctccacaat tagaaggaga  21120
acaatcttga gttctcaatc aaacgttccc aaaattgcca tcgtcggttt agcgactcag  21180
taccccgatg ctgatacgcc agcaaagttc tggcaaaatt tattagataa aaaagactct  21240
cgcagcacca ttagtcagca aaagctcaat gcaaacccag ctgactttca aggtgttcaa  21300
ggccagtctg accgttttta ttgtgacaaa ggtggctaca ttcaagactt tagttttgat  21360
gccaatggtt accgtattcc agctgcgcag tttaatggtc ttgacgacag ttttttatgg  21420
gcaacagaca cggcgcgtaa agcactcaat gatgctggtg tggatatcac taacagtcaa  21480
gataatgcga tattaaatcg cactggtatt gtcatgggta ccttgtcgtt cccaacggca  21540
aaatctaacg aattgtttgt gccgatttat cacagcgccg ttgaaaaagc gctacaagat  21600
aagctgcaac aacccagttt cacattgcag ccttttgata gtgagggata tagcaagcaa  21660
acaacgccag cctctttgtc taatggcgcc attgcacata atgcatcaaa attagtggcc  21720
gatgccctag ggttaggcgc agcacaactc agccttgatg ccgcttgcgc gagctcagtt  21780
tactcattaa agctagcttg tgattacttg catacaggca aagctgacat gatgcttgct  21840
ggtgcggttt caggcgcaga tcccttcttt attaacatgg gtttttctat cttccatgct  21900
tacccagacc atggcatttc agcgcctttt gatagtaatt caaaagggtt atttgcaggt  21960
gaaggtgctg gcgttttagt gctcaaacgt cttgaagatg ctgagcgtga tggcgaccat  22020
atttatgcac tagttagcgg cattggctta tccaacgatg gtaaaggtca atttgtactg  22080
agcccaaaca gtgatggtca agtcaaagcc tttgagcgtg cctatgcaga tgcagccatg  22140
catgatgaac atttcggccc tgataatatt gaggtcatcg agtgtcatgc cactggcaca  22200
ccgctgggtg ataaagttga actgacctcg atggaacgtt tttttaacga caaactcaat  22260
ggtagccata cgccattgat tggctcagct aaatcaaact taggtcattt gctgacggct  22320
gcgggtatgc ctgggatcat gaaaatgatt tttgccatgc gccaaggtat gttgccaccc  22380
agtatcaata ttagttcgcc aattacatca ccaaatcaga tgtttggccc tgctacatta  22440
cctaatgatg tattgccgtg gcctgataaa gcgggcaatc gtgctcgtca tgctggtgtc  22500
tcagtattcg gctttggtgg ttgtaatgcc cacttattga ttgagtcata tcacggacaa  22560
acgtcaacag ctccagctgc taataccatt aatgcacagt tgcctatgca tattacaggc  22620
atggcatcac actttgggcc gctgaataat attaaccgct ttgccaatgc aataaaccag  22680
caacaaacgg cctttactcc gctaccggca aaacgctgga aaggcttaga taaacatcct  22740
gagttattgc agcagcttgg tttggcgcaa acaccgccaa caggggctta tattgatcag  22800
tttgattttg acttcttgcg ttttaaagtg ccaccgaatg aagacgaccg cctgatttcg  22860
cagcagttat tgttgatgaa agttgcagac gaagcgattc atgatgccaa acttgcatct  22920
ggcagcaagg ttgctgtact ggttgcaatg gaaaccgagc ttgaactgca tcaattccgt  22980
gggcgagtta atttgcatac tcaaatcgca gccagcttaa atgcgcacgg tgtcagccta  23040
tctgacgatg agtaccaagc cctcgaaacc cttgcgatgg acagtgtttt agatgcggcc  23100
aagctgaacc aatacactag ctttattggt aatattatgg cgtcgcggat ctcatcgtta  23160
tgggatttta atggcccagc ctttacgatt tcagcaggcg agcagtcggt aaatcgttgt  23220
attgatgtgg cgcaaaacct attggctatg gagtcacgtc aagagccgct agatgccgtg  23280
atcatcgcag cagttgattt atctggcagt attgaaaata tcgtcctgaa aacggcaagt  23340
```

-continued

```
ctcgctaaaa caggtcaact acttccgctc agtattggtg aaggtgcggg tgcaatagta  23400
ctgcaggttg ccgaccaaac agccacagac tctgagccac tggatttaat tcatcaagca  23460
cttggtgctg tggacacacc atctgcggca atatcaggtt caacagaacg aatcagcagt  23520
gattccctta acagccacgg ggcgttaaac agctacgcta caatcaacag tttatcattt  23580
ggtcacatta gccaacttga agccatcagt gatgaattac tcacccctgc gggcttatct  23640
acaagtgata tcggcaagct agagctaaac caagctccag acttaaccca tattgattca  23700
gcgcaagcgc tatcacaact ttatagtcag tcagcaacaa ctcaagccaa atcatgtatc  23760
ggccatactt ttgccgcttc aggaatggca agcttgctgc acggactgct cattcaaaaa  23820
caagatgcgc attcaaacca aacggttcaa cccttaaata cccttgtcgc cacactcagt  23880
gagaaccagt gttcacagct actgatgagt caaactgctg aacagatctc ggctttaaac  23940
agtcgaatta atactgatat tgggcagcaa accgctaaaa aactgagcct tgttaaacaa  24000
gtgagcttag gtggacatga tatttatcag catattgtcg atacgccact agctgacatt  24060
gacaatattc gcgctaaaac ggcaaatctt atccctgccg taaccaatac aacgacgaac  24120
atgcttgagc gaggtcagtt tgtgtctcca caactaactc ctttagcacc aatgttcgac  24180
aagaataacg ctatgacaac agagacttct atgccgtttt cagatcgttc tacccagttt  24240
aatccagctc ctaaagctgc agcgcttaat gccaaagata gtgccaaagc taatgccaac  24300
gttaaagcta acgtgacgac agcaaacgta acaacagcaa accaagtgcc accagcacat  24360
ttaacggctt tcgagcaaaa tcaatggtta gcccataaag cgcaattagc atttttaaac  24420
agccgtgagc aaggcttaaa agtcgctgat gcgcttttaa agcagcaggt agcacaagca  24480
aatggtcagc cttatgttgc ccaaccgatt gcacaaccta ctgcagctgt acaagcagca  24540
aatgtgttag ccgagcctgt agcatctgct ccaatcttgc gtccggatca tgcaaatgtg  24600
ccaccttaca cagcgccgac tcctgctgat aagccatgta tttggaatta cgctgattta  24660
gttgaatacg ctgaaggcga tatcgctaag gtattcggcc ctgattacgc tgtgattgat  24720
aactactcgc gccgtgttcg cctaccgacc actgattatt tgctggtatc tcgcgtgact  24780
aaactcgatg cgaccatgaa tcaatataag ccgtgcagca tgacaacaga gtacgacatc  24840
cctgaagatg cgccgtacct tgtcgatggt caaattccat gggcggtcgc cgttgaatca  24900
ggccaatgtg atttaatgtt gatcagctac ttagggattg attttgaaaa caaaggtgaa  24960
cgtgtttatc gcttacttga ctgtacctta accttcttag atgacttacc acgcggcggt  25020
gacacactgc gctacgacat caagattaat aacttcgcta agaatggcga caccttacta  25080
ttcttcttct cgtatgagtg ttttgttggc gacaagatga ttctgaaaat ggacggcggt  25140
tgtgcaggct tctttaccga ccaagaattg gatgacggta aaggcgttat tcgcaccgac  25200
gatgagatta agctgcgtga aactgcgcta aacaatccta ataagcctcg ctttgagcca  25260
ttattgcatt gcgcccaaac tgagtttgat tatggtcaaa ttcatcattt gttaaatgca  25320
gatataggtg gctgtttcgc gggcgagcat cacaaccatc aacaagcttc aggtaagcaa  25380
gattcactgt gttttgcttc tgaaaagttc ttgatgattg agcaagtagg caaccttgat  25440
gttcatggcg gcgcatgggg cttaggcttt attgaaggtc ataagcaact ggcacctgat  25500
cattggtatt tcccatgtca ctttaaaggt gaccaagtca tggcggggtc attaatggct  25560
gaaggttgtg gtcaattact gcaattcttt atgctgcaca ttggtatgca cacgctcgtt  25620
gaaaatggcc gtttccaacc acttgaaaat gcttcacaaa aagtgcgttg tcgtggtcaa  25680
gttctgccgc agcacggtga actgacttac cggatggaaa tcactgaaat tggcattcac  25740
```

-continued

```
cctcgcccat atgccaaagc gaatattgat attttgctta acggtaaagc ggttgtcgac  25800
ttccaaaact taggtgtcat gatcaaagaa gaaagcgaat gtacgcgcta ccttaatgat  25860
acgcccgctg tcgatgcctc agctgatcga attaattcag caaccaataa tattctatac  25920
ccagcggctt caaccaatgc gccactcatg gctcaactgc ctgatttgaa tgccccaacg  25980
aataaaggcg ttatcccact gcaacatgtt gaagcgccga taattccaga ttatccaaat  26040
cgtactcctg ataccctgcc attcacggcg tatcacatgt tcgaatttgc cactggcaat  26100
attgaaaact gctttggacc ggactttagt atttaccgtg gtttcattcc accgcgcaca  26160
ccatgtggcg acttacagct aacgactcgt attgttgata ttcaaggtaa acgtggcgaa  26220
ttgaaaaagc catcatcgtg tatcgcagaa tatgaagtgc caactgatgc atggtatttc  26280
gctaaaaaca gccacgcctc ggtcatacct tattcagtgt tgatggaaat ttcactgcaa  26340
cctaacggct ttatttcagg ctacatgggc accacattag ggttccctgg tgaagagtta  26400
ttcttccgta acttagacgg tagtggtgaa ctattacgtg atgttgattt acgtggcaaa  26460
accatcgtta atgattcaaa gctattatca accgttattg ctggtagcaa catcattcaa  26520
agcttcacat ttgatttaag tgttgacggc gagcccttct acaaaggcag tgcggtattt  26580
ggctacttta aaggcgatgc gcttaaaaac cagttaggta ttgataacgg ccgtatcact  26640
caaccatggc atgttgaaaa taacgtccct gctgatatca ctgttgattt acttgataag  26700
caatctcgcg tgttccatgc tcccgctaat caaccacatt atcgcttagc tggcggtcaa  26760
cttaacttta tcgacaaagc tgaaatagtt gataaaggcg gtaaaaatgg cttaggttac  26820
ttgtcggcat ctcgcaccat tgacccaagt gattggttct tccaattcca tttccatcaa  26880
gatccagtga tgccaggttc attaggcgtt gaagccatta tcgagttaat gcaaacttac  26940
gccattagca aagacctagg taaaggtttc acaaacccga aatttggcca gatttatct  27000
gacatcaaat ggaagtaccg tggccaaatt aacccattga ataagcaaat gtcgttagat  27060
gtgcacatca gtgcagtcaa agatgaaaac ggcaaacgca tcatcgtagg cgacgccaac  27120
ctgagcaaag acgggttacg catttacgaa gtaaaagata tcgctatctg tatcgaagag  27180
gcataaagga ataataatga ctattagcac tcaaaacgaa aagctttctc catggccttg  27240
gcaagttgcg ccaagtgatg ccagctttga cactgccact atcggtaata aattaaaaga  27300
actcactcaa gcttgttatt tagtgagtca ccctgaaaaa ggcttaggta tttcgcaaaa  27360
cgcacaagta atgactgaaa gcataaacag ccaacaggat ttacctgtca gtgcatttgc  27420
ccctgcttta ggcactcaaa gcctaggcga cagtaacttc cgccgcgttc acggtgttaa  27480
atacgcctat tatgctggtg cgatggccaa tggtatttca tctgaagagt tagtgattgc  27540
attaggtcaa gcaggcattt tatgctcgtt cggcgcagct ggcttaattc catcacgcgt  27600
tgaacaagcc attaaccgca ttcaaaccgc acttccaaat ggcccgtaca tgtttaactt  27660
aatccatagt ccaagtgagc cagcactaga acgtggcagt gttgagctgt ttttaaaaca  27720
taaagtgcgc acggtagaag cttctgcatt tttaggctta accccgcaaa ttgtctatta  27780
ccgcgctgca ggtttaagcc gtgatgccca aggtgaagtg gtaattgcca acaaggttat  27840
tgccaaagtg agccgcacag aagtggcgag taagtttatg caaccagctc ctgctaaaat  27900
gctgcaaaaa ctggttgatg aaggcttaat caccccagag caaatggcgc ttgcccaatt  27960
agtgccaatg gctgatgacg tgactgcaga agccgattct ggcggtcata ctgataaccg  28020
tccattagtg acgctattgc caacaatttt ggcacttaaa gataaaatcc aagccgagta  28080
```

-continued

```
ccaatacaaa acacctattc gtgtcggttg tggcggcggt gtcggcaccc ctgatgcagc  28140
acttgcaacc tttaatatgg gcgcagctta tattgtgaca ggctcaatta accaagcttg  28200
tgttgaagcg ggtgccagtg aacacacgcg taaactactt gctacgactg aaatggccga  28260
tgtcaccatg gcgcctgctg ctgatatgtt cgagatgggc gttaagctac aagtagtaaa  28320
acgtggcacc ttattcccaa tgcgtgctaa taaactttat gaaatttata cccgttatga  28380
gtcgattgaa gccatcccag ccgaagaacg tgaaaagctt gaaaaacaag tcttccgctc  28440
gacccttgat gatatttggg ctggcactgt ggcgcacttt aatgaacgcg atccaaaaca  28500
aatcgagcgc gcagaaggta accctaagcg taaaatggcg cttattttcc gttggtactt  28560
aggtttatca agccgttggt ctaattctgg tgaagctggc cgtgagatgg attatcaaat  28620
ttgggccggt ccagcactgg gcgcgttcaa cgaatgggca aaaggcagct atttagatga  28680
ttatacccag cgaaatgcgg tagacttagc aaaacacttg atgcacggcg cagcttatca  28740
agcgcgtgta aacttactta ccgctcaagg tgtggcactg cctgttgaat tacagcgttg  28800
gagcccgctt gatcaggtta agtaagcctg ccaagcgtca tcaagctaag tcatttggat  28860
ataggtagcg gtaatgagcg aaacacaaaa acttgatttt tcagtggtta atggcacaac  28920
acttgagtcg ttcaaccaac aaaaaaatct gattaaacgc atgctaaaag gcaacagcgc  28980
aacatgtgct gaatgtaaca agccactaac gctgcaatta ccgcctaata ctaaaaatgc  29040
caaacctgcc gaaaaagcac ctgggatata ctgcgcaaaa ggctgcacag atattgaact  29100
ggatatggaa gctgtggcac ttttaaaata atacgatgaa ataacccata gattatttca  29160
tcattaccat ttaaaaaagg catcgaaaga tgccttttta ttgcaattaa ttgaccactt  29220
tatcaagtgg cgacttacct aatcactcac caaaataagt tattcagaat agtgaattta  29280
gaattgagag tttagggaat gctgttactg atacggttca aattaggtaa ttaaaatata  29340
cttcattgct tcacggttcc tgcacggttt ctgcacttta atcacataac attaaaaact  29400
cataatagcc attatcaact acgggttaac ttaggagttt acttatgttc agtccccttc  29460
tctattcgct ttttcaaacg ggatgtaaac catttcggca actattaatt ataccgctta  29520
ctagcttatg cctattaact gcttgtgata gctcagatga taccagcagc gaagagactg  29580
taataacagt acctgacact gaaattgaaa caccggttga ggagtataac gatactgatt  29640
ttgaagcaag cgattggacc gatgacaccc atagcaaaag tgcagatgcc aactttgatg  29700
aagtatttgc tgacaatgaa gtaaaacgcc ttgatgtggt ggtcactgaa gatcgctgga  29760
ccatcatgct taacgatatg actgatactt atggcacttt tggtacaacg actaattcaa  29820
acaaccttgt agatacagat gacaacccca ttatggtgcc agctgatatt tattacgaag  29880
gcaaacagtg gtatcgagtt ggtatccgtt ttaagggaaa ctcgtcactg caaaccagct  29940
ggcaacaagg cgtactcaag ttatctttta agttagattt tgatgagttt gaagactact  30000
acccacaaat cgacaatcaa cgattttatg gctttaaaaa gttaagtctt aaaaataatt  30060
acgatgatga gtcgcagtta cgtgaaaaag ttgccgccga tgtatttaaa gatgcaggtt  30120
tagccgtctc tcacaccgct tttatactt tatatatcga ccatggtgat ggccctgaat  30180
actttggctt atataccctt gtggaagaag tcgatgacac ggtaattgat actcaattta  30240
gcagtgatga tggtaactta tataagcctg aggatgatgg tgcgaccttt attgaaggat  30300
ctttcagtga agacagtttt gaaaagaaaa ccaatgaaga tgatgaagat tggtcagata  30360
ttttagcttt attcgacgca ttacatgatg atacagcgac ttccgatcct gttacttggc  30420
gtgaaaacct tgaagctata tttgatgttg atgtgttctt gaaatatctc gcagtgaatg  30480
```

-continued gcgtaattca aaactgggat acttacggat taatgcccca taattattat ctttacaacg 30540
atccagacac aaacaaatta acttggatcc catgggataa taatgaggca ttacaaacgg 30600
gtaaaatggg cggtgcatta gaacttaatt tctctgattt agactcaaat tcttggccat 30660
tgatagccaa aatctatgct gatgacacat accgggaacg ctataaccag tatttatctg 30720
acgttattag cgatagctat gaaaccaata aaatgcaggc aatttatgac agttactcag 30780
cattaataga gccttatgcc acaacagagt taacaggtta ctcattttta gagtctgcaa 30840
atgactttta tcaagcagtt gatgatttat ctgaacatgc tgaaagtcga acagacgccg 30900
taatcgatta cttaaacacg caataggttg tagatttttt ctgtcatttt gcagatacaa 30960
tgaaaacgaa agcagcactg gctactttcg tttttgttgc tatcaattca aaaccgttta 31020
ctagcgcaca ctttcttatt aaaaaataac accttaacaa gtcattgacc taaatcaaac 31080
ataatgtgaa aaagctaagg cactatgcct ctttattttt tagtttggtt atttccaatg 31140
agtgatatca aggcaaacaa tatagagcaa ccgctgacgg acgagtgcat tttactttct 31200
accactgatt tgaatggtaa tatcaaatac gccaatcaag cctttgcaga tatctctgag 31260
ttcacgacag atgaactcca cggaaaacca cacaatattg ttcgtcaccc tgatatgcct 31320
aaagcagctt ttgaatcctt gtggcaacgg gtcaaagacg gaaaaccttg gtttggtatc 31380
gttaaaaata aaagcaaaac aggcaagtat tattgggtta atgcctatat atcgccagtc 31440
tttgaaaacg gcaaaatgca tgaactacag tctgttcgac gtaaaccttg tcgtgaacac 31500
atcaattccg ctgaaaaaat ttacaaacag ttaaatcaag gtaaagcccc cagagaaacc 31560
acagcaccac tgcttagctt tacgggttca ctttgccttt gggcaaccgt tatttctttg 31620
ataggggtag tgtcttcgct cttcatgcca actttggtcg ccgctttttt cattccctta 31680
atggctggat ttgtcatgta ttacttaacg aggccgttaa aagaacttga aaataaggcc 31740
acaaaaatta tcgacgaccc aattgcttgc gggatttttt catcgagtca acatgagttg 31800
ggcaaaattg aattagcctt aaactactta gtcactgaaa tgggtggtgt tgtcggcagg 31860
atggcagatt cagccacctc cattagcgaa gaaagccagc aacttaatca aactatatcg 31920
accactcgtg aacgggttaa agaacaaaca caccaaaccc gtcaggccgc aacagcaatg 31980
gagcaaatga cggcaagctt cactgaagtt aatcaaaata cccgcaatac agcacaagaa 32040
attaccacca gccaagaggc tgctagtaaa ggtcacgata gtatggacaa agtagtcaat 32100
gcaattggcg agcttagaaa agaagtggtt catttctcaa cggtggtcaa tacaattgaa 32160
aaagacagcc aatcaatcgc atcggtccta ggagagatta aaggcatcgc agaacaaact 32220
aatttattag cgttaaatgc tgccattgaa gcggctcgag caggtgaaac tggccgtggg 32280
tttgccgttg tggcggacga agtaaggcaa ttatcaattc gcaccagtga ttccacatca 32340
gaaattgaac acatagtcac gaactttcaa aaaaccacaa aggaagcgac tcaagcaatg 32400
gagtctggtc agttgcaagc cgatttatca gtatccttag cagaagaagc ggatgacacc 32460
tttgctcagc tccttaactc aattaatcgc atacacgaaa tggctgagct taactcttca 32520
gccatgaacc aacaaacagc ggtcgcagaa gaaattagcc aatctatttt acagatagat 32580
gagatttcaa acctgacctt aattcaaacc gatgacaccc aaaacaagtg tgaacaaatg 32640
agccgattag ccaataaaac tcgtcattta tcgagacaat tttggacgca aacaatcgaa 32700
cgcaccaaat aaatacctcc aatattaccc aaagcgtcat aacctacatg ttgattatga 32760
cgcaatcttg ctcaacactg attaacttcc ccatgtttgc agataacgcg agatttagcg 32820

-continued

```
gctgattgac tattgccccc tctttctgat tgtcattttt tcctgttgtg acagtttatt  32880
ttttgataag actttttaat ttaaaaaatg ccctaatatc atatatacag ttaacgttaa  32940
gccatgctta taaagccgtt taaagcgatt caaagtgagg gtacacaatg acaaacgaat  33000
ttattccacc taaaaaatgg gtaatggaag aggaaaatgg cggcaagttt gccagtataa  33060
accgtcctga ctctggtgcg cgctatgata aagatttacc ggttgggaag catgcactgc  33120
agctttactc tatgggcacc ccaaacggcc aaaaagtcac gattatgttg gaagagctgt  33180
tagccgcagg gatcactgac gcagaatatg atgctcactt gattagcatt ggtgatagcg  33240
atcaattctc atcaggtttt gttagcgtta atccaaattc aaaaataccg gcattattag  33300
ataacagtac ctcaacgcct attaatgtat ttgagtcagg cgctatttta ctttacctcg  33360
ctgaaaaatt tggctgcttc ttaccaacag atttagctgc taaaacccaa gtcatgaatt  33420
ggttgttttg gctgcagggc tcggctcctt atttaggtgg cggttttggt cacttttatg  33480
cttacgcccc tgaaaagttt aaatacccta tcgacaggtt ctctatggag gccaagcgtc  33540
aacttgatgt acttgacaag caattagcta aacaccgctt cttgggtggt gatgagtata  33600
gtattgccga tattgcgaca tggccttggt acggaaattt ggtgcttgga aacctatatg  33660
aagcagcaga gtttttagat gttgaaagct accctaacct aatgcgctgg gcaaaagaca  33720
ttgaacaacg tccagctgtc gcgcgtggca gaatcattaa tcgaacctgg ggggaagagt  33780
gggaacaact agcgaatcgt catagcgccg aagatattga taatgtgctt aaacgtcagc  33840
cataacactc acaatttctc aatccattgg tagatcactc aattttgata atgtgagcct  33900
ttacctttga tgtgattcac tctcattggg aatgaagttt gataaagcgg taggcacacc  33960
atcaagtgct tatcgcatta ttgctaacca acaacccctt taccgattaa ccactttcaa  34020
gcttgttcca acaacataag cacgtcggct gtacgtctgg cggtaaagta atgataaaac  34080
cacaatgcgg gcaaaaatcc ccaatattta aacggacata agattgtgtt tgcttataca  34140
tcagcatcgc tcttcttttc gattatattg aggtgaatac atcgccatta gctgtgcttc  34200
tacagcaccc cttacacaaa caggctcacc atttagcgga ctaggtacag ttacgttagt  34260
cgcaatccat agctccatat cacgtattaa ctcctcttta actaacctgc cagccgtacc  34320
atgtgaccaa atacgttttc caagtagacc actctcgccg acatataaaa cctgatctcc  34380
tttcttgaaa aaatacaccc ccgaaatgtc tcttggtaac agagaaaacc agtgctttct  34440
tgttgcatac tcattaccct caaagtcata taagccataa gtttcgctat tacgattaac  34500
aagccatgct tgagatcaac tgatattagc gatatgagta aatgtaatac tgcccatttt  34560
aaaggtattc atctacgacc tcagcgcagt taaacccctg gtacatctgg ccatcaggcc  34620
tcaacttcga acttgttaca gcattatcac taacaaactt ggtataaatt gtatctactc  34680
ttttaacagg cttaccaaat aacactcgag tatttcctcc gatagcagat accagtcgac  34740
tacctagcat ctgatgttct tcagtttcta tctcatctaa tatggccaca acttgataag  34800
ccactggaat tttacggttt gcattgatga cataaaccca atctcctttt gagattgaac  34860
aaaagtcatc ccagccatgt tggccaggtg ctaaatcgaa aaaagcattg ttaccaagcg  34920
atgcatatat ttttcggtgt ggacgatcag ctatatttga tacaagaaat tttcgcataa  34980
tgaacaaagg cacttaatac acatgtgtat atactaatta agtttcccta caaagtaaac  35040
cgtactaagt acctttattg tttatttcaa tatagatcat attcaaataa cgctaatcat  35100
aacgactttt ttattgattt cattgaattt taggcgcaaa gttaactatg taaaccagct  35160
aattagaacg cttaaagagt aaaaagcgca cactagcaac acagataaaa gcaaaattgc  35220
```

-continued

```
gccagtacta tcagcacctt catatgaggt aaatatgaac aagctactaa tacttagagc  35280
agtgacgagg atttatgaca ccttcaacct ctgcaaaagc acccacttta ataccagcca  35340
actaaacttg ttagcgacag cgaatcacct catcgctgca tgctttaaca gcaaaagtcc  35400
agctaacgct aaaatcaaat cagcaagtat catcatttgt tacttattta acggcattgt  35460
ttttagcgta catgcaacgg atgagcacct taacagtaca aggcatcttc aaacgatttc  35520
cccgcttaaa accgctttgc atttggagac ttatttaggc ggacatagta caaatttagc  35580
taacaaagcc gcactttcgt ttgagttcgg ccagagaaat agtcagcatg tttgccatat  35640
aaccacaaca gaagagcatt taatgcaatc caataattta ctggaaaaca ttaatttaag  35700
tgaaaaacat ttcttctttg actgtcaaat tgataatgat ttttatgtat tatctaacca  35760
ataccgtact tatgcccaag tgataattaa gcaacctgac atcaactttc caatgtcgat  35820
gcatatagag gcgaaacttg tcacaattga tggcaagctg ctcaatgtca ccagtggtga  35880
tatctcactt aaacggaaat agctcacatg gaatttgaca caataagaga ttatttactg  35940
actaaacctt ttgctacaga agactttcca ttcggagaat ctactcacgt ttttaaagtt  36000
cactcgaaga tgtttgcact aatgtcatgg cgaaatgatg ctttgatggt taatgtaaag  36060
tgcgatcctg aagactcatt cgccctaaga gagatattta gcaatattac gacgggatat  36120
catatggaca agaaacattg gatttctatc tatttacagt caactgggag tgataaatct  36180
aaagaatctc gattaattcc agatggtgag gtattgcgca ttattgataa ttcataccta  36240
ttagtcgtcg acaaacttcc taagaagcaa caaacagcca tcaaactgca tttataacaa  36300
acaaatcaaa gcgctttata gggtttgagc aagactattt ttcagaaagc agagctgtgt  36360
gcactatttt ttcgatagta ttgtcttgct cacctaagaa ctgacaacca aactcgacac  36420
cattttcgaa taatttaaca ttacacactc tggctttaat ggtgaggttt tcttgttctg  36480
tagcctctat cacgatttca atctgctctc cctctgttaa ctcatctttt ccaccttcac  36540
taacttcaat atgacaacct gaaagtgaaa catcggtgat tttaacttgc cattggttat  36600
cacctaaagc gatattggcg gttaaatctg tcaacacacg tttggtcgaa cgtaaattgt  36660
gaataaccat attatctggg aaattcaata ccataatacg agatggctga ctcaaggttt  36720
gtttgattgt tgaaataaat gcgattacag atgcctcatg accttccact aaaccacgaa  36780
cagtcacttg tgagccctga gtaatgtact ggctgtagcc tcccaattta tttgcatctg  36840
gaaattgaat tagtatgaat tgttcaggta gataaccgat aaaaatggta cgaaaacgcc  36900
ctttttttacc tgcaggagtc acaatatcaa tattgacagg cgtaccagcc aataagtatt  36960
taaattcttt agacaaaccc tctttagtat tgatttgttt tgtggtcatt ttaccttccc  37020
tgaacctttt atttcccaat caaagattag cacaagattt aacatacaca acagtgagtt  37080
aaccttaatt aaatgttatt catgtgcttg cacctcttgt atctagaggt ctatggtgaa  37140
tatcacaagg ttaaggtttt tgatgtaaaa cataaaagac attgcaccaa acctgaatat  37200
tgacggtcgt cagattcagt cgcctcagcc gttgacataa ggtaacggag ttaacatatg  37260
agaaatctag aattattcag cacagcatct atcgatcact tactttggtc taccagcact  37320
gactcaccca gcttagactc tccagcgtta gacgtattta ctgattttga tgtagcacgt  37380
cctattgtcg ttgatgcatc caccagcgca gtggccacag caataatcat ggaacaaacc  37440
catgcattta tgagattagt tgttgataag aataataaat ttttaggggt gataacgctg  37500
caagaattgt ctgaccataa tttatttgtt accgcgaaaa agctagacct tactgtagat  37560
```

-continued

```
gagcttttag tcacagaagt gatggtgcca agagaagagc tacaagcgtt tgactatcaa  37620
caaatttcaa cagccaaagt cagtgatata gtcaggcttt tgcaacaaaa taatttgcac  37680
cacatgctag tcatcgatca tgaattgcat catatccgag ggctgattgc agcgagtgac  37740
ttagccagaa aactcaatat gccaatagaa atacatcaac ggccttcttt cagccaaatt  37800
ttctctaatg cccattaatg attttgccta aacgatataa atcacggagc cacttacctg  37860
acaaatctca ggtaagtgac gataaacctt attgaatata cgcagaaact agccttgctg  37920
tgttagttgg ctttcttgtt caacaagctg attatcgaaa gcaacacact gatttttacc  37980
ataagtctta gcttgatata gggccaaatc cgctttttga ataatctctt tcgctgaggt  38040
gaagttgcta ggtatgcaag aagtaaaacc taaactcaag gtgacgattt tactttttga  38100
tcttgggtgc gggatgccga gttcggcaat tttcaaacga atatcttcag cgagttgcga  38160
cacactttct tgctgtccgt aacaaataat agcaaactct tcaccgccat aacggcatac  38220
cacatcggtt gaacgcacac atacctcagc tattgcttgc gatacttgta ttaagcattg  38280
atctccttgg tagtggccta agaaatcgtt ataagcttta aaacaatcaa tatcacacat  38340
gattaatgac actaattgtc gctctcttcg tgctagattg ataataaagt ccaattgaga  38400
atcgaactct ctgcgattgt tcagccctgt taatgcatca agctttgaaa gcttaaacaa  38460
tttagcactc gtacgttcac gctcaataat cccaaaaagt aattgtgcat ttccgcaatc  38520
gtctcgaagt attgctctcg ctttactcgt aaagtaaagg atctcacctt ggttagcgtc  38580
ataataagga aaacgattat ggtattcatc gatacgtcct aagcgcaagt cacagtaatc  38640
ttcaaaaatt cgcttagctt tatgggcatc ttttaccgca atatttttat tgtaatcccc  38700
agcgatagga caagtcttac taacagaatg ttgaagggta tttgagtcta aagagaacat  38760
gtcacgcatg ttactgttgc agtaaaaaac attactatta tcttctaagt ctattagcca  38820
ccaggaaaca cctgaaaagc ttaataactc ttgataaagc gtataatatt tttcaattcg  38880
cttatttgga aacgtcataa ttgattagcc actttgttca agctaaccat tagtcactta  38940
cgcaactaac tttcccttta gcaaaatgaa tcagcaaaac tactatgatt atagaccctg  39000
tttacgtaat ttcctgtttg cctctcattt agctcaaaac aatgtcgtta ataaatgccg  39060
ctaataaatg cattaaaccg ctgtccacct atgttcgata cacggcttta tttgggatac  39120
ttgctcagct aactgctctt gtgatgaata atcgacattg gcccaaagct taatctcaaa  39180
caccgcccct aaagcaacct ggccaacgcc tttaggtgta cctgtcatca caatgtcgcc  39240
atccactaac gtcataaatt cattcaccga agctagaata tcgtcagcac tgtacatcat  39300
taaatcgcta tgaccgagtt gcctgacttc accatcgatt gtcaattgaa agcaaaatgt  39360
agctccggca gttaacgaca atgaagataa actgacaaaa tcactaaata gagccgagcc  39420
gtcaaatgcc ttagctcgct cccatggtag ctgttgtgat ttaagtttgg actgcaattc  39480
tctcttggtt aggtctaatc ccacccctac cccatgaaac atcccattac gcactgaaaa  39540
acatagctct gtttcaaaat gaatcggctc ttgatgaaat gagatcagct gcgtggaaat  39600
cgcagagtta ggttttaaaa aaaccaccat atctgaaggc acctcattac ccagctcatg  39660
gatatgatc                                                          39669
```

<210> SEQ ID NO 2
<211> LENGTH: 2787
<212> TYPE: PRT
<213> ORGANISM: Sh. japonica

<400> SEQUENCE: 2

```
Met Ser Gln Ala Pro Thr Asn Pro Glu Thr Ser Ser Gln Asp Asn Asn
1               5                   10                  15

Glu Ser Gln Asp Thr Arg Leu Asn Lys Arg Leu Lys Asp Met Pro Ile
            20                  25                  30

Ala Ile Val Gly Met Ala Ser Ile Phe Ala Asn Ser Arg Tyr Leu Asn
        35                  40                  45

Lys Phe Trp Asp Leu Ile Ser Glu Lys Ile Asp Ala Ile Thr Glu Val
    50                  55                  60

Pro Asp Thr His Trp Arg Ala Glu Asp Tyr Phe Asp Ala Asp Lys Ser
65                  70                  75                  80

Thr Pro Asp Lys Ser Tyr Cys Lys Arg Gly Gly Phe Ile Pro Glu Val
                85                  90                  95

Asp Phe Asn Pro Met Glu Phe Gly Leu Pro Pro Asn Ile Leu Glu Leu
            100                 105                 110

Thr Asp Thr Ser Gln Leu Leu Ser Leu Val Ile Ala Lys Glu Val Leu
        115                 120                 125

Ala Asp Ala Gly Val Thr Ser Glu Tyr Asp Thr Asp Lys Ile Gly Ile
    130                 135                 140

Thr Leu Gly Val Gly Gly Gln Lys Ile Asn Ala Ser Leu Thr Ala
145                 150                 155                 160

Arg Leu Gln Tyr Pro Val Leu Lys Lys Val Phe Lys Ser Ser Gly Leu
                165                 170                 175

Ser Asp Ala Asp Ser Asp Met Leu Ile Lys Lys Phe Gln Asp Gln Tyr
            180                 185                 190

Ile His Trp Glu Glu Asn Ser Phe Pro Gly Ser Leu Gly Asn Val Ile
        195                 200                 205

Ala Gly Arg Ile Ala Asn Arg Phe Asp Leu Gly Gly Met Asn Cys Val
    210                 215                 220

Val Asp Ala Ala Cys Ala Gly Ser Leu Ala Ala Met Arg Met Ala Leu
225                 230                 235                 240

Thr Glu Leu Val Glu Gly Arg Ser Glu Met Met Ile Thr Gly Gly Val
                245                 250                 255

Cys Thr Asp Asn Ser Pro Ser Met Tyr Met Ser Phe Ser Lys Thr Pro
            260                 265                 270

Ala Phe Thr Thr Asn Glu Thr Ile Gln Pro Phe Asp Ile Asp Ser Lys
        275                 280                 285

Gly Met Met Ile Gly Glu Gly Ile Gly Met Val Ala Leu Lys Arg Leu
    290                 295                 300

Glu Asp Ala Glu Arg Asp Gly Asp Arg Ile Tyr Ser Val Ile Lys Gly
305                 310                 315                 320

Val Gly Ala Ser Ser Asp Gly Lys Phe Lys Ser Ile Tyr Ala Pro Arg
                325                 330                 335

Pro Glu Gly Gln Ala Lys Ala Leu Lys Arg Ala Tyr Asp Asp Ala Gly
            340                 345                 350

Phe Ala Pro Glu Thr Val Gly Leu Ile Glu Ala His Gly Thr Gly Thr
        355                 360                 365

Ala Ala Gly Asp Val Ala Glu Phe Asn Gly Leu Lys Ser Val Phe Gly
    370                 375                 380

Glu Asn Asp Ser Thr Lys Gln His Ile Ala Leu Gly Ser Val Lys Ser
385                 390                 395                 400

Gln Val Gly His Thr Lys Ser Thr Ala Gly Thr Ala Gly Val Ile Lys
                405                 410                 415
```

-continued

```
Ala Ala Leu Ala Leu His His Lys Val Leu Pro Pro Thr Ile Asn Val
            420                 425                 430

Ser Lys Pro Asn Pro Lys Leu Asn Val Glu Asp Ser Pro Phe Phe Ile
        435                 440                 445

Asn Thr Glu Thr Arg Pro Trp Met Pro Arg Pro Asp Gly Thr Pro Arg
    450                 455                 460

Arg Ala Gly Ile Ser Ser Phe Gly Phe Gly Gly Thr Asn Phe His Leu
465                 470                 475                 480

Val Leu Glu Glu Tyr Ser Pro Glu His Ser Arg Asp Glu Lys Tyr Arg
                485                 490                 495

Gln Arg Gln Val Ala Gln Ser Leu Leu Ile Ser Ala Asp Asn Lys Ala
            500                 505                 510

Glu Leu Ile Ala Glu Ile Asn Lys Leu Asn Ala Asp Ile Ser Ala Leu
        515                 520                 525

Lys Gly Thr Asp Asn Ser Ser Ile Glu Gln Ala Glu Leu Ala Arg Ile
    530                 535                 540

Ala Lys Leu Tyr Ala Val Arg Thr Leu Asp Thr Ser Ala Ala Arg Leu
545                 550                 555                 560

Gly Leu Val Val Ser Ser Leu Asn Glu Leu Thr Thr Gln Leu Gly Leu
                565                 570                 575

Ala Leu Lys Gln Leu Ser Asn Asp Ala Glu Ala Trp Gln Leu Pro Ser
            580                 585                 590

Gly Thr Ser Tyr Arg Ser Ser Ala Leu Ile Thr Ile Asn Ala Asn Gln
        595                 600                 605

Lys Thr Thr Lys Gly Lys Lys Ala Ala Asn Thr Pro Lys Val Ala Ala
    610                 615                 620

Leu Phe Ala Gly Gln Gly Ser Gln Tyr Val Asn Met Gly Ile Asp Val
625                 630                 635                 640

Ala Cys His Phe Pro Glu Met Arg Gln Gln Leu Ile Lys Ala Asp Lys
                645                 650                 655

Val Phe Ala Ser Phe Asp Lys Thr Pro Leu Ser Gln Val Met Phe Pro
            660                 665                 670

Ile Pro Ala Phe Glu Lys Ala Asp Lys Asp Ala Gln Ala Ala Leu Leu
        675                 680                 685

Thr Ser Thr Asp Asn Ala Gln Ser Ala Ile Gly Val Met Ser Met Ser
    690                 695                 700

Gln Tyr Gln Leu Phe Thr Gln Ser Gly Phe Ser Ala Asp Met Phe Ala
705                 710                 715                 720

Gly His Ser Phe Gly Glu Leu Ser Ala Leu Cys Ala Ala Gly Val Ile
                725                 730                 735

Ser Asn Asp Asp Tyr Tyr Gln Leu Ser Tyr Ala Arg Gly Ala Ser Met
            740                 745                 750

Ala Ala Ser Ala Val Asp Lys Asp Gly Asn Glu Leu Asp Lys Gly Thr
        755                 760                 765

Met Tyr Ala Ile Ile Leu Pro Ala Asn Glu Asn Asp Ala Ala Asn Ser
    770                 775                 780

Asp Asn Ile Ala Lys Leu Glu Ser Cys Ile Ser Glu Phe Glu Gly Val
785                 790                 795                 800

Lys Val Ala Asn Tyr Asn Ser Ala Thr Gln Leu Val Ile Ala Gly Pro
                805                 810                 815

Thr Gln Ser Cys Ala Asp Ala Ala Lys Ala Ile Ala Ala Leu Gly Phe
            820                 825                 830

Lys Ala Ile Ala Leu Pro Val Ser Gly Ala Phe His Thr Pro Leu Val
```

-continued

```
        835                 840                 845

Gly His Ala Gln Lys Pro Phe Ala Lys Ala Ile Asp Lys Ala Lys Phe
    850                 855                 860

Thr Ala Ser Lys Val Asp Leu Phe Ser Asn Ala Thr Gly Asp Lys His
865                 870                 875                 880

Pro Ser Asp Ala Lys Ser Ile Lys Ala Ala Phe Lys Gln His Met Leu
                885                 890                 895

Gln Ser Val Arg Phe Thr Asp Gln Leu Asn Asn Met Tyr Asp Ala Gly
            900                 905                 910

Ala Arg Val Phe Val Glu Phe Gly Pro Lys Asn Ile Leu Gln Lys Leu
        915                 920                 925

Val Glu Ala Thr Leu Gly Asn Lys Ala Glu Ala Val Ser Val Ile Ser
    930                 935                 940

Ile Asn Pro Asn Pro Lys Gly Asn Ser Asp Val Gln Leu Arg Val Ala
945                 950                 955                 960

Ala Met Gln Leu Ser Val Leu Gly Ala Pro Leu Ser Ser Ile Asp Pro
                965                 970                 975

Tyr Gln Ala Glu Ile Ala Ala Pro Ala Val Pro Lys Gly Met Asn Val
            980                 985                 990

Lys Leu Asn Ala Thr Asn His Ile  Ser Ala Pro Thr Arg  Ala Lys Met
        995                 1000                1005

Glu Lys  Ser Leu Ala Thr Gly  Gln Val Thr Ser Gln  Val Val Glu
    1010                 1015                 1020

Thr Ile  Val Glu Lys Val Ile  Glu Lys Pro Val Glu  Lys Val Val
    1025                 1030                 1035

Glu Lys  Ile Val Glu Lys Glu  Val Ile Lys Thr Glu  Tyr Val Glu
    1040                 1045                 1050

Val Ala  Thr Ser Gly Ala Thr  Thr Val Ser Asn Val  Ala Pro Gln
    1055                 1060                 1065

Ala Ile  Ala Pro His Ala Ser  Ala Gln Ala Ala Pro  Ala Ser Gly
    1070                 1075                 1080

Ser Leu  Glu Ala Phe Phe Asn  Ala Gln Gln Gln Ala  Ala Asp Leu
    1085                 1090                 1095

His Gln  Gln Phe Leu Ala Ile  Pro Gln Gln Tyr Gly  Asp Thr Phe
    1100                 1105                 1110

Thr His  Leu Met Ala Glu Gln  Ser Lys Met Val Ala  Ala Gly Gln
    1115                 1120                 1125

Ala Ile  Pro Glu Ser Leu Gln  Arg Ser Ile Glu Leu  Phe His Gln
    1130                 1135                 1140

His Gln  Ala Gln Thr Leu Gln  Ser His Thr Leu Phe  Leu Glu Gln
    1145                 1150                 1155

Gln Ala  Gln Ala Ser Gln Asn  Ala Leu Asn Met Leu  Thr Gly Gln
    1160                 1165                 1170

Thr Pro  Val Thr Ala Pro Val  Val Asn Ala Pro Ile  Val Asn Ser
    1175                 1180                 1185

Pro Val  Val Glu Ala Val Lys  Val Ala Pro Pro Val  Gln Thr Pro
    1190                 1195                 1200

Val Val  Asn Thr Pro Val Val  Pro Ala Val Lys Ala  Thr Pro Val
    1205                 1210                 1215

Ala Gln  Pro Ala Ala Met Ala  Ala Pro Thr Pro Pro  Val Glu Pro
    1220                 1225                 1230

Ile Lys  Ala Pro Ala Pro Val  Ala Ala Pro Val Val  Ser Ala Pro
    1235                 1240                 1245
```

```
Val Val  Pro Thr Pro Ala Gly  Leu Ser Ala Gln Thr  Ala Leu Ser
    1250                 1255                 1260

Ser Gln  Lys Val Leu Asp Thr  Met Leu Glu Val Val  Ala Glu Lys
    1265                 1270                 1275

Thr Gly  Tyr Pro Thr Glu Met  Leu Glu Leu Ser Met  Asp Met Glu
    1280                 1285                 1290

Ala Asp  Leu Gly Ile Asp Ser  Ile Lys Arg Val Glu  Ile Leu Gly
    1295                 1300                 1305

Thr Val  Gln Asp Glu Leu Pro  Thr Leu Pro Glu Leu  Ser Pro Glu
    1310                 1315                 1320

Asp Leu  Ala Glu Cys Arg Thr  Leu Gly Glu Ile Val  Asp Tyr Met
    1325                 1330                 1335

Gly Ser  Lys Leu Pro Ala Ala  Gly Ala Met Asn Ser  Asp Thr Ala
    1340                 1345                 1350

Asn Ala  Thr His Thr Ala Val  Ser Ala Pro Ala Ala  Ser Gly Leu
    1355                 1360                 1365

Ser Ala  Glu Thr Val Leu Asn  Thr Met Leu Glu Val  Val Ala Glu
    1370                 1375                 1380

Lys Thr  Gly Tyr Pro Thr Glu  Met Leu Glu Leu Ser  Met Asp Met
    1385                 1390                 1395

Glu Ala  Asp Leu Gly Ile Asp  Ser Ile Lys Arg Val  Glu Ile Leu
    1400                 1405                 1410

Gly Thr  Val Gln Asp Glu Leu  Pro Thr Pro Pro Glu  Leu Ser Pro
    1415                 1420                 1425

Glu Asp  Leu Ala Glu Cys Arg  Thr Leu Gly Glu Ile  Val Ser Tyr
    1430                 1435                 1440

Met Gly  Ser Lys Leu Pro Ala  Ala Gly Ala Met Asn  Ser Lys Leu
    1445                 1450                 1455

Pro Ala  Ser Ala Ala Glu Val  Ala Gln Pro Gln Thr  Ala Pro Val
    1460                 1465                 1470

Gln Ala  Ala Ser Gly Leu Ser  Ala Glu Thr Val Leu  Asn Thr Met
    1475                 1480                 1485

Leu Glu  Val Val Ala Glu Lys  Thr Gly Tyr Pro Thr  Glu Met Leu
    1490                 1495                 1500

Glu Leu  Ser Met Asp Met Glu  Ala Asp Leu Gly Ile  Asp Ser Ile
    1505                 1510                 1515

Lys Arg  Val Glu Ile Leu Gly  Thr Val Gln Asp Glu  Leu Pro Thr
    1520                 1525                 1530

Leu Pro  Glu Leu Ser Pro Glu  Asp Leu Ala Glu Cys  Arg Thr Leu
    1535                 1540                 1545

Gly Glu  Ile Val Asp Tyr Met  Asn Ser Lys Leu Pro  Ala Ala Gly
    1550                 1555                 1560

Ser Ala  Pro Val Ala Ser Pro  Val Gln Ser Ala Thr  Pro Val Ser
    1565                 1570                 1575

Gly Leu  Ser Ala Glu Thr Val  Leu Asn Thr Met Leu  Glu Val Val
    1580                 1585                 1590

Ala Glu  Lys Thr Gly Tyr Pro  Thr Asp Met Leu Glu  Leu Ser Met
    1595                 1600                 1605

Asp Met  Glu Ala Asp Leu Gly  Ile Asp Ser Ile Lys  Arg Val Glu
    1610                 1615                 1620

Ile Leu  Gly Thr Val Gln Asp  Glu Leu Pro Thr Leu  Pro Glu Leu
    1625                 1630                 1635
```

-continued

```
Ser Pro Glu Asp Leu Ala Glu Cys Arg Thr Leu Gly Glu Ile Val
    1640                1645                1650

Asp Tyr Met Gly Ser Lys Leu Pro Ala Ala Gly Ala Met Asn Thr
    1655                1660                1665

Lys Leu Pro Ala Glu Gly Ala Asn Thr Gln Ala Ala Ala Gly Ala
    1670                1675                1680

Ala Gln Val Ala Ala Thr Gln Thr Ser Gly Leu Ser Ala Glu Gln
    1685                1690                1695

Val Gln Ser Thr Met Met Thr Val Val Ala Glu Lys Thr Gly Tyr
    1700                1705                1710

Pro Thr Glu Met Leu Glu Leu Ser Met Asp Met Glu Ala Asp Leu
    1715                1720                1725

Gly Ile Asp Ser Ile Lys Arg Val Glu Ile Leu Gly Thr Val Gln
    1730                1735                1740

Asp Glu Leu Pro Thr Leu Pro Glu Leu Asn Pro Glu Asp Leu Ala
    1745                1750                1755

Glu Cys Arg Thr Leu Gly Glu Ile Val Ser Tyr Met Gly Gly Lys
    1760                1765                1770

Leu Pro Ala Ala Gly Ala Met Asn Thr Lys Leu Pro Ala Glu Gly
    1775                1780                1785

Ala Asn Thr Gln Ala Ala Ala Gly Ala Ser Gln Val Ala Ala Ser
    1790                1795                1800

Thr Ala Glu Thr Ala Leu Ser Ala Glu Gln Val Gln Ser Thr Met
    1805                1810                1815

Met Thr Val Val Ala Glu Lys Thr Gly Tyr Pro Thr Glu Met Leu
    1820                1825                1830

Glu Leu Ser Met Asp Met Glu Ala Asp Leu Gly Ile Asp Ser Ile
    1835                1840                1845

Lys Arg Val Glu Ile Leu Gly Thr Val Gln Asp Glu Leu Pro Gly
    1850                1855                1860

Leu Pro Glu Leu Asn Pro Glu Asp Leu Ala Glu Cys Arg Thr Leu
    1865                1870                1875

Gly Glu Ile Val Ser Tyr Met Gly Ala Lys Leu Pro Ala Ala Gly
    1880                1885                1890

Ala Met Asn Lys Lys Gln Ala Ser Val Glu Thr Gln Ser Ala Pro
    1895                1900                1905

Ala Ala Glu Leu Ala Thr Asp Leu Pro Pro His Gln Glu Val Ala
    1910                1915                1920

Leu Lys Lys Leu Pro Ala Ala Asp Lys Leu Val Asp Gly Phe Ser
    1925                1930                1935

Lys Asp Ala Cys Ile Val Ile Asn Asp Asp Gly His Asn Ala Gly
    1940                1945                1950

Val Leu Ala Glu Lys Leu Val Ala Thr Gly Leu Thr Val Ala Val
    1955                1960                1965

Ile Arg Ser Pro Glu Ser Val Thr Ser Ala Gln Ser Pro Leu Ser
    1970                1975                1980

Ser Asp Ile Ala Ser Phe Thr Leu Ser Ala Val Asn Asp Asp Ala
    1985                1990                1995

Ile Ser Asp Val Ile Ala Gln Ile Ser Lys Gln His Lys Ile Ala
    2000                2005                2010

Gly Phe Val His Leu Gln Pro Gln Leu Thr Ala Gln Gly Ala Leu
    2015                2020                2025

Pro Leu Ser Asp Ala Gly Phe Val Ala Val Glu Gln Ala Phe Leu
```

-continued

```
    2030                2035                2040

Met Ala  Lys His Leu Gln Lys  Pro Phe Ala Glu Leu  Ala Lys Thr
    2045                2050                2055

Glu Arg  Val Ser Phe Met Thr  Val Ser Arg Ile Asp  Gly Gly Phe
    2060                2065                2070

Gly Tyr  Leu Asn Thr Ala Glu  Leu Ala Lys Ala Glu  Leu Asn Gln
    2075                2080                2085

Ala Ala  Leu Ser Gly Leu Thr  Lys Thr Leu Gly His  Glu Trp Pro
    2090                2095                2100

Thr Val  Phe Cys Arg Ala Leu  Asp Ile Thr Pro Ser  Phe Glu Ala
    2105                2110                2115

Val Glu  Leu Ala Gln Ala Val  Ile Ala Glu Leu Phe  Asp Val Asp
    2120                2125                2130

Thr Ala  Thr Ala Glu Val Gly  Ile Ser Asp Gln Gly  Arg His Thr
    2135                2140                2145

Leu Ser  Ala Thr Ala Thr Ala  Gln Thr Arg Tyr Gln  Thr Thr Ser
    2150                2155                2160

Leu Asn  Ser Glu Asp Thr Val  Leu Val Thr Gly Gly  Ala Lys Gly
    2165                2170                2175

Val Thr  Phe Glu Cys Ala Leu  Thr Leu Ala Lys Gln  Thr Gln Ser
    2180                2185                2190

His Phe  Ile Leu Ala Gly Arg  Ser Glu His Leu Ala  Gly Asn Leu
    2195                2200                2205

Pro Thr  Trp Ala Lys Ser Val  Ile Ala Ala Ala Pro  Asn Val Ser
    2210                2215                2220

Glu Val  Asn Thr Ser Gln Leu  Lys Ala Ala Ala Ile  Gly Phe Ile
    2225                2230                2235

Gln Ser  Gln Gly Asn Lys Pro  Thr Pro Lys Gln Ile  Asp Ala Leu
    2240                2245                2250

Val Trp  Pro Ile Thr Ser Ser  Leu Glu Ile Asp Arg  Ser Leu Ala
    2255                2260                2265

Ala Phe  Lys Ala Val Gly Ala  Ser Ala Glu Tyr Ile  Ser Met Asp
    2270                2275                2280

Val Ser  Ser Asp Ala Ala Ile  Lys Gln Ser Leu Ala  Gly Val Lys
    2285                2290                2295

Pro Ile  Thr Gly Ile Ile His  Gly Ala Gly Val Leu  Ala Asp Lys
    2300                2305                2310

His Ile  Gln Asp Lys Thr Leu  Ala Glu Leu Gly Arg  Val Tyr Gly
    2315                2320                2325

Thr Lys  Val Ser Gly Phe Ala  Gly Ile Ile Asn Ala  Ile Asp Ala
    2330                2335                2340

Ser Lys  Leu Lys Leu Val Ala  Met Phe Ser Ser Ala  Ala Gly Phe
    2345                2350                2355

Tyr Gly  Asn Thr Gly Gln Ser  Asp Tyr Ser Met Ser  Asn Glu Ile
    2360                2365                2370

Leu Asn  Lys Thr Ala Leu Gln  Leu Ala Ala Asn Tyr  Pro Gln Ala
    2375                2380                2385

Lys Val  Met Ser Phe Asn Trp  Gly Pro Trp Asp Gly  Gly Met Val
    2390                2395                2400

Ser Ser  Ala Leu Lys Lys Met  Phe Val Glu Arg Gly  Val Tyr Val
    2405                2410                2415

Ile Pro  Leu Asp Lys Gly Ala  Asn Leu Phe Ala His  Ser Leu Leu
    2420                2425                2430
```

```
Ser Glu  Ser Gly Val Gln Leu  Leu Ile Gly Ser Ser  Met Gln Gly
    2435                2440                2445

Ser Ser  Ser Ala Asp Lys Thr  Gly Ala Ala Val Lys  Lys Leu Asn
    2450                2455                2460

Ala Asp  Ser Ser Leu Asn Ala  Glu Gly Ser Leu Ile  Leu Ser Phe
    2465                2470                2475

Thr Thr  Pro Ala Asn Arg Val  Val Asn Asn Ala Val  Thr Val Glu
    2480                2485                2490

Arg Val  Leu Asn Pro Val Ala  Met Pro Phe Leu Glu  Asp His Cys
    2495                2500                2505

Ile Ala  Gly Asn Pro Val Leu  Pro Thr Val Cys Ala  Ile Gln Trp
    2510                2515                2520

Met Arg  Glu Thr Ala Gln Gln  Leu Cys Gly Leu Pro  Val Thr Val
    2525                2530                2535

Gln Asp  Tyr Lys Leu Leu Lys  Gly Ile Ile Phe Glu  Thr Lys Glu
    2540                2545                2550

Pro Gln  Val Leu Thr Leu Thr  Leu Thr Gln Thr Glu  Ser Gly Leu
    2555                2560                2565

Lys Ala  Leu Ile Ala Ser Arg  Met His Arg Asp Pro  Met Asp Ser
    2570                2575                2580

Leu Leu  Arg Pro Gln Tyr Gln  Ala Asn Leu Val Ile  Asn Glu Ala
    2585                2590                2595

Val Ile  Asn Gly Gln Thr Leu  Thr Thr Gln Pro Thr  Ile Val Ala
    2600                2605                2610

Asp Ala  Gln Gln Leu Ala Ser  Ala Gly Lys Val Ile  Ser Thr Asp
    2615                2620                2625

Ser Glu  Leu Tyr Ser Asn Gly  Ser Leu Phe His Gly  Pro Arg Leu
    2630                2635                2640

Gln Gly  Ile Lys Gln Val Leu  Ile Ala Asp Asp Thr  Gln Leu Val
    2645                2650                2655

Cys Asn  Val Glu Leu Pro His  Ile Ser Ser Ala Asp  Cys Ala Gly
    2660                2665                2670

Phe Ala  Pro Asn Leu Ser Ile  Gly Gly Ser Gln Ala  Phe Ala Glu
    2675                2680                2685

Asp Leu  Leu Leu Gln Ala Met  Leu Val Trp Ala Arg  Ile Asn His
    2690                2695                2700

Asp Ala  Ala Ser Leu Pro Ser  Thr Ile Gly Lys Leu  Thr Thr Tyr
    2705                2710                2715

Ser Pro  Phe Ala Ser Gly Asp  Lys Gly Tyr Leu Val  Leu Ser Val
    2720                2725                2730

Leu Lys  Ser Thr Ser Arg Ser  Leu Thr Ala Asp Ile  Ala Leu Tyr
    2735                2740                2745

His Gln  Asp Gly Arg Leu Ser  Cys Thr Met Ser Ser  Ala Lys Thr
    2750                2755                2760

Thr Ile  Ser Lys Ser Leu Asn  Glu Ala Phe Leu Ala  Pro Ala Lys
    2765                2770                2775

Ala Ile  Ala Asp Leu Gln Glu  Ser Val
    2780                2785
```

<210> SEQ ID NO 3
<211> LENGTH: 759
<212> TYPE: PRT
<213> ORGANISM: Sh. japonica

<400> SEQUENCE: 3

```
Val Ser Thr Gln Leu Thr Ala Lys Thr Ala Ala Ile Asn Ser Ile Arg
1               5                   10                  15

Ile Ala Leu Lys Leu Val Ala Asn Asp Gln Thr Ser Phe Ala Pro Ala
            20                  25                  30

Gln Asn Ala Asp Asp Ile Phe Ser Ala Ile Lys Pro Cys Ser Leu Ala
        35                  40                  45

Gln Val Ile Gly Glu Ser Ala Ile Asp Leu Glu Ile Asp Val Ser Ser
    50                  55                  60

Leu Asp Ala Gly Ile Asp Asn Leu Ala Thr Ala Ser Gln Gln Thr Leu
65                  70                  75                  80

Ser Phe Ser Asp Tyr Phe Ala Gln Ala Ile Ala His Ile Glu Gln Gln
                85                  90                  95

His Thr Val Leu Leu Ser His Pro Ala Ile Pro Tyr Arg Val Leu Met
            100                 105                 110

Met Pro Ala Ile Val Ala Ala Lys His Arg Cys His Pro His Ala Tyr
        115                 120                 125

Leu Thr Gly Leu Gly Glu Ala Asp Asp Met Gln Cys Ala Met Gln Asn
    130                 135                 140

Ala Leu Ala Gln Ala Lys Arg Glu His Ile Thr Pro Thr Leu Val Asp
145                 150                 155                 160

Val Thr Glu Leu Thr Cys Tyr Lys Asp Lys Phe Thr Gln Leu Val Met
                165                 170                 175

Leu Ile Ser Arg Ile Ala Ala Arg Arg Leu Pro Asp Thr Thr Leu Pro
            180                 185                 190

Thr Val Thr Ser Asp Lys Gln Asn Asn Ser Asn Gln Ala Asn Ala Lys
        195                 200                 205

Tyr Trp Phe Thr Gln Met His Gln Asn Arg Val Ala Ser Phe Asn Phe
    210                 215                 220

Thr Glu Asn Gly Lys Gln His Ala Ala Val Phe Val Gln Gly Thr Glu
225                 230                 235                 240

Leu Ala Gln Ala Ser Ser Met Leu Asp Glu Asn Arg Leu Phe Phe Pro
                245                 250                 255

Leu Ala Ala Asn Thr Ser Ala Cys Met Ile Gln Ser Leu His Glu Leu
            260                 265                 270

Leu Val Ala Leu Asn Arg Leu Asn Gln Gln Gln Ser Asn Pro Leu Asp
        275                 280                 285

Ser Gln Arg Leu Leu Asn Lys Pro Ser His Val Ile Ser Leu Met Leu
    290                 295                 300

Asn Tyr Leu Lys Ala Phe Asp Gln Thr Lys Ser Leu Ser Ala Val Ile
305                 310                 315                 320

Ile Ala Asn Ser Val Val Thr Ala Ile Ala Glu Ile Glu Ala Met Leu
                325                 330                 335

Ala Lys Ile Ser Thr Ala Ser Asp Asp Thr Ser Gly Ser Ile Asn Glu
            340                 345                 350

Leu Glu Tyr Lys Thr Pro Ser Gly Ser Cys Leu Thr Ile Thr His His
        355                 360                 365

Glu Ala Leu Gly Arg Ser Gly Val Cys Phe Val Tyr Pro Gly Val Gly
    370                 375                 380

Thr Val Tyr Pro Gln Met Phe Ala Gln Leu Pro Gln Tyr Phe Pro Ala
385                 390                 395                 400

Leu Phe Ala Gln Leu Glu Arg Asp Gly Asp Val Lys Ala Met Leu Gln
                405                 410                 415
```

-continued

```
Ala Asp Cys Ile Tyr Ala Glu Asn Ala Lys Thr Ser Asp Met Asn Leu
            420                 425                 430

Gly Glu Leu Ala Ile Ala Gly Val Gly Ala Ser Tyr Ile Leu Thr Lys
        435                 440                 445

Val Leu Thr Glu His Phe Ala Ile Lys Pro Asp Phe Ala Met Gly Tyr
    450                 455                 460

Ser Met Gly Glu Ala Ser Met Trp Ala Ser Leu Asn Val Trp Lys Thr
465                 470                 475                 480

Pro His Asn Met Ile Glu Ala Thr Gln Thr Asn Ser Ile Phe Thr Ser
                485                 490                 495

Asp Ile Ser Gly Arg Leu Asp Cys Val Arg Gln Ala Trp Gln Leu Glu
            500                 505                 510

Gln Gly Glu Asp Ile Val Trp Asn Ser Phe Val Val Arg Ala Ala Pro
        515                 520                 525

Thr Glu Ile Glu Ala Val Leu Ala Asp Tyr Pro Arg Ala Tyr Leu Ala
    530                 535                 540

Ile Ile Gln Gly Asp Thr Cys Val Leu Ala Gly Cys Glu Gln Ser Cys
545                 550                 555                 560

Lys Ala Leu Leu Lys Gln Ile Gly Lys Arg Gly Ile Ala Ala Asn Arg
                565                 570                 575

Val Thr Ala Met His Thr Gln Pro Ala Met Leu Ile Arg Asp Asn Val
            580                 585                 590

Gln Ala Phe Tyr Gln Gln Ala Leu His Asp Gln Asp Val Leu Asp Ala
        595                 600                 605

Gln Ala Ser Ser Ile Lys Phe Ile Ser Ala Ala Ser Gln Ile Pro Ile
    610                 615                 620

Ser Leu Thr Ser Gln Asp Ile Ala Asn Ser Ile Ala Asp Thr Phe Cys
625                 630                 635                 640

Gln Pro Leu Asn Phe Thr Lys Leu Val Asn Asn Ala Arg His Leu Gly
                645                 650                 655

Ala Arg Leu Phe Val Glu Ile Gly Ala Asp Arg Gln Thr Ser Thr Leu
            660                 665                 670

Ile Asp Lys Ile Ala Arg Thr Ala Ala Asn Thr Asp Ser His Leu Asn
        675                 680                 685

Ala Pro Leu Ser Ala Ile Ala Ile Asn Ala Lys Gly Asp Asp Gln Thr
    690                 695                 700

Ala Leu Leu Lys Cys Ile Ala Gln Leu Ile Ser His Lys Val Pro Leu
705                 710                 715                 720

Ser Leu Gln Tyr Leu Thr Glu Asn Leu Ser His Leu Leu Thr Ala Ser
                725                 730                 735

Ile Thr Arg Glu Asn Arg Gln Gln Ser Gln Thr Ala Gln Leu Ala Pro
            740                 745                 750

Gln Leu Glu Gly Glu Gln Ser
        755


<210> SEQ ID NO 4
<211> LENGTH: 2019
<212> TYPE: PRT
<213> ORGANISM: Sh. japonica

<400> SEQUENCE: 4

Leu Ser Ser Gln Ser Asn Val Pro Lys Ile Ala Ile Val Gly Leu Ala
1               5                   10                  15

Thr Gln Tyr Pro Asp Ala Asp Thr Pro Ala Lys Phe Trp Gln Asn Leu
```

-continued

```
            20                  25                  30

Leu Asp Lys Lys Asp Ser Arg Ser Thr Ile Ser Gln Gln Lys Leu Asn
        35                  40                  45

Ala Asn Pro Ala Asp Phe Gln Gly Val Gln Gly Gln Ser Asp Arg Phe
    50                  55                  60

Tyr Cys Asp Lys Gly Gly Tyr Ile Gln Asp Phe Ser Phe Asp Ala Asn
65                  70                  75                  80

Gly Tyr Arg Ile Pro Ala Ala Gln Phe Asn Gly Leu Asp Asp Ser Phe
                85                  90                  95

Leu Trp Ala Thr Asp Thr Ala Arg Lys Ala Leu Asn Asp Ala Gly Val
            100                 105                 110

Asp Ile Thr Asn Ser Gln Asp Asn Ala Ile Leu Asn Arg Thr Gly Ile
        115                 120                 125

Val Met Gly Thr Leu Ser Phe Pro Thr Ala Lys Ser Asn Glu Leu Phe
    130                 135                 140

Val Pro Ile Tyr His Ser Ala Val Glu Lys Ala Leu Gln Asp Lys Leu
145                 150                 155                 160

Gln Gln Pro Ser Phe Thr Leu Gln Pro Phe Asp Ser Glu Gly Tyr Ser
                165                 170                 175

Lys Gln Thr Thr Pro Ala Ser Leu Ser Asn Gly Ala Ile Ala His Asn
            180                 185                 190

Ala Ser Lys Leu Val Ala Asp Ala Leu Gly Leu Gly Ala Ala Gln Leu
        195                 200                 205

Ser Leu Asp Ala Ala Cys Ala Ser Ser Val Tyr Ser Leu Lys Leu Ala
    210                 215                 220

Cys Asp Tyr Leu His Thr Gly Lys Ala Asp Met Met Leu Ala Gly Ala
225                 230                 235                 240

Val Ser Gly Ala Asp Pro Phe Phe Ile Asn Met Gly Phe Ser Ile Phe
                245                 250                 255

His Ala Tyr Pro Asp His Gly Ile Ser Ala Pro Phe Asp Ser Asn Ser
            260                 265                 270

Lys Gly Leu Phe Ala Gly Glu Gly Ala Gly Val Leu Val Leu Lys Arg
        275                 280                 285

Leu Glu Asp Ala Glu Arg Asp Gly Asp His Ile Tyr Ala Leu Val Ser
    290                 295                 300

Gly Ile Gly Leu Ser Asn Asp Gly Lys Gly Gln Phe Val Leu Ser Pro
305                 310                 315                 320

Asn Ser Asp Gly Gln Val Lys Ala Phe Glu Arg Ala Tyr Ala Asp Ala
                325                 330                 335

Ala Met His Asp Glu His Phe Gly Pro Asp Asn Ile Glu Val Ile Glu
            340                 345                 350

Cys His Ala Thr Gly Thr Pro Leu Gly Asp Lys Val Glu Leu Thr Ser
        355                 360                 365

Met Glu Arg Phe Phe Asn Asp Lys Leu Asn Gly Ser His Thr Pro Leu
    370                 375                 380

Ile Gly Ser Ala Lys Ser Asn Leu Gly His Leu Leu Thr Ala Ala Gly
385                 390                 395                 400

Met Pro Gly Ile Met Lys Met Ile Phe Ala Met Arg Gln Gly Met Leu
                405                 410                 415

Pro Pro Ser Ile Asn Ile Ser Ser Pro Ile Thr Ser Pro Asn Gln Met
            420                 425                 430

Phe Gly Pro Ala Thr Leu Pro Asn Asp Val Leu Pro Trp Pro Asp Lys
        435                 440                 445
```

-continued

```
Ala Gly Asn Arg Ala Arg His Ala Gly Val Ser Val Phe Gly Phe Gly
    450                 455                 460

Gly Cys Asn Ala His Leu Leu Ile Glu Ser Tyr His Gly Gln Thr Ser
465                 470                 475                 480

Thr Ala Pro Ala Ala Asn Thr Ile Asn Ala Gln Leu Pro Met His Ile
                485                 490                 495

Thr Gly Met Ala Ser His Phe Gly Pro Leu Asn Asn Ile Asn Arg Phe
            500                 505                 510

Ala Asn Ala Ile Asn Gln Gln Gln Thr Ala Phe Thr Pro Leu Pro Ala
        515                 520                 525

Lys Arg Trp Lys Gly Leu Asp Lys His Pro Glu Leu Leu Gln Gln Leu
    530                 535                 540

Gly Leu Ala Gln Thr Pro Pro Thr Gly Ala Tyr Ile Asp Gln Phe Asp
545                 550                 555                 560

Phe Asp Phe Leu Arg Phe Lys Val Pro Pro Asn Glu Asp Asp Arg Leu
                565                 570                 575

Ile Ser Gln Gln Leu Leu Leu Met Lys Val Ala Asp Glu Ala Ile His
            580                 585                 590

Asp Ala Lys Leu Ala Ser Gly Ser Lys Val Ala Val Leu Val Ala Met
        595                 600                 605

Glu Thr Glu Leu Glu Leu His Gln Phe Arg Gly Arg Val Asn Leu His
    610                 615                 620

Thr Gln Ile Ala Ala Ser Leu Asn Ala His Gly Val Ser Leu Ser Asp
625                 630                 635                 640

Asp Glu Tyr Gln Ala Leu Glu Thr Leu Ala Met Asp Ser Val Leu Asp
                645                 650                 655

Ala Ala Lys Leu Asn Gln Tyr Thr Ser Phe Ile Gly Asn Ile Met Ala
            660                 665                 670

Ser Arg Ile Ser Ser Leu Trp Asp Phe Asn Gly Pro Ala Phe Thr Ile
        675                 680                 685

Ser Ala Gly Glu Gln Ser Val Asn Arg Cys Ile Asp Val Ala Gln Asn
    690                 695                 700

Leu Leu Ala Met Glu Ser Arg Gln Glu Pro Leu Asp Ala Val Ile Ile
705                 710                 715                 720

Ala Ala Val Asp Leu Ser Gly Ser Ile Glu Asn Ile Val Leu Lys Thr
                725                 730                 735

Ala Ser Leu Ala Lys Thr Gly Gln Leu Leu Pro Leu Ser Ile Gly Glu
            740                 745                 750

Gly Ala Gly Ala Ile Val Leu Gln Val Ala Asp Gln Thr Ala Thr Asp
        755                 760                 765

Ser Glu Pro Leu Asp Leu Ile His Gln Ala Leu Gly Ala Val Asp Thr
    770                 775                 780

Pro Ser Ala Ala Ile Ser Gly Ser Thr Glu Arg Ile Ser Ser Asp Ser
785                 790                 795                 800

Leu Asn Ser His Gly Ala Leu Asn Ser Tyr Ala Thr Ile Asn Ser Leu
                805                 810                 815

Ser Phe Gly His Ile Ser Gln Leu Glu Ala Ile Ser Asp Glu Leu Leu
            820                 825                 830

Thr Pro Ala Gly Leu Ser Thr Ser Asp Ile Gly Lys Leu Glu Leu Asn
        835                 840                 845

Gln Ala Pro Asp Leu Thr His Ile Asp Ser Ala Gln Ala Leu Ser Gln
    850                 855                 860
```

-continued

```
Leu Tyr Ser Gln Ser Ala Thr Thr Gln Ala Lys Ser Cys Ile Gly His
865                 870                 875                 880

Thr Phe Ala Ala Ser Gly Met Ala Ser Leu Leu His Gly Leu Leu Ile
                885                 890                 895

Gln Lys Gln Asp Ala His Ser Asn Gln Thr Val Gln Pro Leu Asn Thr
            900                 905                 910

Leu Val Ala Thr Leu Ser Glu Asn Gln Cys Ser Gln Leu Leu Met Ser
        915                 920                 925

Gln Thr Ala Glu Gln Ile Ser Ala Leu Asn Ser Arg Ile Asn Thr Asp
    930                 935                 940

Ile Gly Gln Gln Thr Ala Lys Lys Leu Ser Leu Val Lys Gln Val Ser
945                 950                 955                 960

Leu Gly Gly His Asp Ile Tyr Gln His Ile Val Asp Thr Pro Leu Ala
                965                 970                 975

Asp Ile Asp Asn Ile Arg Ala Lys Thr Ala Asn Leu Ile Pro Ala Val
            980                 985                 990

Thr Asn Thr Thr Thr Asn Met Leu  Glu Arg Gly Gln Phe  Val Ser Pro
        995                 1000                1005

Gln Leu  Thr Pro Leu Ala Pro  Met Phe Asp Lys Asn  Asn Ala Met
    1010                1015                1020

Thr Thr  Glu Thr Ser Met Pro  Phe Ser Asp Arg Ser  Thr Gln Phe
    1025                1030                1035

Asn Pro  Ala Pro Lys Ala Ala  Ala Leu Asn Ala Lys  Asp Ser Ala
    1040                1045                1050

Lys Ala  Asn Ala Asn Val Lys  Ala Asn Val Thr Thr  Ala Asn Val
    1055                1060                1065

Thr Thr  Ala Asn Gln Val Pro  Pro Ala His Leu Thr  Ala Phe Glu
    1070                1075                1080

Gln Asn  Gln Trp Leu Ala His  Lys Ala Gln Leu Ala  Phe Leu Asn
    1085                1090                1095

Ser Arg  Glu Gln Gly Leu Lys  Val Ala Asp Ala Leu  Leu Lys Gln
    1100                1105                1110

Gln Val  Ala Gln Ala Asn Gly  Gln Pro Tyr Val Ala  Gln Pro Ile
    1115                1120                1125

Ala Gln  Pro Thr Ala Ala Val  Gln Ala Ala Asn Val  Leu Ala Glu
    1130                1135                1140

Pro Val  Ala Ser Ala Pro Ile  Leu Arg Pro Asp His  Ala Asn Val
    1145                1150                1155

Pro Pro  Tyr Thr Ala Pro Thr  Pro Ala Asp Lys Pro  Cys Ile Trp
    1160                1165                1170

Asn Tyr  Ala Asp Leu Val Glu  Tyr Ala Glu Gly Asp  Ile Ala Lys
    1175                1180                1185

Val Phe  Gly Pro Asp Tyr Ala  Val Ile Asp Asn Tyr  Ser Arg Arg
    1190                1195                1200

Val Arg  Leu Pro Thr Thr Asp  Tyr Leu Leu Val Ser  Arg Val Thr
    1205                1210                1215

Lys Leu  Asp Ala Thr Met Asn  Gln Tyr Lys Pro Cys  Ser Met Thr
    1220                1225                1230

Thr Glu  Tyr Asp Ile Pro Glu  Asp Ala Pro Tyr Leu  Val Asp Gly
    1235                1240                1245

Gln Ile  Pro Trp Ala Val Ala  Val Glu Ser Gly Gln  Cys Asp Leu
    1250                1255                1260

Met Leu  Ile Ser Tyr Leu Gly  Ile Asp Phe Glu Asn  Lys Gly Glu
```

-continued

```
    1265                1270                1275

Arg Val  Tyr Arg Leu Leu Asp  Cys Thr Leu Thr Phe  Leu Asp Asp
    1280                1285                1290

Leu Pro  Arg Gly Gly Asp Thr  Leu Arg Tyr Asp Ile  Lys Ile Asn
    1295                1300                1305

Asn Phe  Ala Lys Asn Gly Asp  Thr Leu Leu Phe Phe  Phe Ser Tyr
    1310                1315                1320

Glu Cys  Phe Val Gly Asp Lys  Met Ile Leu Lys Met  Asp Gly Gly
    1325                1330                1335

Cys Ala  Gly Phe Phe Thr Asp  Gln Glu Leu Asp Asp  Gly Lys Gly
    1340                1345                1350

Val Ile  Arg Thr Asp Asp Glu  Ile Lys Leu Arg Glu  Thr Ala Leu
    1355                1360                1365

Asn Asn  Pro Asn Lys Pro Arg  Phe Glu Pro Leu Leu  His Cys Ala
    1370                1375                1380

Gln Thr  Glu Phe Asp Tyr Gly  Gln Ile His His Leu  Leu Asn Ala
    1385                1390                1395

Asp Ile  Gly Gly Cys Phe Ala  Gly Glu His His Asn  His Gln Gln
    1400                1405                1410

Ala Ser  Gly Lys Gln Asp Ser  Leu Cys Phe Ala Ser  Glu Lys Phe
    1415                1420                1425

Leu Met  Ile Glu Gln Val Gly  Asn Leu Asp Val His  Gly Gly Ala
    1430                1435                1440

Trp Gly  Leu Gly Phe Ile Glu  Gly His Lys Gln Leu  Ala Pro Asp
    1445                1450                1455

His Trp  Tyr Phe Pro Cys His  Phe Lys Gly Asp Gln  Val Met Ala
    1460                1465                1470

Gly Ser  Leu Met Ala Glu Gly  Cys Gly Gln Leu Leu  Gln Phe Phe
    1475                1480                1485

Met Leu  His Ile Gly Met His  Thr Leu Val Glu Asn  Gly Arg Phe
    1490                1495                1500

Gln Pro  Leu Glu Asn Ala Ser  Gln Lys Val Arg Cys  Arg Gly Gln
    1505                1510                1515

Val Leu  Pro Gln His Gly Glu  Leu Thr Tyr Arg Met  Glu Ile Thr
    1520                1525                1530

Glu Ile  Gly Ile His Pro Arg  Pro Tyr Ala Lys Ala  Asn Ile Asp
    1535                1540                1545

Ile Leu  Leu Asn Gly Lys Ala  Val Val Asp Phe Gln  Asn Leu Gly
    1550                1555                1560

Val Met  Ile Lys Glu Glu Ser  Glu Cys Thr Arg Tyr  Leu Asn Asp
    1565                1570                1575

Thr Pro  Ala Val Asp Ala Ser  Ala Asp Arg Ile Asn  Ser Ala Thr
    1580                1585                1590

Asn Asn  Ile Leu Tyr Pro Ala  Ala Ser Thr Asn Ala  Pro Leu Met
    1595                1600                1605

Ala Gln  Leu Pro Asp Leu Asn  Ala Pro Thr Asn Lys  Gly Val Ile
    1610                1615                1620

Pro Leu  Gln His Val Glu Ala  Pro Ile Ile Pro Asp  Tyr Pro Asn
    1625                1630                1635

Arg Thr  Pro Asp Thr Leu Pro  Phe Thr Ala Tyr His  Met Phe Glu
    1640                1645                1650

Phe Ala  Thr Gly Asn Ile Glu  Asn Cys Phe Gly Pro  Asp Phe Ser
    1655                1660                1665
```

```
Ile Tyr  Arg Gly Phe Ile Pro  Pro Arg Thr Pro Cys  Gly Asp Leu
    1670                 1675                 1680

Gln Leu  Thr Thr Arg Ile Val  Asp Ile Gln Gly Lys  Arg Gly Glu
    1685                 1690                 1695

Leu Lys  Lys Pro Ser Ser Cys  Ile Ala Glu Tyr Glu  Val Pro Thr
    1700                 1705                 1710

Asp Ala  Trp Tyr Phe Ala Lys  Asn Ser His Ala Ser  Val Ile Pro
    1715                 1720                 1725

Tyr Ser  Val Leu Met Glu Ile  Ser Leu Gln Pro Asn  Gly Phe Ile
    1730                 1735                 1740

Ser Gly  Tyr Met Gly Thr Thr  Leu Gly Phe Pro Gly  Glu Glu Leu
    1745                 1750                 1755

Phe Phe  Arg Asn Leu Asp Gly  Ser Gly Glu Leu Leu  Arg Asp Val
    1760                 1765                 1770

Asp Leu  Arg Gly Lys Thr Ile  Val Asn Asp Ser Lys  Leu Leu Ser
    1775                 1780                 1785

Thr Val  Ile Ala Gly Ser Asn  Ile Ile Gln Ser Phe  Thr Phe Asp
    1790                 1795                 1800

Leu Ser  Val Asp Gly Glu Pro  Phe Tyr Lys Gly Ser  Ala Val Phe
    1805                 1810                 1815

Gly Tyr  Phe Lys Gly Asp Ala  Leu Lys Asn Gln Leu  Gly Ile Asp
    1820                 1825                 1830

Asn Gly  Arg Ile Thr Gln Pro  Trp His Val Glu Asn  Asn Val Pro
    1835                 1840                 1845

Ala Asp  Ile Thr Val Asp Leu  Leu Asp Lys Gln Ser  Arg Val Phe
    1850                 1855                 1860

His Ala  Pro Ala Asn Gln Pro  His Tyr Arg Leu Ala  Gly Gly Gln
    1865                 1870                 1875

Leu Asn  Phe Ile Asp Lys Ala  Glu Ile Val Asp Lys  Gly Gly Lys
    1880                 1885                 1890

Asn Gly  Leu Gly Tyr Leu Ser  Ala Ser Arg Thr Ile  Asp Pro Ser
    1895                 1900                 1905

Asp Trp  Phe Phe Gln Phe His  Phe His Gln Asp Pro  Val Met Pro
    1910                 1915                 1920

Gly Ser  Leu Gly Val Glu Ala  Ile Ile Glu Leu Met  Gln Thr Tyr
    1925                 1930                 1935

Ala Ile  Ser Lys Asp Leu Gly  Lys Gly Phe Thr Asn  Pro Lys Phe
    1940                 1945                 1950

Gly Gln  Ile Leu Ser Asp Ile  Lys Trp Lys Tyr Arg  Gly Gln Ile
    1955                 1960                 1965

Asn Pro  Leu Asn Lys Gln Met  Ser Leu Asp Val His  Ile Ser Ala
    1970                 1975                 1980

Val Lys  Asp Glu Asn Gly Lys  Arg Ile Ile Val Gly  Asp Ala Asn
    1985                 1990                 1995

Leu Ser  Lys Asp Gly Leu Arg  Ile Tyr Glu Val Lys  Asp Ile Ala
    2000                 2005                 2010

Ile Cys  Ile Glu Glu Ala
    2015

<210> SEQ ID NO 5
<211> LENGTH: 542
<212> TYPE: PRT
<213> ORGANISM: Sh. japonica
```

<400> SEQUENCE: 5

```
Met Thr Ile Ser Thr Gln Asn Glu Lys Leu Ser Pro Trp Pro Trp Gln
1               5                   10                  15

Val Ala Pro Ser Asp Ala Ser Phe Asp Thr Ala Thr Ile Gly Asn Lys
            20                  25                  30

Leu Lys Glu Leu Thr Gln Ala Cys Tyr Leu Val Ser His Pro Glu Lys
        35                  40                  45

Gly Leu Gly Ile Ser Gln Asn Ala Gln Val Met Thr Glu Ser Ile Asn
    50                  55                  60

Ser Gln Gln Asp Leu Pro Val Ser Ala Phe Ala Pro Ala Leu Gly Thr
65                  70                  75                  80

Gln Ser Leu Gly Asp Ser Asn Phe Arg Arg Val His Gly Val Lys Tyr
                85                  90                  95

Ala Tyr Tyr Ala Gly Ala Met Ala Asn Gly Ile Ser Ser Glu Glu Leu
            100                 105                 110

Val Ile Ala Leu Gly Gln Ala Gly Ile Leu Cys Ser Phe Gly Ala Ala
        115                 120                 125

Gly Leu Ile Pro Ser Arg Val Glu Gln Ala Ile Asn Arg Ile Gln Thr
    130                 135                 140

Ala Leu Pro Asn Gly Pro Tyr Met Phe Asn Leu Ile His Ser Pro Ser
145                 150                 155                 160

Glu Pro Ala Leu Glu Arg Gly Ser Val Glu Leu Phe Leu Lys His Lys
                165                 170                 175

Val Arg Thr Val Glu Ala Ser Ala Phe Leu Gly Leu Thr Pro Gln Ile
            180                 185                 190

Val Tyr Tyr Arg Ala Ala Gly Leu Ser Arg Asp Ala Gln Gly Glu Val
        195                 200                 205

Val Ile Ala Asn Lys Val Ile Ala Lys Val Ser Arg Thr Glu Val Ala
    210                 215                 220

Ser Lys Phe Met Gln Pro Ala Pro Ala Lys Met Leu Gln Lys Leu Val
225                 230                 235                 240

Asp Glu Gly Leu Ile Thr Pro Glu Gln Met Ala Leu Ala Gln Leu Val
                245                 250                 255

Pro Met Ala Asp Asp Val Thr Ala Glu Ala Asp Ser Gly Gly His Thr
            260                 265                 270

Asp Asn Arg Pro Leu Val Thr Leu Leu Pro Thr Ile Leu Ala Leu Lys
        275                 280                 285

Asp Lys Ile Gln Ala Glu Tyr Gln Tyr Lys Thr Pro Ile Arg Val Gly
    290                 295                 300

Cys Gly Gly Gly Val Gly Thr Pro Asp Ala Ala Leu Ala Thr Phe Asn
305                 310                 315                 320

Met Gly Ala Ala Tyr Ile Val Thr Gly Ser Ile Asn Gln Ala Cys Val
                325                 330                 335

Glu Ala Gly Ala Ser Glu His Thr Arg Lys Leu Leu Ala Thr Thr Glu
            340                 345                 350

Met Ala Asp Val Thr Met Ala Pro Ala Ala Asp Met Phe Glu Met Gly
        355                 360                 365

Val Lys Leu Gln Val Val Lys Arg Gly Thr Leu Phe Pro Met Arg Ala
    370                 375                 380

Asn Lys Leu Tyr Glu Ile Tyr Thr Arg Tyr Glu Ser Ile Glu Ala Ile
385                 390                 395                 400

Pro Ala Glu Glu Arg Glu Lys Leu Glu Lys Gln Val Phe Arg Ser Thr
                405                 410                 415
```

-continued

```
Leu Asp Asp Ile Trp Ala Gly Thr Val Ala His Phe Asn Glu Arg Asp
            420                 425                 430

Pro Lys Gln Ile Glu Arg Ala Glu Gly Asn Pro Lys Arg Lys Met Ala
        435                 440                 445

Leu Ile Phe Arg Trp Tyr Leu Gly Leu Ser Ser Arg Trp Ser Asn Ser
    450                 455                 460

Gly Glu Ala Gly Arg Glu Met Asp Tyr Gln Ile Trp Ala Gly Pro Ala
465                 470                 475                 480

Leu Gly Ala Phe Asn Glu Trp Ala Lys Gly Ser Tyr Leu Asp Asp Tyr
                485                 490                 495

Thr Gln Arg Asn Ala Val Asp Leu Ala Lys His Leu Met His Gly Ala
            500                 505                 510

Ala Tyr Gln Ala Arg Val Asn Leu Leu Thr Ala Gln Gly Val Ala Leu
        515                 520                 525

Pro Val Glu Leu Gln Arg Trp Ser Pro Leu Asp Gln Val Lys
    530                 535                 540


<210> SEQ ID NO 6
<211> LENGTH: 303
<212> TYPE: PRT
<213> ORGANISM: Sh. japonica

<400> SEQUENCE: 6

Met Ser Tyr Cys Tyr Tyr Lys Cys Glu Phe Gly Leu Ser Pro Leu Pro
1               5                   10                  15

Thr Ile Gln Leu Phe Phe Cys Pro Leu Asp Thr Asn Leu Leu Asp Glu
            20                  25                  30

Lys Thr Val Ser Thr Val Arg Ser Trp Leu Ser Asp Ala Glu Ile Asn
        35                  40                  45

Lys Val Asp Arg Phe Ile Gln Gln Ala Ala Gln Gln Gly Leu Met
    50                  55                  60

Val Arg Gly Tyr Leu Arg Ser Val Leu Ser Asn Phe Ala Asn Ile Glu
65                  70                  75                  80

Pro Asp Asp Trp Gln Phe Glu Tyr Gly Glu Lys Gly Lys Pro Arg Leu
                85                  90                  95

Ser Ala Val Gln Tyr Lys Gln Thr Gly Leu Gln Phe Asn Leu Ser His
            100                 105                 110

Ser Gly Asn Trp Leu Leu Ile Gly Val Ile His Ser Lys Glu Asp Ala
        115                 120                 125

Ser Met Pro Ile Gln Leu Gly Val Asp Ile Glu Arg Arg Arg Glu Ser
    130                 135                 140

Thr Asn Ile His Ser Ile Leu His His Tyr Phe Ser Lys Pro Glu Glu
145                 150                 155                 160

Thr Ala Leu Leu Ala Leu Pro Glu Ser Gln Gln Arg Glu Arg Phe Phe
                165                 170                 175

Asp Leu Trp Ala Leu Lys Glu Ser Tyr Ile Lys Ala Lys Gly Leu Gly
            180                 185                 190

Leu Ala Leu Ser Leu Lys Ser Phe Ala Phe Asp Leu Ser Ala Pro Ser
        195                 200                 205

Leu Ala Asn Leu Thr Ile Asp Asp Gln Leu Leu Pro Ile Gln His Asp
    210                 215                 220

Ile Ser Leu Ser Leu Leu Lys Pro Thr Asp Val Asp Glu Leu Glu Gln
225                 230                 235                 240

Thr Asn Asp Val Glu Ser Phe Tyr Glu Val Ser Pro Leu Trp Gln Cys
```

-continued

```
            245                 250                 255

Cys Leu Gly Lys Leu Asn Asn Ser Tyr Arg Phe Ala Val Ser Val Gly
            260                 265                 270

Glu Phe Ala Phe Gly Glu Lys Pro Leu Thr Leu Gln Leu Lys Ala Lys
        275                 280                 285

Lys Ile Ser Trp His Glu Gln Ile Lys Met Phe Ile Lys Thr Asn
    290                 295                 300


<210> SEQ ID NO 7
<211> LENGTH: 38794
<212> TYPE: DNA
<213> ORGANISM: Sh. olleyana

<400> SEQUENCE: 7

gatccagtgt tattcaacca aattgaagca ttgaatactc cttatccttt tccaattcaa     60

ggccatgctc aattcgccat cgtgttttgg cgagaagatg agataccgtt tatttggttt    120

ttaaagcttc cgcttgatga acaagggtta ttgtctccag ctcaacgtag ccaattcatc    180

aaaatgatcc tcgaagcctt aggccgagat cctaccaaag cgctttctga tgaagaacaa    240

gagcgttatg ctaatcatcc gttcagcttc aaaccgagtc aggagaagct agccttattt    300

aacgcattag taaaaaaaca gttaagccaa caagcctcgg cgcagtacga atatgctgct    360

cagtactttg aaaatttgaa tgaaaaaaac gctcaagatg acagctggca gcaactgggt    420

ttacaaggca tcgccgatgt ctgtgtccgc ttagataagt ttgaccatga taagcatatt    480

aatacggcaa tgaagcttgc tcccttagaa gtacaagccg caatttgcca atgtttagaa    540

catgttgctg tttcaaatac attagctgaa accttatacg ataatttgtc atctgctgaa    600

gtggaacata aacatatcta ccttcgcgct cttgcttcac agcctgaatt gactcaaaaa    660

gcgattcagc aactggttaa tttacagcaa ctcgatgaga atttattaat cactattgca    720

gcaagaagtt ggacggcttt aaaagatgat gcaactcgca aactttatct tgaagtctta    780

gctaaccaac cacaaaactt ctttaatcaa gtttttgctg atatcgtagc tattccaagt    840

ctacggaact cactgctact tgatttaaga agtgctgatc gtagtgaaaa actttcttcc    900

gccatcggcg gattatttag ggccgttagc caatgatgtc agactttatt ttaatcgttg    960

ctgttgtggt tgttgctgca ttcttttggc agttacgcca gatggctgaa atcagtcgcc   1020

gatatgctga gagatcttgt gccaatcaaa aagtacaatt actcgcgatt gcgatggaat   1080

cagctagacc tagtattggc ggttcaacag gtttatgttg gcgagcaaaa tttatgtttg   1140

aattcagcac cgatggtatt aaccaatacc gcggtcatat caacatgcac agcaaaaaaa   1200

tagagaaaat taattggcct attttccctg agcccgaatg gatggatgcg ccaatggcaa   1260

aaggcaaatt cggtggttgt ggcggcgcat cgagctgtaa ctcaggtaag tgtcgttaag   1320

cctcaacaac tgcctaatca gtgagtcatt gtagagttaa tgtcactcgt atttactcaa   1380

aatatagtta caacaaaact gattattatc gtaataaaat aagcgctatt aggagaaatt   1440

cactcttaat ggcgtttttt attggctaag tgatttttttg tacgattgtt ggaaaacaca   1500

caagtcaaaa aatacttcac gtatggttat atatttagcc caaaagaaag accgcggcaa   1560

taaattgtcg cggcctcttg tacttttgtt aagccatcca gctatatctg tgctccctgc   1620

accatccatg cgtctaactt gctccgtgcg ctatccttat tctatccttg atgttccatg   1680

tacatttaag tactgtcctt cttactcgat tatcctttga ccgagcctgc tcaaatcctt   1740

aagcgtgtcc tttaattcgt ccgtggtttt cttccatgac atccttgatt caatttactg   1800
```

-continued

```
catccattgc aatcactgtt ttccttaaca gctcaaatcc attttattga tgtccaattt   1860
ataaaatcca tttaaccata aagtctttca tcatcttcga tgtcagtgtc atccataaac   1920
actatcgttt tccttaacga cgctttatcg tccacttaat taatgtgcct tagtcatcat   1980
cctgatgagc aacaacaata attaaggttc atcctgagca agccagcaca ataatctatt   2040
gtaacgctct gttgtaacaa tctcatgtta caaccacctg caaaaatcct attcagctgc   2100
agtctgaatt caaactgcta aacacttcct gtgcttattt gcttccttgt gattaatttt   2160
aatcgatatg tgagcaaata aatatgcaca aaacacacaa ttaacatcaa cccaacaaac   2220
aagcttggca cccataaaat taaactattt aaatacagta acttaaataa aaacacttca   2280
acatcgttat ggttaaagcg tttaatctca caacttttgt gagatatatc tcacaaagag   2340
tataggaaag acagaaggta agtcttttgg cctattcaca catttaacat ttgttaggta   2400
aaagtgcata aatattgatt tgaactgaac ataaaaaagc ccgaccttat aaataaggtc   2460
aggctcattt tactctttgt tagctatcct gctaaattgt gctccctgct ccatccatgc   2520
gactatatgt gcttcctgct ccatttatcc atttcaactc aatttccttg tattgcccca   2580
aatagagcat tacatgagtt ttcattcctt tgaatcagtc tatccatttg actgaaagtc   2640
ttactcctag atataccatc ctggtatttg cttcctgcaa tccttcatct tcctgatgag   2700
ggtcatcctt gtttcagtta atcattaact gagcttatgc ccattccttg agcgtgtcct   2760
tgtttcatcc tgaattggtt gttactcacc cagcatttac tcgataaata actaaattca   2820
cttaagcagc aatattcact taaaccaaat agttaattaa ctgttcttgt cttgcggcta   2880
cttcctgtaa ctcactaagt taatatattg attgcttaat gagttcattg taataaatgg   2940
atgaaataga gataggtaaa aaacgagcag aaacaaaaac ttcacaaacc tgaaattcag   3000
accaaaaact caagcacttg ttttatatcc acaaattaat aaaaaagtaa gatattgagt   3060
atttgggcta aacgaatacc tacatcaatg tgagataagt ctcacaaacg gaagtaacag   3120
ttagcttgaa taatttccca acttaaactg ttttttaac atttgtgcaa acatcaccca   3180
atcagctaat agactataaa acgggtactc gaatgttgct ggtcggtttt tctcaaacac   3240
aaaatggcca acccacgcaa aaccatagcc aatcacgggt aaaagccaca attgccacca   3300
ctgctgatta atgagcgtta taacaatcaa tattatgatt aatccacttc caacataatg   3360
cagccttcta caagtggcat cttgatgttg tgataaatag aaagggtaaa aagatttaaa   3420
gtcttggtat ttttttcgc tcatcttatc gtctccactt atatattatt gtttttgaga   3480
aagatgctaa acagaactgt agacaacata tggttcacaa aatgacagtt ttatttactt   3540
ggataaatga gaatttcacc atcgacactg ccaattgtta attcagacaa atgattaaag   3600
ccttcacgag caaataattc tgcatgctta gggttattca cgaaaacacc gataccatca   3660
agttctggct gctcatcaca ccaacttaac actgcctgga tcagcttagc gccattacct   3720
ttactttgct caattggcga taaagcaata aattgcaaaa taccatactg cttactcggc   3780
aagctttcta agatactgtg ctcttttttc atgagcgctt gggtcgagtt ccaaccggta   3840
cctaacacca ttttcaaacg ccaatgccaa taacggctct cacctaatgg cacttgatga   3900
gttatgacac aggcgactcc aatgagcctt tcaccatcga accagccaat taaaggttgt   3960
tcttgttgcc aaagttccgt taactcctcg cgaatagagg cacgtagttt ctgctcgtaa   4020
ctagcttggt tagtagtagc aagagcttca ataaagaaag gatcatcatg gtaagcgtta   4080
taaataattg atgcagccac gcgtaaatct tctgcagtta aataaacagc tctgtgttct   4140
tctaacgtgt tttgttccat gtttacactc tttactaaac caagttaata gttacaactt   4200
```

-continued

```
aacaagttta aaacatattg caattttaat gctgtcacct aggcttaaag atatctcgat   4260
agccaagtac acgataaatt ggggatgaaa atggatacaa cttcagcaac acttgctcac   4320
ttgtttgaac agctaggatt ggattcatca gatgctggaa taagcgtttt tctatcgcaa   4380
cataccatca aagcaagtac aaatttaact gaggctgact tttggaataa tgctcaaaga   4440
gcatttttag aagagagttt aaaagatgac gcccagtggt cagaactggt agaccaactg   4500
gacgttttgt taaggcaata gccacaagct tttaataagg caattgccaa aagcaaaggc   4560
cactctttga aacacattaa aaagtgacag tgcttaatag tttatttaaa ttttttgata   4620
cgcagtgtca ccccaaccca ctagcttatt atcactaatg acaaccggcg tacactcatc   4680
ttttgtggtc ttgccgtcac ctttactcca ttgagtacga taaaagagta cgtttacttc   4740
ttttttcggg ctttcggcgt ctgcctgagt aacgtatgcc tcactaaaat ctgcagttcc   4800
cattaatata gtgacttgat ctctcgccat acccatagtg agttttgata aattggctct   4860
gttagtttgt tgctgtgttt cccaataaga atcactatgg ttaccttcgc tgccaccaac   4920
atgaaataca caaccactta atgtaaggct acttgcagcc attaaaaatg ctaaacccaa   4980
ttttgttttc atgatacttc cttattatta aaatgattct cacgtaattt ctactcaaac   5040
tgcttttgag atacgttata atgttgtcta ttatcattaa gctaaaaaca tgccaaagtt   5100
tatacttttg attttattga atattattta atgaacatta ataagtaagt attttcacta   5160
atccatattg aggattttca ccaattatga gtccaatcga acaagtcctc gctgcagcga   5220
aaaccattgc attgaatggc catacaccga cgatggcatt agttaaaggt aagctcggtg   5280
gcaaagtgcc catgcctttg cttatccaag ggttacaaca atttaaagct attccgaaag   5340
accaatggca aactctgcct gacttaggtg attcacttga atcaaataag cctgcagcca   5400
acacagatac ccaagccata gaacaaaagc tactgactca aatgcagcaa atgaaaaccg   5460
aatttgaaag caaaatttcg ttattagaac aacgtattgc ccaacttgaa aacaaagcgt   5520
aaatacataa ataactgtcg ttagcgctgt taatcattgg cacgattgac tactagtacg   5580
attaaccact gcctaataac gctgacgcat cgcgcttata accccaaagt taaacggaac   5640
cccatgtttg tcacagagct aagatttgaa tgttttgcgg ataccacaat caccgcagcc   5700
gaaaaagcca ttaaccatta cctcgaatct ttgcgagcca acggccaagc cttgggaaga   5760
gaatttgccg tcgcatttaa tgaaggtgag tttaaagtta ggttattaat gccagaaaaa   5820
accagtctat cgactcgtca taatagtcct tggacgaaac aagcgttaaa ccagctcacc   5880
gaagctaaat tacttgcccc tcgtgaaaag tttattggcc aagatatcaa ctctgaagtc   5940
agtaattcag aaacacctag ctggcaggtg ctttatacta gctacgttca tatgtgctcg   6000
cctataagaa gtggcgataa cttgttgcct attccgcttt atcagatccc agccagcttt   6060
aatggcgatc ataaacgggt tatccgctgg caaacagaat ggcaagcttg tgatgaatta   6120
caaatggctg cagccacaaa agccgaattt gccgctttag aagagattac ctcccataaa   6180
agtgacttat tcagacgagg ttgggacata cgcggtagag ttgaattcat cactaagata   6240
ccgacttact attatctata ccgagtaggc ggcgacagtt tagctagtga aaaagagcgt   6300
gcctgccctc gttgtggttc taaagaatgg cgtttagatg aaccattact cgatatgttc   6360
catttcagat gtgagccttg ccgcatagta tctaacatct cttgggatca tcaataagtt   6420
gttatgaaat ccaaataata aagccagaca tttgtctggc tttattataa ttaatcattc   6480
atcaactgat taaattaaga cttcttacct ttaatcaaat cagcccacat cattttcatg   6540
```

-continued

```
cgttgccaaa tgcctgggtg cgcgacatag ttatcttcaa caataggttc aacaggtggc   6600
atcacgcgcg gggttaatcc atcaataaac tcagctaaac tgtcagcgag tttatcttta   6660
ggcttatcac caggaatttc aatccacaca ctgccatctt cgttatcaac agtaatcatt   6720
tgatcgccat cacctaatac gccaacaaac caagtgggtg cttgtttgag ctttttcttc   6780
ataatcagat gaccaatcac attttgttgc aaagattcaa agtcttgctg attccaaact   6840
tgcaatagct caccttctcc ccaagttgaa tcaaaatata aaggcgcaga aaaatattcg   6900
ccataaaacg catttatatc ttggtgcaac ttaagctcta aagcatgttc tacattactg   6960
aaatttgagc tatttttacg tttaatcgct ttccaaaaaa ccgcatcatc tgaatcaaga   7020
tcatacttac cttcaataca ggcggatcct tgcccaagtg ggaaataacg ggaaactcg   7080
cctaatacat cctgataagc ttgaaaataa cggctagaaa aatgatccaa tgaagttgaa   7140
caagacactt aagatgctcc aattttgggt tataatataa gtctattttg acacggaaac   7200
agactagatg acacacaatc acgatcccta tagtgatgca gatgcactta aaggactgac   7260
tttaggtcaa acgacacaat atcaagcaga atatgatgct tcactgctac aaggggttcc   7320
tcgtaaactc aatcgtgatg ccatagcatt aaccgattcg ctcccttttc agggcgcaga   7380
tatctggacc ggctatgaat tatcttggct aaatgccaaa ggcaaaccaa tggttgccat   7440
tattgaagtt tacctcgcta tcgaaagtga taatttaatc gaatctaaat cgtttaaact   7500
gtatctcaac agctttaacc aaacacgttt tgagtcagtt gagcaggtac agcaaacatt   7560
agtcactgac ttaagccatt gtgctaatgg cgaagtgaca gttaaagtga ttgaacctaa   7620
acattttaat actcaacgta ttgtcgaatt accaggtaat tgtatcgacg aacttgatat   7680
tgaagtggat gactacgagt ttaatcctga ctatctacaa gacagtactg aagataaaaa   7740
cgttgtcgaa acagtcacat ctaacttatt gaaatcaaac tgtcttatta cctctcagcc   7800
agattggggt agtgtcatga tccgttatca agggcctaaa attaatcatg agaagttgct   7860
tcgctacttg atttctttcc gccaacataa cgaattccat gagcagtgtg ttgaacgtat   7920
atttactgac ttaaaacgct actgtaactg cactaaacta acggtatatg cccgttatac   7980
tcgacgtggc ggtttagaca ttaatccttt cagaagtgat tttgaacaac cacctgaaac   8040
ccatcgttta gcaagacagt aatgggtttc taataataaa aagcctgcaa ttgcaggctt   8100
ttatattgtt tatagtcggc actaaaattt ttacgcataa tgcccaataa tagccgctaa   8160
atcatctacc gtattggcaa tatgatcagg tttaacatgc cagctttctg gctctgattg   8220
gctataagct gctgcaacag aaatgacctt ggcatcgctg cctaattcta attgcaaatt   8280
acgggcaaat tgtgcatccg cttcatgatc cccgatgtac atcagtaagt tactatttgc   8340
gtgacccagt attgattcaa cacatttcag gccgccgaat gggtgtggtt tttgattacc   8400
gttaggtaca tcgtcatagc caataatcgc tttaaacggt gcaccaattt cattgctatt   8460
gagaacacgg cgaatattat tttgcgaatt ttgcgaacag atcccgtgat caaaatgaga   8520
aaactgttca acaacccct taatgccgtc aaatagcatg acttctgttt cattcttttc   8580
ttgaaactca gcccacatgc ttccagcttg aagcatttca ttttcagtta acccatagta   8640
atcaacatag agttgctgcc aatttttagc accatgatta gcttcatggt aattagcttc   8700
gcttagtaag tacttaggca agttttcgcc agttaaatgc ggtgcaacga tagacagtat   8760
tgctttggtg atatcaatat ttttcggtac agaattgact agagttccat cataatccca   8820
aagtattgcg tctaatttca ttgcatcatc tcattgttta ataaacggta ttaaggagta   8880
cactgttggt gtaaaaagtg gctcagatga atctcgttaa atacctttaa attatgtaac   8940
```

```
gagaaatctg gcgattaaaa taagcttcat cgtgttaaaa aacaactgtt atcacctcag    9000
tctgagctac ctgttaagtt tttactgctc gcgtcatcat cttaaaaaat tggttaaaac    9060
tgacttcatg agggttcagt gcatctcctg caaatggacc atataataag gaaccgtata    9120
atatagcctc attgaggttt atagattaag agcaataaca ctactcatgc caaaaccaac    9180
ctgtttaacg gaattaaatc aagagtcgct caatgactct caagagcatc agcactttaa    9240
aatatttaaa ccttatggat ttttgagcca gtttgttcct gaaacacgaa agaaaaagca    9300
cttacttgca gagctctcaa acttccccga aaaaaccatg gcgattggtc gcttagatca    9360
cgattccgaa ggcttactct tgctcacaac agacggcatg atgagtcata aagtaagaag    9420
caaaggcata gaaaaagagt attacgtgca agtggatggc gatattaacg atgaggctgt    9480
atctctgtta caaaatgggg ttgaaattgg catcaatggc acaaaatatc ttaccctgcc    9540
ttgtaaagca ttcaagctaa acgcagagcc aatgcttccc tcacgcggta aaaaaattcg    9600
cgatccaagg catgggccaa ccagttgggt atcgatcacc ttatgtgaag gtaaaaatcg    9660
tcaaataaga aagatgacag cagcagtagg ttttgcgacc ttaaggctag taagagtcag    9720
aattggcgat attcatattg atgccatgca agcaggcgat gttatttctc tgagcaattt    9780
tgacgcggct attaatagcg ataattaacg gtcactttct agcaaataca ccttttccat    9840
tgctgtttca actaactcac gtaaccactt cgttgccggg tcttgttgat tacgggtcgg    9900
ccaaatgctg taaattgata tcaattggct ttcgaacggt aaatccatca aggttaaatt    9960
aaaagtagat tgatagtttt tagcataggt atatggcgca atgcagattg catcagattt   10020
gctgactccc gataacatgg tgagcaaaga tgatttttcg ccatacatat ggcgttcagg   10080
taaatgctct gtagaaataa tctctgctac tcgctgatta tgtcgatgta atcggtaaaa   10140
caaatgttta gccgtaaaat acgactgctc atcaatacca tttttaaatt gaggatggtt   10200
cgccctcgcg acacaaacga gcttttcggt agcaatttgt ttgctggaaa atgatgcttc   10260
gctcggcgcc acaatatcta acgctaaatc aatatgctgt ttttgaagcg cttgatataa   10320
attaccttca tcaataatcg cttcagtaaa gatgatttca acgcctttat cagccaccga   10380
tttttcaata tcggcctcaa tcaaatcaat aattgattca tttgcactga catgaaaaac   10440
acgttttgat tgctgcgggt caaacacttt aacgctatta atacactgct ctatatcgat   10500
taaagatggt cctaaggttt ggtgcaaatg ttggcctatt gcggtaagag caatacctcg   10560
accttgcctg acaaataact ccgcccccaac aagggtttta aagcggttaa ttgcattgct   10620
gacagaagat tgggttagtg aaaggtgctc tgctgcaagt gtaattgatt gataatcaca   10680
tacactacaa aataccctaa caagattaag atcgagctta tgcagctctt gttggctcct   10740
ttcttgttgc agttgttcta attgcaattg ccctaaacct tgcttcactt ttaccacctt   10800
aatacgtcat ttgaacaaat agatttccaa tacaaatgct cattcaagtc attgattctc   10860
gcctaataca ttcacacagt aaatgtatta actattctta gccatagtta tctttgccaa   10920
ttttgttgtt aacttatatt caacaacaat aaatcctaga ggcttacatg agaaaatcat   10980
tacttggttt agcgattacc ctaacgttta ccacccaagc ttttgcagct caacatgaac   11040
acgaccatat cactgttgat taccatggta agcccgcaac tcctatcact gctgaacata   11100
ataagtcagt agcaaaaacc ttaaactttg atgataaagc cgcttttgag cgatttagca   11160
aaaacaaaat cgcctcattt gatgaagcta cagccaaaat tctacgagca gaatttagct   11220
ttattagtga agagttaccg gactctgtaa acccatcatt atatcgtcaa gcacagctga   11280
```

-continued

```
atatggtgcc aaacggacta tataaagtca caggtggtat ctaccaagtc cgtggtacag  11340
acttatctaa cctaaccctt atccgaggca aaactggctg gattgcttat gatgtattac  11400
tcaccaaaga agcagcgcag caatcgttaa agtttgcttt tgctaactta ccagaaggtc  11460
aggatttacc tgttgtcgcg atgatttact ctcatagcca tgccgaccac tttggcggtg  11520
cccgtggagt gcaggaacta tatcctgatg tgaaagtcta tggttcaaac aatatcacct  11580
cagaaattgt tgatgagaat gttcttgctg gtaacgtgat gagccgccgc gcagcatatc  11640
aatatggcgc cacactgggt aaacacgacc acggtattgt ggatgcagca cttgccaaag  11700
gtttatcaaa aggtgaaatc acttacgtta aacccgacta tgaacttaat cataaaggta  11760
aatgggaaac cttaaccatt gatggtcttg aaatggtatt tatggatgcc tctggcactg  11820
aagccgccag tgaaatgatc acctacattc cgtcaatgaa agcgctatgg tcaggtgaat  11880
taacttatga tggcatgcac aatgtataca ccttaagagg agctaaagta cgcgactctt  11940
taaaatggtc taaagacatt aatgaaatga ttaacgcctt tggtgaagac gtaaacgtat  12000
tatttgcctc tcattcagcg ccagtttggg gcaataaaga ggttaatcat taccttcgca  12060
tgcagcgtga taactatggt ttagttcata accagtcaat gcgtttagcc aatgacggca  12120
tagttattca agatattggc gacgctatca tggagaccat acctcaaaac gttcaagacg  12180
aatggtacac caatggttat cacggcacct atagtcataa tgccaaagct gtatacaaca  12240
tgtacttagg ctactttgac atgaatccag ccaatttaaa tccattaacc actaaagcag  12300
aagcaacaaa atttgttgaa tatatgggcg gtgcagataa cgtggtgaaa aaatcaaaac  12360
atgattttag ccaaggagag tatcgctttg ttgccacagc acttaataaa gtcgttatgg  12420
cagatccaca acacgatgca gcccgagagt tacttgcaga cacctacgaa cagctaggtt  12480
atcaagctga aggggctggg tggcgtaata tttatctcac tggtgctcaa gagttacgag  12540
tgggtattaa gcctggcgcg ccaaagtcgg cctctgctga tgtgatcagc gaaatggaca  12600
tgtcgacctt atttgatttc ttagcagtaa aagtcgacag cattaaagct gcggcacttg  12660
gtaacattac cttgaatgta gtgacacaag atggaagcca aaccaacacc ttatttgttg  12720
agttaagtaa cggtaactta agcaatattg ctgtcgagtc tccaaaacaa gctgatgcaa  12780
ctctgactgt aaataaagct gatgtggttg gcatactatt aggcaagacg aatatgaaag  12840
cgctgatgca atcaggtgcg gcgacaatgg aaggtgacaa acaggctttc gctaaaatcg  12900
cttcgactct agtgcaattt aatcctgact ttgaaatcgt tccattaaag catgctcatt  12960
aattagggct tgttaaatga tgagagtcta gtggctcaga ataaacagtt ttaaaacgaa  13020
acagttttac ctatcagttg gtttgaaggc gtgatttaca acttcaagcc aactgatttt  13080
ttttgctttc agctccggag gtaactcgtc tgaatttgta gacgcacgac ccacactcac  13140
agcaaaacga tacaaatcat caagctttcc taaataacaa tgccactgcg gggcaatgac  13200
aaaatcctct aataaaccat cagagtcact cgcctttagt aagcttaact tgacattttg  13260
ttggatggtg attgtctcac tgttaacttg tagttcaccc acacttgagg cagataaatc  13320
aaacgcaaaa gattttagcg ataaagctag acctaagcct ttcgctttta tataagactc  13380
cttaagcgcc cataaatcaa aaaagcgttc tctgtgttta tcttcagcta aagccagtaa  13440
tgcactctct tctggttttg aaaaatagtg atttagaatc gaatgaatat tcgttgtttc  13500
acgacggcgt tcaatgtcta caccaagttc tatatctgtt tgttgttgag ctgttccata  13560
tgtgtttgcc accccgatta acaaccagtc accactgtga ctcagattaa actgcaaacc  13620
agtttgcgca aactgctccg ccgttaacct cggcttgccc ttctcaccat attcaaattg  13680
```

-continued

```
ccattgctgc ggctcaacac tagcaaagcg cgataacaca ctgcgtaaat agcctcgcac  13740
cattaaacct tgttctctag atgattgctg aataaaacga tcaacctttt tgacctcatc  13800
ttcaggcagc catgaacgca caatagacgc agtcgattca tctaataaat cagtattaag  13860
gggacagaaa aataattgaa tgacggttgg cggcttcaaa ctaggctcag gctaaattgg  13920
caatgtacca ttgtcgcttg ttttaggaag cgatttcaac aagcaaggtt acttatcgat  13980
atggttgcgg cgttaatacg ctgatgtgtc aacgccaaaa cgtgggttca ctgaactaaa  14040
acagtcttga actaacttta attaatccaa aacaaactta atttacctga tgaaaaaaag  14100
ggttgagcaa tgctcaaccc tctatgggtt ttatcctata acaggcattt aaaaattact  14160
ctgccagtgc ttttactgcc ttttgaggaa gcacatcgta gcggctgaaa tgcatcgaga  14220
attgcccttc gccacctgtc atcgacttaa gccgagtgga gtaattactc acgttagcca  14280
gtggcgcttc aacactcact tccactaaac cattgctact tgcttgggta ccgcaaacga  14340
tacctcttga agaactaata tcccccgtaa tttcacccac atggttttga gccacatgaa  14400
tttgcatatc aacgataggt tctaaaataa ccggctgagc cagttttacc gcttccataa  14460
aggctttttt gcccgccata acaaaagcaa tctcctttga atcgacactg tgatgcttgc  14520
catcaagcaa agttaccttc acatcctgta atgggtatcc acccatttcg cccgctaaca  14580
tggcttcgcg tacacctttc tcaacggctg gaatgtactg ggttggcaca gaaccgccca  14640
ccacttggga gacaaactca aaaccttgtc cacgcgctaa cggttcaact tttaattcaa  14700
cttcgccaaa ttggccagat ccacctgatt gctttttatg acgatatcga tactctgcct  14760
cagccataat ggtttcacgg taagccacag ccggcgtatc agtttccata tccacattaa  14820
ataaattttg cgctttctct aaggcaattt gaaggtgtaa gtcaccttgt ccttgcagca  14880
cggtttgacc ttcagcttcg ttgcgactga tttgtaaact tggatcttcg gccaccagct  14940
tatttaatac ttccgatatt ttctgctcat caccacggcg tttagctgat actgccagac  15000
caaaaatagg ttgcgggaat ttaagctcgg gtaaatggaa ttcatcttca tcatgactat  15060
cgtgaagcac agctcccaca gataactctt caagcttagc aatggcgcaa atatcaccag  15120
gtaacgcttg attgacatta atttgtttgt cgccttgaag tttcattaag tgagacactt  15180
taaacggctt gcgtccgcta ccaatgaaca atttcattcc cacagaaatc gtaccttgat  15240
acaagcggaa aacccccata cgtccaaaga acggatctat cgccacccta aatacatgcg  15300
ctaaaacatg atcagaggct ttttgagtga catcaatcgg cttagcttca tcaccgtagc  15360
ctttaataaa ttgcggcgga ttcgcttcaa gtggattcgg cattaactta accagaatct  15420
ctaacaacga actgatgcca atatcttgct ctgcgctagt aaaacaaact ggcaccaagt  15480
gccccattct taacgctgtt tccaatggcg catgcagttg ctctggcgta agtgattcgc  15540
cttgttctaa ataaagctcc attaaagctt catcttcttc aagtacggta tcaaccagct  15600
catctcttgc tgtagcggca ttgctaaaca aagtattgaa agtttcatca caatgtaagt  15660
agcagtcaac cacatcatcg accaaaccat cagctgtaac attgggtaaa ttaaccggta  15720
agcatctgtg gccaaattga tgttgaatat ccatcatcac atcaaacacc ttggcttcat  15780
ttccatccat gtgatttatc gcaatgatga ctgctttacc ttggcttcga gcagcttcaa  15840
atgctcgttt tgtcacggat tcaatgccaa cacttgcgtt caccactaac aatacagatt  15900
caacaccagg taatggtaat agcgcacgtc caaagaagtc gggtaatcca ggagtatcga  15960
tgaaattgat gtggtgagat tgataatcga gatttaaaaa tgaaggttct aaactgtgac  16020
```

-continued

```
gatgagattt ttcttgggca gtgaaatcag catgatttgt acccttatcg accctgcctt  16080
ttaaacttat agcatcagcg ctaaagagta acgcctcaag taacgaggat ttacctgcgc  16140
ctgtgtgtcc gagcactgcc agattgcgga tttgctcagt ggtaaactca gccatgatgg  16200
cctcctttgt tcacattatt aaactatcca tatctttgtc ttactatgtt tacatttgac  16260
gataaaacac ccataaattc agtatagatc ggtaacattg ttgaataatt gacacagatc  16320
actctttaca cccgcaacgt tttttataac aaaatcaccc attcagctta caagtgttag  16380
ctctttctgg tcgtatcagt aattaattag tttcgggtga ttgtatcgac ctgaaacctc  16440
aggtactctg catgctcgat tgtgataaaa cgctaataat gaagatgaac aaacgttaat  16500
cttcagtatt ttttagagag tcccaataga ttgtacggag tgttcattct gctatggccg  16560
tccttaaatg actgcaaacc gacaagctaa atcagccact aaaacagtgg taaaaaaatc  16620
ctcttccgat tgtgatgtag cgagcacacc tgtgcgccat cgtaatgcga caacgacccc  16680
cgaaatgcgt caatttatcc aaacttccga ctttagtgtc agccagttgg ctaaaattct  16740
gaacatatca gaagccacgg taagaaaatg gcgcaaacgt gactccatca gcgatacacc  16800
caatacgcca catcacttaa aaaccaccct ttcacctatg gaagagtatg tggttgttgg  16860
cttacgttat cagctgaaaa tgccgttaga cagattgcta aaagtcactc aacagttcat  16920
caataaagat gtttctcgtt caggacttgc ccgctgctta aaacgctacg gtgtatcgaa  16980
actcgatgaa ttcgaaagcc cctatgttcc agaacgctat ttcaaccaat taccgattgt  17040
tcagggtaca gatgtagcga cttacacact gaaccctgaa actcttgcta aaaccctgtc  17100
attgcctgaa gccacaccag acaatgtggt gcaagtggta tccctaacga ttccacctca  17160
actgactcaa gcagacagct attccatttt actcggtgtc gactttgcaa ccgactgggt  17220
gtatctcgac atttatcaag acaaccacac acaagcaacc aatcgctata tcgcttatgt  17280
gttaaagcac ggaccgttcc atttacgtaa attactcgtc aaaaattatc atactttttt  17340
agcccgtttt cctggtgcaa cagtgttgca ctctgtggaa gcggcgaacc aaaaaaataa  17400
atcagctaag gatcagctga acactggaga ctcaaaatga gccaagcccc tacaaatcct  17460
gagacctcat ctcaagataa caacgagtcg caagatacaa gactgaacaa acgtcttaaa  17520
gacatgccta ttgccatcgt cggcatggca agtatctttg ctaattctcg ttacctgaat  17580
aagttttggg acttaatcag cgagaagatt gatgccatca cagaagtgcc tgatacccat  17640
tggcgcgctg aagattactt tgatgccgat aaaagcaccc cagataaaag ctactgtaaa  17700
cgtggtggat ttatcccaga agttgatttc aacccaatgg aattcggcct gccaccaaat  17760
attttagaac tgactgatac ttcgcaattg ctatcattag tgattgccaa agaagtgctt  17820
gcagatgcgg gcgttacctc tgagtacgat accgacaaaa tcggtattac gctgggtgtg  17880
ggtggcggtc aaaagattaa tgcaagctta accgcgcgcc tacaataccc agtacttaaa  17940
aaagtattta agagcagtgg tctaagtgat gctgacagcg atatgctgat caaaaagttc  18000
caagaccaat acattcactg ggaagaaaat tcattcccag gctcactagg taatgttatt  18060
gctggtcgta ttgctaaccg cttcgatttg ggcggcatga actgtgtagt agatgctgca  18120
tgtgcgggct ctcttgctgc aatgcgtatg gcgttaactg agctagttga aggccgcagt  18180
gaaatgatga tcacaggtgg tgtgtgtacc gataactcac catcaatgta tatgagtttc  18240
tctaaaacgc ctgcgttcac caccaatgaa accattcagc catttgatat cgactcaaaa  18300
ggcatgatga ttggtgaagg tatcggcatg gtagcactta agcgcctaga agatgctgag  18360
cgtgatggcg accgtattta ttctgtgatt aaaggtgtcg gcgcttcatc agacggtaaa  18420
```

-continued

```
tttaagagta tttatgcacc gcgccctgaa ggccaagcaa aagcattaaa acgagcttat  18480
gatgacgctg gttttgcccc tgaaacagtt ggcttaatcg aagctcacgg tacgggtact  18540
gctgcaggtg atgtagccga atttaacggc cttaaatctg tatttggtga aaacgatcca  18600
actaagcaac acatcgcttt aggttcagtg aaatcacaag tgggtcacac gaaatcaacc  18660
gctggtactg ctggcgtgat taaagctgcc cttgccctgc accataaagt attgccaccg  18720
accattaacg tctctaagcc aaaccctaag cttaatgttg aggattcacc gtttttcgtt  18780
aataccgaaa cacgcccatg gatgcctcgc cctgacggca ctcctcgccg tgctggtatt  18840
agctcgttcg gttttggtgg aactaacttc cacttagtat tagaagaata cacccctgag  18900
cacagccatg atgagaaata ccgtcaacgc caagtggctc aaagcttatt aatgagtgct  18960
gataataaag cagccttgat tgcagaagtg aataagctaa ctgcagacat cagcgcgctt  19020
aaaggcacag ataacagcag cattgaacaa gctgaacttg ctcgcattgc taaactatat  19080
gctgttcgca ccatagatac ttcagcagcc cgtttaggtc ttgtggtatc aagccttaat  19140
gaattaacca ctcagcttgg tttagcgtta aagcagctta ataatgatgt tgatgcatgg  19200
caactgccat cagggactag ctaccgctct tcagcactca tcacgattaa tgcaaaccaa  19260
aaggcgacta aaggtaaaaa agcgactaac gcaccgaaag ttgcagcatt gtttgcaggt  19320
caaggctctc agtacgtcaa catgggtatt gaagtcgctt gtcacttccc tgaaatgcgt  19380
cagcaattaa tcaaggccga taaagtattc gcaagctttg ataaaacccc gctgtctcag  19440
gtgatgttcc cgattccagc ctttgaaaaa gcagataaag atgcacaagc agctttactc  19500
accagcactg ataacgcgca aagcgccatt ggtgtaatga gcatgagcca ataccaattg  19560
tttactcagt ctggtttcag tgcggatatg tttgcaggtc acagctttgg tgaactgtcg  19620
gctttatgtg ctgctggcgt tatctctaat gacgattact accagttatc atttgctcgt  19680
ggtgcagcta tggcttcatc agcagttgat aaagatggca atgagctaga taaaggcacc  19740
atgtacgcca ttatcttgcc agccaatgaa gctgatgctg caaacagcga taacatcgcc  19800
aagctagaaa cctgtatctg tgagtttgat ggcgtgaaag tcgctaacta caactctgcg  19860
actcaattag tgattgctgg cccaacggac tcttgtgcaa atgcagccaa agccattagt  19920
gctttaggct ttaaagccat tgcgcttcct gtatcaggtg ccttccatac tccacttgtt  19980
gggcatgcgc aaaaaccttt tgcaaaggca attgataaag ctaaatttac tgccagcaaa  20040
gttgatttat tctctaatgc gacaggtgaa aagcatcctg ctgatgctaa atcaattaaa  20100
gcggcgttca aacagcacat gttgcaatca gtgcgtttca ctgaccaatt aaacaatatg  20160
tatgatgctg gtgcccgtgt atttgttgag ttcggaccta agaatatttt acaaaagctg  20220
gttgaagcaa cgctaggtaa taaagctgaa gctgtatctg tgattagcat taaccctaat  20280
cctaaaggca atagcgatgt gcaattacgt gtcgctgcta tgcaacttag cgtattaggc  20340
gctccgctta ctgaagttga cccttaccaa gctgaaatcg cagcccctgc tgtaccaaaa  20400
ggtatgaacg tcaagttaac tgcgtcaaac cacatcagcg caccaactcg tgccaagatg  20460
gaaaaatcat tagcaacagg ccaagtcact tcacaaatcg ttgaaacgat tgtagagaaa  20520
gttatcgaaa tgccagttga aaaagtagta gagaaaatcg tggaaaaaga agttatcaaa  20580
actgaatatg ttgaagttgc cgcatctggc gcaacagcag tgcctaacgc cgctgcacca  20640
gtggctcaag cttctcaagt aatagcacct caaatgcaag ttcaggcaac gcctgtagct  20700
ggcagcttag aagcgttctt taatgcacaa cagcaagccg ctgatttaca tcagcaattc  20760
```

-continued

```
ttagccattc cacaacagta tggtgacacc tttacacacc taatggccga gcaaagtaaa  20820
atggccgctg ctggacatgc tattcctgag agcctacaac gttcaatgga gctattccac  20880
caacatcaag ctcaaacact acaaagtcat actttgttcc ttgagcagca agcacaatca  20940
agccaaaacg cattaagcat gctgactggc caagcaccag ctacaacaac gccagctgtt  21000
aatgctccta gagttaatgc gcctatcact gaaaatccag tagttgctgc gccagtcgtt  21060
gaagctgtta aagtagccgc tacggttcaa actccgacgg cacaagctcc agctgttcaa  21120
gcgtcaatta ctcaaactgc tgccaaacca gccgctatgg ccgctccagc gccacgtatt  21180
gaaccagtaa aagcaactgc cccagttgca gctcctgtcg ttgcgccagc agttgcagca  21240
gcacctgcag gtttaagcgc agaaacagtt ctgaatacta tgttagaagt ggttgcagaa  21300
aaaacaggtt acccaactga aatgcttgaa ttaagcatgg atatggaagc tgatcttggt  21360
attgattcta tcaaacgtgt tgagatctta ggtactgttc aagacgaact gccaacacta  21420
cctgaactaa gccctgaaga tttagccgag tgtcgtacgc ttggtgaaat cgttgactac  21480
atgaactcta aacttcctaa aagtgacgct tcaggaactc aaacgcaagt cgcgccagtt  21540
caagcagcat caggccttag cgctgaaaca gttctgaata ccatgcttga agtggttgct  21600
gaaaagaccg gttacccaac tgaaatgctt gaattaagca tggatatgga ggctgatctt  21660
ggtattgatt ctatcaaacg tgttgagatc ttaggtactg ttcaagacga actgccaaca  21720
ctgccagaac taagccctga agatttagct gaatgtcgta ctcttggcga aatcgttgac  21780
tacatgaaca gcaagcttcc tgctgctggc tctactccag ttgcatcacc agttcagtct  21840
gcggctccgg tatctggcct tagcgctgaa acagttctga ataccatgtt agaagtggtt  21900
gctgaaaaga ctggttaccc aactgaaatg cttgaattaa gcatggatat ggaagccgat  21960
ttaggtatcg attcaatcaa gcgtgttgag attctaggaa ccgttcaaga tgaactgcca  22020
acactgccag agcttagccc tgaagattta gctgagtgtc gtactcttgg tgaaatcgtt  22080
gactacatga actctaagct tcctacaagt tcagccgcag gcgctaatac acaggctgta  22140
gctccagttg ctcaagaatc aggtttaagt gctgaaacag ccttgagcgc gcaagaagtt  22200
caaagcacta tgatgactgt agttgctgaa aaaaccggtt acccaactga aatgcttgaa  22260
ttaagcatgg atatggaagc cgatttaggc atcgattcaa tcaagcgagt tgaaattcta  22320
ggtacagttc aagacgaatt accaacacta cctgagctaa gtcctgaaga tctagctgaa  22380
tgtcgtactc ttggtgaaat cgtatcttat atgaattcta agttacccgc cgcaggcgct  22440
atgaacagca cagccgttgt agctcaagct tctggtttaa gtgctgaaac agccttgagc  22500
gcgcaagaag tacaaagcac catgatgact gtggttgctg aaaaaaccgg ttacccaact  22560
gaaatgcttg agctaagcat ggatatggaa gcggatttag gcatcgattc aatcaaacga  22620
gttgagatct taggtacagt tcaagatgaa ctaccaacgc taccagagct taaccctgaa  22680
gatttagctg agtgtcgtac ccttggcgaa atcgtgagct acatgaacag caagcttcct  22740
gctgtcagtg cgacaactgc cgcagggact caaacacaag cagccgcagg cgctactcaa  22800
gcttctggtt taagtgcaga gcaagtgcaa agcactatga tgacagtcgt tgctgaaaaa  22860
accggttacc caactgaaat gcttgagcta agcatggata tggaagcaga tttaggcatc  22920
gattcaatca aacgtgttga aattttaggg acggttcaag acgagcttcc aggcttacct  22980
gaattaaacc ctgaagattt agcagagtgt cgcaccctag gtgaaatcgt tagctatatg  23040
aacagcaaac tttcaacaag tgcagctgaa ggctctcagc caacgctaag ctcaactgac  23100
acttcaccag caacagccac agctgagtta gcaacagact tacctcctca tcaggaagtt  23160
```

-continued

```
gctctaaaaa agctaccagc ggcggataag ttagttgacg tttttcaaa agacgcatgt  23220
atcgttatca atgatgacgg ccataacgca ggtgttttag ctgaaaaatt agtagcaaca  23280
ggcctaaccg tcgccgttat tcgtagccct gagtcagtga catctgcgca atcaccgctt  23340
agcagtgata ttgccagctt cactttatct gcggtcaatg acgacgcgat tagcgatgtc  23400
attgctcaaa ttagcaagca acataagatc gccggctttg ttcacctgca acctcaacta  23460
acagcacaag gtgctttgcc attaagtgat gcaggttttg tagcagtgga gcaagctttc  23520
ttgatggcta aacacctaca gaaaccattt gctgagctag ctaaaactga gcgcgtaagc  23580
tttatgactg ttagccgcat tgatggcgga tttggttact taaacagtaa cgaacttgca  23640
aaggctgagc taaaccaagc tgcattatct ggtttaacta aaacattagg tcatgagtgg  23700
ccaactgtgt tctgtagagc attggatatt accccaagct ttgaggcagt tgagttagca  23760
caagccgtta ttgaagagtt atttgatctt gatactgcaa ctgctgaagt gggtattagc  23820
gaccaaggtc gtcatacctt atctgctacc actgcagctc aaacccgtta ccaaaccaca  23880
tcattaaaca atgaagatac agtgttggtg actggcggag caaaaggcgt cacattcgaa  23940
tgtgccctta cccttgcgaa acaaactcag tcacacttta tcttagcggg tcgcagtgag  24000
catttagccg gtaatttacc gacttgggct caaggcaaac aggctaaaga attgaaagct  24060
gctgcaattg gatttattca atctcaaggt aataagccaa caccaaagca aattgatgcc  24120
ttagtttggc cgattaccag cagtttagaa attgatcgct cattagcagc atttaaagct  24180
gtcggtgcaa gtgctgaata catcagcatg gatgtcagct cagatgcagc catcaagcaa  24240
tcacttgctg gcctcaaacc gattacaggc atcattcatg gtgcgggggt actcgccgat  24300
aaacacattc aagacaaaac attagctgag ttaggccgtg tatatggcac taaagtctcg  24360
ggctttgccg gcatcatcaa tgcgattgat gcaagtaaat tgaagctagt tgctatgttc  24420
tcatcagcag cgggtttcta tggcaacact ggtcaaagtg attactcaat gtcgaatgag  24480
atcctaaaca agacagcact acaacttgca gcgaactacc cgcaagcaaa agtgatgagc  24540
tttaactggg gaccttggga cggcggtatg gtcagttcag cgttaaagaa aatgtttgtt  24600
gagcgcggcg tatacgttat tccactcgat aaaggcgcaa acttgtttgc tcacagccta  24660
ttgtctgaat ctggcgtaca gctattaatt ggttcaagta tgcagggctc aagctcagca  24720
gctaaaacag gcgcagctgt aaaaaagctt aatgcggact cttcgcttaa tgccgagggt  24780
tcgctgattc tttcttttac tgctccagat aaccgtgttg ttaacaacgc ggttactgtt  24840
gaacgagtac taaacccagt tgcaatgccc ttccttgaag atcattgcat cgcgggtaat  24900
ccagtactgc caacagtgtg cgctatacaa tggatgcgtg aaactgcgca aaaactgtgt  24960
ggcctacctg tgacggttca agattataaa ttgctgaaag gcattatttt cgagactaaa  25020
gagccacaag tattaacgct gacattgacg caaacagaat caggcttaaa agcactgatt  25080
gcgagtcgta tgcaaagtga tgccgttgat agcttgctta gacctcagta tcaagcaaac  25140
ctgattgtta acgagaagat tgttaacgag aaggttgcta aagaagcggt ttcaaccacg  25200
ctaccaactg cagcaaaaaa tgcgcagcaa ttagcaagct caggtaaagt cattagcact  25260
gatagcgagc tatatagcaa tggcagctta ttccacggcc ctcgccttca aggaataaag  25320
cagttgttaa ttgccaacga tgagcaattg gtttgctcag ttgagttgcc tcaaattacc  25380
gctgtagatt gcgcaagctt tacaccgcaa acaggtttag gtggtagtca ggctttcgct  25440
gaagacttac ttttacaagc catgttagtg tgggcgcgta tcaaacacga tgcagcgagc  25500
```

-continued

```
ttaccgtcaa ccattggtga attaaccaca tacgccccat tcgcctcggg tgataaaggt  25560
tacttagtgt taactgtgct taaaagtact agccgttcat tgactgctga tattgcgctt  25620
tatcatcaag atggccgctt aagctgcact atgctaagcg caaaaacgac catcagcaaa  25680
agcttgaatg aggccttttt agccccagcc aaagcattag ctgatttgca ggagtctgtg  25740
tgagtaatca actgcctcct tcaacgtctg ctattaaaag catgcgaata gccttaaaga  25800
tggttgcgaa tgagcaagtc tcattcgcaa catcttcagg caatgatttt agtgccaata  25860
gctttgcagc gattaagcct tgctcattag ctgaggccat tggcgcttca gcaattgatc  25920
ttgaaattga tgtatcaagc ctagatgcga gtttgagtga aaacgctgtt aataaagcac  25980
ttagctttaa tgactatttt gctcaagcca tcatccatat cgagcaacaa catacggttt  26040
tactcagtca ccctgaatta ccgtatcgct tattaatgat gccagcgatt gtggcggcta  26100
aacatcgttg ccatcctcat gcctacttaa ccggtttggg tgaagctgat gatatgccaa  26160
gtgcaataaa tgcggcttta gttcaagcca agcgtgcaca cattaaacct actcatgtcg  26220
atgcgactca attaacttgt tataaagata agtttgccca gttggttatg ctgataggca  26280
gcattgccac tcgcagtgtg ccaaatacag tttcagaaaa tcagtcagct gatgctcaat  26340
actggttcac tgaaatgcac caaaatcgcg ttgccagctt taattttagt gaaggcaata  26400
agcaacacag tgcagtcttt gtccaaggca ctgagcttgc tcaagcaagt tctttggtag  26460
atgacaatcg actattttg cctgtatcag ccaatgacct tggaatgatg aaacagcagc  26520
tgcaagcatt aagcagtcaa ttggctgcgc tgcctgcaca acatgacaag agtgacagtt  26580
ccgctatctc cttcatgctt agccagctaa agcaatttga tcagacccag cctttatcgg  26640
cagttgttat ggcaaattca gtgactaatg cagtaagtga aatcaatgtc atgcttagca  26700
cgattggtaa agctgaagcc actgcggcaa atgaagttca agctaaaagc aacttaagca  26760
ttgaacacaa aaccccgtca ggaagctgct ttcatctcac ttcagataaa gtacttggca  26820
ataatggcct gtgttttgtt taccctggcg tgggcacggt atacccgcaa atgtttgctc  26880
aactgccgcg ctactttcca gcattatttg cccagctaga gcgcgatggt gatgtcaaag  26940
ccatgctgca agcggatagt atttatgctg aaaatgctaa aaccactgac atgagcttag  27000
gtgaactagc tattgcaggt gtaggcgcaa gttacatcct aaccaaagtg ctcactgagc  27060
atttcggcat taagcctaac tttgccatgg gttactcaat gggcgaggca tcaatgtggg  27120
ccagtcttga tgtgtggaaa acaccccaca atatgattga agcaacgcaa actaacagta  27180
tttttaccac tgacatttcg ggccgcttag actgcgttcg tcaagcatgg cagctagaac  27240
atggcgaaga cattgtttgg aatagctttg tggttcgtgc agcgcctgct gatatcgaaa  27300
aagtattagc tgatttccca cgtgcatacc ttgctatcat ccaaggtgat acttgtgtgc  27360
ttgcaggctg tgaggaaagc tgtaaagcgc tacttaaaca aattggtaaa cgtggcatag  27420
cagcgaatcg agtaaccgca atgcacacta aacctgcgat gcttattcga gacaacgtac  27480
aagcctttta tcagcagcct ttgcatgagc aagatgttat tgcacctttc gcaagccaaa  27540
ttaaatttat cagcgctgca agccaatcgc cgattaattt aaccagtgaa gcgattgcaa  27600
catccattgc tgataccttt tgtcagccgt tagattttac acaattagtc aataatgcac  27660
gtcatttagg cgcctcgctt tttgtcgaaa tcggcgctga cagacaaacg acaacactga  27720
ttgacaaaat ctcgcgtacc tctgaaatgg cgcaaacatg ccaagccatt tcagtgaatg  27780
caaaaggcga tgaccaaact gcgctactta aatgtattgc tcaactgatt actcataaaa  27840
ccccaatttc gctcgattat cttactgaga ccttgtcgag tttactgacg acaacattgg  27900
```

-continued

```
cggcagaaaa acgaagtaat caccacacag gcaatatgtt ggcccctcaa ttagaaggag  27960
aacaatcttg agttctcaat caactaatct aaatacaaca gtcccaaaga ttgccattgt  28020
aggtttagcg actcaatatc ccgatgcgga tacgcccgct aaattctggc aaaacttatt  28080
agacaaaaaa gactctcgaa gcacgattaa cagccaaaag ctcaatgcaa acccagctga  28140
ctatcaaggt gtgcaaggtg agtctgaccg tttttattgt gataaaggcg gctacattca  28200
aaacttcagt tttgatgcta atggctatcg tattcctgcc gagcaattta gcggccttga  28260
tgacagtttt ttatgggcaa ccgatacagc acgtaaagca ttgaatgatg ctggtgttga  28320
tattacaaac ccacaaaaca atggcgcatt aaaccgcacc ggtattgtca tgggaacact  28380
atcgtttcca acggctaaat ccaatgaact gttcgtaccg atttatcaca gcgcagtaga  28440
aaaagcgttg caagataaac tgcaacaacc aagtttcaca ttgcagccat ttgatagtga  28500
aggatatagt cagcaaacaa cgtcagcttc tttgtctaat ggcgccattg ctcacaatgc  28560
atctaaacta gtcgccgatg cgctaggctt aggtgcagcg caattaagcc ttgatgctgc  28620
ttgtgcaagt tctgtttact cattaaagct tgcctgtgat tatttgcata ctggcaaagc  28680
tgacatgatg ttagctggcg cagtttctgg cgctgaccca ttctttatta acatgggttt  28740
ctccattttc cacgcctacc ctgaccacgg tatttcagcg ccatttgata gtaattcaaa  28800
aggtttgttt gctggtgaag gtgctggtgt tttagtcctt aaacgccttg aagatgctga  28860
gcgcgatggc gaccatattt atgcactcgt tagcggtatc ggtttatcaa atgacggcaa  28920
aggccaattt gtattaagcc caaacagcga cggccaagtt aaagcattcg aacgtgctta  28980
tgctgatgct gctatgcatg atgaaaactt tggcccaaac aacatagaag tgcttgagtg  29040
tcacgcaaca ggtacgccat taggtgacaa agttgagctg acgtcaatgg agcgcttttt  29100
tagcgacaaa ctcaatggca gtaacacgcc gttaattggt tcagctaagt ctaacttagg  29160
ccacttgctg actgctgcag gtatgccagg gatcatgaaa atgatttttg cgatgcgcca  29220
aggtgttctg ccgccaagta ttaatattag cgcaccgatt gcttcaccat cagaaatgtt  29280
tggccctgca accttaccta atgatgttct cccttggcct gataaagctg gcaatacagc  29340
ccgccatgcg ggtgtgtcag tatttggttt tggcggttgt aatgcccatt tattagttga  29400
gtcatacttt gcgaagagtc atggccagcc ttctagcaca gagttagtta aaccagcgac  29460
aacgaccatc aatgcgcaaa tgccaatgca cattaccggt atggcatcac actttggttc  29520
gttgtcgaac gtaaatgact ttgctgatgc ggtaaataac aatcaaaccg catttacctc  29580
attgccagct aaacgctgga aaggtttaga taaacaccca gagttattac aaaaattcgg  29640
actgagtcaa gctgcgccaa caggtgctta tattgatcaa tttgatttcg acttcttacg  29700
ctttaaagtg ccacccaatg aagatgaccg tttaatctcg cagcaattgt tattaatgaa  29760
agtagcagat gaagccattc atgatgccaa acttgagtca ggtagcaaag tggcggtttt  29820
ggttgcaatg gaaacagaac ttgaattaca tcagttccgt ggccgcgtta acttacatac  29880
ccaaatagct gccagcttaa cagcccatgg cgtgagctta tctgatagcg aataccaagc  29940
attagaaacc attgcgatgg acagcgtgtt agatgccgcc aagcttaacc aatacaccag  30000
ctttattggt aatattatgg cgtcacgcat ctcatcatta tgggatttta atggccctgc  30060
ctttacgatt tcagcaggcg agcaatcagt taaccgctgt attgatgtgg cgcaaaacct  30120
actggcgatg gagtctcgtc aagagcctct agatgcagcg attattgccg cagtggattt  30180
atctggcagt attgaaaata tcgtgcttaa aacggcgaac attaataaaa caggctcaac  30240
```

-continued

```
tgaagcactc aatattggtg aaggggctgg cgcaattgta ttgcaagcag ccgctattga  30300

tagcgagcac tgcgacctaa tacatcaagg tttaggcgcg ttagatacgc tagattcagc  30360

aagcacccac agttatggca ccatcgacag tttggcattt ggtcatacag accagctttc  30420

aaccattagc gatgacgtgt taactcctgt tggattggct gcaactgata ttgatttatt  30480

agagttaaac caagcacctg atttgctcaa tattgataat gcgcaaatgc tatcgcagct  30540

atttaaccaa tcgagcacca gcaaagcgca atcttgtatc gggcacactt ttgccgcttc  30600

cggtattgcc agcttattgc atggcttatt gaaaactcga ttgaatgctt ctgtgcagaa  30660

cgctaactcg gatagcaaac tgagcaataa gcccaaccaa aaggccataa tcgctacttt  30720

gagcgaaaac cagtgttcgc agcttcttat cagccaaaac gctgaacaag caagcgcgat  30780

gagcactcgt attgacactg atatacaagc gcaaacggcc aagaaattga gcctagttaa  30840

gcaagtcagt ttaggtggtc gtgacatcta ccagcatatt gttgatgcgc cactggctaa  30900

cattgacagt attagagcga aagttgccaa gcttaaccct gttgcaccta caactgtgat  30960

gaacttacat gaccgcggcc aatttatcgc gccagctcat gccaattcag cgcctatgtc  31020

cgctaacaat aattcaatga ctacagagac ttctatgccg ttttctgatc gttcaaccca  31080

gtttaaccct acacctaaag tggctacgcc tactgcactt tccactcagg cagctcaggc  31140

aactcagtca gctcaaacgt cttcagtgac gagctctgtc gcagcaatta gccaagtgcc  31200

acctacgcat ttaagcgctt ttgagcaaaa ccaatggtta gcacatcaag cgcaattagc  31260

atttttaaag agccgcgaac aaggcttaaa agtcgctgat gcacttttaa agcaagagat  31320

tgcacaagca aatggtcagc cttatgttgc ccaatcgacg gcacaagctg tagcgcccgt  31380

ccaagcggca aacgtgttag cgcagccaat agcatctgcg tcaatcttgc gtccagatca  31440

tgcaaatgtg ccaccctaca cagcgcctat cccagcgaat aagccatgta tttggaacta  31500

cgctgattta gtagaatatg ccgaaggtga tattgccaaa gtatttggcc cagattacgc  31560

cgtgattgat aactactctc gccgcgtacg ccttcctaca actgattact tattggtatc  31620

tcgcgttact aaactcgatg caacaatgaa ccaatataag ccttgtagca tgaccacaga  31680

gtatgacatc ccagaagatg caccttactt agtcgatggc caaatccctt gggcggtagc  31740

cgttgaatca ggccagtgtg atttaatgct gatcagttat ttaggcattg attttgaaaa  31800

caaaggtgag cgtgtttacc gtttacttga ttgtacgctg accttcttag gcgacttacc  31860

tcgtggcggc gacacattgc gttacgacat taaaatcaat aacttcgcta agaatggcga  31920

gacactatta ttcttcttct cctacgaatg tttcgtcggc gataagatgg tcttaaaaat  31980

ggatggcggc tgtgctggct tctttaccga ccaagagtta gatgacggta aaggggttat  32040

ttacaccgaa gatgaaatca aaacccgtga agcggcgtta aatacgccaa acaaaccgcg  32100

ttttgaaccg ctattacatt gtgctcagac tcaatttgac tatggtcaaa tccatcattt  32160

actcaatgct gatattggca gctgttttgc tggcgaacac cataaccacc agcaagcatc  32220

aggtaagcaa gactcattat gttttgcctc tgaaaagttc ttgatgattg agcaagtggg  32280

caatttagaa gtccatggcg gcgcttgggg cttaggcttt atcgaaggcc ataaacaatt  32340

agcacctgat cattggtact tcccttgtca tttccaaggc gaccaagtaa tggctggctc  32400

attaatggct gaaggttgtg gccaattatt gcagttcttc atgctgcaca ttggtatgca  32460

caccttagtt gaaaacggac gtttccagcc tttagaaaat gcttcacaaa aagtacgttg  32520

tcgtggccaa gtactgccac aacatggtga actgacgtac cgcatggaag tcacagaaat  32580

tggtactcac cctcgcccat acgccaaagc caatattgaa atattgctca atggtaaagc  32640
```

-continued

```
ggtcgtggac ttccaaaatc ttggggtgat gattaaagaa gaaggtgaat gtactcgtta  32700
cactgccgac tctactgaaa cacatacaac ctcaggcaca gtccaaaaaa acaacagcca  32760
caacacacca gcatcattaa atgcaccgtt aatggcacaa gtgccagact taagtgaacc  32820
agccaataaa ggcgttatcc cgctgcaaca tgttgaagcg cctatgctgc cagactaccc  32880
aaatcgaacc cctgatacgc tgccgttcac cgcgtaccat atgtttgagt ttgcaacagg  32940
tgacatcgaa aactgttttg gacctgactt tagtatttac cggggcttta ttccgccgcg  33000
cacgccatgt ggtgacttac agctaacaac ccgtgttgtt gatattcaag gtaaacgtgg  33060
cgagcttaaa aaaccgtcat cgtgtatcgc tgaatatgaa gtgccaaccg atgcgtggta  33120
ttttgctaaa aacagtcacg cttcagtgat gccttactcg gtattaatgg aaatatcact  33180
gcaaccaaac ggatttattt cgggttacat gggcacaacc cttggtttcc cagggcaaga  33240
gctattcttc cgtaaccttg atggtagcgg tgagttattg tgtgatgtag atttacgcgg  33300
caaaaccatt gtcaatgatt ctaagctatt atctaccgtt attgccggca gtaacatcat  33360
ccaaagtttc agctttgatt taagtgttga tggcgagcct ttctatactg gtagcgctgt  33420
atttggttac tttaaaggtg atgcacttaa aaaccagcta ggtattgata atggccgtat  33480
tactcagcca tggcatgttg aaaataacgt agcggctgat atcaccgttg atttgcttga  33540
taagcagtcc cgcgtattcc atgcaccagc aaaccagcca cattatcgtt tagctggcgg  33600
tcaacttaac tttatcgaca aagctgaaat cgttgataaa ggcggtaaaa atggtttagg  33660
ttacttgtct gcctcacgca ccattgaccc aagtgattgg ttcttccagt tccacttcca  33720
tcaagatcct gtgatgccag gttcattagg cgttgaagca attatcgagt taatgcaaac  33780
ttacgccatc agtaaagacc taggtaaagg tttcactaac ccgaaatttg gtcagatttt  33840
gtctgacatc aaatggaagt accgtggcca aatcaaccca ctaaataagc aaatgtcgct  33900
ggatgtgcac atcagtgcag tcaaagatga aaacggcaaa cgtatcattg tgggtgacgc  33960
aaacctcagc aaagacggtt tacgtattta cgaagtaaaa gacatcgcta tctgtatcga  34020
agaggcataa aggaataata atgactatta gcactcaaaa cgaaaagctt tctccatggc  34080
cttggcaagt agccccaagt gatgccagct ttgagaatgc cgctatcggt aaaaaattaa  34140
aagaactgtc tcaggcgtgt tatttaatta accaccctga aaaaggctta ggtatttcgc  34200
aaaacgcaca agtaatgact gaaagcatga acagccagca agacttacca gttagtgcat  34260
ttgcacctgc tttaggcact caaagcttag gcgacagtaa tttccgccgc gttcacggag  34320
taaaatacgc ctactacgct ggcgcgatgg ccaatggtat ttcatctgaa gagttagtga  34380
ttgcattagg ccaagctggt attttgtgtt catttggcgc agcaggatta attccatctc  34440
gcgtagaaca agccattaat cgcattcaaa cggcgctacc caatggcccg tacatgttta  34500
acttaatcca cagcccaagt gagccagcat tagaacgtgg cagtgttgag ttatttttaa  34560
aacataaagt gcgcacggtt gaagcatcag catttttagg gttaaccccg caaattgtct  34620
attaccgcgc tgcaggttta agccgtgatg ctcaaggtga agtggttata gccaacaagg  34680
ttatcgctaa agtaagccgc acagaagtag cgagtaagtt catgcaacct gcacctgcta  34740
aaatgctgca aaagctggtt gatgaaggct taatcacacc tgagcaaatg gagctcgcac  34800
aattagtccc aatggcagat gatgtgacag cagaggctga ttctggtggt cataccgata  34860
accgtccatt agtgacgcta ttgccaacaa ttttggcgct taaagataaa attcaagccg  34920
agtaccaata caagacgcct attcgtgtcg gttgcggcgg cggcgtggga acacctgatg  34980
```

-continued

```
cagcattagc gacctttaac atgggcgcag cgtatatcgt taccggctca atcaaccaag  35040

cgtgtgttga agctggtgcc agtgaacata ctcgtaaatt attagcgaca acagaaatgg  35100

ccgatgtcac catggcacct gctgctgata tgtttgaaat gggcgttaaa ctacaagtgg  35160

ttaagcgcgg tacactattc ccaatgcgtg ccaacaagct ttatgagatt tacactcgtt  35220

atgaatcaat tgaagcgatt ccagctgaag aacgtgaaaa actagagaaa caagttttcc  35280

gttcaaccct tgatgatatt tgggcaggca ctgtggctca ctttaacgaa cgcgacccta  35340

agcaaatcga acgcgcagaa ggaaacccta agcgtaaaat ggcactgatt ttccgttggt  35400

acttaggttt atcaagccgc tggtcaaatt cgggcgaagt cggccgtgaa atggattacc  35460

aaatttgggc aggtcctgca cttggtgcgt tcaatgaatg ggcaaaaggc agctatttag  35520

atgattatac ccagcgaaat gcggtagact tggccaaaca cttgatgcat ggcgcagctt  35580

atcaagcccg cgttaactta ttaactgctc aaggcgtggc actgccggtt gaattgcaac  35640

gctggagccc gctagatcag gttaagtaac ggacgttgta gctttataac gtcagcagtg  35700

atactcgcca tattgcgatc aagttaacca ttactattgt gccactcact caacatgagt  35760

ggcacattga tatttagttt gcagttaggt aacagtatga gcgaaaccca aaagttagat  35820

ttttcagcgg taaatggcac aacactagcc tcgtttaatc agcataaaaa cttgatcaaa  35880

cgtatgctaa aaggcaacag cgctgaatgt agcgagtgta aaaaaccact cactttgcaa  35940

ttaccgccta acattaagaa cgctaaacca agtgataaag caccaggcat atattgcgca  36000

aaaggctgta ccgatatcga gctagatatg gaagcagtgg cattaatgaa gtagccgaag  36060

ataagaacac agttctttag gtataagcct ttataagcac aattacgaag caccttatgg  36120

gtgcttttac ttttcctatc ccaccaaaga tattgtttta actaacttaa gaagggttag  36180

tatgtggcat aactaactca gctaaccatt cataatattt ttcattccca tgaatccaat  36240

ccacttgtcc atttgaataa gttattgggc tgataaattc atgaaagtca taaccttctt  36300

cgataaaaat acgagcagca ttgacaaacg ttatatcaaa ttgtgctagt acgtaatcta  36360

tcgcctcaaa atatgcaaaa ataatatttg ccataggttt agcttcttca acaaatttac  36420

taaaaggagg atctgaaaca acaattactt tatggccaat acttttcaat ttgatcaaaa  36480

tagataattg atcctgaatg tcatcatgaa agtaatctac aaattcctta gtctcaatat  36540

tactaatccc ttgtggatat tgacgtttca cccagtctac aaatctagct gcactttgat  36600

gtgtctgtag acccacatta catataactg tagattgact aaccgtttta ttattttcat  36660

gtatagataa gttatttaat acatctttcc aaagtgttct agacgctgca ctttctaaag  36720

gcacgaatat ctcagtatca catatagcaa acttcttttg cgcgaaccct gatccattca  36780

ttatcattcc tcctgtatga ggaatattcc ttaatttcat tgcattagaa agttttccca  36840

tatgactatc accaaatatg gaaatggaat ccccgtcatt cgatagttgt ttagagttca  36900

actttctaga agcttgtaaa aactcttcat cgcaaactac ttcatcactt actgttttat  36960

caactttatc ggtaattgaa atatctttac ttaatgtttc accaaaatgc ttcatgacat  37020

aactgaccat ctctgctgta acagttctta gattttcctt aaatctatag tctgtagaaa  37080

tgggtaatgt aactaattca taagaaggaa aataactaaa tactgcctca tattcactta  37140

gttcacctgc aacagctcgt aatgtcgact tagagtattg gttagcgatt gctatatgat  37200

ttgacgtagc tgtagctgtt aatggtacgg gtgagacagt gagtacaatc tgaatgttag  37260

gatttataca ttctacaact ttagctattt ctttaagatc attttgaatt tcagcgaatg  37320

taaaattatg aaaattataa tttttttgtt tatattctcc ttggataacc ccgggacaac  37380
```

```
taggatagca aaccccattt atatcaaacc atgcttctgt taatcccaat gtaaaaatta  37440
acacatcagt cttcgcaatt gtttgcttca tttcatcaac ggcagctttt cttgcctgaa  37500
ttaaagcact ctcggatgag taacctaact cgttatataa aggtcttagc aaatcataga  37560
atcttgtttc attgtgataa attgagtgat ctgtcttgaa gctctgatta tcacaattaa  37620
gccactgtaa aaaacacctt ggcgtataaa catttccaaa agcaaaacta gatacattag  37680
cttcgtctaa ttcactttga ttaaaattaa aattattgtc atttagccac ttaccgacat  37740
gctgagcaaa acatgaacca actgacgata ttctgggcac attagttttg aaatttatat  37800
caaccaaatt agatattgtt tcttcaaaat agttttgaga aacaacgcca gttttccaaa  37860
agtgctggga agctttatgt gtataaggtg tcaatttaaa ctccaaaaat gatatggtta  37920
agctcatagt caaattagtg actttcatta aagtaagcat tatatatgcc atttaaatac  37980
taactataaa actgaaattc gacttgccac tcacccacca aatagccttg ctaaatctat  38040
tcctctcgtc ataaagtctc atttttacca acaaaaataa tgcgttaaca ttttttttgac  38100
ctgtatcaat aataagtctt attagctaag gcactatgcc tcattatttt taatgtggtt  38160
atattttta tgagtcaaat caaggctaac aacaatattg agcaagcgct aactgacaat  38220
tgcattcttt tgtcgaccac agatctgaat ggcaacataa aatacgccaa taaagcattt  38280
gccgatattt cagaatacag cactgaagag ctacatggac agcctcataa tattgttcgt  38340
caccctgata tgcctaaagc tgcatttaaa gcactttggg atcgtgtaaa agatggcaaa  38400
ccatggtgtg gcatcgttaa aaataaaacc aaatctggca aatattactg ggtgaatgcg  38460
tatatttcgc cagtttttga aaatggccgt ttacatgaac ttcaatcaat cagacgtaaa  38520
ccatgtcagg cacatatcaa atcagctgaa agcatctacc aacaacttaa tgaaggtaaa  38580
gaacctgctg cgatatcacc accactcttt agcttcacgg gtgcactctg cctatgggca  38640
gtgtttatct cgttaattgg cgttatttct tcgttattaa tgcctacgct agttgcagca  38700
ttttttatcc cgttactggc aggttttggt atttactttc taacaagacc ccttaaagaa  38760
cttgaaacta aagccaccaa tattattgat gatc                              38794
```

```
<210> SEQ ID NO 8
<211> LENGTH: 2768
<212> TYPE: PRT
<213> ORGANISM: Sh. olleyana

<400> SEQUENCE: 8

Met Ser Gln Ala Pro Thr Asn Pro Glu Thr Ser Ser Gln Asp Asn Asn
1               5                   10                  15

Glu Ser Gln Asp Thr Arg Leu Asn Lys Arg Leu Lys Asp Met Pro Ile
            20                  25                  30

Ala Ile Val Gly Met Ala Ser Ile Phe Ala Asn Ser Arg Tyr Leu Asn
        35                  40                  45

Lys Phe Trp Asp Leu Ile Ser Glu Lys Ile Asp Ala Ile Thr Glu Val
    50                  55                  60

Pro Asp Thr His Trp Arg Ala Glu Asp Tyr Phe Asp Ala Asp Lys Ser
65                  70                  75                  80

Thr Pro Asp Lys Ser Tyr Cys Lys Arg Gly Gly Phe Ile Pro Glu Val
                85                  90                  95

Asp Phe Asn Pro Met Glu Phe Gly Leu Pro Pro Asn Ile Leu Glu Leu
            100                 105                 110

Thr Asp Thr Ser Gln Leu Leu Ser Leu Val Ile Ala Lys Glu Val Leu
```

-continued

```
        115                 120                 125

Ala Asp Ala Gly Val Thr Ser Glu Tyr Asp Thr Asp Lys Ile Gly Ile
    130                 135                 140

Thr Leu Gly Val Gly Gly Gly Gln Lys Ile Asn Ala Ser Leu Thr Ala
145                 150                 155                 160

Arg Leu Gln Tyr Pro Val Leu Lys Lys Val Phe Lys Ser Ser Gly Leu
                165                 170                 175

Ser Asp Ala Asp Ser Asp Met Leu Ile Lys Lys Phe Gln Asp Gln Tyr
            180                 185                 190

Ile His Trp Glu Glu Asn Ser Phe Pro Gly Ser Leu Gly Asn Val Ile
        195                 200                 205

Ala Gly Arg Ile Ala Asn Arg Phe Asp Leu Gly Gly Met Asn Cys Val
    210                 215                 220

Val Asp Ala Ala Cys Ala Gly Ser Leu Ala Ala Met Arg Met Ala Leu
225                 230                 235                 240

Thr Glu Leu Val Glu Gly Arg Ser Glu Met Met Ile Thr Gly Gly Val
                245                 250                 255

Cys Thr Asp Asn Ser Pro Ser Met Tyr Met Ser Phe Ser Lys Thr Pro
            260                 265                 270

Ala Phe Thr Thr Asn Glu Thr Ile Gln Pro Phe Asp Ile Asp Ser Lys
        275                 280                 285

Gly Met Met Ile Gly Glu Gly Ile Gly Met Val Ala Leu Lys Arg Leu
    290                 295                 300

Glu Asp Ala Glu Arg Asp Gly Asp Arg Ile Tyr Ser Val Ile Lys Gly
305                 310                 315                 320

Val Gly Ala Ser Ser Asp Gly Lys Phe Lys Ser Ile Tyr Ala Pro Arg
                325                 330                 335

Pro Glu Gly Gln Ala Lys Ala Leu Lys Arg Ala Tyr Asp Asp Ala Gly
            340                 345                 350

Phe Ala Pro Glu Thr Val Gly Leu Ile Glu Ala His Gly Thr Gly Thr
        355                 360                 365

Ala Ala Gly Asp Val Ala Glu Phe Asn Gly Leu Lys Ser Val Phe Gly
    370                 375                 380

Glu Asn Asp Pro Thr Lys Gln His Ile Ala Leu Gly Ser Val Lys Ser
385                 390                 395                 400

Gln Val Gly His Thr Lys Ser Thr Ala Gly Thr Ala Gly Val Ile Lys
                405                 410                 415

Ala Ala Leu Ala Leu His His Lys Val Leu Pro Pro Thr Ile Asn Val
            420                 425                 430

Ser Lys Pro Asn Pro Lys Leu Asn Val Glu Asp Ser Pro Phe Phe Val
        435                 440                 445

Asn Thr Glu Thr Arg Pro Trp Met Pro Arg Pro Asp Gly Thr Pro Arg
    450                 455                 460

Arg Ala Gly Ile Ser Ser Phe Gly Phe Gly Gly Thr Asn Phe His Leu
465                 470                 475                 480

Val Leu Glu Glu Tyr Thr Pro Glu His Ser His Asp Glu Lys Tyr Arg
                485                 490                 495

Gln Arg Gln Val Ala Gln Ser Leu Leu Met Ser Ala Asp Asn Lys Ala
            500                 505                 510

Ala Leu Ile Ala Glu Val Asn Lys Leu Thr Ala Asp Ile Ser Ala Leu
        515                 520                 525

Lys Gly Thr Asp Asn Ser Ser Ile Glu Gln Ala Glu Leu Ala Arg Ile
    530                 535                 540
```

-continued

```
Ala Lys Leu Tyr Ala Val Arg Thr Ile Asp Thr Ser Ala Ala Arg Leu
545                 550                 555                 560

Gly Leu Val Val Ser Ser Leu Asn Glu Leu Thr Thr Gln Leu Gly Leu
                565                 570                 575

Ala Leu Lys Gln Leu Asn Asn Asp Val Asp Ala Trp Gln Leu Pro Ser
            580                 585                 590

Gly Thr Ser Tyr Arg Ser Ser Ala Leu Ile Thr Ile Asn Ala Asn Gln
        595                 600                 605

Lys Ala Thr Lys Gly Lys Lys Ala Thr Asn Ala Pro Lys Val Ala Ala
    610                 615                 620

Leu Phe Ala Gly Gln Gly Ser Gln Tyr Val Asn Met Gly Ile Glu Val
625                 630                 635                 640

Ala Cys His Phe Pro Glu Met Arg Gln Gln Leu Ile Lys Ala Asp Lys
                645                 650                 655

Val Phe Ala Ser Phe Asp Lys Thr Pro Leu Ser Gln Val Met Phe Pro
            660                 665                 670

Ile Pro Ala Phe Glu Lys Ala Asp Lys Asp Ala Gln Ala Ala Leu Leu
        675                 680                 685

Thr Ser Thr Asp Asn Ala Gln Ser Ala Ile Gly Val Met Ser Met Ser
    690                 695                 700

Gln Tyr Gln Leu Phe Thr Gln Ser Gly Phe Ser Ala Asp Met Phe Ala
705                 710                 715                 720

Gly His Ser Phe Gly Glu Leu Ser Ala Leu Cys Ala Ala Gly Val Ile
                725                 730                 735

Ser Asn Asp Asp Tyr Tyr Gln Leu Ser Phe Ala Arg Gly Ala Ala Met
            740                 745                 750

Ala Ser Ser Ala Val Asp Lys Asp Gly Asn Glu Leu Asp Lys Gly Thr
        755                 760                 765

Met Tyr Ala Ile Ile Leu Pro Ala Asn Glu Ala Asp Ala Ala Asn Ser
    770                 775                 780

Asp Asn Ile Ala Lys Leu Glu Thr Cys Ile Cys Glu Phe Asp Gly Val
785                 790                 795                 800

Lys Val Ala Asn Tyr Asn Ser Ala Thr Gln Leu Val Ile Ala Gly Pro
                805                 810                 815

Thr Asp Ser Cys Ala Asn Ala Ala Lys Ala Ile Ser Ala Leu Gly Phe
            820                 825                 830

Lys Ala Ile Ala Leu Pro Val Ser Gly Ala Phe His Thr Pro Leu Val
        835                 840                 845

Gly His Ala Gln Lys Pro Phe Ala Lys Ala Ile Asp Lys Ala Lys Phe
    850                 855                 860

Thr Ala Ser Lys Val Asp Leu Phe Ser Asn Ala Thr Gly Glu Lys His
865                 870                 875                 880

Pro Ala Asp Ala Lys Ser Ile Lys Ala Ala Phe Lys Gln His Met Leu
                885                 890                 895

Gln Ser Val Arg Phe Thr Asp Gln Leu Asn Asn Met Tyr Asp Ala Gly
            900                 905                 910

Ala Arg Val Phe Val Glu Phe Gly Pro Lys Asn Ile Leu Gln Lys Leu
        915                 920                 925

Val Glu Ala Thr Leu Gly Asn Lys Ala Glu Ala Val Ser Val Ile Ser
    930                 935                 940

Ile Asn Pro Asn Pro Lys Gly Asn Ser Asp Val Gln Leu Arg Val Ala
945                 950                 955                 960
```

-continued

```
Ala Met Gln Leu Ser Val Leu Gly Ala Pro Leu Thr Glu Val Asp Pro
                965                 970                 975

Tyr Gln Ala Glu Ile Ala Ala Pro Ala Val Pro Lys Gly Met Asn Val
            980                 985                 990

Lys Leu Thr Ala Ser Asn His Ile  Ser Ala Pro Thr Arg  Ala Lys Met
        995                 1000                1005

Glu Lys  Ser Leu Ala Thr Gly  Gln Val Thr Ser Gln  Ile Val Glu
    1010                 1015                 1020

Thr Ile  Val Glu Lys Val Ile  Glu Met Pro Val Glu  Lys Val Val
    1025                 1030                 1035

Glu Lys  Ile Val Glu Lys Glu  Val Ile Lys Thr Glu  Tyr Val Glu
    1040                 1045                 1050

Val Ala  Ala Ser Gly Ala Thr  Ala Val Pro Asn Ala  Ala Ala Pro
    1055                 1060                 1065

Val Ala  Gln Ala Ser Gln Val  Ile Ala Pro Gln Met  Gln Val Gln
    1070                 1075                 1080

Ala Thr  Pro Val Ala Gly Ser  Leu Glu Ala Phe Phe  Asn Ala Gln
    1085                 1090                 1095

Gln Gln  Ala Ala Asp Leu His  Gln Gln Phe Leu Ala  Ile Pro Gln
    1100                 1105                 1110

Gln Tyr  Gly Asp Thr Phe Thr  His Leu Met Ala Glu  Gln Ser Lys
    1115                 1120                 1125

Met Ala  Ala Ala Gly His Ala  Ile Pro Glu Ser Leu  Gln Arg Ser
    1130                 1135                 1140

Met Glu  Leu Phe His Gln His  Gln Ala Gln Thr Leu  Gln Ser His
    1145                 1150                 1155

Thr Leu  Phe Leu Glu Gln Gln  Ala Gln Ser Ser Gln  Asn Ala Leu
    1160                 1165                 1170

Ser Met  Leu Thr Gly Gln Ala  Pro Ala Thr Thr Thr  Pro Ala Val
    1175                 1180                 1185

Asn Ala  Pro Arg Val Asn Ala  Pro Ile Thr Glu Asn  Pro Val Val
    1190                 1195                 1200

Ala Ala  Pro Val Val Glu Ala  Val Lys Val Ala Ala  Thr Val Gln
    1205                 1210                 1215

Thr Pro  Thr Ala Gln Ala Pro  Ala Val Gln Ala Ser  Ile Thr Gln
    1220                 1225                 1230

Thr Ala  Ala Lys Pro Ala Ala  Met Ala Ala Pro Ala  Pro Arg Ile
    1235                 1240                 1245

Glu Pro  Val Lys Ala Thr Ala  Pro Val Ala Ala Pro  Val Val Ala
    1250                 1255                 1260

Pro Ala  Val Ala Ala Ala Pro  Ala Gly Leu Ser Ala  Glu Thr Val
    1265                 1270                 1275

Leu Asn  Thr Met Leu Glu Val  Val Ala Glu Lys Thr  Gly Tyr Pro
    1280                 1285                 1290

Thr Glu  Met Leu Glu Leu Ser  Met Asp Met Glu Ala  Asp Leu Gly
    1295                 1300                 1305

Ile Asp  Ser Ile Lys Arg Val  Glu Ile Leu Gly Thr  Val Gln Asp
    1310                 1315                 1320

Glu Leu  Pro Thr Leu Pro Glu  Leu Ser Pro Glu Asp  Leu Ala Glu
    1325                 1330                 1335

Cys Arg  Thr Leu Gly Glu Ile  Val Asp Tyr Met Asn  Ser Lys Leu
    1340                 1345                 1350

Pro Lys  Ser Asp Ala Ser Gly  Thr Gln Thr Gln Val  Ala Pro Val
```

-continued

```
    1355                1360                1365

Gln Ala  Ala Ser Gly Leu Ser  Ala Glu Thr Val Leu  Asn Thr Met
    1370                1375                1380

Leu Glu  Val Val Ala Glu Lys  Thr Gly Tyr Pro Thr  Glu Met Leu
    1385                1390                1395

Glu Leu  Ser Met Asp Met Glu  Ala Asp Leu Gly Ile  Asp Ser Ile
    1400                1405                1410

Lys Arg  Val Glu Ile Leu Gly  Thr Val Gln Asp Glu  Leu Pro Thr
    1415                1420                1425

Leu Pro  Glu Leu Ser Pro Glu  Asp Leu Ala Glu Cys  Arg Thr Leu
    1430                1435                1440

Gly Glu  Ile Val Asp Tyr Met  Asn Ser Lys Leu Pro  Ala Ala Gly
    1445                1450                1455

Ser Thr  Pro Val Ala Ser Pro  Val Gln Ser Ala Ala  Pro Val Ser
    1460                1465                1470

Gly Leu  Ser Ala Glu Thr Val  Leu Asn Thr Met Leu  Glu Val Val
    1475                1480                1485

Ala Glu  Lys Thr Gly Tyr Pro  Thr Glu Met Leu Glu  Leu Ser Met
    1490                1495                1500

Asp Met  Glu Ala Asp Leu Gly  Ile Asp Ser Ile Lys  Arg Val Glu
    1505                1510                1515

Ile Leu  Gly Thr Val Gln Asp  Glu Leu Pro Thr Leu  Pro Glu Leu
    1520                1525                1530

Ser Pro  Glu Asp Leu Ala Glu  Cys Arg Thr Leu Gly  Glu Ile Val
    1535                1540                1545

Asp Tyr  Met Asn Ser Lys Leu  Pro Thr Ser Ser Ala  Ala Gly Ala
    1550                1555                1560

Asn Thr  Gln Ala Val Ala Pro  Val Ala Gln Glu Ser  Gly Leu Ser
    1565                1570                1575

Ala Glu  Thr Ala Leu Ser Ala  Gln Glu Val Gln Ser  Thr Met Met
    1580                1585                1590

Thr Val  Val Ala Glu Lys Thr  Gly Tyr Pro Thr Glu  Met Leu Glu
    1595                1600                1605

Leu Ser  Met Asp Met Glu Ala  Asp Leu Gly Ile Asp  Ser Ile Lys
    1610                1615                1620

Arg Val  Glu Ile Leu Gly Thr  Val Gln Asp Glu Leu  Pro Thr Leu
    1625                1630                1635

Pro Glu  Leu Ser Pro Glu Asp  Leu Ala Glu Cys Arg  Thr Leu Gly
    1640                1645                1650

Glu Ile  Val Ser Tyr Met Asn  Ser Lys Leu Pro Ala  Ala Gly Ala
    1655                1660                1665

Met Asn  Ser Thr Ala Val Val  Ala Gln Ala Ser Gly  Leu Ser Ala
    1670                1675                1680

Glu Thr  Ala Leu Ser Ala Gln  Glu Val Gln Ser Thr  Met Met Thr
    1685                1690                1695

Val Val  Ala Glu Lys Thr Gly  Tyr Pro Thr Glu Met  Leu Glu Leu
    1700                1705                1710

Ser Met  Asp Met Glu Ala Asp  Leu Gly Ile Asp Ser  Ile Lys Arg
    1715                1720                1725

Val Glu  Ile Leu Gly Thr Val  Gln Asp Glu Leu Pro  Thr Leu Pro
    1730                1735                1740

Glu Leu  Asn Pro Glu Asp Leu  Ala Glu Cys Arg Thr  Leu Gly Glu
    1745                1750                1755
```

-continued

```
Ile Val  Ser Tyr Met Asn Ser  Lys Leu Pro Ala Val  Ser Ala Thr
    1760                 1765                 1770

Thr Ala  Ala Gly Thr Gln Thr  Gln Ala Ala Ala Gly  Ala Thr Gln
    1775                 1780                 1785

Ala Ser  Gly Leu Ser Ala Glu  Gln Val Gln Ser Thr  Met Met Thr
    1790                 1795                 1800

Val Val  Ala Glu Lys Thr Gly  Tyr Pro Thr Glu Met  Leu Glu Leu
    1805                 1810                 1815

Ser Met  Asp Met Glu Ala Asp  Leu Gly Ile Asp Ser  Ile Lys Arg
    1820                 1825                 1830

Val Glu  Ile Leu Gly Thr Val  Gln Asp Glu Leu Pro  Gly Leu Pro
    1835                 1840                 1845

Glu Leu  Asn Pro Glu Asp Leu  Ala Glu Cys Arg Thr  Leu Gly Glu
    1850                 1855                 1860

Ile Val  Ser Tyr Met Asn Ser  Lys Leu Ser Thr Ser  Ala Ala Glu
    1865                 1870                 1875

Gly Ser  Gln Pro Thr Leu Ser  Ser Thr Asp Thr Ser  Pro Ala Thr
    1880                 1885                 1890

Ala Thr  Ala Glu Leu Ala Thr  Asp Leu Pro Pro His  Gln Glu Val
    1895                 1900                 1905

Ala Leu  Lys Lys Leu Pro Ala  Ala Asp Lys Leu Val  Asp Val Phe
    1910                 1915                 1920

Ser Lys  Asp Ala Cys Ile Val  Ile Asn Asp Asp Gly  His Asn Ala
    1925                 1930                 1935

Gly Val  Leu Ala Glu Lys Leu  Val Ala Thr Gly Leu  Thr Val Ala
    1940                 1945                 1950

Val Ile  Arg Ser Pro Glu Ser  Val Thr Ser Ala Gln  Ser Pro Leu
    1955                 1960                 1965

Ser Ser  Asp Ile Ala Ser Phe  Thr Leu Ser Ala Val  Asn Asp Asp
    1970                 1975                 1980

Ala Ile  Ser Asp Val Ile Ala  Gln Ile Ser Lys Gln  His Lys Ile
    1985                 1990                 1995

Ala Gly  Phe Val His Leu Gln  Pro Gln Leu Thr Ala  Gln Gly Ala
    2000                 2005                 2010

Leu Pro  Leu Ser Asp Ala Gly  Phe Val Ala Val Glu  Gln Ala Phe
    2015                 2020                 2025

Leu Met  Ala Lys His Leu Gln  Lys Pro Phe Ala Glu  Leu Ala Lys
    2030                 2035                 2040

Thr Glu  Arg Val Ser Phe Met  Thr Val Ser Arg Ile  Asp Gly Gly
    2045                 2050                 2055

Phe Gly  Tyr Leu Asn Ser Asn  Glu Leu Ala Lys Ala  Glu Leu Asn
    2060                 2065                 2070

Gln Ala  Ala Leu Ser Gly Leu  Thr Lys Thr Leu Gly  His Glu Trp
    2075                 2080                 2085

Pro Thr  Val Phe Cys Arg Ala  Leu Asp Ile Thr Pro  Ser Phe Glu
    2090                 2095                 2100

Ala Val  Glu Leu Ala Gln Ala  Val Ile Glu Glu Leu  Phe Asp Leu
    2105                 2110                 2115

Asp Thr  Ala Thr Ala Glu Val  Gly Ile Ser Asp Gln  Gly Arg His
    2120                 2125                 2130

Thr Leu  Ser Ala Thr Thr Ala  Ala Gln Thr Arg Tyr  Gln Thr Thr
    2135                 2140                 2145
```

-continued

```
Ser Leu  Asn Asn Glu Asp Thr  Val Leu Val Thr Gly  Gly Ala Lys
    2150                 2155                 2160

Gly Val  Thr Phe Glu Cys Ala  Leu Thr Leu Ala Lys  Gln Thr Gln
    2165                 2170                 2175

Ser His  Phe Ile Leu Ala Gly  Arg Ser Glu His Leu  Ala Gly Asn
    2180                 2185                 2190

Leu Pro  Thr Trp Ala Gln Gly  Lys Gln Ala Lys Glu  Leu Lys Ala
    2195                 2200                 2205

Ala Ala  Ile Gly Phe Ile Gln  Ser Gln Gly Asn Lys  Pro Thr Pro
    2210                 2215                 2220

Lys Gln  Ile Asp Ala Leu Val  Trp Pro Ile Thr Ser  Ser Leu Glu
    2225                 2230                 2235

Ile Asp  Arg Ser Leu Ala Ala  Phe Lys Ala Val Gly  Ala Ser Ala
    2240                 2245                 2250

Glu Tyr  Ile Ser Met Asp Val  Ser Ser Asp Ala Ala  Ile Lys Gln
    2255                 2260                 2265

Ser Leu  Ala Gly Leu Lys Pro  Ile Thr Gly Ile Ile  His Gly Ala
    2270                 2275                 2280

Gly Val  Leu Ala Asp Lys His  Ile Gln Asp Lys Thr  Leu Ala Glu
    2285                 2290                 2295

Leu Gly  Arg Val Tyr Gly Thr  Lys Val Ser Gly Phe  Ala Gly Ile
    2300                 2305                 2310

Ile Asn  Ala Ile Asp Ala Ser  Lys Leu Lys Leu Val  Ala Met Phe
    2315                 2320                 2325

Ser Ser  Ala Ala Gly Phe Tyr  Gly Asn Thr Gly Gln  Ser Asp Tyr
    2330                 2335                 2340

Ser Met  Ser Asn Glu Ile Leu  Asn Lys Thr Ala Leu  Gln Leu Ala
    2345                 2350                 2355

Ala Asn  Tyr Pro Gln Ala Lys  Val Met Ser Phe Asn  Trp Gly Pro
    2360                 2365                 2370

Trp Asp  Gly Gly Met Val Ser  Ser Ala Leu Lys Lys  Met Phe Val
    2375                 2380                 2385

Glu Arg  Gly Val Tyr Val Ile  Pro Leu Asp Lys Gly  Ala Asn Leu
    2390                 2395                 2400

Phe Ala  His Ser Leu Leu Ser  Glu Ser Gly Val Gln  Leu Leu Ile
    2405                 2410                 2415

Gly Ser  Ser Met Gln Gly Ser  Ser Ser Ala Ala Lys  Thr Gly Ala
    2420                 2425                 2430

Ala Val  Lys Lys Leu Asn Ala  Asp Ser Ser Leu Asn  Ala Glu Gly
    2435                 2440                 2445

Ser Leu  Ile Leu Ser Phe Thr  Ala Pro Asp Asn Arg  Val Val Asn
    2450                 2455                 2460

Asn Ala  Val Thr Val Glu Arg  Val Leu Asn Pro Val  Ala Met Pro
    2465                 2470                 2475

Phe Leu  Glu Asp His Cys Ile  Ala Gly Asn Pro Val  Leu Pro Thr
    2480                 2485                 2490

Val Cys  Ala Ile Gln Trp Met  Arg Glu Thr Ala Gln  Lys Leu Cys
    2495                 2500                 2505

Gly Leu  Pro Val Thr Val Gln  Asp Tyr Lys Leu Leu  Lys Gly Ile
    2510                 2515                 2520

Ile Phe  Glu Thr Lys Glu Pro  Gln Val Leu Thr Leu  Thr Leu Thr
    2525                 2530                 2535

Gln Thr  Glu Ser Gly Leu Lys  Ala Leu Ile Ala Ser  Arg Met Gln
```

```
    2540                2545                2550

Ser Asp  Ala Val Asp Ser Leu  Leu Arg Pro Gln Tyr  Gln Ala Asn
    2555                2560                2565

Leu Ile  Val Asn Glu Lys Ile  Val Asn Glu Lys Val  Ala Lys Glu
    2570                2575                2580

Ala Val  Ser Thr Thr Leu Pro  Thr Ala Ala Lys Asn  Ala Gln Gln
    2585                2590                2595

Leu Ala  Ser Ser Gly Lys Val  Ile Ser Thr Asp Ser  Glu Leu Tyr
    2600                2605                2610

Ser Asn  Gly Ser Leu Phe His  Gly Pro Arg Leu Gln  Gly Ile Lys
    2615                2620                2625

Gln Leu  Leu Ile Ala Asn Asp  Glu Gln Leu Val Cys  Ser Val Glu
    2630                2635                2640

Leu Pro  Gln Ile Thr Ala Val  Asp Cys Ala Ser Phe  Thr Pro Gln
    2645                2650                2655

Thr Gly  Leu Gly Gly Ser Gln  Ala Phe Ala Glu Asp  Leu Leu Leu
    2660                2665                2670

Gln Ala  Met Leu Val Trp Ala  Arg Ile Lys His Asp  Ala Ala Ser
    2675                2680                2685

Leu Pro  Ser Thr Ile Gly Glu  Leu Thr Thr Tyr Ala  Pro Phe Ala
    2690                2695                2700

Ser Gly  Asp Lys Gly Tyr Leu  Val Leu Thr Val Leu  Lys Ser Thr
    2705                2710                2715

Ser Arg  Ser Leu Thr Ala Asp  Ile Ala Leu Tyr His  Gln Asp Gly
    2720                2725                2730

Arg Leu  Ser Cys Thr Met Leu  Ser Ala Lys Thr Thr  Ile Ser Lys
    2735                2740                2745

Ser Leu  Asn Glu Ala Phe Leu  Ala Pro Ala Lys Ala  Leu Ala Asp
    2750                2755                2760

Leu Gln  Glu Ser Val
    2765


<210> SEQ ID NO 9
<211> LENGTH: 743
<212> TYPE: PRT
<213> ORGANISM: Sh. olleyana

<400> SEQUENCE: 9

Val Ser Asn Gln Leu Pro Pro Ser Thr Ser Ala Ile Lys Ser Met Arg
1               5                   10                  15

Ile Ala Leu Lys Met Val Ala Asn Glu Gln Val Ser Phe Ala Thr Ser
            20                  25                  30

Ser Gly Asn Asp Phe Ser Ala Asn Ser Phe Ala Ala Ile Lys Pro Cys
        35                  40                  45

Ser Leu Ala Glu Ala Ile Gly Ala Ser Ala Ile Asp Leu Glu Ile Asp
    50                  55                  60

Val Ser Ser Leu Asp Ala Ser Leu Ser Glu Asn Ala Val Asn Lys Ala
65                  70                  75                  80

Leu Ser Phe Asn Asp Tyr Phe Ala Gln Ala Ile Ile His Ile Glu Gln
                85                  90                  95

Gln His Thr Val Leu Leu Ser His Pro Glu Leu Pro Tyr Arg Leu Leu
            100                 105                 110

Met Met Pro Ala Ile Val Ala Ala Lys His Arg Cys His Pro His Ala
        115                 120                 125
```

-continued

```
Tyr Leu Thr Gly Leu Gly Glu Ala Asp Asp Met Pro Ser Ala Ile Asn
    130                 135                 140

Ala Ala Leu Val Gln Ala Lys Arg Ala His Ile Lys Pro Thr His Val
145                 150                 155                 160

Asp Ala Thr Gln Leu Thr Cys Tyr Lys Asp Lys Phe Ala Gln Leu Val
                165                 170                 175

Met Leu Ile Gly Ser Ile Ala Thr Arg Ser Val Pro Asn Thr Val Ser
            180                 185                 190

Glu Asn Gln Ser Ala Asp Ala Gln Tyr Trp Phe Thr Glu Met His Gln
        195                 200                 205

Asn Arg Val Ala Ser Phe Asn Phe Ser Glu Gly Asn Lys Gln His Ser
    210                 215                 220

Ala Val Phe Val Gln Gly Thr Glu Leu Ala Gln Ala Ser Ser Leu Val
225                 230                 235                 240

Asp Asp Asn Arg Leu Phe Leu Pro Val Ser Ala Asn Asp Leu Gly Met
                245                 250                 255

Met Lys Gln Gln Leu Gln Ala Leu Ser Ser Gln Leu Ala Ala Leu Pro
            260                 265                 270

Ala Gln His Asp Lys Ser Asp Ser Ser Ala Ile Ser Phe Met Leu Ser
        275                 280                 285

Gln Leu Lys Gln Phe Asp Gln Thr Gln Pro Leu Ser Ala Val Val Met
    290                 295                 300

Ala Asn Ser Val Thr Asn Ala Val Ser Glu Ile Asn Val Met Leu Ser
305                 310                 315                 320

Thr Ile Gly Lys Ala Glu Ala Thr Ala Ala Asn Glu Val Gln Ala Lys
                325                 330                 335

Ser Asn Leu Ser Ile Glu His Lys Thr Pro Ser Gly Ser Cys Phe His
            340                 345                 350

Leu Thr Ser Asp Lys Val Leu Gly Asn Asn Gly Leu Cys Phe Val Tyr
        355                 360                 365

Pro Gly Val Gly Thr Val Tyr Pro Gln Met Phe Ala Gln Leu Pro Arg
    370                 375                 380

Tyr Phe Pro Ala Leu Phe Ala Gln Leu Glu Arg Asp Gly Asp Val Lys
385                 390                 395                 400

Ala Met Leu Gln Ala Asp Ser Ile Tyr Ala Glu Asn Ala Lys Thr Thr
                405                 410                 415

Asp Met Ser Leu Gly Glu Leu Ala Ile Ala Gly Val Gly Ala Ser Tyr
            420                 425                 430

Ile Leu Thr Lys Val Leu Thr Glu His Phe Gly Ile Lys Pro Asn Phe
        435                 440                 445

Ala Met Gly Tyr Ser Met Gly Glu Ala Ser Met Trp Ala Ser Leu Asp
    450                 455                 460

Val Trp Lys Thr Pro His Asn Met Ile Glu Ala Thr Gln Thr Asn Ser
465                 470                 475                 480

Ile Phe Thr Thr Asp Ile Ser Gly Arg Leu Asp Cys Val Arg Gln Ala
                485                 490                 495

Trp Gln Leu Glu His Gly Glu Asp Ile Val Trp Asn Ser Phe Val Val
            500                 505                 510

Arg Ala Ala Pro Ala Asp Ile Glu Lys Val Leu Ala Asp Phe Pro Arg
        515                 520                 525

Ala Tyr Leu Ala Ile Ile Gln Gly Asp Thr Cys Val Leu Ala Gly Cys
    530                 535                 540

Glu Glu Ser Cys Lys Ala Leu Leu Lys Gln Ile Gly Lys Arg Gly Ile
```

-continued

```
545                 550                 555                 560

Ala Ala Asn Arg Val Thr Ala Met His Thr Lys Pro Ala Met Leu Ile
                565                 570                 575

Arg Asp Asn Val Gln Ala Phe Tyr Gln Gln Pro Leu His Glu Gln Asp
            580                 585                 590

Val Ile Ala Pro Phe Ala Ser Gln Ile Lys Phe Ile Ser Ala Ala Ser
        595                 600                 605

Gln Ser Pro Ile Asn Leu Thr Ser Glu Ala Ile Ala Thr Ser Ile Ala
    610                 615                 620

Asp Thr Phe Cys Gln Pro Leu Asp Phe Thr Gln Leu Val Asn Asn Ala
625                 630                 635                 640

Arg His Leu Gly Ala Ser Leu Phe Val Glu Ile Gly Ala Asp Arg Gln
                645                 650                 655

Thr Thr Thr Leu Ile Asp Lys Ile Ser Arg Thr Ser Glu Met Ala Gln
            660                 665                 670

Thr Cys Gln Ala Ile Ser Val Asn Ala Lys Gly Asp Asp Gln Thr Ala
        675                 680                 685

Leu Leu Lys Cys Ile Ala Gln Leu Ile Thr His Lys Thr Pro Ile Ser
    690                 695                 700

Leu Asp Tyr Leu Thr Glu Thr Leu Ser Ser Leu Leu Thr Thr Thr Leu
705                 710                 715                 720

Ala Ala Glu Lys Arg Ser Asn His His Thr Gly Asn Met Leu Ala Pro
                725                 730                 735

Gln Leu Glu Gly Glu Gln Ser
            740


<210> SEQ ID NO 10
<211> LENGTH: 2020
<212> TYPE: PRT
<213> ORGANISM: Sh. olleyana

<400> SEQUENCE: 10

Leu Ser Ser Gln Ser Thr Asn Leu Asn Thr Thr Val Pro Lys Ile Ala
1               5                   10                  15

Ile Val Gly Leu Ala Thr Gln Tyr Pro Asp Ala Asp Thr Pro Ala Lys
            20                  25                  30

Phe Trp Gln Asn Leu Leu Asp Lys Lys Asp Ser Arg Ser Thr Ile Asn
        35                  40                  45

Ser Gln Lys Leu Asn Ala Asn Pro Ala Asp Tyr Gln Gly Val Gln Gly
    50                  55                  60

Glu Ser Asp Arg Phe Tyr Cys Asp Lys Gly Gly Tyr Ile Gln Asn Phe
65                  70                  75                  80

Ser Phe Asp Ala Asn Gly Tyr Arg Ile Pro Ala Glu Gln Phe Ser Gly
                85                  90                  95

Leu Asp Asp Ser Phe Leu Trp Ala Thr Asp Thr Ala Arg Lys Ala Leu
            100                 105                 110

Asn Asp Ala Gly Val Asp Ile Thr Asn Pro Gln Asn Asn Gly Ala Leu
        115                 120                 125

Asn Arg Thr Gly Ile Val Met Gly Thr Leu Ser Phe Pro Thr Ala Lys
    130                 135                 140

Ser Asn Glu Leu Phe Val Pro Ile Tyr His Ser Ala Val Glu Lys Ala
145                 150                 155                 160

Leu Gln Asp Lys Leu Gln Gln Pro Ser Phe Thr Leu Gln Pro Phe Asp
                165                 170                 175
```

-continued

```
Ser Glu Gly Tyr Ser Gln Gln Thr Thr Ser Ala Ser Leu Ser Asn Gly
            180                 185                 190

Ala Ile Ala His Asn Ala Ser Lys Leu Val Ala Asp Ala Leu Gly Leu
        195                 200                 205

Gly Ala Ala Gln Leu Ser Leu Asp Ala Ala Cys Ala Ser Ser Val Tyr
    210                 215                 220

Ser Leu Lys Leu Ala Cys Asp Tyr Leu His Thr Gly Lys Ala Asp Met
225                 230                 235                 240

Met Leu Ala Gly Ala Val Ser Gly Ala Asp Pro Phe Phe Ile Asn Met
                245                 250                 255

Gly Phe Ser Ile Phe His Ala Tyr Pro Asp His Gly Ile Ser Ala Pro
            260                 265                 270

Phe Asp Ser Asn Ser Lys Gly Leu Phe Ala Gly Glu Gly Ala Gly Val
        275                 280                 285

Leu Val Leu Lys Arg Leu Glu Asp Ala Glu Arg Asp Gly Asp His Ile
    290                 295                 300

Tyr Ala Leu Val Ser Gly Ile Gly Leu Ser Asn Asp Gly Lys Gly Gln
305                 310                 315                 320

Phe Val Leu Ser Pro Asn Ser Asp Gly Gln Val Lys Ala Phe Glu Arg
                325                 330                 335

Ala Tyr Ala Asp Ala Ala Met His Asp Glu Asn Phe Gly Pro Asn Asn
            340                 345                 350

Ile Glu Val Leu Glu Cys His Ala Thr Gly Thr Pro Leu Gly Asp Lys
        355                 360                 365

Val Glu Leu Thr Ser Met Glu Arg Phe Phe Ser Asp Lys Leu Asn Gly
    370                 375                 380

Ser Asn Thr Pro Leu Ile Gly Ser Ala Lys Ser Asn Leu Gly His Leu
385                 390                 395                 400

Leu Thr Ala Ala Gly Met Pro Gly Ile Met Lys Met Ile Phe Ala Met
                405                 410                 415

Arg Gln Gly Val Leu Pro Pro Ser Ile Asn Ile Ser Ala Pro Ile Ala
            420                 425                 430

Ser Pro Ser Glu Met Phe Gly Pro Ala Thr Leu Pro Asn Asp Val Leu
        435                 440                 445

Pro Trp Pro Asp Lys Ala Gly Asn Thr Ala Arg His Ala Gly Val Ser
    450                 455                 460

Val Phe Gly Phe Gly Gly Cys Asn Ala His Leu Leu Val Glu Ser Tyr
465                 470                 475                 480

Phe Ala Lys Ser His Gly Gln Pro Ser Ser Thr Glu Leu Val Lys Pro
                485                 490                 495

Ala Thr Thr Thr Ile Asn Ala Gln Met Pro Met His Ile Thr Gly Met
            500                 505                 510

Ala Ser His Phe Gly Ser Leu Ser Asn Val Asn Asp Phe Ala Asp Ala
        515                 520                 525

Val Asn Asn Asn Gln Thr Ala Phe Thr Ser Leu Pro Ala Lys Arg Trp
    530                 535                 540

Lys Gly Leu Asp Lys His Pro Glu Leu Leu Gln Lys Phe Gly Leu Ser
545                 550                 555                 560

Gln Ala Ala Pro Thr Gly Ala Tyr Ile Asp Gln Phe Asp Phe Asp Phe
                565                 570                 575

Leu Arg Phe Lys Val Pro Pro Asn Glu Asp Asp Arg Leu Ile Ser Gln
            580                 585                 590

Gln Leu Leu Leu Met Lys Val Ala Asp Glu Ala Ile His Asp Ala Lys
```

-continued

```
        595                 600                 605

Leu Glu Ser Gly Ser Lys Val Ala Val Leu Val Ala Met Glu Thr Glu
    610                 615                 620

Leu Glu Leu His Gln Phe Arg Gly Arg Val Asn Leu His Thr Gln Ile
625                 630                 635                 640

Ala Ala Ser Leu Thr Ala His Gly Val Ser Leu Ser Asp Ser Glu Tyr
                645                 650                 655

Gln Ala Leu Glu Thr Ile Ala Met Asp Ser Val Leu Asp Ala Ala Lys
            660                 665                 670

Leu Asn Gln Tyr Thr Ser Phe Ile Gly Asn Ile Met Ala Ser Arg Ile
        675                 680                 685

Ser Ser Leu Trp Asp Phe Asn Gly Pro Ala Phe Thr Ile Ser Ala Gly
    690                 695                 700

Glu Gln Ser Val Asn Arg Cys Ile Asp Val Ala Gln Asn Leu Leu Ala
705                 710                 715                 720

Met Glu Ser Arg Gln Glu Pro Leu Asp Ala Ala Ile Ile Ala Ala Val
                725                 730                 735

Asp Leu Ser Gly Ser Ile Glu Asn Ile Val Leu Lys Thr Ala Asn Ile
            740                 745                 750

Asn Lys Thr Gly Ser Thr Glu Ala Leu Asn Ile Gly Glu Gly Ala Gly
        755                 760                 765

Ala Ile Val Leu Gln Ala Ala Ala Ile Asp Ser Glu His Cys Asp Leu
    770                 775                 780

Ile His Gln Gly Leu Gly Ala Leu Asp Thr Leu Asp Ser Ala Ser Thr
785                 790                 795                 800

His Ser Tyr Gly Thr Ile Asp Ser Leu Ala Phe Gly His Thr Asp Gln
                805                 810                 815

Leu Ser Thr Ile Ser Asp Asp Val Leu Thr Pro Val Gly Leu Ala Ala
            820                 825                 830

Thr Asp Ile Asp Leu Leu Glu Leu Asn Gln Ala Pro Asp Leu Leu Asn
        835                 840                 845

Ile Asp Asn Ala Gln Met Leu Ser Gln Leu Phe Asn Gln Ser Ser Thr
    850                 855                 860

Ser Lys Ala Gln Ser Cys Ile Gly His Thr Phe Ala Ala Ser Gly Ile
865                 870                 875                 880

Ala Ser Leu Leu His Gly Leu Leu Lys Thr Arg Leu Asn Ala Ser Val
                885                 890                 895

Gln Asn Ala Asn Ser Asp Ser Lys Leu Ser Asn Lys Pro Asn Gln Lys
            900                 905                 910

Ala Ile Ile Ala Thr Leu Ser Glu Asn Gln Cys Ser Gln Leu Leu Ile
        915                 920                 925

Ser Gln Asn Ala Glu Gln Ala Ser Ala Met Ser Thr Arg Ile Asp Thr
    930                 935                 940

Asp Ile Gln Ala Gln Thr Ala Lys Lys Leu Ser Leu Val Lys Gln Val
945                 950                 955                 960

Ser Leu Gly Gly Arg Asp Ile Tyr Gln His Ile Val Asp Ala Pro Leu
                965                 970                 975

Ala Asn Ile Asp Ser Ile Arg Ala Lys Val Ala Lys Leu Asn Pro Val
            980                 985                 990

Ala Pro Thr Thr Val Met Asn Leu  His Asp Arg Gly Gln  Phe Ile Ala
        995                 1000                1005

Pro Ala  His Ala Asn Ser Ala  Pro Met Ser Ala Asn  Asn Asn Ser
    1010                1015                1020
```

```
Met Thr  Thr Glu Thr Ser Met  Pro Phe Ser Asp Arg  Ser Thr Gln
    1025                 1030                 1035

Phe Asn  Pro Thr Pro Lys Val  Ala Thr Pro Thr Ala  Leu Ser Thr
    1040                 1045                 1050

Gln Ala  Ala Gln Ala Thr Gln  Ser Ala Gln Thr Ser  Ser Val Thr
    1055                 1060                 1065

Ser Ser  Val Ala Ala Ile Ser  Gln Val Pro Pro Thr  His Leu Ser
    1070                 1075                 1080

Ala Phe  Glu Gln Asn Gln Trp  Leu Ala His Gln Ala  Gln Leu Ala
    1085                 1090                 1095

Phe Leu  Lys Ser Arg Glu Gln  Gly Leu Lys Val Ala  Asp Ala Leu
    1100                 1105                 1110

Leu Lys  Gln Glu Ile Ala Gln  Ala Asn Gly Gln Pro  Tyr Val Ala
    1115                 1120                 1125

Gln Ser  Thr Ala Gln Ala Val  Ala Pro Val Gln Ala  Ala Asn Val
    1130                 1135                 1140

Leu Ala  Gln Pro Ile Ala Ser  Ala Ser Ile Leu Arg  Pro Asp His
    1145                 1150                 1155

Ala Asn  Val Pro Pro Tyr Thr  Ala Pro Ile Pro Ala  Asn Lys Pro
    1160                 1165                 1170

Cys Ile  Trp Asn Tyr Ala Asp  Leu Val Glu Tyr Ala  Glu Gly Asp
    1175                 1180                 1185

Ile Ala  Lys Val Phe Gly Pro  Asp Tyr Ala Val Ile  Asp Asn Tyr
    1190                 1195                 1200

Ser Arg  Arg Val Arg Leu Pro  Thr Thr Asp Tyr Leu  Leu Val Ser
    1205                 1210                 1215

Arg Val  Thr Lys Leu Asp Ala  Thr Met Asn Gln Tyr  Lys Pro Cys
    1220                 1225                 1230

Ser Met  Thr Thr Glu Tyr Asp  Ile Pro Glu Asp Ala  Pro Tyr Leu
    1235                 1240                 1245

Val Asp  Gly Gln Ile Pro Trp  Ala Val Ala Val Glu  Ser Gly Gln
    1250                 1255                 1260

Cys Asp  Leu Met Leu Ile Ser  Tyr Leu Gly Ile Asp  Phe Glu Asn
    1265                 1270                 1275

Lys Gly  Glu Arg Val Tyr Arg  Leu Leu Asp Cys Thr  Leu Thr Phe
    1280                 1285                 1290

Leu Gly  Asp Leu Pro Arg Gly  Gly Asp Thr Leu Arg  Tyr Asp Ile
    1295                 1300                 1305

Lys Ile  Asn Asn Phe Ala Lys  Asn Gly Glu Thr Leu  Leu Phe Phe
    1310                 1315                 1320

Phe Ser  Tyr Glu Cys Phe Val  Gly Asp Lys Met Val  Leu Lys Met
    1325                 1330                 1335

Asp Gly  Gly Cys Ala Gly Phe  Phe Thr Asp Gln Glu  Leu Asp Asp
    1340                 1345                 1350

Gly Lys  Gly Val Ile Tyr Thr  Glu Asp Glu Ile Lys  Thr Arg Glu
    1355                 1360                 1365

Ala Ala  Leu Asn Thr Pro Asn  Lys Pro Arg Phe Glu  Pro Leu Leu
    1370                 1375                 1380

His Cys  Ala Gln Thr Gln Phe  Asp Tyr Gly Gln Ile  His His Leu
    1385                 1390                 1395

Leu Asn  Ala Asp Ile Gly Ser  Cys Phe Ala Gly Glu  His His Asn
    1400                 1405                 1410
```

-continued

```
His Gln  Gln Ala Ser Gly Lys  Gln Asp Ser Leu Cys  Phe Ala Ser
    1415                 1420                 1425

Glu Lys  Phe Leu Met Ile Glu  Gln Val Gly Asn Leu  Glu Val His
    1430                 1435                 1440

Gly Gly  Ala Trp Gly Leu Gly  Phe Ile Glu Gly His  Lys Gln Leu
    1445                 1450                 1455

Ala Pro  Asp His Trp Tyr Phe  Pro Cys His Phe Gln  Gly Asp Gln
    1460                 1465                 1470

Val Met  Ala Gly Ser Leu Met  Ala Glu Gly Cys Gly  Gln Leu Leu
    1475                 1480                 1485

Gln Phe  Phe Met Leu His Ile  Gly Met His Thr Leu  Val Glu Asn
    1490                 1495                 1500

Gly Arg  Phe Gln Pro Leu Glu  Asn Ala Ser Gln Lys  Val Arg Cys
    1505                 1510                 1515

Arg Gly  Gln Val Leu Pro Gln  His Gly Glu Leu Thr  Tyr Arg Met
    1520                 1525                 1530

Glu Val  Thr Glu Ile Gly Thr  His Pro Arg Pro Tyr  Ala Lys Ala
    1535                 1540                 1545

Asn Ile  Glu Ile Leu Leu Asn  Gly Lys Ala Val Val  Asp Phe Gln
    1550                 1555                 1560

Asn Leu  Gly Val Met Ile Lys  Glu Glu Gly Glu Cys  Thr Arg Tyr
    1565                 1570                 1575

Thr Ala  Asp Ser Thr Glu Thr  His Thr Thr Ser Gly  Thr Val Gln
    1580                 1585                 1590

Lys Asn  Asn Ser His Asn Thr  Pro Ala Ser Leu Asn  Ala Pro Leu
    1595                 1600                 1605

Met Ala  Gln Val Pro Asp Leu  Ser Glu Pro Ala Asn  Lys Gly Val
    1610                 1615                 1620

Ile Pro  Leu Gln His Val Glu  Ala Pro Met Leu Pro  Asp Tyr Pro
    1625                 1630                 1635

Asn Arg  Thr Pro Asp Thr Leu  Pro Phe Thr Ala Tyr  His Met Phe
    1640                 1645                 1650

Glu Phe  Ala Thr Gly Asp Ile  Glu Asn Cys Phe Gly  Pro Asp Phe
    1655                 1660                 1665

Ser Ile  Tyr Arg Gly Phe Ile  Pro Pro Arg Thr Pro  Cys Gly Asp
    1670                 1675                 1680

Leu Gln  Leu Thr Thr Arg Val  Val Asp Ile Gln Gly  Lys Arg Gly
    1685                 1690                 1695

Glu Leu  Lys Lys Pro Ser Ser  Cys Ile Ala Glu Tyr  Glu Val Pro
    1700                 1705                 1710

Thr Asp  Ala Trp Tyr Phe Ala  Lys Asn Ser His Ala  Ser Val Met
    1715                 1720                 1725

Pro Tyr  Ser Val Leu Met Glu  Ile Ser Leu Gln Pro  Asn Gly Phe
    1730                 1735                 1740

Ile Ser  Gly Tyr Met Gly Thr  Thr Leu Gly Phe Pro  Gly Gln Glu
    1745                 1750                 1755

Leu Phe  Phe Arg Asn Leu Asp  Gly Ser Gly Glu Leu  Leu Cys Asp
    1760                 1765                 1770

Val Asp  Leu Arg Gly Lys Thr  Ile Val Asn Asp Ser  Lys Leu Leu
    1775                 1780                 1785

Ser Thr  Val Ile Ala Gly Ser  Asn Ile Ile Gln Ser  Phe Ser Phe
    1790                 1795                 1800

Asp Leu  Ser Val Asp Gly Glu  Pro Phe Tyr Thr Gly  Ser Ala Val
```

-continued

```
    1805                1810                1815

Phe Gly  Tyr Phe Lys Gly Asp  Ala Leu Lys Asn Gln  Leu Gly Ile
    1820                1825                1830

Asp Asn  Gly Arg Ile Thr Gln  Pro Trp His Val Glu  Asn Asn Val
    1835                1840                1845

Ala Ala  Asp Ile Thr Val Asp  Leu Leu Asp Lys Gln  Ser Arg Val
    1850                1855                1860

Phe His  Ala Pro Ala Asn Gln  Pro His Tyr Arg Leu  Ala Gly Gly
    1865                1870                1875

Gln Leu  Asn Phe Ile Asp Lys  Ala Glu Ile Val Asp  Lys Gly Gly
    1880                1885                1890

Lys Asn  Gly Leu Gly Tyr Leu  Ser Ala Ser Arg Thr  Ile Asp Pro
    1895                1900                1905

Ser Asp  Trp Phe Phe Gln Phe  His Phe His Gln Asp  Pro Val Met
    1910                1915                1920

Pro Gly  Ser Leu Gly Val Glu  Ala Ile Ile Glu Leu  Met Gln Thr
    1925                1930                1935

Tyr Ala  Ile Ser Lys Asp Leu  Gly Lys Gly Phe Thr  Asn Pro Lys
    1940                1945                1950

Phe Gly  Gln Ile Leu Ser Asp  Ile Lys Trp Lys Tyr  Arg Gly Gln
    1955                1960                1965

Ile Asn  Pro Leu Asn Lys Gln  Met Ser Leu Asp Val  His Ile Ser
    1970                1975                1980

Ala Val  Lys Asp Glu Asn Gly  Lys Arg Ile Ile Val  Gly Asp Ala
    1985                1990                1995

Asn Leu  Ser Lys Asp Gly Leu  Arg Ile Tyr Glu Val  Lys Asp Ile
    2000                2005                2010

Ala Ile  Cys Ile Glu Glu Ala
    2015                2020


<210> SEQ ID NO 11
<211> LENGTH: 542
<212> TYPE: PRT
<213> ORGANISM: Sh. olleyana

<400> SEQUENCE: 11

Met Thr Ile Ser Thr Gln Asn Glu Lys Leu Ser Pro Trp Pro Trp Gln
1               5                   10                  15

Val Ala Pro Ser Asp Ala Ser Phe Glu Asn Ala Ala Ile Gly Lys Lys
            20                  25                  30

Leu Lys Glu Leu Ser Gln Ala Cys Tyr Leu Ile Asn His Pro Glu Lys
        35                  40                  45

Gly Leu Gly Ile Ser Gln Asn Ala Gln Val Met Thr Glu Ser Met Asn
    50                  55                  60

Ser Gln Gln Asp Leu Pro Val Ser Ala Phe Ala Pro Ala Leu Gly Thr
65                  70                  75                  80

Gln Ser Leu Gly Asp Ser Asn Phe Arg Arg Val His Gly Val Lys Tyr
                85                  90                  95

Ala Tyr Tyr Ala Gly Ala Met Ala Asn Gly Ile Ser Ser Glu Glu Leu
            100                 105                 110

Val Ile Ala Leu Gly Gln Ala Gly Ile Leu Cys Ser Phe Gly Ala Ala
        115                 120                 125

Gly Leu Ile Pro Ser Arg Val Glu Gln Ala Ile Asn Arg Ile Gln Thr
    130                 135                 140
```

-continued

```
Ala Leu Pro Asn Gly Pro Tyr Met Phe Asn Leu Ile His Ser Pro Ser
145                 150                 155                 160

Glu Pro Ala Leu Glu Arg Gly Ser Val Glu Leu Phe Leu Lys His Lys
                165                 170                 175

Val Arg Thr Val Glu Ala Ser Ala Phe Leu Gly Leu Thr Pro Gln Ile
            180                 185                 190

Val Tyr Tyr Arg Ala Ala Gly Leu Ser Arg Asp Ala Gln Gly Glu Val
        195                 200                 205

Val Ile Ala Asn Lys Val Ile Ala Lys Val Ser Arg Thr Glu Val Ala
    210                 215                 220

Ser Lys Phe Met Gln Pro Ala Pro Ala Lys Met Leu Gln Lys Leu Val
225                 230                 235                 240

Asp Glu Gly Leu Ile Thr Pro Glu Gln Met Glu Leu Ala Gln Leu Val
                245                 250                 255

Pro Met Ala Asp Asp Val Thr Ala Glu Ala Asp Ser Gly Gly His Thr
            260                 265                 270

Asp Asn Arg Pro Leu Val Thr Leu Leu Pro Thr Ile Leu Ala Leu Lys
        275                 280                 285

Asp Lys Ile Gln Ala Glu Tyr Gln Tyr Lys Thr Pro Ile Arg Val Gly
    290                 295                 300

Cys Gly Gly Gly Val Gly Thr Pro Asp Ala Ala Leu Ala Thr Phe Asn
305                 310                 315                 320

Met Gly Ala Ala Tyr Ile Val Thr Gly Ser Ile Asn Gln Ala Cys Val
                325                 330                 335

Glu Ala Gly Ala Ser Glu His Thr Arg Lys Leu Leu Ala Thr Thr Glu
            340                 345                 350

Met Ala Asp Val Thr Met Ala Pro Ala Ala Asp Met Phe Glu Met Gly
        355                 360                 365

Val Lys Leu Gln Val Val Lys Arg Gly Thr Leu Phe Pro Met Arg Ala
    370                 375                 380

Asn Lys Leu Tyr Glu Ile Tyr Thr Arg Tyr Glu Ser Ile Glu Ala Ile
385                 390                 395                 400

Pro Ala Glu Glu Arg Glu Lys Leu Glu Lys Gln Val Phe Arg Ser Thr
                405                 410                 415

Leu Asp Asp Ile Trp Ala Gly Thr Val Ala His Phe Asn Glu Arg Asp
            420                 425                 430

Pro Lys Gln Ile Glu Arg Ala Glu Gly Asn Pro Lys Arg Lys Met Ala
        435                 440                 445

Leu Ile Phe Arg Trp Tyr Leu Gly Leu Ser Ser Arg Trp Ser Asn Ser
    450                 455                 460

Gly Glu Val Gly Arg Glu Met Asp Tyr Gln Ile Trp Ala Gly Pro Ala
465                 470                 475                 480

Leu Gly Ala Phe Asn Glu Trp Ala Lys Gly Ser Tyr Leu Asp Asp Tyr
                485                 490                 495

Thr Gln Arg Asn Ala Val Asp Leu Ala Lys His Leu Met His Gly Ala
            500                 505                 510

Ala Tyr Gln Ala Arg Val Asn Leu Leu Thr Ala Gln Gly Val Ala Leu
        515                 520                 525

Pro Val Glu Leu Gln Arg Trp Ser Pro Leu Asp Gln Val Lys
    530                 535                 540
```

<210> SEQ ID NO 12
<211> LENGTH: 290
<212> TYPE: PRT

-continued

<213> ORGANISM: Sh. olleyana

<400> SEQUENCE: 12

Leu Lys Pro Pro Thr Val Ile Gln Leu Phe Phe Cys Pro Leu Asn Thr
1 5 10 15

Asp Leu Leu Asp Glu Ser Thr Ala Ser Ile Val Arg Ser Trp Leu Pro
20 25 30

Glu Asp Glu Val Lys Lys Val Asp Arg Phe Ile Gln Gln Ser Ser Arg
35 40 45

Glu Gln Gly Leu Met Val Arg Gly Tyr Leu Arg Ser Val Leu Ser Arg
50 55 60

Phe Ala Ser Val Glu Pro Gln Gln Trp Gln Phe Glu Tyr Gly Glu Lys
65 70 75 80

Gly Lys Pro Arg Leu Thr Ala Glu Gln Phe Ala Gln Thr Gly Leu Gln
85 90 95

Phe Asn Leu Ser His Ser Gly Asp Trp Leu Leu Ile Gly Val Ala Asn
100 105 110

Thr Tyr Gly Thr Ala Gln Gln Gln Thr Asp Ile Glu Leu Gly Val Asp
115 120 125

Ile Glu Arg Arg Arg Glu Thr Thr Asn Ile His Ser Ile Leu Asn His
130 135 140

Tyr Phe Ser Lys Pro Glu Glu Ser Ala Leu Leu Ala Leu Ala Glu Asp
145 150 155 160

Lys His Arg Glu Arg Phe Phe Asp Leu Trp Ala Leu Lys Glu Ser Tyr
165 170 175

Ile Lys Ala Lys Gly Leu Gly Leu Ala Leu Ser Leu Lys Ser Phe Ala
180 185 190

Phe Asp Leu Ser Ala Ser Ser Val Gly Glu Leu Gln Val Asn Ser Glu
195 200 205

Thr Ile Thr Ile Gln Gln Asn Val Lys Leu Ser Leu Leu Lys Ala Ser
210 215 220

Asp Ser Asp Gly Leu Leu Glu Asp Phe Val Ile Ala Pro Gln Trp His
225 230 235 240

Cys Tyr Leu Gly Lys Leu Asp Asp Leu Tyr Arg Phe Ala Val Ser Val
245 250 255

Gly Arg Ala Ser Thr Asn Ser Asp Glu Leu Pro Pro Glu Leu Lys Ala
260 265 270

Lys Lys Ile Ser Trp Leu Glu Val Val Asn His Ala Phe Lys Pro Thr
275 280 285

Asp Arg
290

<210> SEQ ID NO 13
<211> LENGTH: 8730
<212> TYPE: DNA
<213> ORGANISM: Schizochytrium sp.

<400> SEQUENCE: 13
atggcggccc gtctgcagga gcaaaaggga ggcgagatgg atacccgcat tgccatcatc 60
ggcatgtcgg ccatcctccc ctgcggcacg accgtgcgcg agtcgtggga gaccatccgc 120
gccggcatcg actgcctgtc ggatctcccc gaggaccgcg tcgacgtgac ggcgtacttt 180
gaccccgtca agaccaccaa ggacaagatc tactgcaagc gcggtggctt cattcccgag 240
tacgactttg acgcccgcga gttcggactc aacatgttcc agatggagga ctcggacgca 300

-continued

```
aaccagacca tctcgcttct caaggtcaag gaggccctcc aggacgccgg catcgacgcc    360
ctcggcaagg aaaagaagaa catcggctgc gtgctcggca ttggcggcgg ccaaaagtcc    420
agccacgagt tctactcgcg ccttaattat gttgtcgtgg agaaggtcct ccgcaagatg    480
ggcatgcccg aggaggacgt caaggtcgcc gtcgaaaagt acaaggccaa cttccccgag    540
tggcgcctcg actccttccc tggcttcctc ggcaacgtca ccgccggtcg ctgcaccaac    600
accttcaacc tcgacggcat gaactgcgtt gtcgacgccg catgcgcctc gtccctcatc    660
gccgtcaagg tcgccatcga cgagctgctc tacggtgact gcgacatgat ggtcaccggt    720
gccacctgca cggataactc catcggcatg tacatggcct tctccaagac ccccgtgttc    780
tccacggacc ccagcgtgcg cgcctacgac gaaaagacaa agggcatgct catcggcgag    840
ggctccgcca tgctcgtcct caagcgctac gccgacgccg tccgcgacgg cgatgagatc    900
cacgctgtta ttcgcggctg cgcctcctcc agtgatggca aggccgccgg catctacacg    960
cccaccattt cgggccagga ggaggccctc cgccgcgcct acaaccgcgc ctgtgtcgac   1020
ccggccaccg tcactctcgt cgagggtcac ggcaccggta ctcccgttgg cgaccgcatc   1080
gagctcaccg ccttgcgcaa cctctttgac aaggcctacg gcgagggcaa caccgaaaag   1140
gtcgctgtgg gcagcatcaa gtccagcatc ggccatctca aggccgtcgc cggtctcgcc   1200
ggtatgatca aggtcatcat ggcgctcaag cacaagactc tcccgggcac catcaacgtc   1260
gacaacccac ccaacctcta cgacaacacg cccatcaacg agtcctcgct ctacattaac   1320
accatgaacc gcccctggtt cccgcccccct ggtgtgcccc gccgcgccgg catttcgagc   1380
tttggctttg gtggcgccaa ctaccacgcc gtcctcgagg aggccgagcc cgagcacacg   1440
accgcgtacc gcctcaacaa gcgcccgcag cccgtgctca tgatggccgc cacgcccgcg   1500
gccctccagt cgctctgcga ggcccagctc aaggagttcg aggccgccat caaggagaac   1560
gagaccgtca agaacaccgc ctacatcaag tgcgtcaagt tcggcgagca gttcaaattc   1620
cctggctcca tcccggccac aaacgcgcgc ctcggcttcc tcgtcaagga tgctgaggat   1680
gcctgctcca ccctccgtgc catctgcgcc caattcgcca aggatgtcac caaggaggcc   1740
tggcgcctcc cccgcgaggg cgtcagcttc cgcgccaagg gcatcgccac caacggcgct   1800
gtcgccgcgc tcttctccgg ccagggcgcg cagtacacgc acatgtttag cgaggtggcc   1860
atgaactggc cccagttccg ccagagcatt gccgccatgg acgccgccca gtccaaggtc   1920
gctggaagcg acaaggactt tgagcgcgtc tcccaggtcc tctacccgcg caagccgtac   1980
gagcgtgagc ccgagcagaa ccccaagaag atctccctca ccgcctactc gcagccctcg   2040
accctggcct gcgctctcgg tgcctttgag atcttcaagg aggccggctt caccccggac   2100
tttgccgccg gccattcgct cggtgagttc gccgccctct acgccgcggg ctgcgtcgac   2160
cgcgacgagc tctttgagct tgtctgccgc cgcgcccgca tcatgggcgg caaggacgca   2220
ccggccaccc ccaagggatg catggccgcc gtcattggcc ccaacgccga gaacatcaag   2280
gtccaggccg ccaacgtctg gctcggcaac tccaactcgc cttcgcagac cgtcatcacc   2340
ggctccgtcg aaggtatcca ggccgagagc gcccgcctcc agaaggaggg cttccgcgtc   2400
gtgcctcttg cctgcgagag cgccttccac tcgccccaga tggagaacgc ctcgtcggcc   2460
ttcaaggacg tcatctccaa ggtctccttc cgcacccccca aggccgagac caagctcttc   2520
agcaacgtct ctggcgagac ctaccccacg gacgcccgcg agatgcttac gcagcacatg   2580
accagcagcg tcaagttcct cacccaggtc cgcaacatgc accaggccgg tgcgcgcatc   2640
tttgtcgagt tcggacccaa gcaggtgctc tccaagcttg tctccgagac cctcaaggat   2700
```

-continued

```
gaccccctcgg ttgtcaccgt ctctgtcaac ccggcctcgg gcacggattc ggacatccag   2760
ctccgcgacg cggccgtcca gctcgttgtc gctggcgtca accttcaggg ctttgacaag   2820
tgggacgccc ccgatgccac ccgcatgcag gccatcaaga agaagcgcac taccctccgc   2880
ctttcggccg ccacctacgt ctcggacaag accaagaagg tccgcgacgc cgccatgaac   2940
gatggccgct gcgtcaccta cctcaagggc gccgcaccgc tcatcaaggc cccggagccc   3000
gttgtcgacg aggccgccaa gcgcgaggcc gagcgtctcc agaaggagct tcaggatgcc   3060
cagcgccagc tcgacgacgc caagcgcgcc gccgccgagg ccaactccaa gctcgccgct   3120
gccaaggagg aggccaagac cgccgctgct tcggccaagc ccgcagttga cactgctgtt   3180
gtcgaaaagc atcgtgccat cctcaagtcc atgctcgcgg agctcgatgg ctacggatcg   3240
gtcgacgctt cttccctcca gcagcagcag cagcagcaga cggcccccgc cccggtcaag   3300
gctgctgcgc ctgccgcccc cgttgcctcg gcccctgccc cggctgtctc gaacgagctt   3360
cttgagaagg ccgagactgt cgtcatggag gtcctcgccg ccaagaccgg ctacgagacc   3420
gacatgatcg aggctgacat ggagctcgag accgagctcg gcattgactc catcaagcgt   3480
gtcgagatcc tctccgaggt ccaggccatg ctcaatgtcg aggccaagga tgtcgatgcc   3540
ctcagccgca ctcgcactgt tggtgaggtt gtcaacgcca tgaaggccga gatcgctggc   3600
agctctgccc cggcgcctgc tgccgctgct ccggctccgg ccaaggctgc ccctgccgcc   3660
gctgcgcctg ctgtctcgaa cgagcttctc gagaaggccg agaccgtcgt catggaggtc   3720
ctcgccgcca agactggcta cgagactgac atgatcgagt ccgacatgga gctcgagact   3780
gagctcggca ttgactccat caagcgtgtc gagatcctct ccgaggttca ggccatgctc   3840
aacgtcgagg ccaaggacgt cgacgctctc agccgcactc gcactgtggg tgaggtcgtc   3900
aacgccatga aggctgagat cgctggtggc tctgccccgg cgcctgccgc cgctgcccca   3960
ggtccggctg ctgccgcccc tgcgcctgcc gccgccgccc ctgctgtctc gaacgagctt   4020
cttgagaagg ccgagaccgt cgtcatggag gtcctcgccg ccaagactgg ctacgagact   4080
gacatgatcg agtccgacat ggagctcgag accgagctcg gcattgactc catcaagcgt   4140
gtcgagattc tctccgaggt ccaggccatg ctcaacgtcg aggccaagga cgtcgacgct   4200
ctcagccgca cccgcactgt tggcgaggtc gtcgatgcca tgaaggccga gatcgctggt   4260
ggctctgccc cggcgcctgc cgccgctgct cctgctccgg ctgctgccgc ccctgcgcct   4320
gccgcccctg cgcctgctgt ctcgagcgag cttctcgaga aggccgagac tgtcgtcatg   4380
gaggtcctcg ccgccaagac tggctacgag actgacatga tcgagtccga catggagctc   4440
gagaccgagc tcggcattga ctccatcaag cgtgtcgaga ttctctccga ggtccaggcc   4500
atgctcaacg tcgaggccaa ggacgtcgac gctctcagcc gcacccgcac tgttggcgag   4560
gtcgtcgatg ccatgaaggc cgagatcgct ggtggctctg ccccggcgcc tgccgccgct   4620
gctcctgctc cggctgctgc cgcccctgcg cctgccgccc ctgcgcctgc cgcccctgcg   4680
cctgctgtct cgagcgagct tctcgagaag gccgagactg tcgtcatgga ggtcctcgcc   4740
gccaagactg gctacgagac tgacatgatt gagtccgaca tggagctcga gaccgagctc   4800
ggcattgact ccatcaagcg tgtcgagatt ctctccgagg ttcaggccat gctcaacgtc   4860
gaggccaagg acgtcgacgc tctcagccgc actcgcactg ttggtgaggt cgtcgatgcc   4920
atgaaggctg agatcgctgg cagctccgcc tcggcgcctg ccgccgctgc tcctgctccg   4980
gctgctgccg ctcctgcgcc cgctgccgcc gcccctgctg tctcgaacga gcttctcgag   5040
```

-continued

```
aaagccgaga ctgtcgtcat ggaggtcctc gccgccaaga ctggctacga gactgacatg   5100
atcgagtccg acatggagct cgagactgag ctcggcattg actccatcaa gcgtgtcgag   5160
atcctctccg aggttcaggc catgctcaac gtcgaggcca aggacgtcga tgccctcagc   5220
cgcacccgca ctgttggcga ggttgtcgat gccatgaagg ccgagatcgc tggtggctct   5280
gccccggcgc ctgccgccgc tgcccctgct ccggctgccg ccgcccctgc tgtctcgaac   5340
gagcttctcg agaaggccga gactgtcgtc atggaggtcc tcgccgccaa gactggctac   5400
gagaccgaca tgatcgagtc cgacatggag ctcgagaccg agctcggcat tgactccatc   5460
aagcgtgtcg agattctctc cgaggttcag gccatgctca acgtcgaggc caaggacgtc   5520
gatgctctca gccgcactcg cactgttggc gaggtcgtcg atgccatgaa ggctgagatc   5580
gccggcagct ccgccccggc gcctgccgcc gctgctcctg ctccggctgc tgccgctcct   5640
gcgcccgctg ccgctgcccc tgctgtctcg agcgagcttc tcgagaaggc cgagaccgtc   5700
gtcatggagg tcctcgccgc caagactggc tacgagactg acatgattga gtccgacatg   5760
gagctcgaga ctgagctcgg cattgactcc atcaagcgtg tcgagatcct ctccgaggtt   5820
caggccatgc tcaacgtcga ggccaaggac gtcgatgccc tcagccgcac ccgcactgtt   5880
ggcgaggttg tcgatgccat gaaggccgag atcgctggtg gctctgcccc ggcgcctgcc   5940
gccgctgccc ctgctccggc tgccgccgcc cctgctgtct cgaacgagct tcttgagaag   6000
gccgagaccg tcgtcatgga ggtcctcgcc gccaagactg gctacgagac cgacatgatc   6060
gagtccgaca tggagctcga gaccgagctc ggcattgact ccatcaagcg tgtcgagatt   6120
ctctccgagg ttcaggccat gctcaacgtc gaggccaagg acgtcgacgc tctcagccgc   6180
actcgcactg ttggcgaggt cgtcgatgcc atgaaggctg agatcgctgg tggctctgcc   6240
ccggcgcctg ccgccgctgc tcctgcctcg gctggcgccg cgcctgcggt caagattgac   6300
tcggtccacg gcgctgactg tgatgatctt tccctgatgc acgccaaggt ggttgacatc   6360
cgccgcccgg acgagctcat cctggagcgc cccgagaacc gccccgttct cgttgtcgat   6420
gacggcagcg agctcaccct cgccctggtc cgcgtcctcg gcgcctgcgc cgttgtcctg   6480
acctttgagg gtctccagct cgctcagcgc gctggtgccg ctgccatccg ccacgtgctc   6540
gccaaggatc tttccgcgga gagcgccgag aaggccatca aggaggccga gcagcgcttt   6600
ggcgctctcg gcggcttcat ctcgcagcag gcggagcgct tcgagcccgc cgaaatcctc   6660
ggcttcacgc tcatgtgcgc caagttcgcc aaggcttccc tctgcacggc tgtggctggc   6720
ggccgcccgg cctttatcgg tgtggcgcgc cttgacggcc gcctcggatt cacttcgcag   6780
ggcacttctg acgcgctcaa gcgtgcccag cgtggtgcca tctttggcct ctgcaagacc   6840
atcggcctcg agtggtccga gtctgacgtc ttttcccgcg gcgtggacat tgctcagggc   6900
atgcaccccg aggatgccgc cgtggcgatt gtgcgcgaga tggcgtgcgc tgacattcgc   6960
attcgcgagg tcggcattgg cgcaaaccag cagcgctgca cgatccgtgc cgccaagctc   7020
gagaccggca acccgcagcg ccagatcgcc aaggacgacg tgctgctcgt ttctggcggc   7080
gctcgcggca tcacgcctct ttgcatccgg gagatcacgc gccagatcgc gggcggcaag   7140
tacattctgc ttggccgcag caaggtctct gcgagcgaac cggcatggtg cgctggcatc   7200
actgacgaga aggctgtgca aaaggctgct acccaggagc tcaagcgcgc ctttagcgct   7260
ggcgagggcc ccaagcccac gccccgcgct gtcactaagc ttgtgggctc tgttcttggc   7320
gctcgcgagg tgcgcagctc tattgctgcg attgaagcgc tcggcggcaa ggccatctac   7380
tcgtcgtgcg acgtgaactc tgccgccgac gtggccaagg ccgtgcgcga tgccgagtcc   7440
```

-continued

```
cagctcggtg cccgcgtctc gggcatcgtt catgcctcgg gcgtgctccg cgaccgtctc   7500

atcgagaaga agctccccga cgagttcgac gccgtctttg gcaccaaggt caccggtctc   7560

gagaacctcc tcgccgccgt cgaccgcgcc aacctcaagc acatggtcct cttcagctcg   7620

ctcgccggct tccacggcaa cgtcggccag tctgactacg ccatggccaa cgaggccctt   7680

aacaagatgg gcctcgagct cgccaaggac gtctcggtca agtcgatctg cttcggtccc   7740

tgggacggtg gcatggtgac gccgcagctc aagaagcagt tccaggagat gggcgtgcag   7800

atcatccccc gcgagggcgg cgctgatacc gtggcgcgca tcgtgctcgg ctcctcgccg   7860

gctgagatcc ttgtcggcaa ctggcgcacc ccgtccaaga aggtcggctc ggacaccatc   7920

accctgcacc gcaagatttc cgccaagtcc aacccccttcc tcgaggacca cgtcatccag   7980

ggccgccgcg tgctgcccat gacgctggcc attggctcgc tcgcggagac ctgcctcggc   8040

ctcttccccg gctactcgct ctgggccatt gacgacgccc agctcttcaa gggtgtcact   8100

gtcgacggcg acgtcaactg cgaggtgacc ctcaccccgt cgacggcgcc ctcgggccgc   8160

gtcaacgtcc aggccacgct caagaccttt tccagcggca agctggtccc ggcctaccgc   8220

gccgtcatcg tgctctccaa ccagggcgcg cccccggcca acgccaccat gcagccgccc   8280

tcgctcgatg ccgatccggc gctccagggc tccgtctacg acggcaagac cctcttccac   8340

ggcccggcct tccgcggcat cgatgacgtg ctctcgtgca ccaagagcca gcttgtggcc   8400

aagtgcagcg ctgtccccgg ctccgacgcc gctcgcggcg agtttgccac ggacactgac   8460

gcccatgacc ccttcgtgaa cgacctggcc tttcaggcca tgctcgtctg ggtgcgccgc   8520

acgctcggcc aggctgcgct ccccaactcg atccagcgca tcgtccagca ccgcccggtc   8580

ccgcaggaca agcccttcta cattaccctc cgctccaacc agtcgggcgg tcactcccag   8640

cacaagcacg cccttcagtt ccacaacgag cagggcgatc tcttcattga tgtccaggct   8700

tcggtcatcg ccacggacag ccttgccttc                                    8730
```

<210> SEQ ID NO 14
<211> LENGTH: 2910
<212> TYPE: PRT
<213> ORGANISM: Schizochytrium sp.

<400> SEQUENCE: 14

```
Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gly Gln Lys Ser Ser His Glu Phe
    130                 135                 140
```

-continued

```
Tyr Ser Arg Leu Asn Tyr Val Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
    210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
    290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
        355                 360                 365

Phe Asp Lys Ala Tyr Gly Glu Gly Asn Thr Glu Lys Val Ala Val Gly
    370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Pro Asn Leu Tyr Asp Asn Thr Pro Ile
            420                 425                 430

Asn Glu Ser Ser Leu Tyr Ile Asn Thr Met Asn Arg Pro Trp Phe Pro
        435                 440                 445

Pro Pro Gly Val Pro Arg Arg Ala Gly Ile Ser Ser Phe Gly Phe Gly
    450                 455                 460

Gly Ala Asn Tyr His Ala Val Leu Glu Glu Ala Glu Pro Glu His Thr
465                 470                 475                 480

Thr Ala Tyr Arg Leu Asn Lys Arg Pro Gln Pro Val Leu Met Met Ala
                485                 490                 495

Ala Thr Pro Ala Ala Leu Gln Ser Leu Cys Glu Ala Gln Leu Lys Glu
            500                 505                 510

Phe Glu Ala Ala Ile Lys Glu Asn Glu Thr Val Lys Asn Thr Ala Tyr
        515                 520                 525

Ile Lys Cys Val Lys Phe Gly Glu Gln Phe Lys Phe Pro Gly Ser Ile
    530                 535                 540

Pro Ala Thr Asn Ala Arg Leu Gly Phe Leu Val Lys Asp Ala Glu Asp
545                 550                 555                 560
```

-continued

```
Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590

Lys Gly Ile Ala Thr Asn Gly Ala Val Ala Ala Leu Phe Ser Gly Gln
        595                 600                 605

Gly Ala Gln Tyr Thr His Met Phe Ser Glu Val Ala Met Asn Trp Pro
    610                 615                 620

Gln Phe Arg Gln Ser Ile Ala Ala Met Asp Ala Ala Gln Ser Lys Val
625                 630                 635                 640

Ala Gly Ser Asp Lys Asp Phe Glu Arg Val Ser Gln Val Leu Tyr Pro
                645                 650                 655

Arg Lys Pro Tyr Glu Arg Glu Pro Glu Gln Asn Pro Lys Lys Ile Ser
            660                 665                 670

Leu Thr Ala Tyr Ser Gln Pro Ser Thr Leu Ala Cys Ala Leu Gly Ala
        675                 680                 685

Phe Glu Ile Phe Lys Glu Ala Gly Phe Thr Pro Asp Phe Ala Ala Gly
    690                 695                 700

His Ser Leu Gly Glu Phe Ala Ala Leu Tyr Ala Ala Gly Cys Val Asp
705                 710                 715                 720

Arg Asp Glu Leu Phe Glu Leu Val Cys Arg Arg Ala Arg Ile Met Gly
                725                 730                 735

Gly Lys Asp Ala Pro Ala Thr Pro Lys Gly Cys Met Ala Ala Val Ile
            740                 745                 750

Gly Pro Asn Ala Glu Asn Ile Lys Val Gln Ala Ala Asn Val Trp Leu
        755                 760                 765

Gly Asn Ser Asn Ser Pro Ser Gln Thr Val Ile Thr Gly Ser Val Glu
    770                 775                 780

Gly Ile Gln Ala Glu Ser Ala Arg Leu Gln Lys Glu Gly Phe Arg Val
785                 790                 795                 800

Val Pro Leu Ala Cys Glu Ser Ala Phe His Ser Pro Gln Met Glu Asn
                805                 810                 815

Ala Ser Ser Ala Phe Lys Asp Val Ile Ser Lys Val Ser Phe Arg Thr
            820                 825                 830

Pro Lys Ala Glu Thr Lys Leu Phe Ser Asn Val Ser Gly Glu Thr Tyr
        835                 840                 845

Pro Thr Asp Ala Arg Glu Met Leu Thr Gln His Met Thr Ser Ser Val
    850                 855                 860

Lys Phe Leu Thr Gln Val Arg Asn Met His Gln Ala Gly Ala Arg Ile
865                 870                 875                 880

Phe Val Glu Phe Gly Pro Lys Gln Val Leu Ser Lys Leu Val Ser Glu
                885                 890                 895

Thr Leu Lys Asp Asp Pro Ser Val Val Thr Val Ser Val Asn Pro Ala
            900                 905                 910

Ser Gly Thr Asp Ser Asp Ile Gln Leu Arg Asp Ala Ala Val Gln Leu
        915                 920                 925

Val Val Ala Gly Val Asn Leu Gln Gly Phe Asp Lys Trp Asp Ala Pro
    930                 935                 940

Asp Ala Thr Arg Met Gln Ala Ile Lys Lys Lys Arg Thr Thr Leu Arg
945                 950                 955                 960

Leu Ser Ala Ala Thr Tyr Val Ser Asp Lys Thr Lys Lys Val Arg Asp
                965                 970                 975

Ala Ala Met Asn Asp Gly Arg Cys Val Thr Tyr Leu Lys Gly Ala Ala
```

-continued

```
            980                 985                 990

Pro Leu Ile Lys Ala Pro Glu Pro  Val Val Asp Glu Ala  Ala Lys Arg
        995                 1000                1005

Glu Ala  Glu Arg Leu Gln Lys  Glu Leu Gln Asp Ala  Gln Arg Gln
    1010                 1015                 1020

Leu Asp  Asp Ala Lys Arg Ala  Ala Ala Glu Ala Asn  Ser Lys Leu
    1025                 1030                 1035

Ala Ala  Ala Lys Glu Glu Ala  Lys Thr Ala Ala Ala  Ser Ala Lys
    1040                 1045                 1050

Pro Ala  Val Asp Thr Ala Val  Val Glu Lys His Arg  Ala Ile Leu
    1055                 1060                 1065

Lys Ser  Met Leu Ala Glu Leu  Asp Gly Tyr Gly Ser  Val Asp Ala
    1070                 1075                 1080

Ser Ser  Leu Gln Gln Gln Gln  Gln Gln Gln Thr Ala  Pro Ala Pro
    1085                 1090                 1095

Val Lys  Ala Ala Ala Pro Ala  Ala Pro Val Ala Ser  Ala Pro Ala
    1100                 1105                 1110

Pro Ala  Val Ser Asn Glu Leu  Leu Glu Lys Ala Glu  Thr Val Val
    1115                 1120                 1125

Met Glu  Val Leu Ala Ala Lys  Thr Gly Tyr Glu Thr  Asp Met Ile
    1130                 1135                 1140

Glu Ala  Asp Met Glu Leu Glu  Thr Glu Leu Gly Ile  Asp Ser Ile
    1145                 1150                 1155

Lys Arg  Val Glu Ile Leu Ser  Glu Val Gln Ala Met  Leu Asn Val
    1160                 1165                 1170

Glu Ala  Lys Asp Val Asp Ala  Leu Ser Arg Thr Arg  Thr Val Gly
    1175                 1180                 1185

Glu Val  Val Asn Ala Met Lys  Ala Glu Ile Ala Gly  Ser Ser Ala
    1190                 1195                 1200

Pro Ala  Pro Ala Ala Ala Ala  Pro Ala Pro Ala Lys  Ala Ala Pro
    1205                 1210                 1215

Ala Ala  Ala Ala Pro Ala Val  Ser Asn Glu Leu Leu  Glu Lys Ala
    1220                 1225                 1230

Glu Thr  Val Val Met Glu Val  Leu Ala Ala Lys Thr  Gly Tyr Glu
    1235                 1240                 1245

Thr Asp  Met Ile Glu Ser Asp  Met Glu Leu Glu Thr  Glu Leu Gly
    1250                 1255                 1260

Ile Asp  Ser Ile Lys Arg Val  Glu Ile Leu Ser Glu  Val Gln Ala
    1265                 1270                 1275

Met Leu  Asn Val Glu Ala Lys  Asp Val Asp Ala Leu  Ser Arg Thr
    1280                 1285                 1290

Arg Thr  Val Gly Glu Val Val  Asn Ala Met Lys Ala  Glu Ile Ala
    1295                 1300                 1305

Gly Gly  Ser Ala Pro Ala Pro  Ala Ala Ala Ala Pro  Gly Pro Ala
    1310                 1315                 1320

Ala Ala  Ala Pro Ala Pro Ala  Ala Ala Ala Pro Ala  Val Ser Asn
    1325                 1330                 1335

Glu Leu  Leu Glu Lys Ala Glu  Thr Val Val Met Glu  Val Leu Ala
    1340                 1345                 1350

Ala Lys  Thr Gly Tyr Glu Thr  Asp Met Ile Glu Ser  Asp Met Glu
    1355                 1360                 1365

Leu Glu  Thr Glu Leu Gly Ile  Asp Ser Ile Lys Arg  Val Glu Ile
    1370                 1375                 1380
```

```
Leu Ser Glu Val Gln Ala Met Leu Asn Val Glu Ala Lys Asp Val
    1385                1390                1395

Asp Ala Leu Ser Arg Thr Arg Thr Val Gly Glu Val Val Asp Ala
    1400                1405                1410

Met Lys Ala Glu Ile Ala Gly Gly Ser Ala Pro Ala Pro Ala Ala
    1415                1420                1425

Ala Ala Pro Ala Pro Ala Ala Ala Ala Pro Ala Pro Ala Ala Pro
    1430                1435                1440

Ala Pro Ala Val Ser Ser Glu Leu Leu Glu Lys Ala Glu Thr Val
    1445                1450                1455

Val Met Glu Val Leu Ala Ala Lys Thr Gly Tyr Glu Thr Asp Met
    1460                1465                1470

Ile Glu Ser Asp Met Glu Leu Glu Thr Glu Leu Gly Ile Asp Ser
    1475                1480                1485

Ile Lys Arg Val Glu Ile Leu Ser Glu Val Gln Ala Met Leu Asn
    1490                1495                1500

Val Glu Ala Lys Asp Val Asp Ala Leu Ser Arg Thr Arg Thr Val
    1505                1510                1515

Gly Glu Val Val Asp Ala Met Lys Ala Glu Ile Ala Gly Gly Ser
    1520                1525                1530

Ala Pro Ala Pro Ala Ala Ala Ala Pro Ala Pro Ala Ala Ala Ala
    1535                1540                1545

Pro Ala Pro Ala Ala Pro Ala Pro Ala Ala Pro Ala Pro Ala Val
    1550                1555                1560

Ser Ser Glu Leu Leu Glu Lys Ala Glu Thr Val Val Met Glu Val
    1565                1570                1575

Leu Ala Ala Lys Thr Gly Tyr Glu Thr Asp Met Ile Glu Ser Asp
    1580                1585                1590

Met Glu Leu Glu Thr Glu Leu Gly Ile Asp Ser Ile Lys Arg Val
    1595                1600                1605

Glu Ile Leu Ser Glu Val Gln Ala Met Leu Asn Val Glu Ala Lys
    1610                1615                1620

Asp Val Asp Ala Leu Ser Arg Thr Arg Thr Val Gly Glu Val Val
    1625                1630                1635

Asp Ala Met Lys Ala Glu Ile Ala Gly Ser Ser Ala Ser Ala Pro
    1640                1645                1650

Ala Ala Ala Ala Pro Ala Pro Ala Ala Ala Ala Pro Ala Pro Ala
    1655                1660                1665

Ala Ala Ala Pro Ala Val Ser Asn Glu Leu Leu Glu Lys Ala Glu
    1670                1675                1680

Thr Val Val Met Glu Val Leu Ala Ala Lys Thr Gly Tyr Glu Thr
    1685                1690                1695

Asp Met Ile Glu Ser Asp Met Glu Leu Glu Thr Glu Leu Gly Ile
    1700                1705                1710

Asp Ser Ile Lys Arg Val Glu Ile Leu Ser Glu Val Gln Ala Met
    1715                1720                1725

Leu Asn Val Glu Ala Lys Asp Val Asp Ala Leu Ser Arg Thr Arg
    1730                1735                1740

Thr Val Gly Glu Val Val Asp Ala Met Lys Ala Glu Ile Ala Gly
    1745                1750                1755

Gly Ser Ala Pro Ala Pro Ala Ala Ala Ala Pro Ala Pro Ala Ala
    1760                1765                1770
```

-continued

```
Ala Ala  Pro Ala Val Ser Asn  Glu Leu Leu Glu Lys  Ala Glu Thr
    1775                 1780                 1785

Val Val  Met Glu Val Leu Ala  Ala Lys Thr Gly Tyr  Glu Thr Asp
    1790                 1795                 1800

Met Ile  Glu Ser Asp Met Glu  Leu Glu Thr Glu Leu  Gly Ile Asp
    1805                 1810                 1815

Ser Ile  Lys Arg Val Glu Ile  Leu Ser Glu Val Gln  Ala Met Leu
    1820                 1825                 1830

Asn Val  Glu Ala Lys Asp Val  Asp Ala Leu Ser Arg  Thr Arg Thr
    1835                 1840                 1845

Val Gly  Glu Val Val Asp Ala  Met Lys Ala Glu Ile  Ala Gly Ser
    1850                 1855                 1860

Ser Ala  Pro Ala Pro Ala Ala  Ala Ala Pro Ala Pro  Ala Ala Ala
    1865                 1870                 1875

Ala Pro  Ala Pro Ala Ala Ala  Ala Pro Ala Val Ser  Ser Glu Leu
    1880                 1885                 1890

Leu Glu  Lys Ala Glu Thr Val  Val Met Glu Val Leu  Ala Ala Lys
    1895                 1900                 1905

Thr Gly  Tyr Glu Thr Asp Met  Ile Glu Ser Asp Met  Glu Leu Glu
    1910                 1915                 1920

Thr Glu  Leu Gly Ile Asp Ser  Ile Lys Arg Val Glu  Ile Leu Ser
    1925                 1930                 1935

Glu Val  Gln Ala Met Leu Asn  Val Glu Ala Lys Asp  Val Asp Ala
    1940                 1945                 1950

Leu Ser  Arg Thr Arg Thr Val  Gly Glu Val Val Asp  Ala Met Lys
    1955                 1960                 1965

Ala Glu  Ile Ala Gly Gly Ser  Ala Pro Ala Pro Ala  Ala Ala Ala
    1970                 1975                 1980

Pro Ala  Pro Ala Ala Ala Ala  Pro Ala Val Ser Asn  Glu Leu Leu
    1985                 1990                 1995

Glu Lys  Ala Glu Thr Val Val  Met Glu Val Leu Ala  Ala Lys Thr
    2000                 2005                 2010

Gly Tyr  Glu Thr Asp Met Ile  Glu Ser Asp Met Glu  Leu Glu Thr
    2015                 2020                 2025

Glu Leu  Gly Ile Asp Ser Ile  Lys Arg Val Glu Ile  Leu Ser Glu
    2030                 2035                 2040

Val Gln  Ala Met Leu Asn Val  Glu Ala Lys Asp Val  Asp Ala Leu
    2045                 2050                 2055

Ser Arg  Thr Arg Thr Val Gly  Glu Val Val Asp Ala  Met Lys Ala
    2060                 2065                 2070

Glu Ile  Ala Gly Gly Ser Ala  Pro Ala Pro Ala Ala  Ala Ala Pro
    2075                 2080                 2085

Ala Ser  Ala Gly Ala Ala Pro  Ala Val Lys Ile Asp  Ser Val His
    2090                 2095                 2100

Gly Ala  Asp Cys Asp Asp Leu  Ser Leu Met His Ala  Lys Val Val
    2105                 2110                 2115

Asp Ile  Arg Arg Pro Asp Glu  Leu Ile Leu Glu Arg  Pro Glu Asn
    2120                 2125                 2130

Arg Pro  Val Leu Val Val Asp  Asp Gly Ser Glu Leu  Thr Leu Ala
    2135                 2140                 2145

Leu Val  Arg Val Leu Gly Ala  Cys Ala Val Val Leu  Thr Phe Glu
    2150                 2155                 2160

Gly Leu  Gln Leu Ala Gln Arg  Ala Gly Ala Ala Ala  Ile Arg His
```

-continued

```
    2165                2170                2175

Val Leu  Ala Lys Asp Leu Ser  Ala Glu Ser Ala Glu  Lys Ala Ile
    2180                2185                2190

Lys Glu  Ala Glu Gln Arg Phe  Gly Ala Leu Gly Gly  Phe Ile Ser
    2195                2200                2205

Gln Gln  Ala Glu Arg Phe Glu  Pro Ala Glu Ile Leu  Gly Phe Thr
    2210                2215                2220

Leu Met  Cys Ala Lys Phe Ala  Lys Ala Ser Leu Cys  Thr Ala Val
    2225                2230                2235

Ala Gly  Gly Arg Pro Ala Phe  Ile Gly Val Ala Arg  Leu Asp Gly
    2240                2245                2250

Arg Leu  Gly Phe Thr Ser Gln  Gly Thr Ser Asp Ala  Leu Lys Arg
    2255                2260                2265

Ala Gln  Arg Gly Ala Ile Phe  Gly Leu Cys Lys Thr  Ile Gly Leu
    2270                2275                2280

Glu Trp  Ser Glu Ser Asp Val  Phe Ser Arg Gly Val  Asp Ile Ala
    2285                2290                2295

Gln Gly  Met His Pro Glu Asp  Ala Ala Val Ala Ile  Val Arg Glu
    2300                2305                2310

Met Ala  Cys Ala Asp Ile Arg  Ile Arg Glu Val Gly  Ile Gly Ala
    2315                2320                2325

Asn Gln  Gln Arg Cys Thr Ile  Arg Ala Ala Lys Leu  Glu Thr Gly
    2330                2335                2340

Asn Pro  Gln Arg Gln Ile Ala  Lys Asp Asp Val Leu  Leu Val Ser
    2345                2350                2355

Gly Gly  Ala Arg Gly Ile Thr  Pro Leu Cys Ile Arg  Glu Ile Thr
    2360                2365                2370

Arg Gln  Ile Ala Gly Gly Lys  Tyr Ile Leu Leu Gly  Arg Ser Lys
    2375                2380                2385

Val Ser  Ala Ser Glu Pro Ala  Trp Cys Ala Gly Ile  Thr Asp Glu
    2390                2395                2400

Lys Ala  Val Gln Lys Ala Ala  Thr Gln Glu Leu Lys  Arg Ala Phe
    2405                2410                2415

Ser Ala  Gly Glu Gly Pro Lys  Pro Thr Pro Arg Ala  Val Thr Lys
    2420                2425                2430

Leu Val  Gly Ser Val Leu Gly  Ala Arg Glu Val Arg  Ser Ser Ile
    2435                2440                2445

Ala Ala  Ile Glu Ala Leu Gly  Gly Lys Ala Ile Tyr  Ser Ser Cys
    2450                2455                2460

Asp Val  Asn Ser Ala Ala Asp  Val Ala Lys Ala Val  Arg Asp Ala
    2465                2470                2475

Glu Ser  Gln Leu Gly Ala Arg  Val Ser Gly Ile Val  His Ala Ser
    2480                2485                2490

Gly Val  Leu Arg Asp Arg Leu  Ile Glu Lys Lys Leu  Pro Asp Glu
    2495                2500                2505

Phe Asp  Ala Val Phe Gly Thr  Lys Val Thr Gly Leu  Glu Asn Leu
    2510                2515                2520

Leu Ala  Ala Val Asp Arg Ala  Asn Leu Lys His Met  Val Leu Phe
    2525                2530                2535

Ser Ser  Leu Ala Gly Phe His  Gly Asn Val Gly Gln  Ser Asp Tyr
    2540                2545                2550

Ala Met  Ala Asn Glu Ala Leu  Asn Lys Met Gly Leu  Glu Leu Ala
    2555                2560                2565
```

-continued

```
Lys Asp  Val Ser Val Lys Ser  Ile Cys Phe Gly Pro  Trp Asp Gly
    2570                 2575                 2580

Gly Met  Val Thr Pro Gln Leu  Lys Lys Gln Phe Gln  Glu Met Gly
    2585                 2590                 2595

Val Gln  Ile Ile Pro Arg Glu  Gly Gly Ala Asp Thr  Val Ala Arg
    2600                 2605                 2610

Ile Val  Leu Gly Ser Ser Pro  Ala Glu Ile Leu Val  Gly Asn Trp
    2615                 2620                 2625

Arg Thr  Pro Ser Lys Lys Val  Gly Ser Asp Thr Ile  Thr Leu His
    2630                 2635                 2640

Arg Lys  Ile Ser Ala Lys Ser  Asn Pro Phe Leu Glu  Asp His Val
    2645                 2650                 2655

Ile Gln  Gly Arg Arg Val Leu  Pro Met Thr Leu Ala  Ile Gly Ser
    2660                 2665                 2670

Leu Ala  Glu Thr Cys Leu Gly  Leu Phe Pro Gly Tyr  Ser Leu Trp
    2675                 2680                 2685

Ala Ile  Asp Asp Ala Gln Leu  Phe Lys Gly Val Thr  Val Asp Gly
    2690                 2695                 2700

Asp Val  Asn Cys Glu Val Thr  Leu Thr Pro Ser Thr  Ala Pro Ser
    2705                 2710                 2715

Gly Arg  Val Asn Val Gln Ala  Thr Leu Lys Thr Phe  Ser Ser Gly
    2720                 2725                 2730

Lys Leu  Val Pro Ala Tyr Arg  Ala Val Ile Val Leu  Ser Asn Gln
    2735                 2740                 2745

Gly Ala  Pro Pro Ala Asn Ala  Thr Met Gln Pro Pro  Ser Leu Asp
    2750                 2755                 2760

Ala Asp  Pro Ala Leu Gln Gly  Ser Val Tyr Asp Gly  Lys Thr Leu
    2765                 2770                 2775

Phe His  Gly Pro Ala Phe Arg  Gly Ile Asp Asp Val  Leu Ser Cys
    2780                 2785                 2790

Thr Lys  Ser Gln Leu Val Ala  Lys Cys Ser Ala Val  Pro Gly Ser
    2795                 2800                 2805

Asp Ala  Ala Arg Gly Glu Phe  Ala Thr Asp Thr Asp  Ala His Asp
    2810                 2815                 2820

Pro Phe  Val Asn Asp Leu Ala  Phe Gln Ala Met Leu  Val Trp Val
    2825                 2830                 2835

Arg Arg  Thr Leu Gly Gln Ala  Ala Leu Pro Asn Ser  Ile Gln Arg
    2840                 2845                 2850

Ile Val  Gln His Arg Pro Val  Pro Gln Asp Lys Pro  Phe Tyr Ile
    2855                 2860                 2865

Thr Leu  Arg Ser Asn Gln Ser  Gly Gly His Ser Gln  His Lys His
    2870                 2875                 2880

Ala Leu  Gln Phe His Asn Glu  Gln Gly Asp Leu Phe  Ile Asp Val
    2885                 2890                 2895

Gln Ala  Ser Val Ile Ala Thr  Asp Ser Leu Ala Phe
    2900                 2905                 2910

<210> SEQ ID NO 15
<211> LENGTH: 6177
<212> TYPE: DNA
<213> ORGANISM: Schizochytrium sp.

<400> SEQUENCE: 15

atggccgctc ggaatgtgag cgccgcgcat gagatgcacg atgaaaagcg catcgccgtc     60
```

-continued

```
gtcggcatgg ccgtccagta cgccggatgc aaaaccaagg acgagttctg ggaggtgctc    120
atgaacggca aggtcgagtc caaggtgatc agcgacaaac gactcggctc caactaccgc    180
gccgagcact acaaagcaga gcgcagcaag tatgccgaca ccttttgcaa cgaaacgtac    240
ggcacccttg acgagaacga gatcgacaac gagcacgaac tcctcctcaa cctcgccaag    300
caggcactcg cagagacatc cgtcaaagac tcgacacgct gcggcatcgt cagcggctgc    360
ctctcgttcc ccatggacaa cctccagggt gaactcctca acgtgtacca aaaccatgtc    420
gagaaaaagc tcggggcccg cgtcttcaag gacgcctccc attggtccga acgcgagcag    480
tccaacaaac ccgaggccgg tgaccgccgc atcttcatgg acccggcctc cttcgtcgcc    540
gaagaactca acctcggcgc ccttcactac tccgtcgacg cagcatgcgc cacggcgctc    600
tacgtgctcc gcctcgcgca ggatcatctc gtctccggcg ccgccgacgt catgctctgc    660
ggtgccacct gcctgccgga gccctttttc atcctttcgg gcttttccac cttccaggcc    720
atgcccgtcg gcacgggcca gaacgtgtcc atgccgctgc acaaggacag ccagggcctc    780
accccgggtg agggcggctc catcatggtc ctcaagcgtc tcgatgatgc catccgcgac    840
ggcgaccaca tttacggcac ccttctcggc gccaatgtca gcaactccgg cacaggtctg    900
cccctcaagc cccttctccc cagcgagaaa aagtgcctca tggacaccta cacgcgcatt    960
aacgtgcacc cgcacaagat tcagtacgtc gagtgccacg ccaccggcac gccccagggt   1020
gatcgtgtgg aaatcgacgc cgtcaaggcc tgctttgaag gcaaggtccc ccgtttcggt   1080
accacaaagg gcaactttgg acacaccctS gyCgcagccg gctttgccgg tatgtgcaag   1140
gtcctcctct ccatgaagca tggcatcatc ccgcccaccc cgggtatcga tgacgagacc   1200
aagatggacc ctctcgtcgt ctccggtgag gccatcccat ggccagagac caacggcgag   1260
cccaagcgcg ccggtctctc ggcctttggc tttggtggca ccaacgccca tgccgtcttt   1320
gaggagcatg accccctccaa cgccgcctgc acgggccacg actccatttc tgcgctctcg   1380
gcccgctgcg gcggtgaaag caacatgcgc atcgccatca ctggtatgga cgccaccttt   1440
ggcgctctca agggactcga cgccttcgag cgcgccattt acaccggcgc tcacggtgcc   1500
atcccactcc cagaaaagcg ctggcgcttt ctcggcaagg acaaggactt tcttgacctc   1560
tgcggcgtca aggccacccc gcacggctgc tacattgaag atgttgaggt cgacttccag   1620
cgcctccgca cgcccatgac ccctgaagac atgctcctcc ctcagcagct tctggccgtc   1680
accaccattg accgcgccat cctcgactcg ggaatgaaaa agggtggcaa tgtcgccgtc   1740
tttgtcggcc tcggcaccga cctcgagctc taccgtcacc gtgctcgcgt cgctctcaag   1800
gagcgcgtcc gccctgaagc ctccaagaag ctcaatgaca tgatgcagta cattaacgac   1860
tgcggcacat ccacatcgta cacctcgtac attggcaacc tcgtcgccac gcgcgtctcg   1920
tcgcagtggg gcttcacggg cccctccttt acgatcaccg agggcaacaa ctccgtctac   1980
cgctgcgccg agctcggcaa gtacctcctc gagaccggcg aggtcgatgg cgtcgtcgtt   2040
gcgggtgtcg atctctgcgg cagtgccgaa aacctttacg tcaagtctcg ccgcttcaag   2100
gtgtccacct ccgataccccc gcgcgccagc tttgacgccg ccgccgatgg ctactttgtc   2160
ggcgagggct gcggtgcctt tgtgctcaag cgtgagacta gctgcaccaa ggacgaccgt   2220
atctacgctt gcatggatgc catcgtccct ggcaacgtcc ctagcgcctg cttgcgcgag   2280
gccctcgacc aggcgcgcgt caagccgggc gatatcgaga tgctcgagct cagcgccgac   2340
tccgcccgcc acctcaagga cccgtccgtc ctgcccaagg agctcactgc cgaggaggaa   2400
```

-continued

```
atcggcggcc ttcagacgat ccttcgtgac gatgacaagc tcccgcgcaa cgtcgcaacg   2460
ggcagtgtca aggccaccgt cggtgacacc ggttatgcct ctggtgctgc cagcctcatc   2520
aaggctgcgc tttgcatcta caaccgctac ctgcccagca acggcgacga ctgggatgaa   2580
cccgcccctg aggcgccctg ggacagcacc ctctttgcgt gccagacctc gcgcgcttgg   2640
ctcaagaacc ctggcgagcg tcgctatgcg gccgtctcgg gcgtctccga gacgcgctcg   2700
tgctattccg tgctcctctc cgaagccgag ggccactacg agcgcgagaa ccgcatctcg   2760
ctcgacgagg aggcgcccaa gctcattgtg cttcgcgccg actcccacga ggagatcctt   2820
ggtcgcctcg acaagatccg cgagcgcttc ttgcagccca cgggcgccgc cccgcgcgag   2880
tccgagctca aggcgcaggc ccgccgcatc ttcctcgagc tcctcggcga gacccttgcc   2940
caggatgccg cttcttcagg ctcgcaaaag cccctcgctc tcagcctcgt ctccacgccc   3000
tccaagctcc agcgcgaggt cgagctcgcg gccaagggta tcccgcgctg cctcaagatg   3060
cgccgcgatt ggagctcccc tgctggcagc cgctacgcgc ctgagccgct cgccagcgac   3120
cgcgtcgcct tcatgtacgg cgaaggtcgc agcccttact acggcatcac ccaagacatt   3180
caccgcattt ggcccgaact ccacgaggtc atcaacgaaa agacgaaccg tctctgggcc   3240
gaaggcgacc gctgggtcat gccgcgcgcc agcttcaagt cggagctcga gagccagcag   3300
caagagtttg atcgcaacat gattgaaatg ttccgtcttg gaatcctcac ctcaattgcc   3360
ttcaccaatc tggcgcgcga cgttctcaac atcacgccca aggccgcctt tggcctcagt   3420
cttggcgaga tttccatgat ttttgccttt tccaagaaga acggtctcat ctccgaccag   3480
ctcaccaagg atcttcgcga gtccgacgtg tggaacaagg ctctggccgt tgaatttaat   3540
gcgctgcgcg aggcctgggg cattccacag agtgtcccca aggacgagtt ctggcaaggc   3600
tacattgtgc gcggcaccaa gcaggatatc gaggcggcca tcgccccgga cagcaagtac   3660
gtgcgcctca ccatcatcaa tgatgccaac accgccctca ttagcggcaa gcccgacgcc   3720
tgcaaggctg cgatcgcgcg tctcggtggc aacattcctg cgcttcccgt gacccagggc   3780
atgtgcggcc actgccccga ggtgggacct tataccaagg atatcgccaa gatccatgcc   3840
aaccttgagt tccccgttgt cgacggcctt gacctctgga ccacaatcaa ccagaagcgc   3900
ctcgtgccac gcgccacggg cgccaaggac gaatgggccc cttcttcctt tggcgagtac   3960
gccggccagc tctacgagaa gcaggctaac ttcccccaaa tcgtcgagac catttacaag   4020
caaaactacg acgtctttgt cgaggttggg cccaacaacc accgtagcac cgcagtgcgc   4080
accacgcttg gtccccagcg caaccacctt gctggcgcca tcgacaagca gaacgaggat   4140
gcttggacga ccatcgtcaa gcttgtggct tcgctcaagg cccaccttgt tcctggcgtc   4200
acgatctcgc cgctgtacca ctccaagctt gtggcggagg ctcaggcttg ctacgctgcg   4260
ctctgcaagg gtgaaaagcc caagaagaac aagtttgtgc gcaagattca gctcaacggt   4320
cgcttcaaca gcaaggcgga ccccatctcc tcggccgatc ttgccagctt tccgcctgcg   4380
gaccctgcca ttgaagccgc catctcgagc cgcatcatga agcctgtcgc tcccaagttc   4440
tacgcgcgtc tcaacattga cgagcaggac gagacccgag atccgatcct caacaaggac   4500
aacgcgccgt cttcttcttc ttcttcttct tcttcttctt cttcttcttc ttctccgtcg   4560
cctgctcctt cggcccccgt gcaaaagaag gctgctcccg ccgcggagac caaggctgtt   4620
gcttcggctg acgcacttcg cagtgccctg ctcgatctcg acagtatgct tgcgctgagc   4680
tctgccagtg cctccggcaa ccttgttgag actgcgccta gcgacgcctc ggtcattgtg   4740
ccgccctgca acattgcgga tctcggcagc cgcgccttca tgaaaacgta cggtgtttcg   4800
```

```
gcgcctctgt acacgggcgc catggccaag ggcattgcct ctgcggacct cgtcattgcc   4860

gccggccgcc agggcatcct tgcgtccttt ggcgccggcg gacttcccat gcaggttgtg   4920

cgtgagtcca tcgaaaagat tcaggccgcc ctgcccaatg gcccgtacgc tgtcaacctt   4980

atccattctc cctttgacag caacctcgaa aagggcaatg tcgatctctt cctcgagaag   5040

ggtgtcacct ttgtcgaggc ctcggccttt atgacgctca ccccgcaggt cgtgcggtac   5100

cgcgcggctg gcctcacgcg caacgccgac ggctcggtca acatccgcaa ccgtatcatt   5160

ggcaaggtct cgcgcaccga gctcgccgag atgttcatgc gtcctgcgcc cgagcacctt   5220

cttcagaagc tcattgcttc cggcgagatc aaccaggagc aggccgagct cgcccgccgt   5280

gttcccgtcg ctgacgacat cgcggtcgaa gctgactcgg gtggccacac cgacaaccgc   5340

cccatccacg tcattctgcc cctcatcatc aaccttcgcg accgccttca ccgcgagtgc   5400

ggctacccgg ccaaccttcg cgtccgtgtg ggcgccggcg gtggcattgg gtgcccccag   5460

gcggcgctgg ccaccttcaa catgggtgcc tcctttattg tcaccggcac cgtgaaccag   5520

gtcgccaagc agtcgggcac gtgcgacaat gtgcgcaagc agctcgcgaa ggccacttac   5580

tcggacgtat gcatggcccc ggctgccgac atgttcgagg aaggcgtcaa gcttcaggtc   5640

ctcaagaagg gaaccatgtt tccctcgcgc gccaacaagc tctacgagct cttttgcaag   5700

tacgactcgt tcgagtccat gccccccgca gagcttgcgc gcgtcgagaa gcgcatcttc   5760

agccgcgcgc tcgaagaggt ctgggacgag accaaaaact tttacattaa ccgtcttcac   5820

aacccggaga agatccagcg cgccgagcgc gaccccaagc tcaagatgtc gctgtgcttt   5880

cgctggtacc tgagcctggc gagccgctgg gccaacactg gagcttccga tcgcgtcatg   5940

gactaccagg tctggtgcgg tcctgccatt ggttccttca acgatttcat caagggaact   6000

taccttgatc cggccgtcgc aaacgagtac ccgtgcgtcg ttcagattaa caagcagatc   6060

cttcgtggag cgtgcttctt gcgccgtctc gaaattctgc gcaacgcacg cctttccgat   6120

ggcgctgccg ctcttgtggc cagcatcgat gacacatacg tcccggccga gaagctg      6177
```

<210> SEQ ID NO 16
<211> LENGTH: 2059
<212> TYPE: PRT
<213> ORGANISM: Schizochytrium sp.
<220> FEATURE:
<221> NAME/KEY: misc_feature
<222> LOCATION: (1)..(2059)
<223> OTHER INFORMATION: Xaa = Ala or Val

<400> SEQUENCE: 16

```
Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110
```

-continued

```
Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Leu Xaa Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys Thr Gly His Asp Ser Ile Ser Ala Leu Ser Ala Arg Cys Gly
    450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
            500                 505                 510

Lys Asp Lys Asp Phe Leu Asp Leu Cys Gly Val Lys Ala Thr Pro His
        515                 520                 525
```

-continued

```
Gly Cys Tyr Ile Glu Asp Val Glu Val Asp Phe Gln Arg Leu Arg Thr
    530                 535                 540

Pro Met Thr Pro Glu Asp Met Leu Leu Pro Gln Gln Leu Leu Ala Val
545                 550                 555                 560

Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
            580                 585                 590

His Arg Ala Arg Val Ala Leu Lys Glu Arg Val Arg Pro Glu Ala Ser
        595                 600                 605

Lys Lys Leu Asn Asp Met Met Gln Tyr Ile Asn Asp Cys Gly Thr Ser
    610                 615                 620

Thr Ser Tyr Thr Ser Tyr Ile Gly Asn Leu Val Ala Thr Arg Val Ser
625                 630                 635                 640

Ser Gln Trp Gly Phe Thr Gly Pro Ser Phe Thr Ile Thr Glu Gly Asn
                645                 650                 655

Asn Ser Val Tyr Arg Cys Ala Glu Leu Gly Lys Tyr Leu Leu Glu Thr
            660                 665                 670

Gly Glu Val Asp Gly Val Val Val Ala Gly Val Asp Leu Cys Gly Ser
        675                 680                 685

Ala Glu Asn Leu Tyr Val Lys Ser Arg Arg Phe Lys Val Ser Thr Ser
    690                 695                 700

Asp Thr Pro Arg Ala Ser Phe Asp Ala Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
            740                 745                 750

Val Pro Ser Ala Cys Leu Arg Glu Ala Leu Asp Gln Ala Arg Val Lys
        755                 760                 765

Pro Gly Asp Ile Glu Met Leu Glu Leu Ser Ala Asp Ser Ala Arg His
    770                 775                 780

Leu Lys Asp Pro Ser Val Leu Pro Lys Glu Leu Thr Ala Glu Glu Glu
785                 790                 795                 800

Ile Gly Gly Leu Gln Thr Ile Leu Arg Asp Asp Asp Lys Leu Pro Arg
                805                 810                 815

Asn Val Ala Thr Gly Ser Val Lys Ala Thr Val Gly Asp Thr Gly Tyr
            820                 825                 830

Ala Ser Gly Ala Ala Ser Leu Ile Lys Ala Ala Leu Cys Ile Tyr Asn
        835                 840                 845

Arg Tyr Leu Pro Ser Asn Gly Asp Asp Trp Asp Glu Pro Ala Pro Glu
    850                 855                 860

Ala Pro Trp Asp Ser Thr Leu Phe Ala Cys Gln Thr Ser Arg Ala Trp
865                 870                 875                 880

Leu Lys Asn Pro Gly Glu Arg Arg Tyr Ala Ala Val Ser Gly Val Ser
                885                 890                 895

Glu Thr Arg Ser Cys Tyr Ser Val Leu Leu Ser Glu Ala Glu Gly His
            900                 905                 910

Tyr Glu Arg Glu Asn Arg Ile Ser Leu Asp Glu Glu Ala Pro Lys Leu
        915                 920                 925

Ile Val Leu Arg Ala Asp Ser His Glu Glu Ile Leu Gly Arg Leu Asp
    930                 935                 940

Lys Ile Arg Glu Arg Phe Leu Gln Pro Thr Gly Ala Ala Pro Arg Glu
```

-continued

```
945                 950                 955                 960

Ser Glu Leu Lys Ala Gln Ala Arg Arg Ile Phe Leu Glu Leu Leu Gly
                965                 970                 975

Glu Thr Leu Ala Gln Asp Ala Ala Ser Ser Gly Ser Gln Lys Pro Leu
            980                 985                 990

Ala Leu Ser Leu Val Ser Thr Pro  Ser Lys Leu Gln Arg  Glu Val Glu
        995                 1000                1005

Leu Ala  Ala Lys Gly Ile Pro  Arg Cys Leu Lys Met  Arg Arg Asp
    1010                 1015                1020

Trp Ser  Ser Pro Ala Gly Ser  Arg Tyr Ala Pro Glu  Pro Leu Ala
    1025                 1030                1035

Ser Asp  Arg Val Ala Phe Met  Tyr Gly Glu Gly Arg  Ser Pro Tyr
    1040                 1045                1050

Tyr Gly  Ile Thr Gln Asp Ile  His Arg Ile Trp Pro  Glu Leu His
    1055                 1060                1065

Glu Val  Ile Asn Glu Lys Thr  Asn Arg Leu Trp Ala  Glu Gly Asp
    1070                 1075                1080

Arg Trp  Val Met Pro Arg Ala  Ser Phe Lys Ser Glu  Leu Glu Ser
    1085                 1090                1095

Gln Gln  Gln Glu Phe Asp Arg  Asn Met Ile Glu Met  Phe Arg Leu
    1100                 1105                1110

Gly Ile  Leu Thr Ser Ile Ala  Phe Thr Asn Leu Ala  Arg Asp Val
    1115                 1120                1125

Leu Asn  Ile Thr Pro Lys Ala  Ala Phe Gly Leu Ser  Leu Gly Glu
    1130                 1135                1140

Ile Ser  Met Ile Phe Ala Phe  Ser Lys Lys Asn Gly  Leu Ile Ser
    1145                 1150                1155

Asp Gln  Leu Thr Lys Asp Leu  Arg Glu Ser Asp Val  Trp Asn Lys
    1160                 1165                1170

Ala Leu  Ala Val Glu Phe Asn  Ala Leu Arg Glu Ala  Trp Gly Ile
    1175                 1180                1185

Pro Gln  Ser Val Pro Lys Asp  Glu Phe Trp Gln Gly  Tyr Ile Val
    1190                 1195                1200

Arg Gly  Thr Lys Gln Asp Ile  Glu Ala Ala Ile Ala  Pro Asp Ser
    1205                 1210                1215

Lys Tyr  Val Arg Leu Thr Ile  Ile Asn Asp Ala Asn  Thr Ala Leu
    1220                 1225                1230

Ile Ser  Gly Lys Pro Asp Ala  Cys Lys Ala Ala Ile  Ala Arg Leu
    1235                 1240                1245

Gly Gly  Asn Ile Pro Ala Leu  Pro Val Thr Gln Gly  Met Cys Gly
    1250                 1255                1260

His Cys  Pro Glu Val Gly Pro  Tyr Thr Lys Asp Ile  Ala Lys Ile
    1265                 1270                1275

His Ala  Asn Leu Glu Phe Pro  Val Val Asp Gly Leu  Asp Leu Trp
    1280                 1285                1290

Thr Thr  Ile Asn Gln Lys Arg  Leu Val Pro Arg Ala  Thr Gly Ala
    1295                 1300                1305

Lys Asp  Glu Trp Ala Pro Ser  Ser Phe Gly Glu Tyr  Ala Gly Gln
    1310                 1315                1320

Leu Tyr  Glu Lys Gln Ala Asn  Phe Pro Gln Ile Val  Glu Thr Ile
    1325                 1330                1335

Tyr Lys  Gln Asn Tyr Asp Val  Phe Val Glu Val Gly  Pro Asn Asn
    1340                 1345                1350
```

-continued

```
His Arg  Ser Thr Ala Val Arg  Thr Thr Leu Gly Pro  Gln Arg Asn
    1355                 1360                 1365

His Leu  Ala Gly Ala Ile Asp  Lys Gln Asn Glu Asp  Ala Trp Thr
    1370                 1375                 1380

Thr Ile  Val Lys Leu Val Ala  Ser Leu Lys Ala His  Leu Val Pro
    1385                 1390                 1395

Gly Val  Thr Ile Ser Pro Leu  Tyr His Ser Lys Leu  Val Ala Glu
    1400                 1405                 1410

Ala Gln  Ala Cys Tyr Ala Ala  Leu Cys Lys Gly Glu  Lys Pro Lys
    1415                 1420                 1425

Lys Asn  Lys Phe Val Arg Lys  Ile Gln Leu Asn Gly  Arg Phe Asn
    1430                 1435                 1440

Ser Lys  Ala Asp Pro Ile Ser  Ser Ala Asp Leu Ala  Ser Phe Pro
    1445                 1450                 1455

Pro Ala  Asp Pro Ala Ile Glu  Ala Ala Ile Ser Ser  Arg Ile Met
    1460                 1465                 1470

Lys Pro  Val Ala Pro Lys Phe  Tyr Ala Arg Leu Asn  Ile Asp Glu
    1475                 1480                 1485

Gln Asp  Glu Thr Arg Asp Pro  Ile Leu Asn Lys Asp  Asn Ala Pro
    1490                 1495                 1500

Ser Ser  Ser Ser Ser Ser Ser  Ser Ser Ser Ser Ser  Ser Ser Ser
    1505                 1510                 1515

Pro Ser  Pro Ala Pro Ser Ala  Pro Val Gln Lys Lys  Ala Ala Pro
    1520                 1525                 1530

Ala Ala  Glu Thr Lys Ala Val  Ala Ser Ala Asp Ala  Leu Arg Ser
    1535                 1540                 1545

Ala Leu  Leu Asp Leu Asp Ser  Met Leu Ala Leu Ser  Ser Ala Ser
    1550                 1555                 1560

Ala Ser  Gly Asn Leu Val Glu  Thr Ala Pro Ser Asp  Ala Ser Val
    1565                 1570                 1575

Ile Val  Pro Pro Cys Asn Ile  Ala Asp Leu Gly Ser  Arg Ala Phe
    1580                 1585                 1590

Met Lys  Thr Tyr Gly Val Ser  Ala Pro Leu Tyr Thr  Gly Ala Met
    1595                 1600                 1605

Ala Lys  Gly Ile Ala Ser Ala  Asp Leu Val Ile Ala  Ala Gly Arg
    1610                 1615                 1620

Gln Gly  Ile Leu Ala Ser Phe  Gly Ala Gly Gly Leu  Pro Met Gln
    1625                 1630                 1635

Val Val  Arg Glu Ser Ile Glu  Lys Ile Gln Ala Ala  Leu Pro Asn
    1640                 1645                 1650

Gly Pro  Tyr Ala Val Asn Leu  Ile His Ser Pro Phe  Asp Ser Asn
    1655                 1660                 1665

Leu Glu  Lys Gly Asn Val Asp  Leu Phe Leu Glu Lys  Gly Val Thr
    1670                 1675                 1680

Phe Val  Glu Ala Ser Ala Phe  Met Thr Leu Thr Pro  Gln Val Val
    1685                 1690                 1695

Arg Tyr  Arg Ala Ala Gly Leu  Thr Arg Asn Ala Asp  Gly Ser Val
    1700                 1705                 1710

Asn Ile  Arg Asn Arg Ile Ile  Gly Lys Val Ser Arg  Thr Glu Leu
    1715                 1720                 1725

Ala Glu  Met Phe Met Arg Pro  Ala Pro Glu His Leu  Leu Gln Lys
    1730                 1735                 1740
```

-continued

```
Leu Ile  Ala Ser Gly Glu Ile  Asn Gln Glu Gln Ala  Glu Leu Ala
    1745                 1750                 1755

Arg Arg  Val Pro Val Ala Asp  Asp Ile Ala Val Glu  Ala Asp Ser
    1760                 1765                 1770

Gly Gly  His Thr Asp Asn Arg  Pro Ile His Val Ile  Leu Pro Leu
    1775                 1780                 1785

Ile Ile  Asn Leu Arg Asp Arg  Leu His Arg Glu Cys  Gly Tyr Pro
    1790                 1795                 1800

Ala Asn  Leu Arg Val Arg Val  Gly Ala Gly Gly Gly  Ile Gly Cys
    1805                 1810                 1815

Pro Gln  Ala Ala Leu Ala Thr  Phe Asn Met Gly Ala  Ser Phe Ile
    1820                 1825                 1830

Val Thr  Gly Thr Val Asn Gln  Val Ala Lys Gln Ser  Gly Thr Cys
    1835                 1840                 1845

Asp Asn  Val Arg Lys Gln Leu  Ala Lys Ala Thr Tyr  Ser Asp Val
    1850                 1855                 1860

Cys Met  Ala Pro Ala Ala Asp  Met Phe Glu Glu Gly  Val Lys Leu
    1865                 1870                 1875

Gln Val  Leu Lys Lys Gly Thr  Met Phe Pro Ser Arg  Ala Asn Lys
    1880                 1885                 1890

Leu Tyr  Glu Leu Phe Cys Lys  Tyr Asp Ser Phe Glu  Ser Met Pro
    1895                 1900                 1905

Pro Ala  Glu Leu Ala Arg Val  Glu Lys Arg Ile Phe  Ser Arg Ala
    1910                 1915                 1920

Leu Glu  Glu Val Trp Asp Glu  Thr Lys Asn Phe Tyr  Ile Asn Arg
    1925                 1930                 1935

Leu His  Asn Pro Glu Lys Ile  Gln Arg Ala Glu Arg  Asp Pro Lys
    1940                 1945                 1950

Leu Lys  Met Ser Leu Cys Phe  Arg Trp Tyr Leu Ser  Leu Ala Ser
    1955                 1960                 1965

Arg Trp  Ala Asn Thr Gly Ala  Ser Asp Arg Val Met  Asp Tyr Gln
    1970                 1975                 1980

Val Trp  Cys Gly Pro Ala Ile  Gly Ser Phe Asn Asp  Phe Ile Lys
    1985                 1990                 1995

Gly Thr  Tyr Leu Asp Pro Ala  Val Ala Asn Glu Tyr  Pro Cys Val
    2000                 2005                 2010

Val Gln  Ile Asn Lys Gln Ile  Leu Arg Gly Ala Cys  Phe Leu Arg
    2015                 2020                 2025

Arg Leu  Glu Ile Leu Arg Asn  Ala Arg Leu Ser Asp  Gly Ala Ala
    2030                 2035                 2040

Ala Leu  Val Ala Ser Ile Asp  Asp Thr Tyr Val Pro  Ala Glu Lys
    2045                 2050                 2055

Leu

<210> SEQ ID NO 17
<211> LENGTH: 4509
<212> TYPE: DNA
<213> ORGANISM: Schizochytrium sp.

<400> SEQUENCE: 17

atggcgctcc gtgtcaagac gaacaagaag ccatgctggg agatgaccaa ggaggagctg      60

accagcggca agaccgaggt gttcaactat gaggaactcc tcgagttcgc agagggcgac     120

atcgccaagg tcttcggacc cgagttcgcc gtcatcgaca agtacccgcg ccgcgtgcgc     180
```

-continued

```
ctgcccgccc gcgagtacct gctcgtgacc cgcgtcaccc tcatggacgc cgaggtcaac    240

aactaccgcg tcggcgcccg catggtcacc gagtacgatc tccccgtcaa cggagagctc    300

tccgagggcg gagactgccc ctgggccgtc ctggtcgaga gtggccagtg cgatctcatg    360

ctcatctcct acatgggcat tgacttccag aaccagggcg accgcgtcta ccgcctgctc    420

aacaccacgc tcacctttta cggcgtggcc cacgagggcg agaccctcga gtacgacatt    480

cgcgtcaccg gcttcgccaa gcgtctcgac ggcggcatct ccatgttctt cttcgagtac    540

gactgctacg tcaacggccg cctcctcatc gagatgcgcg atggctgcgc cggcttcttc    600

accaacgagg agctcgacgc cggcaagggc gtcgtcttca cccgcggcga cctcgccgcc    660

cgcgccaaga tcccaaagca ggacgtctcc ccctacgccg tcgccccctg cctccacaag    720

accaagctca acgaaaagga gatgcagacc ctcgtcgaca aggactgggc atccgtcttt    780

ggctccaaga acggcatgcc ggaaatcaac tacaaactct gcgcgcgtaa gatgctcatg    840

attgaccgcg tcaccagcat tgaccacaag ggcggtgtct acggcctcgg tcagctcgtc    900

ggtgaaaaga tcctcgagcg cgaccactgg tactttccct gccactttgt caaggatcag    960

gtcatggccg gatccctcgt ctccgacggc tgcagccaga tgctcaagat gtacatgatc   1020

tggctcggcc tccacctcac caccggaccc tttgacttcc gcccggtcaa cggccacccc   1080

aacaaggtcc gctgccgcgg ccaaatctcc ccgcacaagg gcaagctcgt ctacgtcatg   1140

gagatcaagg agatgggctt cgacgaggac aacgacccgt acgccattgc cgacgtcaac   1200

atcattgatg tcgacttcga aaagggccag gactttagcc tcgaccgcat cagcgactac   1260

ggcaagggcg acctcaacaa gaagatcgtc gtcgacttta agggcatcgc tctcaagatg   1320

cagaagcgct ccaccaacaa gaacccctcc aaggttcagc ccgtctttgc caacggcgcc   1380

gccactgtcg gccccgaggc ctccaaggct tcctccggcg ccagcgccag cgccagcgcc   1440

gccccggcca agcctgcctt cagcgccgat gttcttgcgc ccaagcccgt tgcccttccc   1500

gagcacatcc tcaagggcga cgccctcgcc cccaaggaga tgtcctggca ccccatggcc   1560

cgcatcccgg gcaacccgac gccctctttt gcgccctcgg cctacaagcc gcgcaacatc   1620

gcctttacgc ccttccccgg caaccccaac gataacgacc acaccccggg caagatgccg   1680

ctcacctggt tcaacatggc cgagttcatg gccggcaagg tcagcatgtg cctcggcccc   1740

gagttcgcca agttcgacga ctcgaacacc agccgcagcc ccgcttggga cctcgctctc   1800

gtcacccgcg ccgtgtctgt gtctgacctc aagcacgtca actaccgcaa catcgacctc   1860

gacccctcca agggtaccat ggtcggcgag ttcgactgcc ccgcggacgc ctggttctac   1920

aagggcgcct gcaacgatgc ccacatgccg tactcgatcc tcatggagat cgccctccag   1980

acctcgggtg tgctcacctc ggtgctcaag gcgcccctga ccatggagaa ggacgacatc   2040

ctcttccgca acctcgacgc caacgccgag ttcgtgcgcg ccgacctcga ctaccgcggc   2100

aagactatcc gcaacgtcac caagtgcact ggctacagca tgctcggcga gatgggcgtc   2160

caccgcttca cctttgagct ctacgtcgat gatgtgctct tttacaaggg ctcgacctcg   2220

ttcggctggt tcgtgcccga ggtctttgcc gcccaggccg gcctcgacaa cggccgcaag   2280

tcggagccct ggttcattga gaacaaggtt ccggcctcgc aggtctcctc ctttgacgtg   2340

cgccccaacg gcagcggccg caccgccatc ttcgccaacg cccccagcgg cgcccagctc   2400

aaccgccgca cggaccaggg ccagtacctc gacgccgtcg acattgtctc cggcagcggc   2460

aagaagagcc tcggctacgc ccacggttcc aagacggtca acccgaacga ctggttcttc   2520

tcgtgccact tttggtttga ctcggtcatg cccggaagtc tcggtgtcga gtccatgttc   2580
```

```
cagctcgtcg aggccatcgc cgcccacgag gatctcgctg gcaaagcacg gcattgccaa   2640

ccccaccttt gtgcacgccc ccgggcaaga tcaagctgga agtaccgcgg ccagctcacg   2700

cccaagagca agaagatgga ctcggaggtc cacatcgtgt ccgtggacgc ccacgacggc   2760

gttgtcgacc tcgtcgccga cggcttcctc tgggccgaca gcctccgcgt ctactcggtg   2820

agcaacattc gcgtgcgcat cgcctccggt gaggcccctg ccgccgcctc ctccgccgcc   2880

tctgtgggct cctcggcttc gtccgtcgag cgcacgcgct cgagccccgc tgtcgcctcc   2940

ggcccggccc agaccatcga cctcaagcag ctcaagaccg agctcctcga gctcgatgcc   3000

ccgctctacc tctcgcagga cccgaccagc ggccagctca agaagcacac cgacgtggcc   3060

tccggccagg ccaccatcgt gcagccctgc acgctcggcg acctcggtga ccgctccttc   3120

atggagacct acggcgtcgt cgccccgctg tacacgggcg ccatggccaa gggcattgcc   3180

tcggcggacc tcgtcatcgc cgccggcaag cgcaagatcc tcggctcctt tggcgccggc   3240

ggcctcccca tgcaccacgt gcgcgccgcc ctcgagaaga tccaggccgc cctgcctcag   3300

ggcccctacg ccgtcaacct catccactcg ccttttgaca gcaacctcga gaagggcaac   3360

gtcgatctct tcctcgagaa gggcgtcact gtggtggagg cctcggcatt catgaccctc   3420

accccgcagg tcgtgcgcta ccgcgccgcc ggcctctcgc gcaacgccga cggttcggtc   3480

aacatccgca accgcatcat cggcaaggtc tcgcgcaccg agctcgccga gatgttcatc   3540

cgcccggccc cggagcacct cctcgagaag ctcatcgcct cgggcgagat cacccaggag   3600

caggccgagc tcgcgcgccg cgttcccgtc gccgacgata tcgctgtcga ggctgactcg   3660

ggcggccaca ccgacaaccg ccccatccac gtcatcctcc cgctcatcat caacctccgc   3720

aaccgcctgc accgcgagtg cggctacccc gcgcacctcc gcgtccgcgt tggcgccggc   3780

ggtggcgtcg gctgcccgca ggccgccgcc gccgcgctca ccatgggcgc cgccttcatc   3840

gtcaccggca ctgtcaacca ggtcgccaag cagtccggca cctgcgacaa cgtgcgcaag   3900

cagctctcgc aggccaccta ctcggatatc tgcatggccc cggccgccga catgttcgag   3960

gagggcgtca agctccaggt cctcaagaag ggaaccatgt tcccctcgcg cgccaacaag   4020

ctctacgagc tcttttgcaa gtacgactcc ttcgactcca tgcctcctgc cgagctcgag   4080

cgcatcgaga agcgtatctt caagcgcgca ctccaggagg tctgggagga gaccaaggac   4140

ttttacatta acggtctcaa gaacccggag aagatccagc gcgccgagca cgaccccaag   4200

ctcaagatgt cgctctgctt ccgctggtac cttggtcttg ccagccgctg ggccaacatg   4260

ggcgccccgg accgcgtcat ggactaccag gtctggtgtg gcccggccat tggcgccttc   4320

aacgacttca tcaagggcac ctacctcgac cccgctgtct ccaacgagta cccctgtgtc   4380

gtccagatca acctgcaaat cctccgtggt gcctgctacc tgcgccgtct caacgccctg   4440

cgcaacgacc cgcgcattga cctcgagacc gaggatgctg cctttgtcta cgagcccacc   4500

aacgcgctc                                                           4509
```

<210> SEQ ID NO 18
<211> LENGTH: 1503
<212> TYPE: PRT
<213> ORGANISM: Schizochytrium sp.

<400> SEQUENCE: 18

```
Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
```

-continued

```
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile
    210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
            260                 265                 270

Leu Cys Ala Arg Lys Met Leu Met Ile Asp Arg Val Thr Ser Ile Asp
        275                 280                 285

His Lys Gly Gly Val Tyr Gly Leu Gly Gln Leu Val Gly Glu Lys Ile
    290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335

Met Tyr Met Ile Trp Leu Gly Leu His Leu Thr Thr Gly Pro Phe Asp
            340                 345                 350

Phe Arg Pro Val Asn Gly His Pro Asn Lys Val Arg Cys Arg Gly Gln
        355                 360                 365

Ile Ser Pro His Lys Gly Lys Leu Val Tyr Val Met Glu Ile Lys Glu
    370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415

Ile Ser Asp Tyr Gly Lys Gly Asp Leu Asn Lys Lys Ile Val Val Asp
            420                 425                 430

Phe Lys Gly Ile Ala Leu Lys Met Gln Lys Arg Ser Thr Asn Lys Asn
        435                 440                 445
```

```
Pro Ser Lys Val Gln Pro Val Phe Ala Asn Gly Ala Ala Thr Val Gly
    450                 455                 460

Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
                485                 490                 495

Val Ala Leu Pro Glu His Ile Leu Lys Gly Asp Ala Leu Ala Pro Lys
            500                 505                 510

Glu Met Ser Trp His Pro Met Ala Arg Ile Pro Gly Asn Pro Thr Pro
        515                 520                 525

Ser Phe Ala Pro Ser Ala Tyr Lys Pro Arg Asn Ile Ala Phe Thr Pro
    530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
            580                 585                 590

Ser Pro Ala Trp Asp Leu Ala Leu Val Thr Arg Ala Val Ser Val Ser
        595                 600                 605

Asp Leu Lys His Val Asn Tyr Arg Asn Ile Asp Leu Asp Pro Ser Lys
    610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
            660                 665                 670

Leu Thr Met Glu Lys Asp Asp Ile Leu Phe Arg Asn Leu Asp Ala Asn
        675                 680                 685

Ala Glu Phe Val Arg Ala Asp Leu Asp Tyr Arg Gly Lys Thr Ile Arg
    690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
                725                 730                 735

Gly Ser Thr Ser Phe Gly Trp Phe Val Pro Glu Val Phe Ala Ala Gln
            740                 745                 750

Ala Gly Leu Asp Asn Gly Arg Lys Ser Glu Pro Trp Phe Ile Glu Asn
        755                 760                 765

Lys Val Pro Ala Ser Gln Val Ser Ser Phe Asp Val Arg Pro Asn Gly
    770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
            820                 825                 830

Val Asn Pro Asn Asp Trp Phe Phe Ser Cys His Phe Trp Phe Asp Ser
        835                 840                 845

Val Met Pro Gly Ser Leu Gly Val Glu Ser Met Phe Gln Leu Val Glu
    850                 855                 860
```

-continued

```
Ala Ile Ala Ala His Glu Asp Leu Ala Gly Lys Ala Arg His Cys Gln
865                 870                 875                 880

Pro His Leu Cys Ala Arg Pro Arg Ala Arg Ser Ser Trp Lys Tyr Arg
                885                 890                 895

Gly Gln Leu Thr Pro Lys Ser Lys Lys Met Asp Ser Glu Val His Ile
            900                 905                 910

Val Ser Val Asp Ala His Asp Gly Val Val Asp Leu Val Ala Asp Gly
        915                 920                 925

Phe Leu Trp Ala Asp Ser Leu Arg Val Tyr Ser Val Ser Asn Ile Arg
    930                 935                 940

Val Arg Ile Ala Ser Gly Glu Ala Pro Ala Ala Ala Ser Ser Ala Ala
945                 950                 955                 960

Ser Val Gly Ser Ser Ala Ser Ser Val Glu Arg Thr Arg Ser Ser Pro
                965                 970                 975

Ala Val Ala Ser Gly Pro Ala Gln Thr Ile Asp Leu Lys Gln Leu Lys
            980                 985                 990

Thr Glu Leu Leu Glu Leu Asp Ala  Pro Leu Tyr Leu Ser  Gln Asp Pro
        995                 1000                1005

Thr Ser  Gly Gln Leu Lys Lys  His Thr Asp Val Ala  Ser Gly Gln
    1010                1015                1020

Ala Thr  Ile Val Gln Pro Cys  Thr Leu Gly Asp Leu  Gly Asp Arg
    1025                1030                1035

Ser Phe  Met Glu Thr Tyr Gly  Val Val Ala Pro Leu  Tyr Thr Gly
    1040                1045                1050

Ala Met  Ala Lys Gly Ile Ala  Ser Ala Asp Leu Val  Ile Ala Ala
    1055                1060                1065

Gly Lys  Arg Lys Ile Leu Gly  Ser Phe Gly Ala Gly  Gly Leu Pro
    1070                1075                1080

Met His  His Val Arg Ala Ala  Leu Glu Lys Ile Gln  Ala Ala Leu
    1085                1090                1095

Pro Gln  Gly Pro Tyr Ala Val  Asn Leu Ile His Ser  Pro Phe Asp
    1100                1105                1110

Ser Asn  Leu Glu Lys Gly Asn  Val Asp Leu Phe Leu  Glu Lys Gly
    1115                1120                1125

Val Thr  Val Val Glu Ala Ser  Ala Phe Met Thr Leu  Thr Pro Gln
    1130                1135                1140

Val Val  Arg Tyr Arg Ala Ala  Gly Leu Ser Arg Asn  Ala Asp Gly
    1145                1150                1155

Ser Val  Asn Ile Arg Asn Arg  Ile Ile Gly Lys Val  Ser Arg Thr
    1160                1165                1170

Glu Leu  Ala Glu Met Phe Ile  Arg Pro Ala Pro Glu  His Leu Leu
    1175                1180                1185

Glu Lys  Leu Ile Ala Ser Gly  Glu Ile Thr Gln Glu  Gln Ala Glu
    1190                1195                1200

Leu Ala  Arg Arg Val Pro Val  Ala Asp Asp Ile Ala  Val Glu Ala
    1205                1210                1215

Asp Ser  Gly Gly His Thr Asp  Asn Arg Pro Ile His  Val Ile Leu
    1220                1225                1230

Pro Leu  Ile Ile Asn Leu Arg  Asn Arg Leu His Arg  Glu Cys Gly
    1235                1240                1245

Tyr Pro  Ala His Leu Arg Val  Arg Val Gly Ala Gly  Gly Gly Val
    1250                1255                1260

Gly Cys  Pro Gln Ala Ala Ala  Ala Ala Leu Thr Met  Gly Ala Ala
```

```
    1265                1270                1275

Phe Ile  Val Thr Gly Thr Val  Asn Gln Val Ala Lys  Gln Ser Gly
    1280                1285                1290

Thr Cys  Asp Asn Val Arg Lys  Gln Leu Ser Gln Ala  Thr Tyr Ser
    1295                1300                1305

Asp Ile  Cys Met Ala Pro Ala  Ala Asp Met Phe Glu  Glu Gly Val
    1310                1315                1320

Lys Leu  Gln Val Leu Lys Lys  Gly Thr Met Phe Pro  Ser Arg Ala
    1325                1330                1335

Asn Lys  Leu Tyr Glu Leu Phe  Cys Lys Tyr Asp Ser  Phe Asp Ser
    1340                1345                1350

Met Pro  Pro Ala Glu Leu Glu  Arg Ile Glu Lys Arg  Ile Phe Lys
    1355                1360                1365

Arg Ala  Leu Gln Glu Val Trp  Glu Glu Thr Lys Asp  Phe Tyr Ile
    1370                1375                1380

Asn Gly  Leu Lys Asn Pro Glu  Lys Ile Gln Arg Ala  Glu His Asp
    1385                1390                1395

Pro Lys  Leu Lys Met Ser Leu  Cys Phe Arg Trp Tyr  Leu Gly Leu
    1400                1405                1410

Ala Ser  Arg Trp Ala Asn Met  Gly Ala Pro Asp Arg  Val Met Asp
    1415                1420                1425

Tyr Gln  Val Trp Cys Gly Pro  Ala Ile Gly Ala Phe  Asn Asp Phe
    1430                1435                1440

Ile Lys  Gly Thr Tyr Leu Asp  Pro Ala Val Ser Asn  Glu Tyr Pro
    1445                1450                1455

Cys Val  Val Gln Ile Asn Leu  Gln Ile Leu Arg Gly  Ala Cys Tyr
    1460                1465                1470

Leu Arg  Arg Leu Asn Ala Leu  Arg Asn Asp Pro Arg  Ile Asp Leu
    1475                1480                1485

Glu Thr  Glu Asp Ala Ala Phe  Val Tyr Glu Pro Thr  Asn Ala Leu
    1490                1495                1500
```

<210> SEQ ID NO 19
<211> LENGTH: 8436
<212> TYPE: DNA
<213> ORGANISM: Thraustochytrium sp.

<400> SEQUENCE: 19

```
atgaaggaca tggaagatag acgggtcgct attgtgggca tgtcagctca cttgccttgt     60

gggacagatg tgaaggaatc atggcaggct attcgcgatg gaatcgactg tctaagtgac    120

ctacccgcgg atcgtctcga cgttacagct tactacaatc ccaacaaagc cacgaaagac    180

aagatctact gcaaacgggg tggcttcatc ccgaactatg acttcgaccc ccgcgaattt    240

gggctcaaca tgtttcaaat ggaagactct gatgcgaatc agacacttac cttgctcaaa    300

gtcaaacaag ctctcgaaga tgcaagcata gagcctttca ccaaggagaa gaagaacatt    360

ggatgtgttt taggtattgg tgggggccaa aaggcgagtc atgagttcta ctctcgtctc    420

aactacgttg tcgttgaaaa ggtacttcgg aaaatgggtt taccagatgc tgatgttgaa    480

gaagctgtgg agaaatacaa ggcaaatttt cccgagtggc gcctagactc tttccctggg    540

tttcttggga atgtaacggc tggtcggtgc agtaacacct tcaacatgga aggtatgaac    600

tgcgttgtgg atgctgcatg tgccagttct ctaattgcaa tcaaggttgc agttgaagag    660

ctactctttg gtgactgtga caccatgatt gcaggtgcca cctgcacgga caattcactt    720
```

-continued

```
ggcatgtaca tggccttctc taaaacgcca gtttttcta ctgacccaag tgtccgcgcg    780
tatgatgaga aaacaaaagg gatgctaatt ggagaaggtt cagcaatgtt cgttcttaaa    840
cgctatgcgg atgccgtacg tgatggcgac acaattcacg cggttctgcg ttcttgctct    900
tcgtctagtg atggaaaagc ggcaggaatt tatactccta ctatatctgg acaagaagaa    960
gctttgcgtc gagcgtatgc ccgtgcgggg gtatgtccat ctacgatcgg gcttgttgag   1020
ggtcacggga cagggacccc tgttggagat cgcattgagt taacagctct gcggaacttg   1080
tttgacaaag cttttggtag caagaaggaa caaatagcag ttggcagcat aaagtctcag   1140
ataggtcacc tgaaatctgt tgccggcttt gccggcttgg tcaaagctgt gcttgcgctt   1200
aaacacaaaa cgctcccagg ttcgattaat gtcgaccagc cacctttgtt gtatgacggt   1260
actcaaattc aagactcttc tttatatatc aacaagacaa atagaccatg gtttacgcaa   1320
aacaagcttc cgcgtcgggc tggtgtctca agttttggat ttggaggtgc aaactaccac   1380
gcggttctgg aagaattcga gcccgagcat gaaaaaccat accgcctcaa tactgttgga   1440
catcctgtcc tcttgtacgc tccgtctgtg gaagccctca aagtactttg caacgaccag   1500
cttgcggagc tcacaattgc attggaagag gcaaaaacac ataaaaatgt tgacaaagtt   1560
tgtggctaca agtttattga cgaatttcag ctccaaggaa gctgtcctcc agaaaatccg   1620
agagtaggat ttttagcaac actgcctact tcaaatatca ttgtcgcgct taaggcaatt   1680
ctcgcgcagc ttgatgcaaa accagatgcg aagaaatggg atttgcctca taaaaaggct   1740
tttggggcta ccttcgcatc gtcttcagtg aaaggctctg ttgctgcgct cttcgcagga   1800
cagggtaccc agtacttaaa catgttctct gatgtggcaa tgaactggcc accgttccgt   1860
gacagcattg tcgcaatgga agaagctcaa actgaggtat ttgagggcca agttgaacca   1920
attagcaaag ttctgtttcc acgagagcgc tatgcatccg aaagtgaaca ggggaatgaa   1980
cttctttgct taacagagta ctctcagcca actacgatag cagccgcagt aggggccttc   2040
gatattttca aagcggctgg ctttaagcca gacatggttg gagggcattc acttggcgaa   2100
tttgctgctt tgtacgcggc tgggtccatt tcgcgtgacg acctgtacaa gcttgtgtgc   2160
aaacgggcaa aggcaatggc gaacgctagt gacggagcta tggcagcagt gattggccca   2220
gatgcacgtc tagttacgcc acaaaatagt gacgtttatg tcgcaaactt caactccgca   2280
actcaagtag tcatcagtgg cactgttcaa ggtgtgaaag aagagtcgaa attgctcatt   2340
tcaaaggggt tccgcgtact gccacttaaa tgccagggcg ccttccattc tcctttgatg   2400
gggccttctg aggatagttt caaatcactt gtggagactt gtaccatctc gccgccaaaa   2460
aatgtgaaat tcttttgcaa tgttagtggc aaggaaagcc caaacccaaa acagaccctc   2520
aagtcacaca tgacgtctag cgttcagttc gaggagcaga ttcgtaacat gtacgatgcc   2580
ggagcacgtg tttttctgga gtttggaccc cgccaagtcc ttgcaaagct tatcgcggaa   2640
atgtttccct cgtgtacagc tatcagcgtt aaccccgcga gcagtggtga cagtgacgtg   2700
caactccgcc tcgccgccgt aaaattcgcg gtctcgggtg cagcccttag cacctttgat   2760
ccatgggagt atcgcaagcc acaagatctt cttattcgaa aaccacgaaa aactgccctt   2820
gttctatcag cagcaacata tgtttcccca aagactcttg cagaacgtaa aaaggctatg   2880
gaagatatca agctagtatc cattacacca agagatagta tggtatcaat tggaaaaatc   2940
gcgcaagaag tacggacagc taaacagcct ttagaaaccg aaattcgaag actcaacaaa   3000
gaattagaac atctcaagag agagctagca gcagccaaag cgagtgtcaa gtctgcatca   3060
aaaagctcta aagagcgatc tgtcctatca aagcaccgcg ctttgcttca aaacattttg   3120
```

-continued

```
caagactacg atgatcttcg tgtggtgcca ttcgctgttc gttctgttgc agtggacaac   3180
accgcgccgt atgctgacca agtttcgacc ccagcgtcag agcggtcggc ttcaccgctt   3240
ttcgagaaac gcagttcggt ttcgtcagca cgcctcgctg aagctgaagc cgcggtactg   3300
agcgttctcg cagacaagac aggctacgac agctcaatga tcgagatgga catggacctg   3360
gagagtgagc ttggcgttga tagcatcaaa cgcgtggaga tcatgagcga ggttcaaacg   3420
ctgctcagcg tggaagtctc cgacgttgac gctctgtcaa gaaccaagac tgttggcgac   3480
gtcatcgagg cgatgaagct ggaactcggt ggaccccaag gccagacttt gaccgcggaa   3540
tcgatccgtc agccaccggt gtccgagcct gctgtaccga cctcatcgtc aagcagtatt   3600
gctaatgttt cgtcagcacg cctcgctgaa gctgaagctg cggtactgag cgttctcgca   3660
gacaagacag gctacgacag ctcaatgatc gagatggaca tggacctgga gagcgagctt   3720
ggcgttgata gcatcaaacg cgtggagatc atgagcgagg ttcaaacgct gctcagcgtg   3780
gaagtctccg acgttgacgc tctgtcaaga actaagactg ttggcgacgt catcgaggcg   3840
atgaagctgg aactcggtgg accccaaggc cagactttga ccgcggaatc gatccgtcag   3900
ccaccggtgt ctgagcctgc tgtaccgacc tcatcgtcaa gcagtattgc taatgtttcg   3960
tcagcacgcc tcgctgaagc tgaagcggcg gtactgagcg ttctcgcaga caagacaggc   4020
tacgacagct caatgatcga gatggacatg gacctggaga gcgagcttgg cgtcgacagc   4080
atcaaacgcg tggagatcat gagcgaggtt caaacgctgc tcagcgtgga agtctccgac   4140
gttgacgctc tgtcaagaac caagactgtt ggcgacgtca tcgaggcgat gaagctggaa   4200
ctcggtggac cccaaggcca gactttgacc gcggaatcga tccgtcagcc accggtgtcc   4260
gagcctgctg taccgacctc atcgtcaagc agtattgcta atgttttgtc agcacgcctc   4320
gctgaagctg aagccgcggt actgagcgtt ctcgcagaca agacaggcta cgacagctca   4380
atgatcgaga tggacatgga cctggagagc gagcttggcg ttgatagcat caaacgcgtg   4440
gagatcatga gcgaggttca aacgttgctc agcgtggaag tctccgacgt tgacgctctg   4500
tcaagaacca agactgttgg cgacgtcatc gaggcgatga agctggaact cggtggaccc   4560
caaggccaga ctttgaccgc ggaatcgatc cgtcagccac cggtgtctga gcctgctgta   4620
ccgacctcat cgtcaagcag tattgctaat gtttcgtcag cacgcctcgc tgaagctgaa   4680
gccgcggtac tgagcgttct cgcagacaag acaggctacg acagctcaat gatcgagatg   4740
gacatggacc tggagagtga gcttggcgtc gacagcatca aacgcgtgga gatcatgagc   4800
gaggttcaaa cgctgctcag cgtggaagtc tccgacgttg acgctctgtc aagaaccaag   4860
actgttggcg acgtcatcga ggcgatgaag ctggaactcg gtggacccca aggccagact   4920
ttgacctctg aaccgatcca tcagccacca gtgtccgagc ctgctgtacc gacctcatcg   4980
tcaagcagta ttgctaatgt ttcttcagca cgcctcgctg aagctgaagc cgcggtactg   5040
agcgttctcg cagacaagac aggctacgac agctcaatga tcgagatgga catggacctg   5100
gagagcgagc ttggcgttga tagcatcaaa cgcgtggaaa tcatgagcga ggttcaaacg   5160
ctgctcagcg tggaagtctc cgacgttgac gctctgtcaa gaaccaagac tgttggcgac   5220
gtcatcgagg cgatgaagat ggaactcggt ggaccccaag gccagacttt gaccgcggaa   5280
tcgatccgtc agccaccggt gtctgagcct gctgtaccga cctcatcgtc aagcagtatt   5340
gctaatgttt cgtcagcacg cctcgctgaa gctgaagcgg cggtactgag cgttctcgca   5400
gacaagacag gctacgacag ctcaatgatc gagatggaca tggacctgga gagcgagctt   5460
```

-continued

```
ggcgttgata gcatcaaacg cgtggagatc atgagcgagg ttcaagcgct gctcagcgtg   5520
gaagtctccg acgttgacgc tctgtcaaga accaagactg ttggcgacgt catcgaggcg   5580
atgaagatgg aactcggtgg accccaaggc cagactttga ccgcagaatc gatccgtgag   5640
ccaccggtgt ctgagcctgc tgtaccgacc tcatcgtcaa gtagtatcgc taatgtttct   5700
tcagctcgcc tcgctgaagc tgaagccgcg gtactgagcg ttctcgcaga caagacaggc   5760
tacgacagct caatgatcga gatggacatg gacctggaga gtgagcttgg cgtcgacagc   5820
atcaaacgcg tggagatcat gagcgaggtt caaacgttgc tcagcgtgga agtctccgac   5880
gttgacgctc tgtcaagaac caagactgtt ggcgacgtca tcgaggcgat gaagctggaa   5940
cttggggaat catcaagtat tgagactctc aattgtaccg aggttgagca cacgagctac   6000
aaaagtgtca aggcttcagg gtgtgagaat gtagataccc gtttcgctaa ggttgtacaa   6060
atctcgcttc ctagcaagct gaaatccact gtgtcgcacg atcgacctgt aattgttgta   6120
gatgatggaa cgcccttaac cacggagctt tgtaaaattc ttgggggtaa tattgtggtt   6180
ctctcttatc aagggaagcc cgctggtcca cggggagtcg aggtgccaga tctttccgag   6240
gaagccctaa ttcaagctct tgcattgatt cggtctacat atggagttcc aattggtttt   6300
atttgtcagc aagtgtctaa tgtgagcacc aaggcacagc tttgttgggc actcctcgca   6360
gcgaagcatc tcaagaagga tttgaatgct gtcttacccg attcaagatc cttcttcgtc   6420
ggagttgtac gcttgaacgg gaaacttgga actttcgaaa acatcagcga cttctctaaa   6480
tttgatttga cgaaagccct agattacgga cagcgtggtt ctctcttagg cctgtgcaag   6540
tcactagact tagaatggga acaggtgttt tgccgtggaa tagatcttgc gtgtgatctt   6600
atgccactcc aggccgcaag gatactcaga aatgagcttc agtgtcccaa tatgcgcctt   6660
cgcgaggttg ggtacgatat ttctggcgcc aggtacacca tttcaaccga tgacctgcta   6720
tgtggaccct cgaaggctaa agtagaggcc gcagacttgt ttcttgtgac aggtggcgca   6780
cgaggtatta cacctcattg tgttcgtgag attgcaagtc gatcccccgg aaccacattt   6840
gtgctggttg gaagaagcga aatgtccgac gagcctgact gggctgttgg ccactacaat   6900
aaagacctgg accaaagcac aatgaaacac ttgaaagcaa cgcatgctgc tggaggggta   6960
aaacctacgc ctaaagcaca tcgtgcactt gtgaacaggg tcactggctc acgggaggta   7020
cgagaatctc ttagagcaat ccaggaggca ggggcaaatg tcgaatatat cgcctgtgat   7080
gtttcggatg aaaacaaggt ccgccaactt gtgcaaagag tggagcaaaa gtatggctgt   7140
gaaataactg ggatttggca tgcaagcggg gttcttcgtg acaaacttgt cgagcaaaag   7200
actacagacg actttgaggc agtttttggg accaaggtga ctggccttgt aaacatcgtg   7260
tcacaagtca atatgtctaa gctacgacac ttcatcctct tcagttcttt ggctggattt   7320
catgggaaca agggccaaac ggattatgca attgctaatg aagccttgaa caaaatcgcg   7380
catactctct cagcgttttt gcccaaactg aatgcaaagg tgctagactt cggtccgtgg   7440
gtaggttcag gaatggtaac cgaaacactt gagaagcatt ttaaagctat gggggttcag   7500
actattcctc tcgagccagg agcacggact gttgcgcaaa tcattttggc aagttcgcca   7560
ccgcaatcgc ttttggggaa ctggggcttt ccagccacca aaccgctaca acgctctaat   7620
gtagtcacgg gcacactctc tccggaagag atagaattca tcgcagacca caaaattcaa   7680
ggccgcaagg tgcttcccat gatggctgca atcgggttca tggcctctat tgcggaagga   7740
ctctacccgg ggtacaatct gcaaggcgtg gaaaatgctc agctctttca aggcttgact   7800
atcaaccaag agacaaaatt tcaaatcact ctcattgagg agcacaactc tgaggaaaac   7860
```

```
ctggatgtcc tgacatccct tggtgtaatg ttggaaagcg ggaaggtgct tcccgcttac   7920

cgatgtgttg tatgcttgaa tacaacccag cagcagccca agctatctcc aaaaattctt   7980

aacttggaag ttgaccctgc atgcgaggtt aacccctatg atggaaagtc gttgttccac   8040

ggtccgcttt tgcaattcgt tcaacaagtg ttgcactcaa gtaccaaagg cctcgttgcc   8100

aagtgccgcg cgcttccaat caaagaagcc atccgagggc catttatcaa gcaaacactc   8160

catgatccaa ttctagacga cgtcattttt cagctaatgc tcgtgtggtg tcgtaatgct   8220

ctaggaagtg catcgctacc caacagaatt gaaaagatgt catactttgg gaatgtctca   8280

gaaggtagca ctttctttgc ctcagttaca cctgtgggac caagagtacc aaaggatccc   8340

gtgatcaaaa tgcagtttct tctccaagat gaatccggca acacattttc atcgggggag   8400

ggctcggttg tgcttagtga cgaactcgtc ttttga                              8436
```

```
<210> SEQ ID NO 20
<211> LENGTH: 2811
<212> TYPE: PRT
<213> ORGANISM: Thraustochytrium sp.

<400> SEQUENCE: 20

Met Lys Asp Met Glu Asp Arg Arg Val Ala Ile Val Gly Met Ser Ala
1               5                   10                  15

His Leu Pro Cys Gly Thr Asp Val Lys Glu Ser Trp Gln Ala Ile Arg
            20                  25                  30

Asp Gly Ile Asp Cys Leu Ser Asp Leu Pro Ala Asp Arg Leu Asp Val
        35                  40                  45

Thr Ala Tyr Tyr Asn Pro Asn Lys Ala Thr Lys Asp Lys Ile Tyr Cys
    50                  55                  60

Lys Arg Gly Gly Phe Ile Pro Asn Tyr Asp Phe Asp Pro Arg Glu Phe
65                  70                  75                  80

Gly Leu Asn Met Phe Gln Met Glu Asp Ser Asp Ala Asn Gln Thr Leu
                85                  90                  95

Thr Leu Leu Lys Val Lys Gln Ala Leu Glu Asp Ala Ser Ile Glu Pro
            100                 105                 110

Phe Thr Lys Glu Lys Lys Asn Ile Gly Cys Val Leu Gly Ile Gly Gly
        115                 120                 125

Gly Gln Lys Ala Ser His Glu Phe Tyr Ser Arg Leu Asn Tyr Val Val
    130                 135                 140

Val Glu Lys Val Leu Arg Lys Met Gly Leu Pro Asp Ala Asp Val Glu
145                 150                 155                 160

Glu Ala Val Glu Lys Tyr Lys Ala Asn Phe Pro Glu Trp Arg Leu Asp
                165                 170                 175

Ser Phe Pro Gly Phe Leu Gly Asn Val Thr Ala Gly Arg Cys Ser Asn
            180                 185                 190

Thr Phe Asn Met Glu Gly Met Asn Cys Val Val Asp Ala Ala Cys Ala
        195                 200                 205

Ser Ser Leu Ile Ala Ile Lys Val Ala Val Glu Glu Leu Leu Phe Gly
    210                 215                 220

Asp Cys Asp Thr Met Ile Ala Gly Ala Thr Cys Thr Asp Asn Ser Leu
225                 230                 235                 240

Gly Met Tyr Met Ala Phe Ser Lys Thr Pro Val Phe Ser Thr Asp Pro
                245                 250                 255

Ser Val Arg Ala Tyr Asp Glu Lys Thr Lys Gly Met Leu Ile Gly Glu
            260                 265                 270
```

-continued

```
Gly Ser Ala Met Phe Val Leu Lys Arg Tyr Ala Asp Ala Val Arg Asp
        275                 280                 285

Gly Asp Thr Ile His Ala Val Leu Arg Ser Cys Ser Ser Ser Ser Asp
    290                 295                 300

Gly Lys Ala Ala Gly Ile Tyr Thr Pro Thr Ile Ser Gly Gln Glu Glu
305                 310                 315                 320

Ala Leu Arg Arg Ala Tyr Ala Arg Ala Gly Val Cys Pro Ser Thr Ile
                325                 330                 335

Gly Leu Val Glu Gly His Gly Thr Gly Thr Pro Val Gly Asp Arg Ile
            340                 345                 350

Glu Leu Thr Ala Leu Arg Asn Leu Phe Asp Lys Ala Phe Gly Ser Lys
        355                 360                 365

Lys Glu Gln Ile Ala Val Gly Ser Ile Lys Ser Gln Ile Gly His Leu
    370                 375                 380

Lys Ser Val Ala Gly Phe Ala Gly Leu Val Lys Ala Val Leu Ala Leu
385                 390                 395                 400

Lys His Lys Thr Leu Pro Gly Ser Ile Asn Val Asp Gln Pro Pro Leu
                405                 410                 415

Leu Tyr Asp Gly Thr Gln Ile Gln Asp Ser Ser Leu Tyr Ile Asn Lys
            420                 425                 430

Thr Asn Arg Pro Trp Phe Thr Gln Asn Lys Leu Pro Arg Arg Ala Gly
        435                 440                 445

Val Ser Ser Phe Gly Phe Gly Gly Ala Asn Tyr His Ala Val Leu Glu
    450                 455                 460

Glu Phe Glu Pro Glu His Glu Lys Pro Tyr Arg Leu Asn Thr Val Gly
465                 470                 475                 480

His Pro Val Leu Leu Tyr Ala Pro Ser Val Glu Ala Leu Lys Val Leu
                485                 490                 495

Cys Asn Asp Gln Leu Ala Glu Leu Thr Ile Ala Leu Glu Glu Ala Lys
            500                 505                 510

Thr His Lys Asn Val Asp Lys Val Cys Gly Tyr Lys Phe Ile Asp Glu
        515                 520                 525

Phe Gln Leu Gln Gly Ser Cys Pro Pro Glu Asn Pro Arg Val Gly Phe
    530                 535                 540

Leu Ala Thr Leu Pro Thr Ser Asn Ile Ile Val Ala Leu Lys Ala Ile
545                 550                 555                 560

Leu Ala Gln Leu Asp Ala Lys Pro Asp Ala Lys Lys Trp Asp Leu Pro
                565                 570                 575

His Lys Lys Ala Phe Gly Ala Thr Phe Ala Ser Ser Ser Val Lys Gly
            580                 585                 590

Ser Val Ala Ala Leu Phe Ala Gly Gln Gly Thr Gln Tyr Leu Asn Met
        595                 600                 605

Phe Ser Asp Val Ala Met Asn Trp Pro Pro Phe Arg Asp Ser Ile Val
    610                 615                 620

Ala Met Glu Glu Ala Gln Thr Glu Val Phe Glu Gly Gln Val Glu Pro
625                 630                 635                 640

Ile Ser Lys Val Leu Phe Pro Arg Glu Arg Tyr Ala Ser Glu Ser Glu
                645                 650                 655

Gln Gly Asn Glu Leu Leu Cys Leu Thr Glu Tyr Ser Gln Pro Thr Thr
            660                 665                 670

Ile Ala Ala Ala Val Gly Ala Phe Asp Ile Phe Lys Ala Ala Gly Phe
        675                 680                 685
```

-continued

```
Lys Pro Asp Met Val Gly Gly His Ser Leu Gly Glu Phe Ala Ala Leu
    690                 695                 700

Tyr Ala Ala Gly Ser Ile Ser Arg Asp Asp Leu Tyr Lys Leu Val Cys
705                 710                 715                 720

Lys Arg Ala Lys Ala Met Ala Asn Ala Ser Asp Gly Ala Met Ala Ala
                725                 730                 735

Val Ile Gly Pro Asp Ala Arg Leu Val Thr Pro Gln Asn Ser Asp Val
            740                 745                 750

Tyr Val Ala Asn Phe Asn Ser Ala Thr Gln Val Val Ile Ser Gly Thr
        755                 760                 765

Val Gln Gly Val Lys Glu Glu Ser Lys Leu Leu Ile Ser Lys Gly Phe
    770                 775                 780

Arg Val Leu Pro Leu Lys Cys Gln Gly Ala Phe His Ser Pro Leu Met
785                 790                 795                 800

Gly Pro Ser Glu Asp Ser Phe Lys Ser Leu Val Glu Thr Cys Thr Ile
                805                 810                 815

Ser Pro Pro Lys Asn Val Lys Phe Phe Cys Asn Val Ser Gly Lys Glu
            820                 825                 830

Ser Pro Asn Pro Lys Gln Thr Leu Lys Ser His Met Thr Ser Ser Val
        835                 840                 845

Gln Phe Glu Glu Gln Ile Arg Asn Met Tyr Asp Ala Gly Ala Arg Val
    850                 855                 860

Phe Leu Glu Phe Gly Pro Arg Gln Val Leu Ala Lys Leu Ile Ala Glu
865                 870                 875                 880

Met Phe Pro Ser Cys Thr Ala Ile Ser Val Asn Pro Ala Ser Ser Gly
                885                 890                 895

Asp Ser Asp Val Gln Leu Arg Leu Ala Ala Val Lys Phe Ala Val Ser
            900                 905                 910

Gly Ala Ala Leu Ser Thr Phe Asp Pro Trp Glu Tyr Arg Lys Pro Gln
        915                 920                 925

Asp Leu Leu Ile Arg Lys Pro Arg Lys Thr Ala Leu Val Leu Ser Ala
    930                 935                 940

Ala Thr Tyr Val Ser Pro Lys Thr Leu Ala Glu Arg Lys Lys Ala Met
945                 950                 955                 960

Glu Asp Ile Lys Leu Val Ser Ile Thr Pro Arg Asp Ser Met Val Ser
                965                 970                 975

Ile Gly Lys Ile Ala Gln Glu Val Arg Thr Ala Lys Gln Pro Leu Glu
            980                 985                 990

Thr Glu Ile Arg Arg Leu Asn Lys  Glu Leu Glu His Leu  Lys Arg Glu
        995                 1000                 1005

Leu Ala  Ala Ala Lys Ala Ser  Val Lys Ser Ala Ser  Lys Ser Ser
    1010                 1015                 1020

Lys Glu  Arg Ser Val Leu Ser  Lys His Arg Ala Leu  Leu Gln Asn
    1025                 1030                 1035

Ile Leu  Gln Asp Tyr Asp Asp  Leu Arg Val Val Pro  Phe Ala Val
    1040                 1045                 1050

Arg Ser  Val Ala Val Asp Asn  Thr Ala Pro Tyr Ala  Asp Gln Val
    1055                 1060                 1065

Ser Thr  Pro Ala Ser Glu Arg  Ser Ala Ser Pro Leu  Phe Glu Lys
    1070                 1075                 1080

Arg Ser  Ser Val Ser Ser Ala  Arg Leu Ala Glu Ala  Glu Ala Ala
    1085                 1090                 1095

Val Leu  Ser Val Leu Ala Asp  Lys Thr Gly Tyr Asp  Ser Ser Met
```

-continued

```
    1100                1105                1110

Ile Glu  Met Asp Met Asp Leu  Glu Ser Glu Leu Gly  Val Asp Ser
    1115                1120                1125

Ile Lys  Arg Val Glu Ile Met  Ser Glu Val Gln Thr  Leu Leu Ser
    1130                1135                1140

Val Glu  Val Ser Asp Val Asp  Ala Leu Ser Arg Thr  Lys Thr Val
    1145                1150                1155

Gly Asp  Val Ile Glu Ala Met  Lys Leu Glu Leu Gly  Gly Pro Gln
    1160                1165                1170

Gly Gln  Thr Leu Thr Ala Glu  Ser Ile Arg Gln Pro  Pro Val Ser
    1175                1180                1185

Glu Pro  Ala Val Pro Thr Ser  Ser Ser Ser Ser Ile  Ala Asn Val
    1190                1195                1200

Ser Ser  Ala Arg Leu Ala Glu  Ala Glu Ala Ala Val  Leu Ser Val
    1205                1210                1215

Leu Ala  Asp Lys Thr Gly Tyr  Asp Ser Ser Met Ile  Glu Met Asp
    1220                1225                1230

Met Asp  Leu Glu Ser Glu Leu  Gly Val Asp Ser Ile  Lys Arg Val
    1235                1240                1245

Glu Ile  Met Ser Glu Val Gln  Thr Leu Leu Ser Val  Glu Val Ser
    1250                1255                1260

Asp Val  Asp Ala Leu Ser Arg  Thr Lys Thr Val Gly  Asp Val Ile
    1265                1270                1275

Glu Ala  Met Lys Leu Glu Leu  Gly Gly Pro Gln Gly  Gln Thr Leu
    1280                1285                1290

Thr Ala  Glu Ser Ile Arg Gln  Pro Pro Val Ser Glu  Pro Ala Val
    1295                1300                1305

Pro Thr  Ser Ser Ser Ser Ser  Ile Ala Asn Val Ser  Ser Ala Arg
    1310                1315                1320

Leu Ala  Glu Ala Glu Ala Ala  Val Leu Ser Val Leu  Ala Asp Lys
    1325                1330                1335

Thr Gly  Tyr Asp Ser Ser Met  Ile Glu Met Asp Met  Asp Leu Glu
    1340                1345                1350

Ser Glu  Leu Gly Val Asp Ser  Ile Lys Arg Val Glu  Ile Met Ser
    1355                1360                1365

Glu Val  Gln Thr Leu Leu Ser  Val Glu Val Ser Asp  Val Asp Ala
    1370                1375                1380

Leu Ser  Arg Thr Lys Thr Val  Gly Asp Val Ile Glu  Ala Met Lys
    1385                1390                1395

Leu Glu  Leu Gly Gly Pro Gln  Gly Gln Thr Leu Thr  Ala Glu Ser
    1400                1405                1410

Ile Arg  Gln Pro Pro Val Ser  Glu Pro Ala Val Pro  Thr Ser Ser
    1415                1420                1425

Ser Ser  Ser Ile Ala Asn Val  Leu Ser Ala Arg Leu  Ala Glu Ala
    1430                1435                1440

Glu Ala  Ala Val Leu Ser Val  Leu Ala Asp Lys Thr  Gly Tyr Asp
    1445                1450                1455

Ser Ser  Met Ile Glu Met Asp  Met Asp Leu Glu Ser  Glu Leu Gly
    1460                1465                1470

Val Asp  Ser Ile Lys Arg Val  Glu Ile Met Ser Glu  Val Gln Thr
    1475                1480                1485

Leu Leu  Ser Val Glu Val Ser  Asp Val Asp Ala Leu  Ser Arg Thr
    1490                1495                1500
```

-continued

```
Lys Thr  Val Gly Asp Val Ile  Glu Ala Met Lys Leu  Glu Leu Gly
    1505                 1510                 1515

Gly Pro  Gln Gly Gln Thr Leu  Thr Ala Glu Ser Ile  Arg Gln Pro
    1520                 1525                 1530

Pro Val  Ser Glu Pro Ala Val  Pro Thr Ser Ser Ser  Ser Ser Ile
    1535                 1540                 1545

Ala Asn  Val Ser Ser Ala Arg  Leu Ala Glu Ala Glu  Ala Ala Val
    1550                 1555                 1560

Leu Ser  Val Leu Ala Asp Lys  Thr Gly Tyr Asp Ser  Ser Met Ile
    1565                 1570                 1575

Glu Met  Asp Met Asp Leu Glu  Ser Glu Leu Gly Val  Asp Ser Ile
    1580                 1585                 1590

Lys Arg  Val Glu Ile Met Ser  Glu Val Gln Thr Leu  Leu Ser Val
    1595                 1600                 1605

Glu Val  Ser Asp Val Asp Ala  Leu Ser Arg Thr Lys  Thr Val Gly
    1610                 1615                 1620

Asp Val  Ile Glu Ala Met Lys  Leu Glu Leu Gly Gly  Pro Gln Gly
    1625                 1630                 1635

Gln Thr  Leu Thr Ser Glu Pro  Ile His Gln Pro Pro  Val Ser Glu
    1640                 1645                 1650

Pro Ala  Val Pro Thr Ser Ser  Ser Ser Ser Ile Ala  Asn Val Ser
    1655                 1660                 1665

Ser Ala  Arg Leu Ala Glu Ala  Glu Ala Ala Val Leu  Ser Val Leu
    1670                 1675                 1680

Ala Asp  Lys Thr Gly Tyr Asp  Ser Ser Met Ile Glu  Met Asp Met
    1685                 1690                 1695

Asp Leu  Glu Ser Glu Leu Gly  Val Asp Ser Ile Lys  Arg Val Glu
    1700                 1705                 1710

Ile Met  Ser Glu Val Gln Thr  Leu Leu Ser Val Glu  Val Ser Asp
    1715                 1720                 1725

Val Asp  Ala Leu Ser Arg Thr  Lys Thr Val Gly Asp  Val Ile Glu
    1730                 1735                 1740

Ala Met  Lys Met Glu Leu Gly  Gly Pro Gln Gly Gln  Thr Leu Thr
    1745                 1750                 1755

Ala Glu  Ser Ile Arg Gln Pro  Pro Val Ser Glu Pro  Ala Val Pro
    1760                 1765                 1770

Thr Ser  Ser Ser Ser Ser Ile  Ala Asn Val Ser Ser  Ala Arg Leu
    1775                 1780                 1785

Ala Glu  Ala Glu Ala Ala Val  Leu Ser Val Leu Ala  Asp Lys Thr
    1790                 1795                 1800

Gly Tyr  Asp Ser Ser Met Ile  Glu Met Asp Met Asp  Leu Glu Ser
    1805                 1810                 1815

Glu Leu  Gly Val Asp Ser Ile  Lys Arg Val Glu Ile  Met Ser Glu
    1820                 1825                 1830

Val Gln  Ala Leu Leu Ser Val  Glu Val Ser Asp Val  Asp Ala Leu
    1835                 1840                 1845

Ser Arg  Thr Lys Thr Val Gly  Asp Val Ile Glu Ala  Met Lys Met
    1850                 1855                 1860

Glu Leu  Gly Gly Pro Gln Gly  Gln Thr Leu Thr Ala  Glu Ser Ile
    1865                 1870                 1875

Arg Glu  Pro Pro Val Ser Glu  Pro Ala Val Pro Thr  Ser Ser Ser
    1880                 1885                 1890
```

-continued

```
Ser Ser  Ile Ala Asn Val Ser  Ser Ala Arg Leu Ala  Glu Ala Glu
    1895                 1900                 1905

Ala Ala  Val Leu Ser Val Leu  Ala Asp Lys Thr Gly  Tyr Asp Ser
    1910                 1915                 1920

Ser Met  Ile Glu Met Asp Met  Asp Leu Glu Ser Glu  Leu Gly Val
    1925                 1930                 1935

Asp Ser  Ile Lys Arg Val Glu  Ile Met Ser Glu Val  Gln Thr Leu
    1940                 1945                 1950

Leu Ser  Val Glu Val Ser Asp  Val Asp Ala Leu Ser  Arg Thr Lys
    1955                 1960                 1965

Thr Val  Gly Asp Val Ile Glu  Ala Met Lys Leu Glu  Leu Gly Glu
    1970                 1975                 1980

Ser Ser  Ser Ile Glu Thr Leu  Asn Cys Thr Glu Val  Glu His Thr
    1985                 1990                 1995

Ser Tyr  Lys Ser Val Lys Ala  Ser Gly Cys Glu Asn  Val Asp Thr
    2000                 2005                 2010

Arg Phe  Ala Lys Val Val Gln  Ile Ser Leu Pro Ser  Lys Leu Lys
    2015                 2020                 2025

Ser Thr  Val Ser His Asp Arg  Pro Val Ile Val Val  Asp Asp Gly
    2030                 2035                 2040

Thr Pro  Leu Thr Thr Glu Leu  Cys Lys Ile Leu Gly  Gly Asn Ile
    2045                 2050                 2055

Val Val  Leu Ser Tyr Gln Gly  Lys Pro Ala Gly Pro  Arg Gly Val
    2060                 2065                 2070

Glu Val  Pro Asp Leu Ser Glu  Glu Ala Leu Ile Gln  Ala Leu Ala
    2075                 2080                 2085

Leu Ile  Arg Ser Thr Tyr Gly  Val Pro Ile Gly Phe  Ile Cys Gln
    2090                 2095                 2100

Gln Val  Ser Asn Val Ser Thr  Lys Ala Gln Leu Cys  Trp Ala Leu
    2105                 2110                 2115

Leu Ala  Ala Lys His Leu Lys  Lys Asp Leu Asn Ala  Val Leu Pro
    2120                 2125                 2130

Asp Ser  Arg Ser Phe Phe Val  Gly Val Val Arg Leu  Asn Gly Lys
    2135                 2140                 2145

Leu Gly  Thr Phe Glu Asn Ile  Ser Asp Phe Ser Lys  Phe Asp Leu
    2150                 2155                 2160

Thr Lys  Ala Leu Asp Tyr Gly  Gln Arg Gly Ser Leu  Leu Gly Leu
    2165                 2170                 2175

Cys Lys  Ser Leu Asp Leu Glu  Trp Glu Gln Val Phe  Cys Arg Gly
    2180                 2185                 2190

Ile Asp  Leu Ala Cys Asp Leu  Met Pro Leu Gln Ala  Ala Arg Ile
    2195                 2200                 2205

Leu Arg  Asn Glu Leu Gln Cys  Pro Asn Met Arg Leu  Arg Glu Val
    2210                 2215                 2220

Gly Tyr  Asp Ile Ser Gly Ala  Arg Tyr Thr Ile Ser  Thr Asp Asp
    2225                 2230                 2235

Leu Leu  Cys Gly Pro Ser Lys  Ala Lys Val Glu Ala  Ala Asp Leu
    2240                 2245                 2250

Phe Leu  Val Thr Gly Gly Ala  Arg Gly Ile Thr Pro  His Cys Val
    2255                 2260                 2265

Arg Glu  Ile Ala Ser Arg Ser  Pro Gly Thr Thr Phe  Val Leu Val
    2270                 2275                 2280

Gly Arg  Ser Glu Met Ser Asp  Glu Pro Asp Trp Ala  Val Gly His
```

-continued

```
    2285                2290                2295

Tyr Asn  Lys Asp Leu Asp Gln  Ser Thr Met Lys His  Leu Lys Ala
    2300                2305                2310

Thr His  Ala Ala Gly Gly Val  Lys Pro Thr Pro Lys  Ala His Arg
    2315                2320                2325

Ala Leu  Val Asn Arg Val Thr  Gly Ser Arg Glu Val  Arg Glu Ser
    2330                2335                2340

Leu Arg  Ala Ile Gln Glu Ala  Gly Ala Asn Val Glu  Tyr Ile Ala
    2345                2350                2355

Cys Asp  Val Ser Asp Glu Asn  Lys Val Arg Gln Leu  Val Gln Arg
    2360                2365                2370

Val Glu  Gln Lys Tyr Gly Cys  Glu Ile Thr Gly Ile  Trp His Ala
    2375                2380                2385

Ser Gly  Val Leu Arg Asp Lys  Leu Val Glu Gln Lys  Thr Thr Asp
    2390                2395                2400

Asp Phe  Glu Ala Val Phe Gly  Thr Lys Val Thr Gly  Leu Val Asn
    2405                2410                2415

Ile Val  Ser Gln Val Asn Met  Ser Lys Leu Arg His  Phe Ile Leu
    2420                2425                2430

Phe Ser  Ser Leu Ala Gly Phe  His Gly Asn Lys Gly  Gln Thr Asp
    2435                2440                2445

Tyr Ala  Ile Ala Asn Glu Ala  Leu Asn Lys Ile Ala  His Thr Leu
    2450                2455                2460

Ser Ala  Phe Leu Pro Lys Leu  Asn Ala Lys Val Leu  Asp Phe Gly
    2465                2470                2475

Pro Trp  Val Gly Ser Gly Met  Val Thr Glu Thr Leu  Glu Lys His
    2480                2485                2490

Phe Lys  Ala Met Gly Val Gln  Thr Ile Pro Leu Glu  Pro Gly Ala
    2495                2500                2505

Arg Thr  Val Ala Gln Ile Ile  Leu Ala Ser Ser Pro  Pro Gln Ser
    2510                2515                2520

Leu Leu  Gly Asn Trp Gly Phe  Pro Ala Thr Lys Pro  Leu Gln Arg
    2525                2530                2535

Ser Asn  Val Val Thr Gly Thr  Leu Ser Pro Glu Glu  Ile Glu Phe
    2540                2545                2550

Ile Ala  Asp His Lys Ile Gln  Gly Arg Lys Val Leu  Pro Met Met
    2555                2560                2565

Ala Ala  Ile Gly Phe Met Ala  Ser Ile Ala Glu Gly  Leu Tyr Pro
    2570                2575                2580

Gly Tyr  Asn Leu Gln Gly Val  Glu Asn Ala Gln Leu  Phe Gln Gly
    2585                2590                2595

Leu Thr  Ile Asn Gln Glu Thr  Lys Phe Gln Ile Thr  Leu Ile Glu
    2600                2605                2610

Glu His  Asn Ser Glu Glu Asn  Leu Asp Val Leu Thr  Ser Leu Gly
    2615                2620                2625

Val Met  Leu Glu Ser Gly Lys  Val Leu Pro Ala Tyr  Arg Cys Val
    2630                2635                2640

Val Cys  Leu Asn Thr Thr Gln  Gln Gln Pro Lys Leu  Ser Pro Lys
    2645                2650                2655

Ile Leu  Asn Leu Glu Val Asp  Pro Ala Cys Glu Val  Asn Pro Tyr
    2660                2665                2670

Asp Gly  Lys Ser Leu Phe His  Gly Pro Leu Leu Gln  Phe Val Gln
    2675                2680                2685
```

```
Gln Val  Leu His Ser Ser Thr  Lys Gly Leu Val Ala  Lys Cys Arg
    2690                 2695                 2700

Ala Leu  Pro Ile Lys Glu Ala  Ile Arg Gly Pro Phe  Ile Lys Gln
    2705                 2710                 2715

Thr Leu  His Asp Pro Ile Leu  Asp Asp Val Ile Phe  Gln Leu Met
    2720                 2725                 2730

Leu Val  Trp Cys Arg Asn Ala  Leu Gly Ser Ala Ser  Leu Pro Asn
    2735                 2740                 2745

Arg Ile  Glu Lys Met Ser Tyr  Phe Gly Asn Val Ser  Glu Gly Ser
    2750                 2755                 2760

Thr Phe  Phe Ala Ser Val Thr  Pro Val Gly Pro Arg  Val Pro Lys
    2765                 2770                 2775

Asp Pro  Val Ile Lys Met Gln  Phe Leu Leu Gln Asp  Glu Ser Gly
    2780                 2785                 2790

Asn Thr  Phe Ser Ser Gly Glu  Gly Ser Val Val Leu  Ser Asp Glu
    2795                 2800                 2805

Leu Val  Phe
    2810
```

<210> SEQ ID NO 21
<211> LENGTH: 5808
<212> TYPE: DNA
<213> ORGANISM: Thraustochytrium sp.
<220> FEATURE:
<221> NAME/KEY: misc_feature
<222> LOCATION: (1)..(5808)
<223> OTHER INFORMATION: n = a, c, t, or g

<400> SEQUENCE: 21

```
atgcaacttc ctccagcgca ttctgccgat gagaatcgca tcgcggtcgt gggcatggcc     60
gtcaaatatg cgggctgtga caataaagaa gagttttgga agactttgat gaatggtagt    120
atcaatacca agtcgatttc ggcagcaagg ttgggcagca ataagcgtga cgaacactat    180
gttcctgaac gatcgaaata tgcagatacg ttctgtaacg aaaggtacgg ttgtatccag    240
caaggtacgg ataatgagca tgacctcctc ctaggtcttg ctcaagaagc tctcgctgac    300
gctgccgggc ggatggagaa acaaccttcg gaggcgttcg atctggaaaa tactggcatc    360
gtgagtgggt gcttatcttt tccaatggat aacctgcaag gagagttgtt gaacttgtat    420
caaagccatg tggagaaaca acttccacct agtgccttgg tagaagccgt gaagctttgg    480
tctgagcgac agaaatctac gaaagcacat gcaggggaca agcgccggtt cattgaccca    540
gcttcttttg tagctgataa actgaaccta ggcccactac attatgcgat cgatgcagca    600
tgcgcttctg cattgtacgt gttaaaatta gctcaagacc accttgtttc aggtgccgtt    660
gatatgatgt tatgtggagc gacgtgcttc ccagaaccat tcttcatctt gtctgggttc    720
tcgacttttc aagcgatgcc tgntggggca gatggagtct cactacctct ccataaaacg    780
agtgctgggc tcactccagg tgaagggggg tccattatgg tgctcaagcg actgaaagac    840
gctatcagag atggaaatca catttatggt gtgctccttg aagcaaattt aagtaacgca    900
ggttgtgggc ttccactcag cccgcactta ccgagcgaag aatcatgtat tcgtgatacc    960
taccgccgtg ctggagttgc tgcagatcaa agtattcagt atattgagtg ccacgctacg   1020
ggaacccctc gaggggatgt cgtggaaatt gaggcggttg aaagagtttt caagaaaaac   1080
gttccacgct taggctcgac gaaaggaaat tttggtcact cgttagttgc ggctggtttc   1140
gcaggtatgg caaagcttct tcttgcaatg gaacatggag tgattcctcc cacaccaggt   1200
```

-continued

```
cttgatgctt cgaaccaggc aagtgagcac gttgtgacaa aggctatcac ttggcctgag   1260
acacatgggg ctccaaaacg agctggcctt tcagcatttg gatttggtgg gactaatgcg   1320
catgcactct tcgaagagtt taatgccgag ggcataagtt atcgccctgg aaagcctcca   1380
gtcgaatcga atacccgtcc ttccgtcgta ataactggga tggactgtac ctttgggagc   1440
cttgaaggga ttgatgcgtt cgagactgcc ctgtacgagg ggcgtgacgc agctcgtgac   1500
ttacccgcca aacgttggag gttcctaggt gaggacttgg agtttctccg agccatcagg   1560
ctcaaggaaa agcctagggg ttgtttttgtg gagagtgttg acgttaactt tagacggctg   1620
aaaacgccct tgacaccaga agatatgttg cggccccaac aactcttggc ggtttctacg   1680
atggaccgag caattatcga tgcaggtcta aagaagggcc aacatgtagc agttcttgtt   1740
ggcctaggaa ctgacctgga actttaccgt catcgagcaa gagtcgcgct taaagaggtt   1800
ttgcacccga gcttaaagtc agacactgca attctccaga aaataatgca atatgtgaat   1860
gatgcaggaa cttcgacttc atacacatct tacattggaa acctcgttgc cacgcgtatt   1920
tcgtctcagt ggggattcac agggccgtcc tttactgtca cagaaggaaa taattccgtg   1980
tacagatgtg cacaactagc caaagatatg cttcaggtta accgagttga tgctgtcgtc   2040
atcgcaggcg ttgatctcaa cggaagcgcc gaaagttttt ttgtccgagc aaatcgtcaa   2100
aagatatcca agctaagtca tccatgtgca agcttcgaca gagatgcaga tggatttttc   2160
gcaggtgagg gctgtggtgc cctagttttc aagaggttag aagactgtgc tcctcaggaa   2220
aaaatttatg ctagtataga ctctatcgca atagataaag agcctactag ctcagctgtg   2280
aaagctgtct accaaagtga ttcgagtctc tccgatattg agctgttaga aatcagtgga   2340
gactccaaac ggtttgcagc attcgaaggc gctgtggaaa ttcaatcaag tgtggaagcc   2400
cagctaaaag gactttccaa agtccttgaa cctgcaaaag gccaaggcgt agcggtggga   2460
agtactcgag caaccgttgg ggatataggg tatgctacag gagcggcaag cctgattaaa   2520
actgcactct gcttatataa tcgctacctt ccggcattag caaactggag tggcccatgt   2580
gaacagtccg cctggggctc aaacatgttc gtttgccatg aaacacggcc gtggatgaaa   2640
aaccagaatg aaaagagatg tgccctcatt tctggaacag atccatctca tacatgcttt   2700
tccctcgtac tatcggatac tgggtgttat gaagagcaca atcgaacgtg ctttgatgtg   2760
caagcgccac agctagttct gatacacgga ttcgatggaa aaactattgt gcggcgactt   2820
gaaggatatc tccttgaact tgttgaaggg catgcaagcc cttcagagta tttccacaaa   2880
ctgattggac aaagtctact tgagaactcg aaagaaagta aactcacact ttcgcttgtg   2940
tgcaatccga accagctcca aaaggagctc atgcttgcta tcaaaggagt acaacgaagc   3000
atgttaacag ggaaggattg ggtcagtcca tcaggaagtt gttttgcccc aaatccgtta   3060
tcaagcgcaa aagtggcatt catgtacgga gaaggccgaa gcccgtactg tggtgtaggc   3120
ttgggtctac atcgtttgtg gcccggtctc catgaaaatg tgaacaataa gacagtcgat   3180
ttatggacgg aaggagatgg ttggttatat cctcgaacgt tgacacgaga agagcataca   3240
aaagccatcg aatctttcaa cgcaaatcaa attgaaatgt ttcgcgctgg gattttcatc   3300
tcaatgtgtc agacagacta tgtcatgaat gttctcggtg tccagcctaa ggccggattt   3360
gggctgagct tgggagaaat ttcaatgctc tttgcgatgt caaaggagaa ctgcaggcag   3420
tcacaggaaa tgaccaatcg tttgcgcggt tctccagtgt ggtctaacga gcttgctatc   3480
aacttcaatg caattcgcaa gttatggaaa atcccccgag gagctccctt agaatccttt   3540
```

-continued

```
tggcaaggat acttggttca cggcacaaga gaagaagtag agcatgctat tggtctttct   3600
gagccttatg tacgtctgct tattgtgaac gattcaagga gtgccttgat tgctggaaaa   3660
ccagacgcct gtcaggcagt aatcagtaga ctaaactcca agttcccttc tctgccggta   3720
aagcaaggaa tgattggtca ttgcccagaa gttcgtgcgt tcatcaaaga tattgggtac   3780
atccatgaaa cactccgaat ttccaatgac tattcggatt gtcagctttt ctcagcggta   3840
accaagggcg cacttgacag ctccacaatg gaaatcaaac actttgtggg agaggtctac   3900
tcccggatcg cagactttcc tcaaatcgtc aacacggtgc attcggctgg ttatgacgta   3960
tttcttgagc ttggctgtga tgcttctaga tctgcagcag ttcaaaacat tcttggtggt   4020
caaggaaagt tcttgtctac agctattgac aaaaaaggac actccgcctg gtcacaagta   4080
cttcgggcta ccgcatcatt agctgcacat cgagtaccgg gaatctcaat tttggatttg   4140
tttcacccaa atttccgaga aatgtgctgt acaatggcaa ccacacctaa agtggaagat   4200
aagttcctgc gcacgattca aatcaatggt cggtttgaaa aagaaatgat tcacctagaa   4260
gatacaacat taagttgctt acccgctcca agtgaagcaa atatcgcagc tattcaatct   4320
cggtcaattc gatctgctgc ggcgcgttct ggacaatccc atgattgtgc atcccatagc   4380
catgaagaaa ataaggattc atgccctgaa aagctgaagc ttgattctgt gtccgtcgcc   4440
ataaatttcg acaatgatga ccgcattcag cttgggcacg cgggttttcg ggagatgtac   4500
aatacaagat atagcttgta cacaggggcg atggcaaagg gaattgcatc tgcagatctt   4560
gtcattgccg ctgggaaaga gggcatccta gcttcctatg gagctggagg actacctctt   4620
gctactgttc gaaagggaat agacaaaatt caacaagcct tgccaagtgg cccatatgct   4680
gtaaatctta ttcactctcc ctttgacggc aacttggagc agggaaacgt cgatttgttc   4740
ttggaaaaga acgtccgcgt ggcggaatgt tccgcgttta caacgctaac agtgccagta   4800
gtacactatc gtgctgcagg gcttgttcgg cgccaagatg gaagcatttt gatcaagaac   4860
cgaatcattg ctaaagtatc taggacagaa ctcgctgaga tgttccttcg tccggcacct   4920
caaatcatcc tcgaaaaact ggtagcagca gaaatcattt catctgacca agcgcgtatg   4980
gcagccaaag ttcccatggc ggacgacatc gcagtcgaag ccgactctgg tgggcacacg   5040
gataatcggc ctatgcacgt cattttgccc ctgataattc aactccgcaa tactatactt   5100
gcagagtatg gctgtgccac ggcttttcgt acccgtatag gcgctggagg aggcattggt   5160
tgtccttcag cggccctcgc agcctttgat atgggtgcga gttttgtcgt gactggaagc   5220
ataaatcaaa tttgccgcga ggcagggact tgcgatactg ttcgggagct acttgccaac   5280
tcaagctact cggacgtgac gatggcgcca gcagcagaca tgtttgacca aggtgtgaaa   5340
ctccaagtct taaaacgagg aacgatgttt ccaagcagag caaataaact ccggaagctc   5400
tttgtgaact acgaatctct agaaacactc ccgtcgaaag agttgaaata cctggaaaac   5460
atcatattca agcaagcagt agaccaggtg tgggaggaaa caaagcgctt ttactgtgaa   5520
aaactgaaca atccagataa aattgcaagg gccatgaaag atcctaaatt gaagatgtcg   5580
ctttgctttc ggtggtatct ctccaagagc tctgggtggg ccaacgcagg aattaaatct   5640
cgtgcactcg actaccagat ctggtgtggc ccggcaatgg gctcgttcaa caatttcgcc   5700
agcggcacat ccctcgattg gaaagtgact ggggttttcc ctggcgttgc ggaagtaaac   5760
atggccattt tagatggcgc gcgagaacta gctgctaaac gaaattaa                5808
```

<210> SEQ ID NO 22
<211> LENGTH: 1935

-continued

```
<212> TYPE: PRT
<213> ORGANISM: Thraustochytrium sp.
<220> FEATURE:
<221> NAME/KEY: misc_feature
<222> LOCATION: (1)..(1935)
<223> OTHER INFORMATION: Xaa = Asp, Gly, Ala, or Val

<400> SEQUENCE: 22

Met Gln Leu Pro Pro Ala His Ser Ala Asp Glu Asn Arg Ile Ala Val
1               5                   10                  15

Val Gly Met Ala Val Lys Tyr Ala Gly Cys Asp Asn Lys Glu Glu Phe
            20                  25                  30

Trp Lys Thr Leu Met Asn Gly Ser Ile Asn Thr Lys Ser Ile Ser Ala
        35                  40                  45

Ala Arg Leu Gly Ser Asn Lys Arg Asp Glu His Tyr Val Pro Glu Arg
    50                  55                  60

Ser Lys Tyr Ala Asp Thr Phe Cys Asn Glu Arg Tyr Gly Cys Ile Gln
65                  70                  75                  80

Gln Gly Thr Asp Asn Glu His Asp Leu Leu Leu Gly Leu Ala Gln Glu
                85                  90                  95

Ala Leu Ala Asp Ala Ala Gly Arg Met Glu Lys Gln Pro Ser Glu Ala
            100                 105                 110

Phe Asp Leu Glu Asn Thr Gly Ile Val Ser Gly Cys Leu Ser Phe Pro
        115                 120                 125

Met Asp Asn Leu Gln Gly Glu Leu Leu Asn Leu Tyr Gln Ser His Val
    130                 135                 140

Glu Lys Gln Leu Pro Pro Ser Ala Leu Val Glu Ala Val Lys Leu Trp
145                 150                 155                 160

Ser Glu Arg Gln Lys Ser Thr Lys Ala His Ala Gly Asp Lys Arg Arg
                165                 170                 175

Phe Ile Asp Pro Ala Ser Phe Val Ala Asp Lys Leu Asn Leu Gly Pro
            180                 185                 190

Leu His Tyr Ala Ile Asp Ala Ala Cys Ala Ser Ala Leu Tyr Val Leu
        195                 200                 205

Lys Leu Ala Gln Asp His Leu Val Ser Gly Ala Val Asp Met Met Leu
    210                 215                 220

Cys Gly Ala Thr Cys Phe Pro Glu Pro Phe Phe Ile Leu Ser Gly Phe
225                 230                 235                 240

Ser Thr Phe Gln Ala Met Pro Xaa Gly Ala Asp Gly Val Ser Leu Pro
                245                 250                 255

Leu His Lys Thr Ser Ala Gly Leu Thr Pro Gly Glu Gly Gly Ser Ile
            260                 265                 270

Met Val Leu Lys Arg Leu Lys Asp Ala Ile Arg Asp Gly Asn His Ile
        275                 280                 285

Tyr Gly Val Leu Leu Glu Ala Asn Leu Ser Asn Ala Gly Cys Gly Leu
    290                 295                 300

Pro Leu Ser Pro His Leu Pro Ser Glu Glu Ser Cys Ile Arg Asp Thr
305                 310                 315                 320

Tyr Arg Arg Ala Gly Val Ala Ala Asp Gln Ser Ile Gln Tyr Ile Glu
                325                 330                 335

Cys His Ala Thr Gly Thr Pro Arg Gly Asp Val Val Glu Ile Glu Ala
            340                 345                 350

Val Glu Arg Val Phe Lys Lys Asn Val Pro Arg Leu Gly Ser Thr Lys
        355                 360                 365

Gly Asn Phe Gly His Ser Leu Val Ala Ala Gly Phe Ala Gly Met Ala
```

-continued

```
    370                 375                 380

Lys Leu Leu Leu Ala Met Glu His Gly Val Ile Pro Pro Thr Pro Gly
385                 390                 395                 400

Leu Asp Ala Ser Asn Gln Ala Ser Glu His Val Val Thr Lys Ala Ile
                405                 410                 415

Thr Trp Pro Glu Thr His Gly Ala Pro Lys Arg Ala Gly Leu Ser Ala
            420                 425                 430

Phe Gly Phe Gly Gly Thr Asn Ala His Ala Leu Phe Glu Glu Phe Asn
        435                 440                 445

Ala Glu Gly Ile Ser Tyr Arg Pro Gly Lys Pro Pro Val Glu Ser Asn
    450                 455                 460

Thr Arg Pro Ser Val Val Ile Thr Gly Met Asp Cys Thr Phe Gly Ser
465                 470                 475                 480

Leu Glu Gly Ile Asp Ala Phe Glu Thr Ala Leu Tyr Glu Gly Arg Asp
                485                 490                 495

Ala Ala Arg Asp Leu Pro Ala Lys Arg Trp Arg Phe Leu Gly Glu Asp
            500                 505                 510

Leu Glu Phe Leu Arg Ala Ile Arg Leu Lys Glu Lys Pro Arg Gly Cys
        515                 520                 525

Phe Val Glu Ser Val Asp Val Asn Phe Arg Arg Leu Lys Thr Pro Leu
    530                 535                 540

Thr Pro Glu Asp Met Leu Arg Pro Gln Gln Leu Leu Ala Val Ser Thr
545                 550                 555                 560

Met Asp Arg Ala Ile Ile Asp Ala Gly Leu Lys Lys Gly Gln His Val
                565                 570                 575

Ala Val Leu Val Gly Leu Gly Thr Asp Leu Glu Leu Tyr Arg His Arg
            580                 585                 590

Ala Arg Val Ala Leu Lys Glu Val Leu His Pro Ser Leu Lys Ser Asp
        595                 600                 605

Thr Ala Ile Leu Gln Lys Ile Met Gln Tyr Val Asn Asp Ala Gly Thr
    610                 615                 620

Ser Thr Ser Tyr Thr Ser Tyr Ile Gly Asn Leu Val Ala Thr Arg Ile
625                 630                 635                 640

Ser Ser Gln Trp Gly Phe Thr Gly Pro Ser Phe Thr Val Thr Glu Gly
                645                 650                 655

Asn Asn Ser Val Tyr Arg Cys Ala Gln Leu Ala Lys Asp Met Leu Gln
            660                 665                 670

Val Asn Arg Val Asp Ala Val Val Ile Ala Gly Val Asp Leu Asn Gly
        675                 680                 685

Ser Ala Glu Ser Phe Phe Val Arg Ala Asn Arg Gln Lys Ile Ser Lys
    690                 695                 700

Leu Ser His Pro Cys Ala Ser Phe Asp Arg Asp Ala Asp Gly Phe Phe
705                 710                 715                 720

Ala Gly Glu Gly Cys Gly Ala Leu Val Phe Lys Arg Leu Glu Asp Cys
                725                 730                 735

Ala Pro Gln Glu Lys Ile Tyr Ala Ser Ile Asp Ser Ile Ala Ile Asp
            740                 745                 750

Lys Glu Pro Thr Ser Ser Ala Val Lys Ala Val Tyr Gln Ser Asp Ser
        755                 760                 765

Ser Leu Ser Asp Ile Glu Leu Leu Glu Ile Ser Gly Asp Ser Lys Arg
    770                 775                 780

Phe Ala Ala Phe Glu Gly Ala Val Glu Ile Gln Ser Ser Val Glu Ala
785                 790                 795                 800
```

```
Gln Leu Lys Gly Leu Ser Lys Val Leu Glu Pro Ala Lys Gly Gln Gly
                805                 810                 815

Val Ala Val Gly Ser Thr Arg Ala Thr Val Gly Asp Ile Gly Tyr Ala
            820                 825                 830

Thr Gly Ala Ala Ser Leu Ile Lys Thr Ala Leu Cys Leu Tyr Asn Arg
        835                 840                 845

Tyr Leu Pro Ala Leu Ala Asn Trp Ser Gly Pro Cys Glu Gln Ser Ala
    850                 855                 860

Trp Gly Ser Asn Met Phe Val Cys His Glu Thr Arg Pro Trp Met Lys
865                 870                 875                 880

Asn Gln Asn Glu Lys Arg Cys Ala Leu Ile Ser Gly Thr Asp Pro Ser
                885                 890                 895

His Thr Cys Phe Ser Leu Val Leu Ser Asp Thr Gly Cys Tyr Glu Glu
            900                 905                 910

His Asn Arg Thr Cys Phe Asp Val Gln Ala Pro Gln Leu Val Leu Ile
        915                 920                 925

His Gly Phe Asp Gly Lys Thr Ile Val Arg Arg Leu Glu Gly Tyr Leu
    930                 935                 940

Leu Glu Leu Val Glu Gly His Ala Ser Pro Ser Glu Tyr Phe His Lys
945                 950                 955                 960

Leu Ile Gly Gln Ser Leu Leu Glu Asn Ser Lys Glu Ser Lys Leu Thr
                965                 970                 975

Leu Ser Leu Val Cys Asn Pro Asn Gln Leu Gln Lys Glu Leu Met Leu
            980                 985                 990

Ala Ile Lys Gly Val Gln Arg Ser  Met Leu Thr Gly Lys  Asp Trp Val
        995                 1000                 1005

Ser Pro  Ser Gly Ser Cys Phe  Ala Pro Asn Pro Leu  Ser Ser Ala
    1010                 1015                 1020

Lys Val  Ala Phe Met Tyr Gly  Glu Gly Arg Ser Pro  Tyr Cys Gly
    1025                 1030                 1035

Val Gly  Leu Gly Leu His Arg  Leu Trp Pro Gly Leu  His Glu Asn
    1040                 1045                 1050

Val Asn  Asn Lys Thr Val Asp  Leu Trp Thr Glu Gly  Asp Gly Trp
    1055                 1060                 1065

Leu Tyr  Pro Arg Thr Leu Thr  Arg Glu Glu His Thr  Lys Ala Ile
    1070                 1075                 1080

Glu Ser  Phe Asn Ala Asn Gln  Ile Glu Met Phe Arg  Ala Gly Ile
    1085                 1090                 1095

Phe Ile  Ser Met Cys Gln Thr  Asp Tyr Val Met Asn  Val Leu Gly
    1100                 1105                 1110

Val Gln  Pro Lys Ala Gly Phe  Gly Leu Ser Leu Gly  Glu Ile Ser
    1115                 1120                 1125

Met Leu  Phe Ala Met Ser Lys  Glu Asn Cys Arg Gln  Ser Gln Glu
    1130                 1135                 1140

Met Thr  Asn Arg Leu Arg Gly  Ser Pro Val Trp Ser  Asn Glu Leu
    1145                 1150                 1155

Ala Ile  Asn Phe Asn Ala Ile  Arg Lys Leu Trp Lys  Ile Pro Arg
    1160                 1165                 1170

Gly Ala  Pro Leu Glu Ser Phe  Trp Gln Gly Tyr Leu  Val His Gly
    1175                 1180                 1185

Thr Arg  Glu Glu Val Glu His  Ala Ile Gly Leu Ser  Glu Pro Tyr
    1190                 1195                 1200
```

-continued

```
Val Arg  Leu Leu Ile Val Asn  Asp Ser Arg Ser Ala  Leu Ile Ala
    1205                 1210                 1215

Gly Lys  Pro Asp Ala Cys Gln  Ala Val Ile Ser Arg  Leu Asn Ser
    1220                 1225                 1230

Lys Phe  Pro Ser Leu Pro Val  Lys Gln Gly Met Ile  Gly His Cys
    1235                 1240                 1245

Pro Glu  Val Arg Ala Phe Ile  Lys Asp Ile Gly Tyr  Ile His Glu
    1250                 1255                 1260

Thr Leu  Arg Ile Ser Asn Asp  Tyr Ser Asp Cys Gln  Leu Phe Ser
    1265                 1270                 1275

Ala Val  Thr Lys Gly Ala Leu  Asp Ser Ser Thr Met  Glu Ile Lys
    1280                 1285                 1290

His Phe  Val Gly Glu Val Tyr  Ser Arg Ile Ala Asp  Phe Pro Gln
    1295                 1300                 1305

Ile Val  Asn Thr Val His Ser  Ala Gly Tyr Asp Val  Phe Leu Glu
    1310                 1315                 1320

Leu Gly  Cys Asp Ala Ser Arg  Ser Ala Ala Val Gln  Asn Ile Leu
    1325                 1330                 1335

Gly Gly  Gln Gly Lys Phe Leu  Ser Thr Ala Ile Asp  Lys Lys Gly
    1340                 1345                 1350

His Ser  Ala Trp Ser Gln Val  Leu Arg Ala Thr Ala  Ser Leu Ala
    1355                 1360                 1365

Ala His  Arg Val Pro Gly Ile  Ser Ile Leu Asp Leu  Phe His Pro
    1370                 1375                 1380

Asn Phe  Arg Glu Met Cys Cys  Thr Met Ala Thr Thr  Pro Lys Val
    1385                 1390                 1395

Glu Asp  Lys Phe Leu Arg Thr  Ile Gln Ile Asn Gly  Arg Phe Glu
    1400                 1405                 1410

Lys Glu  Met Ile His Leu Glu  Asp Thr Thr Leu Ser  Cys Leu Pro
    1415                 1420                 1425

Ala Pro  Ser Glu Ala Asn Ile  Ala Ala Ile Gln Ser  Arg Ser Ile
    1430                 1435                 1440

Arg Ser  Ala Ala Ala Arg Ser  Gly Gln Ser His Asp  Cys Ala Ser
    1445                 1450                 1455

His Ser  His Glu Glu Asn Lys  Asp Ser Cys Pro Glu  Lys Leu Lys
    1460                 1465                 1470

Leu Asp  Ser Val Ser Val Ala  Ile Asn Phe Asp Asn  Asp Asp Arg
    1475                 1480                 1485

Ile Gln  Leu Gly His Ala Gly  Phe Arg Glu Met Tyr  Asn Thr Arg
    1490                 1495                 1500

Tyr Ser  Leu Tyr Thr Gly Ala  Met Ala Lys Gly Ile  Ala Ser Ala
    1505                 1510                 1515

Asp Leu  Val Ile Ala Ala Gly  Lys Glu Gly Ile Leu  Ala Ser Tyr
    1520                 1525                 1530

Gly Ala  Gly Gly Leu Pro Leu  Ala Thr Val Arg Lys  Gly Ile Asp
    1535                 1540                 1545

Lys Ile  Gln Gln Ala Leu Pro  Ser Gly Pro Tyr Ala  Val Asn Leu
    1550                 1555                 1560

Ile His  Ser Pro Phe Asp Gly  Asn Leu Glu Gln Gly  Asn Val Asp
    1565                 1570                 1575

Leu Phe  Leu Glu Lys Asn Val  Arg Val Ala Glu Cys  Ser Ala Phe
    1580                 1585                 1590

Thr Thr  Leu Thr Val Pro Val  Val His Tyr Arg Ala  Ala Gly Leu
```

-continued

```
    1595                1600                1605

Val Arg  Arg Gln Asp Gly Ser  Ile Leu Ile Lys Asn  Arg Ile Ile
    1610                1615                1620

Ala Lys  Val Ser Arg Thr Glu  Leu Ala Glu Met Phe  Leu Arg Pro
    1625                1630                1635

Ala Pro  Gln Ile Ile Leu Glu  Lys Leu Val Ala Ala  Glu Ile Ile
    1640                1645                1650

Ser Ser  Asp Gln Ala Arg Met  Ala Ala Lys Val Pro  Met Ala Asp
    1655                1660                1665

Asp Ile  Ala Val Glu Ala Asp  Ser Gly Gly His Thr  Asp Asn Arg
    1670                1675                1680

Pro Met  His Val Ile Leu Pro  Leu Ile Ile Gln Leu  Arg Asn Thr
    1685                1690                1695

Ile Leu  Ala Glu Tyr Gly Cys  Ala Thr Ala Phe Arg  Thr Arg Ile
    1700                1705                1710

Gly Ala  Gly Gly Gly Ile Gly  Cys Pro Ser Ala Ala  Leu Ala Ala
    1715                1720                1725

Phe Asp  Met Gly Ala Ser Phe  Val Val Thr Gly Ser  Ile Asn Gln
    1730                1735                1740

Ile Cys  Arg Glu Ala Gly Thr  Cys Asp Thr Val Arg  Glu Leu Leu
    1745                1750                1755

Ala Asn  Ser Ser Tyr Ser Asp  Val Thr Met Ala Pro  Ala Ala Asp
    1760                1765                1770

Met Phe  Asp Gln Gly Val Lys  Leu Gln Val Leu Lys  Arg Gly Thr
    1775                1780                1785

Met Phe  Pro Ser Arg Ala Asn  Lys Leu Arg Lys Leu  Phe Val Asn
    1790                1795                1800

Tyr Glu  Ser Leu Glu Thr Leu  Pro Ser Lys Glu Leu  Lys Tyr Leu
    1805                1810                1815

Glu Asn  Ile Ile Phe Lys Gln  Ala Val Asp Gln Val  Trp Glu Glu
    1820                1825                1830

Thr Lys  Arg Phe Tyr Cys Glu  Lys Leu Asn Asn Pro  Asp Lys Ile
    1835                1840                1845

Ala Arg  Ala Met Lys Asp Pro  Lys Leu Lys Met Ser  Leu Cys Phe
    1850                1855                1860

Arg Trp  Tyr Leu Ser Lys Ser  Ser Gly Trp Ala Asn  Ala Gly Ile
    1865                1870                1875

Lys Ser  Arg Ala Leu Asp Tyr  Gln Ile Trp Cys Gly  Pro Ala Met
    1880                1885                1890

Gly Ser  Phe Asn Asn Phe Ala  Ser Gly Thr Ser Leu  Asp Trp Lys
    1895                1900                1905

Val Thr  Gly Val Phe Pro Gly  Val Ala Glu Val Asn  Met Ala Ile
    1910                1915                1920

Leu Asp  Gly Ala Arg Glu Leu  Ala Ala Lys Arg Asn
    1925                1930                1935
```

<210> SEQ ID NO 23
<211> LENGTH: 4410
<212> TYPE: DNA
<213> ORGANISM: Thraustochytrium sp.

<400> SEQUENCE: 23

```
atgggcccgc gagtggcgtc aggcaaggtg ccggcttggg agatgagcaa gtccgagctg      60

tgtgatgacc gcacggtagt ctttgactat gaggagctgc tggagttcgc tgagggcgat     120
```

-continued

```
atcagtaagg tttttgggcc ggagttcaaa gtggtggacg ggtttaggcg cagggtgagg    180
ttgcccgctc gagagtacct gctggtgacc cgggttacgc tgatggatgc cgaggtgggc    240
aactttcgag tgggagcacg tatggtgaca gagtatgacg tacctgtgaa cggagagctc    300
tcggaagggg gagatgtgcc gtgggctgtg ttggtggaag ccgggcagtg cgacttgctg    360
ctaatttctt acatgggcat cgatttccag tgcaaaggag agcgggtcta ccggctgctg    420
aacaccacct tgacgttttt tggcgtcgcg aaagaagggg aaacgcttgt gtacgatatt    480
cgcgtcacgg gtttcgccaa gaggccggac ggagatatct ccatgttctt tttcgaatat    540
gattgctact gcaatggcaa gcttctcatc gaaatgcgag atggctctgc aggcttcttc    600
acggacgaag agctcgctgc cggcaaagga gtggtcgtca ctcgtgcaca gcaaaacatg    660
cgggacaaaa ttgtacggca gtccattgag ccttttgcac tggcggcttg cacgcacaaa    720
acgactctga acgagagtga catgcagtcc cttgtggagc gaaactgggc aaacgttttt    780
ggcaccagta acaagatggc ggagctcaac tataaaattt gcgccaggaa aatgctcatg    840
atcgacaggg ttacccacat tgaccaccac ggtggggcgt atggcctcgg actacttgtt    900
ggagagaaga tcttggatcg aaaccattgg tactttcctt gtcactttgt caatgatcaa    960
gtcatggcag ggtcactggt cagcgatggt tgcagccagc tcttaaaact ctatatgatc   1020
tggcttggcc tccacctgaa aatggaggaa tttgattttc tcccagttag cggccacaaa   1080
aacaaggtgc gatgcagggg acaaatttca ccgcataaag gcaagcttgt ctacgtcatg   1140
gaaatcaaaa agatgggtta cgatcaagca tctggaagcc catacgccat cgcggacgtt   1200
gatatcattg acgtcaacga agagctgggt caaagttttg acatcaacga ccttgcgagc   1260
tacggaaaag gtgacctgag caaaaaaatc gtggttgact tcaaaggaat tgctttgcag   1320
ctcaaaggcc gcgctttttc acgcatgagt tccagctcgt ccttgaacga aggatggcaa   1380
tgtgttccaa aaccaagcca gagaatggaa cacgaacagc cccctgctca ctgccttgca   1440
agcgaccccg aagccccttc aactgtgacc tggcacccaa tgtcaaagct tcctggcaac   1500
cctacgccgt tcttctcccc ttcatcttac cctccgaggg caatttgctt catccctttc   1560
ccgggcaatc cccttgacaa caactgcaag gctggagaaa tgcccctgaa ctggtacaac   1620
atgtcagagt tcatgtgtgg caaggtttct aactgcttgg gcccagaatt cgcacgcttt   1680
gacaagtcga acaccagccg gagccctgct tttgacttgg ctctggtgac ccgagttgtt   1740
gaagtcacaa acatggaaca cggcaagttt ctaaacgttg attgcaatcc aagcaaaggc   1800
acaatggtgg gggagtttga ctgtccccaa gacgcgtggt tctttgatgg ttcgtgcaac   1860
gacggccata tgccgtattc cattatcatg gaaatcggac tgcaaacctc aggtgttctc   1920
acctcggtgt tgaaggcacc gctgactatg gacaaggatg acattctctt tcgaaacctc   1980
gatgcaagtg ctgaaatggt gcgtccagac gtggatgttc gcggcaaaac gattcgaaac   2040
gtgaccaagt gtaccggcta tgcaatgttg ggaaagatgg ggattcaccg gttcacgttt   2100
gagttgagcg ttgacggcgt ggtattttat aaaggatcca cttcctttgg atggttcact   2160
cccgaggtgt ttgctcagca agctggactc gacaacggga aaaagacgga gccctggtgc   2220
aagactaaca acacctcggt tcgaagagtt gaaatcgcat ccgccaaagg aaaagagcag   2280
ctgactgaga agcttcccga cgcaactaat gctcaagttc ttcggcgttc agagcagtgt   2340
gaatacctcg attacctcaa tattgcccct gactctgggc tgcatgggaa gggctacgcc   2400
cacggacaca aagacgttaa cccgcaagac tggttcttct cttgccactt ttggttcgat   2460
```

-continued

```
cctgtaatgc caggatcttt aggaattgaa tcaatgttcc agcttatcga ggcctttgcg   2520

gtggaccaaa acattcctgg agagtacaac gtatccaatc cgacctttgc ccatgcacca   2580

ggcaaaacgg cgtggaaata ccgaggccag ctcacaccaa agaaccgtgc gatggactgc   2640

gaggtgcata tcgtttcaat taccgcctcc cccgagaacg ggggctacgt tgacatcgtg   2700

gccgatggag cgctttgggt agatggactt cgcgtgtacg aagccaaaga gcttcgagtt   2760

cgtgtcgttt cggcaaaacc tcaagcaatt ccggatgtac aacaacagcc acctagcgca   2820

aaggcggacc cggggaaaac aggagttgca ctttcgccca ctcagctacg cgacgtcctg   2880

cttgaagtgg acaatccatt gtatcttggt gtagagaact ccaatttggt gcagtttgag   2940

tcgaaacctg caacttcttc acgtatcgtt tcgatcaaac cgtgctcgat tagtgacctt   3000

ggcgataagt cttttatgga aacgtacaac gtgtcagcac ctctgtatac tggagcaatg   3060

gccaagggca ttgcatccgc cgacttggtc attgctgctg ggaaacgcaa gatacttgga   3120

tcgtttggtg cgggagggct gcctatttcc atagtccgtg aagcactgga gaaaattcaa   3180

caacacctgc cccacggccc ctacgctgtt aacctcattc actcgccttt cgacagcaac   3240

ttggaaaagg gcaacgttga cctctttctc gagatgggcg tgacagtggt agaatgcagc   3300

gcgttcatgg aactcacggc ccaggttgtc cggtaccgcg cgtctggtct aagcaaaagt   3360

gcggacggtt cgattcgcat tgctcaccgt attattggca aggtttccag aaccgagctg   3420

gcagaaatgt ttattcgtcc agcaccacag cacctcctcc aaaaactcgt agcctccggc   3480

gagctgacag ctgagcaagc cgagcttgca acacaggttc cggtggcgga tgacattgcg   3540

gtcgaagccg actcgggggg gcataccgac aacaggccta ttcacgtcat tcttcctcta   3600

atcatcaacc tacgcaaccg tttgcataaa gagcttgact acccttcgca tctccgggta   3660

cgtgtgggtg ctggtggtgg tattggatgt cctcaagccg ctcttgcagc atttcaaatg   3720

ggggcagcgt ttttaatcac tggaacggtg aaccagcttg ctcgtgaaag tggcacttgt   3780

gacaacgtcc ggttacagct ctcaaaggcc acgtatagcg acgtgtgtat ggctcctgct   3840

gccgatatgt ttgaccaagg cgtggagctg caagtattga agaaaggcac gctgttccca   3900

agtcgtgcta agaagctgta cgagctgttc tgcaagtatg actcgtttga ggcaatgccg   3960

gctgaagaat tgcaacgggt tgaaaagcgg atttttcaaa agtcgcttgc tgaagtttgg   4020

caggagacca gtgactttta cattcatcgt atcaagaacc ctgagaaaat caatcgtgct   4080

gcaagcgatg gcaaactgaa aatgtcgctt tgctttcgct ggtaccttgg gctttcctca   4140

ttttgggcca actctggggc acaagatcgc gtcatggact atcaaatttg gtgtggccct   4200

gctattggcg ctttcaatga ttttaccaag ggcacgtacc ttgacgtgac tgttgcaaag   4260

agttaccctt gtgtggcaca gatcaatttg caaattttgc aaggagctgc gtatctgaaa   4320

cgccttggtg tcattcgttt tgaccgcatg ctgctgcagg ccgtcgatat cgacgatcct   4380

gtatttactt acgtgccgac ccagccactt                                   4410
```

```
<210> SEQ ID NO 24
<211> LENGTH: 1470
<212> TYPE: PRT
<213> ORGANISM: Thraustochytrium sp.

<400> SEQUENCE: 24

Met Gly Pro Arg Val Ala Ser Gly Lys Val Pro Ala Trp Glu Met Ser
1               5                   10                  15

Lys Ser Glu Leu Cys Asp Asp Arg Thr Val Val Phe Asp Tyr Glu Glu
            20                  25                  30
```

-continued

```
Leu Leu Glu Phe Ala Glu Gly Asp Ile Ser Lys Val Phe Gly Pro Glu
        35                  40                  45

Phe Lys Val Val Asp Gly Phe Arg Arg Arg Val Arg Leu Pro Ala Arg
    50                  55                  60

Glu Tyr Leu Leu Val Thr Arg Val Thr Leu Met Asp Ala Glu Val Gly
65                  70                  75                  80

Asn Phe Arg Val Gly Ala Arg Met Val Thr Glu Tyr Asp Val Pro Val
                85                  90                  95

Asn Gly Glu Leu Ser Glu Gly Gly Asp Val Pro Trp Ala Val Leu Val
            100                 105                 110

Glu Ala Gly Gln Cys Asp Leu Leu Leu Ile Ser Tyr Met Gly Ile Asp
        115                 120                 125

Phe Gln Cys Lys Gly Glu Arg Val Tyr Arg Leu Leu Asn Thr Thr Leu
    130                 135                 140

Thr Phe Phe Gly Val Ala Lys Glu Gly Glu Thr Leu Val Tyr Asp Ile
145                 150                 155                 160

Arg Val Thr Gly Phe Ala Lys Arg Pro Asp Gly Asp Ile Ser Met Phe
                165                 170                 175

Phe Phe Glu Tyr Asp Cys Tyr Cys Asn Gly Lys Leu Leu Ile Glu Met
            180                 185                 190

Arg Asp Gly Ser Ala Gly Phe Phe Thr Asp Glu Glu Leu Ala Ala Gly
        195                 200                 205

Lys Gly Val Val Val Thr Arg Ala Gln Gln Asn Met Arg Asp Lys Ile
    210                 215                 220

Val Arg Gln Ser Ile Glu Pro Phe Ala Leu Ala Ala Cys Thr His Lys
225                 230                 235                 240

Thr Thr Leu Asn Glu Ser Asp Met Gln Ser Leu Val Glu Arg Asn Trp
                245                 250                 255

Ala Asn Val Phe Gly Thr Ser Asn Lys Met Ala Glu Leu Asn Tyr Lys
            260                 265                 270

Ile Cys Ala Arg Lys Met Leu Met Ile Asp Arg Val Thr His Ile Asp
        275                 280                 285

His His Gly Gly Ala Tyr Gly Leu Gly Leu Leu Val Gly Glu Lys Ile
    290                 295                 300

Leu Asp Arg Asn His Trp Tyr Phe Pro Cys His Phe Val Asn Asp Gln
305                 310                 315                 320

Val Met Ala Gly Ser Leu Val Ser Asp Gly Cys Ser Gln Leu Leu Lys
                325                 330                 335

Leu Tyr Met Ile Trp Leu Gly Leu His Leu Lys Met Glu Glu Phe Asp
            340                 345                 350

Phe Leu Pro Val Ser Gly His Lys Asn Lys Val Arg Cys Arg Gly Gln
        355                 360                 365

Ile Ser Pro His Lys Gly Lys Leu Val Tyr Val Met Glu Ile Lys Lys
    370                 375                 380

Met Gly Tyr Asp Gln Ala Ser Gly Ser Pro Tyr Ala Ile Ala Asp Val
385                 390                 395                 400

Asp Ile Ile Asp Val Asn Glu Glu Leu Gly Gln Ser Phe Asp Ile Asn
                405                 410                 415

Asp Leu Ala Ser Tyr Gly Lys Gly Asp Leu Ser Lys Lys Ile Val Val
            420                 425                 430

Asp Phe Lys Gly Ile Ala Leu Gln Leu Lys Gly Arg Ala Phe Ser Arg
        435                 440                 445
```

-continued

```
Met Ser Ser Ser Ser Ser Leu Asn Glu Gly Trp Gln Cys Val Pro Lys
    450                 455                 460

Pro Ser Gln Arg Met Glu His Glu Gln Pro Pro Ala His Cys Leu Ala
465                 470                 475                 480

Ser Asp Pro Glu Ala Pro Ser Thr Val Thr Trp His Pro Met Ser Lys
                485                 490                 495

Leu Pro Gly Asn Pro Thr Pro Phe Phe Ser Pro Ser Ser Tyr Pro Pro
            500                 505                 510

Arg Ala Ile Cys Phe Ile Pro Phe Pro Gly Asn Pro Leu Asp Asn Asn
        515                 520                 525

Cys Lys Ala Gly Glu Met Pro Leu Asn Trp Tyr Asn Met Ser Glu Phe
    530                 535                 540

Met Cys Gly Lys Val Ser Asn Cys Leu Gly Pro Glu Phe Ala Arg Phe
545                 550                 555                 560

Asp Lys Ser Asn Thr Ser Arg Ser Pro Ala Phe Asp Leu Ala Leu Val
                565                 570                 575

Thr Arg Val Val Glu Val Thr Asn Met Glu His Gly Lys Phe Leu Asn
            580                 585                 590

Val Asp Cys Asn Pro Ser Lys Gly Thr Met Val Gly Glu Phe Asp Cys
        595                 600                 605

Pro Gln Asp Ala Trp Phe Phe Asp Gly Ser Cys Asn Asp Gly His Met
    610                 615                 620

Pro Tyr Ser Ile Ile Met Glu Ile Gly Leu Gln Thr Ser Gly Val Leu
625                 630                 635                 640

Thr Ser Val Leu Lys Ala Pro Leu Thr Met Asp Lys Asp Asp Ile Leu
                645                 650                 655

Phe Arg Asn Leu Asp Ala Ser Ala Glu Met Val Arg Pro Asp Val Asp
            660                 665                 670

Val Arg Gly Lys Thr Ile Arg Asn Val Thr Lys Cys Thr Gly Tyr Ala
        675                 680                 685

Met Leu Gly Lys Met Gly Ile His Arg Phe Thr Phe Glu Leu Ser Val
    690                 695                 700

Asp Gly Val Val Phe Tyr Lys Gly Ser Thr Ser Phe Gly Trp Phe Thr
705                 710                 715                 720

Pro Glu Val Phe Ala Gln Gln Ala Gly Leu Asp Asn Gly Lys Lys Thr
                725                 730                 735

Glu Pro Trp Cys Lys Thr Asn Asn Thr Ser Val Arg Arg Val Glu Ile
            740                 745                 750

Ala Ser Ala Lys Gly Lys Glu Gln Leu Thr Glu Lys Leu Pro Asp Ala
        755                 760                 765

Thr Asn Ala Gln Val Leu Arg Arg Ser Glu Gln Cys Glu Tyr Leu Asp
    770                 775                 780

Tyr Leu Asn Ile Ala Pro Asp Ser Gly Leu His Gly Lys Gly Tyr Ala
785                 790                 795                 800

His Gly His Lys Asp Val Asn Pro Gln Asp Trp Phe Phe Ser Cys His
                805                 810                 815

Phe Trp Phe Asp Pro Val Met Pro Gly Ser Leu Gly Ile Glu Ser Met
            820                 825                 830

Phe Gln Leu Ile Glu Ala Phe Ala Val Asp Gln Asn Ile Pro Gly Glu
        835                 840                 845

Tyr Asn Val Ser Asn Pro Thr Phe Ala His Ala Pro Gly Lys Thr Ala
    850                 855                 860

Trp Lys Tyr Arg Gly Gln Leu Thr Pro Lys Asn Arg Ala Met Asp Cys
```

-continued

```
865                 870                 875                 880

Glu Val His Ile Val Ser Ile Thr Ala Ser Pro Glu Asn Gly Gly Tyr
                885                 890                 895

Val Asp Ile Val Ala Asp Gly Ala Leu Trp Val Asp Gly Leu Arg Val
            900                 905                 910

Tyr Glu Ala Lys Glu Leu Arg Val Arg Val Val Ser Ala Lys Pro Gln
        915                 920                 925

Ala Ile Pro Asp Val Gln Gln Gln Pro Pro Ser Ala Lys Ala Asp Pro
    930                 935                 940

Gly Lys Thr Gly Val Ala Leu Ser Pro Thr Gln Leu Arg Asp Val Leu
945                 950                 955                 960

Leu Glu Val Asp Asn Pro Leu Tyr Leu Gly Val Glu Asn Ser Asn Leu
                965                 970                 975

Val Gln Phe Glu Ser Lys Pro Ala Thr Ser Ser Arg Ile Val Ser Ile
            980                 985                 990

Lys Pro Cys Ser Ile Ser Asp Leu  Gly Asp Lys Ser Phe  Met Glu Thr
        995                 1000                1005

Tyr Asn  Val Ser Ala Pro Leu  Tyr Thr Gly Ala Met  Ala Lys Gly
    1010                1015                1020

Ile Ala  Ser Ala Asp Leu Val  Ile Ala Ala Gly Lys  Arg Lys Ile
    1025                1030                1035

Leu Gly  Ser Phe Gly Ala Gly  Gly Leu Pro Ile Ser  Ile Val Arg
    1040                1045                1050

Glu Ala  Leu Glu Lys Ile Gln  Gln His Leu Pro His  Gly Pro Tyr
    1055                1060                1065

Ala Val  Asn Leu Ile His Ser  Pro Phe Asp Ser Asn  Leu Glu Lys
    1070                1075                1080

Gly Asn  Val Asp Leu Phe Leu  Glu Met Gly Val Thr  Val Val Glu
    1085                1090                1095

Cys Ser  Ala Phe Met Glu Leu  Thr Ala Gln Val Val  Arg Tyr Arg
    1100                1105                1110

Ala Ser  Gly Leu Ser Lys Ser  Ala Asp Gly Ser Ile  Arg Ile Ala
    1115                1120                1125

His Arg  Ile Ile Gly Lys Val  Ser Arg Thr Glu Leu  Ala Glu Met
    1130                1135                1140

Phe Ile  Arg Pro Ala Pro Gln  His Leu Leu Gln Lys  Leu Val Ala
    1145                1150                1155

Ser Gly  Glu Leu Thr Ala Glu  Gln Ala Glu Leu Ala  Thr Gln Val
    1160                1165                1170

Pro Val  Ala Asp Asp Ile Ala  Val Glu Ala Asp Ser  Gly Gly His
    1175                1180                1185

Thr Asp  Asn Arg Pro Ile His  Val Ile Leu Pro Leu  Ile Ile Asn
    1190                1195                1200

Leu Arg  Asn Arg Leu His Lys  Glu Leu Asp Tyr Pro  Ser His Leu
    1205                1210                1215

Arg Val  Arg Val Gly Ala Gly  Gly Gly Ile Gly Cys  Pro Gln Ala
    1220                1225                1230

Ala Leu  Ala Ala Phe Gln Met  Gly Ala Ala Phe Leu  Ile Thr Gly
    1235                1240                1245

Thr Val  Asn Gln Leu Ala Arg  Glu Ser Gly Thr Cys  Asp Asn Val
    1250                1255                1260

Arg Leu  Gln Leu Ser Lys Ala  Thr Tyr Ser Asp Val  Cys Met Ala
    1265                1270                1275
```

```
Pro Ala  Ala Asp Met Phe Asp  Gln Gly Val Glu Leu  Gln Val Leu
    1280                 1285                 1290

Lys Lys  Gly Thr Leu Phe Pro  Ser Arg Ala Lys Lys  Leu Tyr Glu
    1295                 1300                 1305

Leu Phe  Cys Lys Tyr Asp Ser  Phe Glu Ala Met Pro  Ala Glu Glu
    1310                 1315                 1320

Leu Gln  Arg Val Glu Lys Arg  Ile Phe Gln Lys Ser  Leu Ala Glu
    1325                 1330                 1335

Val Trp  Gln Glu Thr Ser Asp  Phe Tyr Ile His Arg  Ile Lys Asn
    1340                 1345                 1350

Pro Glu  Lys Ile Asn Arg Ala  Ala Ser Asp Gly Lys  Leu Lys Met
    1355                 1360                 1365

Ser Leu  Cys Phe Arg Trp Tyr  Leu Gly Leu Ser Ser  Phe Trp Ala
    1370                 1375                 1380

Asn Ser  Gly Ala Gln Asp Arg  Val Met Asp Tyr Gln  Ile Trp Cys
    1385                 1390                 1395

Gly Pro  Ala Ile Gly Ala Phe  Asn Asp Phe Thr Lys  Gly Thr Tyr
    1400                 1405                 1410

Leu Asp  Val Thr Val Ala Lys  Ser Tyr Pro Cys Val  Ala Gln Ile
    1415                 1420                 1425

Asn Leu  Gln Ile Leu Gln Gly  Ala Ala Tyr Leu Lys  Arg Leu Gly
    1430                 1435                 1440

Val Ile  Arg Phe Asp Arg Met  Leu Leu Gln Ala Val  Asp Ile Asp
    1445                 1450                 1455

Asp Pro  Val Phe Thr Tyr Val  Pro Thr Gln Pro Leu
    1460                 1465                 1470


<210> SEQ ID NO 25
<211> LENGTH: 20
<212> TYPE: DNA
<213> ORGANISM: Artificial sequence
<220> FEATURE:
<223> OTHER INFORMATION: primer

<400> SEQUENCE: 25

ggyatgmtgr ttggtgaagg                                                  20


<210> SEQ ID NO 26
<211> LENGTH: 22
<212> TYPE: DNA
<213> ORGANISM: Artificial sequence
<220> FEATURE:
<223> OTHER INFORMATION: primer

<400> SEQUENCE: 26

trttsasrta ytgygaacct tg                                               22


<210> SEQ ID NO 27
<211> LENGTH: 20
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: n = a, c, t, or g

<400> SEQUENCE: 27

atgkcngaag gttgtggcca                                                  20
```

<210> SEQ ID NO 28
<211> LENGTH: 23
<212> TYPE: DNA
<213> ORGANISM: Artificial sequence
<220> FEATURE:
<223> OTHER INFORMATION: primer

<400> SEQUENCE: 28
ccwgaratra agccrttdgg ttg 23

<210> SEQ ID NO 29
<211> LENGTH: 192
<212> TYPE: DNA
<213> ORGANISM: Schizochytrium sp.
<220> FEATURE:
<221> NAME/KEY: misc_feature
<222> LOCATION: (1)..(7)
<223> OTHER INFORMATION: BspHI restriction site
<220> FEATURE:
<221> NAME/KEY: misc_feature
<222> LOCATION: (188)..(192)
<223> OTHER INFORMATION: SacII restriction site

<400> SEQUENCE: 29
tcatgaagcc ggttgctccg aagttctacg cgcgtctcaa cattgacgag caggacgaga 60
cccgtgatcc gatcctcaac aaggacaacg cgccgtcttc cagctctagc tcctcttcca 120
gctcttccag ctcttccagc ccgtcgccag ctccgtccgc cccagtgcaa aagaaggctg 180
ctccggccgc gg 192

<210> SEQ ID NO 30
<211> LENGTH: 30
<212> TYPE: DNA
<213> ORGANISM: Artificial sequence
<220> FEATURE:
<223> OTHER INFORMATION: primer

<400> SEQUENCE: 30
cggggtaccc gggagccgcc ttggctttgt 30

<210> SEQ ID NO 31
<211> LENGTH: 35
<212> TYPE: DNA
<213> ORGANISM: Artificial sequence
<220> FEATURE:
<223> OTHER INFORMATION: primer

<400> SEQUENCE: 31
aaactgcagc ccgggtccag ctggcaggca ccctg 35

<210> SEQ ID NO 32
<211> LENGTH: 237
<212> TYPE: PRT
<213> ORGANISM: Nostoc sp.

<400> SEQUENCE: 32

Leu Leu Gln His Thr Trp Leu Pro Lys Pro Pro Asn Leu Thr Leu Leu
1 5 10 15

Ser Asp Glu Val His Leu Trp Arg Ile Pro Leu Asp Gln Pro Glu Ser
20 25 30

Gln Leu Gln Asp Leu Ala Ala Thr Leu Ser Ser Asp Glu Leu Ala Arg
35 40 45

Ala Asn Arg Phe Tyr Phe Pro Glu His Arg Arg Arg Phe Thr Ala Gly

-continued

```
    50                  55                  60

Arg Gly Ile Leu Arg Ser Ile Leu Gly Gly Tyr Leu Gly Val Glu Pro
65                  70                  75                  80

Gly Gln Val Lys Phe Asp Tyr Glu Ser Arg Gly Lys Pro Ile Leu Gly
                85                  90                  95

Asp Arg Phe Ala Glu Ser Gly Leu Leu Phe Asn Leu Ser His Ser Gln
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp His Tyr
225                 230                 235
```

<210> SEQ ID NO 33
<211> LENGTH: 23
<212> TYPE: DNA
<213> ORGANISM: Sh. japonica

<400> SEQUENCE: 33
ctgaacactg gagactcaaa atg 23

<210> SEQ ID NO 34
<211> LENGTH: 23
<212> TYPE: DNA
<213> ORGANISM: Sh. japonica

<400> SEQUENCE: 34
gctgacttgc aggagtctgt gtg 23

<210> SEQ ID NO 35
<211> LENGTH: 23
<212> TYPE: DNA
<213> ORGANISM: Sh. japonica

<400> SEQUENCE: 35
caattagaag gagaacaatc ttg 23

<210> SEQ ID NO 36
<211> LENGTH: 23
<212> TYPE: DNA
<213> ORGANISM: Sh. japonica

<400> SEQUENCE: 36
agaggcataa aggaataata atg 23

<210> SEQ ID NO 37
<211> LENGTH: 23
<212> TYPE: DNA

<213> ORGANISM: Sh. japonica

<400> SEQUENCE: 37
gcgacctaga acaagcgaca atg 23

<210> SEQ ID NO 38
<211> LENGTH: 23
<212> TYPE: DNA
<213> ORGANISM: Sh. olleyana

<400> SEQUENCE: 38
ctgaacactg gagactcaaa atg 23

<210> SEQ ID NO 39
<211> LENGTH: 23
<212> TYPE: DNA
<213> ORGANISM: Sh. olleyana

<400> SEQUENCE: 39
gctgatttgc aggagtctgt gtg 23

<210> SEQ ID NO 40
<211> LENGTH: 23
<212> TYPE: DNA
<213> ORGANISM: Sh. olleyana

<400> SEQUENCE: 40
caattagaag gagaacaatc ttg 23

<210> SEQ ID NO 41
<211> LENGTH: 23
<212> TYPE: DNA
<213> ORGANISM: Sh. olleyana

<400> SEQUENCE: 41
agaggcataa aggaataata atg 23

<210> SEQ ID NO 42
<211> LENGTH: 23
<212> TYPE: DNA
<213> ORGANISM: Sh. olleyana

<400> SEQUENCE: 42
caatttagcc tgagcctagt ttg 23

<210> SEQ ID NO 43
<211> LENGTH: 23
<212> TYPE: DNA
<213> ORGANISM: Sh. japonica

<400> SEQUENCE: 43
taaatcgcac tggtattgtc atg 23

<210> SEQ ID NO 44
<211> LENGTH: 23
<212> TYPE: DNA
<213> ORGANISM: Sh. japonica

<400> SEQUENCE: 44
aagcactcaa tgatgctggt gtg 23

<210> SEQ ID NO 45
<211> LENGTH: 23

<212> TYPE: DNA
<213> ORGANISM: Sh. olleyana

<400> SEQUENCE: 45
taaaccgcac cggtattgtc atg 23

<210> SEQ ID NO 46
<211> LENGTH: 23
<212> TYPE: DNA
<213> ORGANISM: Sh. olleyana

<400> SEQUENCE: 46
acccagctga ctatcaaggt gtg 23

<210> SEQ ID NO 47
<211> LENGTH: 23
<212> TYPE: DNA
<213> ORGANISM: Sh. olleyana

<400> SEQUENCE: 47
atgaatcgac tgcgtctatt gtg 23

<210> SEQ ID NO 48
<211> LENGTH: 23
<212> TYPE: DNA
<213> ORGANISM: Sh. olleyana

<400> SEQUENCE: 48
catctagaga acaaggttta atg 23

<210> SEQ ID NO 49
<211> LENGTH: 27
<212> TYPE: DNA
<213> ORGANISM: artificial sequence
<220> FEATURE:
<223> OTHER INFORMATION: primer

<400> SEQUENCE: 49
cggtacccgc gaatcaagaa ggtaggc 27

<210> SEQ ID NO 50
<211> LENGTH: 27
<212> TYPE: DNA
<213> ORGANISM: artificial sequence
<220> FEATURE:
<223> OTHER INFORMATION: primer

<400> SEQUENCE: 50
cggatcccgt ctctgccgct ttttctt 27

<210> SEQ ID NO 51
<211> LENGTH: 30
<212> TYPE: DNA
<213> ORGANISM: artificial sequence
<220> FEATURE:
<223> OTHER INFORMATION: primer

<400> SEQUENCE: 51
cggatccgaa agtgaacctt gtcctaaccc 30

<210> SEQ ID NO 52
<211> LENGTH: 27
<212> TYPE: DNA
<213> ORGANISM: artificial sequence
<220> FEATURE:

-continued

<223> OTHER INFORMATION: primer

<400> SEQUENCE: 52
ctctagacag atccgcacca tcggccg 27

<210> SEQ ID NO 53
<211> LENGTH: 19
<212> TYPE: DNA
<213> ORGANISM: artificial sequence
<220> FEATURE:
<223> OTHER INFORMATION: primer

<400> SEQUENCE: 53
cactagtacc gctgcggaa 19

<210> SEQ ID NO 54
<211> LENGTH: 34
<212> TYPE: DNA
<213> ORGANISM: artificial sequence
<220> FEATURE:
<223> OTHER INFORMATION: primer

<400> SEQUENCE: 54
cactcgcggg cccatcgtct ctgccgcttt ttct 34

<210> SEQ ID NO 55
<211> LENGTH: 34
<212> TYPE: DNA
<213> ORGANISM: artificial sequence
<220> FEATURE:
<223> OTHER INFORMATION: primer

<400> SEQUENCE: 55
aaagcggcag agacgatggg cccgcgagtg gcgt 34

<210> SEQ ID NO 56
<211> LENGTH: 28
<212> TYPE: DNA
<213> ORGANISM: artificial sequence
<220> FEATURE:
<223> OTHER INFORMATION: primer

<400> SEQUENCE: 56
gatttaaatc cttctttcgc gacgccaa 28

<210> SEQ ID NO 57
<211> LENGTH: 33
<212> TYPE: DNA
<213> ORGANISM: artificial sequence
<220> FEATURE:
<223> OTHER INFORMATION: primer

<400> SEQUENCE: 57
cgatttaaat gcatgctgct gcaggccgtc gat 33

<210> SEQ ID NO 58
<211> LENGTH: 34
<212> TYPE: DNA
<213> ORGANISM: artificial sequence
<220> FEATURE:
<223> OTHER INFORMATION: primer

<400> SEQUENCE: 58
acaaggttca ctttcttaaa gtggctgggt cggc 34

-continued

```
<210> SEQ ID NO 59
<211> LENGTH: 34
<212> TYPE: DNA
<213> ORGANISM: artificial sequence
<220> FEATURE:
<223> OTHER INFORMATION: primer

<400> SEQUENCE: 59

acccagccac tttaagaaag tgaaccttgt ccta                                34


<210> SEQ ID NO 60
<211> LENGTH: 19
<212> TYPE: DNA
<213> ORGANISM: artificial sequence
<220> FEATURE:
<223> OTHER INFORMATION: primer

<400> SEQUENCE: 60

ggtcgacaaa cattttctt                                                 19


<210> SEQ ID NO 61
<211> LENGTH: 7
<212> TYPE: PRT
<213> ORGANISM: Shewanella sp.

<400> SEQUENCE: 61

Met Val Arg Gly Tyr Leu Arg
1               5


<210> SEQ ID NO 62
<211> LENGTH: 54
<212> TYPE: PRT
<213> ORGANISM: Shewanella sp.

<400> SEQUENCE: 62

Leu Ile Ser Leu Tyr Phe Cys Pro Leu Thr Ile Gln Glu Cys Asp Asn
1               5                   10                  15

Gln Thr Thr Glu Leu Val Lys Ser Trp Leu Pro Glu Asp Glu Leu Ile
            20                  25                  30

Lys Val Asn Arg Tyr Ile Lys Gln Glu Ala Lys Thr Gln Gly Leu Met
        35                  40                  45

Val Arg Gly Tyr Leu Arg
    50
```